(12) United States Patent
Khvorova et al.

(10) Patent No.: US 9,303,259 B2
(45) Date of Patent: Apr. 5, 2016

(54) RNA INTERFERENCE IN SKIN INDICATIONS

(71) Applicant: RXi Pharmaceuticals Corporation, Westborough, MA (US)

(72) Inventors: Anastasia Khvorova, Westborough, MA (US); William Salomon, Worcester, MA (US); Joanne Kamens, Newton, MA (US); Dmitry Samarsky, Westborough, MA (US); Tod M. Woolf, Sudbury, MA (US); Pamela A. Pavco, Longmont, CO (US); James Cardia, Franklin, MA (US)

(73) Assignee: RXi Pharmaceuticals Corporation, Marlborough, MA (US)

( * ) Notice: Subject to any disclaimer, the term of this patent is extended or adjusted under 35 U.S.C. 154(b) by 0 days.

(21) Appl. No.: 14/104,450

(22) Filed: Dec. 12, 2013

(65) Prior Publication Data
US 2014/0315974 A1    Oct. 23, 2014

Related U.S. Application Data

(63) Continuation of application No. 13/120,315, filed as application No. PCT/US2009/005246 on Sep. 22, 2009, now Pat. No. 8,664,189.

(60) Provisional application No. 61/224,031, filed on Jul. 8, 2009, provisional application No. 61/149,946, filed on Feb. 4, 2009, provisional application No. 61/192,954, filed on Sep. 22, 2008.

(51) Int. Cl.
*A61K 48/00* (2006.01)
*C12N 15/113* (2010.01)
*C12N 15/11* (2006.01)

(52) U.S. Cl.
CPC ............ *C12N 15/113* (2013.01); *C12N 15/111* (2013.01); *C12N 2310/315* (2013.01); *C12N 2310/321* (2013.01); *C12N 2310/322* (2013.01); *C12N 2310/3515* (2013.01); *C12N 2310/3519* (2013.01); *C12N 2320/32* (2013.01); *C12N 2320/51* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,426,330 A | 1/1984 | Sears |
| 4,897,355 A | 1/1990 | Eppstein et al. |
| 4,904,582 A | 2/1990 | Tullis |
| 4,958,013 A | 9/1990 | Letsinger |
| 5,023,243 A | 6/1991 | Tullis |
| 5,151,510 A | 9/1992 | Stec et al. |
| 5,188,897 A | 2/1993 | Suhadolnik et al. |
| 5,264,423 A | 11/1993 | Cohen et al. |
| 5,264,562 A | 11/1993 | Matteucci |
| 5,405,939 A | 4/1995 | Suhadolnik |
| 5,416,203 A | 5/1995 | Letsinger |
| 5,417,978 A | 5/1995 | Tari et al. |
| 5,453,496 A | 9/1995 | Caruthers et al. |
| 5,466,786 A | 11/1995 | Buhr et al. |
| 5,470,967 A | 11/1995 | Huie et al. |
| 5,489,677 A | 2/1996 | Sanghvi et al. |
| 5,495,009 A | 2/1996 | Matteucci et al. |
| 5,532,130 A | 7/1996 | Alul |
| 5,534,259 A | 7/1996 | Zalipsky et al. |
| 5,556,948 A | 9/1996 | Tagawa et al. |
| 5,561,225 A | 10/1996 | Maddry et al. |
| 5,578,718 A | 11/1996 | Cook et al. |
| 5,591,721 A | 1/1997 | Agrawal et al. |
| 5,596,086 A | 1/1997 | Matteucci et al. |
| 5,599,797 A | 2/1997 | Cook et al. |
| 5,602,240 A | 2/1997 | De Mesmaeker et al. |
| 5,607,923 A | 3/1997 | Cook et al. |
| 5,614,621 A | 3/1997 | Ravikumar et al. |
| 5,623,070 A | 4/1997 | Cook et al. |
| 5,625,050 A | 4/1997 | Beaton et al. |
| 5,633,360 A | 5/1997 | Bischofberger et al. |
| 5,643,889 A | 7/1997 | Suhadolnik et al. |
| 5,646,126 A | 7/1997 | Cheng et al. |
| 5,646,265 A | 7/1997 | McGee |
| 5,658,731 A | 8/1997 | Sproat et al. |
| 5,661,134 A | 8/1997 | Cook et al. |
| 5,663,312 A | 9/1997 | Chaturvedula |
| 5,670,633 A | 9/1997 | Cook et al. |
| 5,684,143 A | 11/1997 | Gryaznov et al. |
| 5,466,786 B1 | 4/1998 | Buhr et al. |
| 5,750,666 A | 5/1998 | Caruthers et al. |
| 5,770,209 A | 6/1998 | Grotendorst et al. |

(Continued)

FOREIGN PATENT DOCUMENTS

| | | |
|---|---|---|
| AU | 2004206255 B2 | 8/2004 |
| CN | 1 568 373 A | 1/2005 |
| EP | 0 552 766 A2 | 1/1993 |
| EP | 1 214 945 A2 | 6/2002 |
| EP | 1 144 623 B9 | 3/2003 |
| EP | 1 352 061 B1 | 10/2003 |
| EP | 0 928 290 B9 | 3/2005 |

(Continued)

OTHER PUBLICATIONS

[No Author Listed] RedChip Small-Cap Investor Conference. RXI Pharmaceuticals (Nasdaq RXII). Jun. 16, 2009 Presentation. 5 pages.

(Continued)

*Primary Examiner* — Kimberly Chong
(74) *Attorney, Agent, or Firm* — Wolf, Greenfield & Sacks, P.C.

(57) ABSTRACT

The present invention relates to RNAi constructs with improved tissue and cellular uptake characteristics and methods of use of these compounds in dermal applications.

12 Claims, 92 Drawing Sheets

(56) References Cited

U.S. PATENT DOCUMENTS

| | | |
|---|---|---|
| 5,770,713 A | 6/1998 | Imbach et al. |
| 5,777,153 A | 7/1998 | Lin et al. |
| 5,792,847 A | 8/1998 | Buhr et al. |
| 5,808,023 A | 9/1998 | Sanghvi et al. |
| 5,817,781 A | 10/1998 | Swaminathan et al. |
| 5,830,430 A | 11/1998 | Unger et al. |
| 5,856,455 A | 1/1999 | Cook |
| 5,914,396 A | 6/1999 | Cook et al. |
| 5,945,521 A | 8/1999 | Just et al. |
| 5,948,767 A | 9/1999 | Scheule et al. |
| 5,981,501 A | 11/1999 | Wheeler et al. |
| 5,986,083 A | 11/1999 | Dwyer et al. |
| 6,015,886 A | 1/2000 | Dale et al. |
| 6,020,475 A | 2/2000 | Capaldi et al. |
| 6,043,352 A | 3/2000 | Manoharan et al. |
| 6,051,699 A | 4/2000 | Ravikumar |
| 6,107,094 A | 8/2000 | Crooke |
| 6,111,085 A | 8/2000 | Cook et al. |
| 6,121,437 A | 9/2000 | Guzaev et al. |
| 6,153,737 A | 11/2000 | Manoharan et al. |
| 6,207,819 B1 | 3/2001 | Manoharan et al. |
| 6,221,911 B1 | 4/2001 | Lavin et al. |
| 6,232,064 B1 | 5/2001 | Grotendorst et al. |
| 6,271,358 B1 | 8/2001 | Manoharan et al. |
| 6,326,358 B1 | 12/2001 | Manoharan |
| 6,328,765 B1 | 12/2001 | Hardwick et al. |
| 6,331,617 B1 | 12/2001 | Weeks et al. |
| 6,395,492 B1 | 5/2002 | Manoharan et al. |
| 6,399,754 B1 | 6/2002 | Cook |
| 6,410,702 B1 | 6/2002 | Swaminathan et al. |
| 6,440,943 B1 | 8/2002 | Cook et al. |
| 6,465,628 B1 | 10/2002 | Ravikumar et al. |
| 6,475,490 B1 | 11/2002 | Srivastava et al. |
| 6,476,205 B1 | 11/2002 | Buhr et al. |
| 6,492,129 B1 | 12/2002 | Grotendorst |
| 6,506,559 B1 | 1/2003 | Fire et al. |
| 6,562,618 B1 | 5/2003 | Tamatani et al. |
| 6,673,611 B2 | 1/2004 | Thompson et al. |
| 6,683,167 B2 | 1/2004 | Metelev et al. |
| 6,706,491 B1 | 3/2004 | Chang et al. |
| 6,753,321 B2 | 6/2004 | Kovesdi |
| 6,794,137 B2 | 9/2004 | Blumenberg |
| 6,965,025 B2 | 11/2005 | Gaarde et al. |
| 7,044,945 B2 | 5/2006 | Sand |
| 7,056,704 B2 | 6/2006 | Tuschl et al. |
| 7,078,196 B2 | 7/2006 | Tuschl et al. |
| 7,108,721 B2 | 9/2006 | Huckle et al. |
| 7,115,390 B1 | 10/2006 | Grotendorst et al. |
| 7,175,844 B2 | 2/2007 | King |
| 7,348,155 B2 | 3/2008 | Kostenis et al. |
| 7,384,634 B2 | 6/2008 | Grotendorst et al. |
| 7,405,274 B2 | 7/2008 | Lin et al. |
| 7,432,250 B2 | 10/2008 | Crooke |
| 7,462,602 B2 | 12/2008 | Schultz et al. |
| 7,534,774 B2 | 5/2009 | Sosnowski et al. |
| 7,538,095 B2 | 5/2009 | Fire et al. |
| 7,560,438 B2 | 7/2009 | Fire et al. |
| 7,579,186 B1 | 8/2009 | Sakamoto et al. |
| 7,595,387 B2 | 9/2009 | Leake et al. |
| 7,622,633 B2 | 11/2009 | Fire et al. |
| 7,629,321 B2 | 12/2009 | Crooke |
| 7,695,902 B2 | 4/2010 | Crooke |
| 7,745,608 B2 | 6/2010 | Manoharan et al. |
| 7,750,144 B2 | 7/2010 | Zamore et al. |
| 7,786,290 B2 | 8/2010 | Woppmann et al. |
| 7,789,841 B2 | 9/2010 | Huckle et al. |
| 7,829,693 B2 | 11/2010 | Kreutzer et al. |
| 7,833,989 B2 | 11/2010 | Khvorova et al. |
| 8,110,674 B2 | 2/2012 | Manoharan et al. |
| 8,258,105 B2 | 9/2012 | Siwkowski et al. |
| 8,263,569 B2 | 9/2012 | Baulcombe et al. |
| 8,329,671 B2 | 12/2012 | Gu et al. |
| 8,664,189 B2 | 3/2014 | Khvorova et al. |
| 8,796,443 B2 | 8/2014 | Khvorova et al. |
| 8,815,818 B2 | 8/2014 | Samarsky et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 2002/0086013 A1 | 7/2002 | King |
| 2002/0132788 A1 | 9/2002 | Lewis et al. |
| 2002/0160393 A1 | 10/2002 | Symonds et al. |
| 2002/0162126 A1 | 10/2002 | Beach et al. |
| 2003/0004325 A1 | 1/2003 | Cook et al. |
| 2003/0077829 A1 | 4/2003 | MacLachlan |
| 2003/0108923 A1 | 6/2003 | Tuschl et al. |
| 2003/0113816 A1 | 6/2003 | Weitz et al. |
| 2003/0144223 A1 | 7/2003 | Gaarde et al. |
| 2003/0148979 A1 | 8/2003 | Sosnowski et al. |
| 2003/0153524 A1 | 8/2003 | Hinton et al. |
| 2003/0157030 A1 | 8/2003 | Davis et al. |
| 2003/0158403 A1 | 8/2003 | Manoharan et al. |
| 2003/0166282 A1 | 9/2003 | Brown et al. |
| 2003/0180300 A1 | 9/2003 | Grotendorst |
| 2004/0005319 A1 | 1/2004 | Grotendorst et al. |
| 2004/0009938 A1 | 1/2004 | Manoharan et al. |
| 2004/0014957 A1 | 1/2004 | Eldrup et al. |
| 2004/0018999 A1 | 1/2004 | Beach et al. |
| 2004/0054155 A1 | 3/2004 | Woolf et al. |
| 2004/0092450 A1 | 5/2004 | Grotendorst et al. |
| 2004/0137471 A1 | 7/2004 | Vickers et al. |
| 2004/0171033 A1 | 9/2004 | Baker et al. |
| 2004/0180351 A1 | 9/2004 | Giese et al. |
| 2004/0192629 A1 | 9/2004 | Xu et al. |
| 2004/0204377 A1 | 10/2004 | Rana |
| 2004/0229266 A1 | 11/2004 | Tuschl et al. |
| 2004/0235031 A1 | 11/2004 | Schultz et al. |
| 2004/0241845 A1 | 12/2004 | Desgroseillers et al. |
| 2004/0248839 A1 | 12/2004 | Kowalik |
| 2004/0259247 A1 | 12/2004 | Tuschl et al. |
| 2005/0008617 A1 | 1/2005 | Chen et al. |
| 2005/0020521 A1 | 1/2005 | Rana |
| 2005/0032733 A1 | 2/2005 | McSwiggen et al. |
| 2005/0059629 A1 | 3/2005 | Gaarde et al. |
| 2005/0080246 A1 | 4/2005 | Allerson et al. |
| 2005/0107325 A1 | 5/2005 | Manoharan et al. |
| 2005/0119202 A1 | 6/2005 | Kreutzer et al. |
| 2005/0142535 A1 | 6/2005 | Damha et al. |
| 2005/0181382 A1 | 8/2005 | Zamore et al. |
| 2005/0245474 A1 | 11/2005 | Baker et al. |
| 2005/0255487 A1 | 11/2005 | Khvorova et al. |
| 2006/0009409 A1 | 1/2006 | Woolf |
| 2006/0069050 A1 | 3/2006 | Rana |
| 2006/0142228 A1 | 6/2006 | Ford et al. |
| 2006/0178324 A1 | 8/2006 | Hadwiger et al. |
| 2006/0178327 A1 | 8/2006 | Yeung |
| 2007/0020623 A1 | 1/2007 | Petersohn et al. |
| 2007/0031844 A1 | 2/2007 | Khvorova et al. |
| 2007/0032441 A1 | 2/2007 | McSwiggen et al. |
| 2007/0166734 A1 | 7/2007 | Bhat et al. |
| 2007/0173476 A1 | 7/2007 | Leake et al. |
| 2007/0254850 A1 | 11/2007 | Lieberman et al. |
| 2007/0269889 A1 | 11/2007 | Leake et al. |
| 2007/0275465 A1 | 11/2007 | Woppmann et al. |
| 2008/0020990 A1 | 1/2008 | Yano et al. |
| 2008/0070856 A1 | 3/2008 | Kreutzer et al. |
| 2008/0085869 A1 | 4/2008 | Yamada et al. |
| 2008/0193443 A1 | 8/2008 | Beskrovnaya et al. |
| 2008/0254487 A1 | 10/2008 | Klaus et al. |
| 2008/0300147 A1 | 12/2008 | Chegini et al. |
| 2009/0012021 A1 | 1/2009 | Sood et al. |
| 2009/0023216 A1 | 1/2009 | Woolf |
| 2009/0069623 A1 | 3/2009 | Oh |
| 2009/0131360 A1 | 5/2009 | Woolf et al. |
| 2009/0202520 A1 | 8/2009 | Lupher, Jr. et al. |
| 2009/0208564 A1 | 8/2009 | Li et al. |
| 2010/0035964 A1 | 2/2010 | Gaarde et al. |
| 2010/0069620 A1 | 3/2010 | Zon |
| 2010/0130595 A1 | 5/2010 | Dean et al. |
| 2010/0136695 A1 | 6/2010 | Woolf |
| 2010/0158907 A1 | 6/2010 | Grotendorst et al. |
| 2010/0190838 A1 | 7/2010 | Grotendorst |
| 2011/0039914 A1 | 2/2011 | Pavco et al. |
| 2011/0054004 A1 | 3/2011 | Mustoe et al. |

(56) References Cited

U.S. PATENT DOCUMENTS

| | | |
|---|---|---|
| 2011/0237522 A1 | 9/2011 | Khvorova et al. |
| 2011/0251258 A1 | 10/2011 | Samarsky et al. |
| 2011/0263680 A1 | 10/2011 | Khvorova et al. |
| 2012/0016005 A1 | 1/2012 | Samarsky et al. |
| 2012/0040459 A1 | 2/2012 | Khvorova et al. |
| 2012/0059046 A1 | 3/2012 | Woolf et al. |
| 2012/0065243 A1 | 3/2012 | Woolf et al. |
| 2013/0131141 A1 | 5/2013 | Khvorova et al. |
| 2013/0131142 A1 | 5/2013 | Libertine et al. |
| 2013/0197055 A1 | 8/2013 | Kamens et al. |
| 2014/0113950 A1 | 4/2014 | Khvorova et al. |
| 2014/0364482 A1 | 12/2014 | Khvorova et al. |

FOREIGN PATENT DOCUMENTS

| | | |
|---|---|---|
| EP | 1 407 044 B1 | 9/2007 |
| EP | 1 605 978 B1 | 1/2010 |
| JP | 4 095 895 B2 | 9/2004 |
| JP | 2005-512976 | 5/2005 |
| JP | 2009-519033 | 5/2009 |
| WO | WO 90/14074 A1 | 11/1990 |
| WO | WO 91/16024 A1 | 10/1991 |
| WO | WO 91/17424 A1 | 11/1991 |
| WO | WO 92/03464 A1 | 3/1992 |
| WO | WO 94/23028 A2 | 10/1994 |
| WO | WO 95/11910 A1 | 5/1995 |
| WO | WO 95/23162 A1 | 8/1995 |
| WO | WO 96/40964 A2 | 12/1996 |
| WO | WO 99/13915 A1 | 3/1999 |
| WO | WO 03/012052 A2 | 2/2003 |
| WO | WO 03/053340 A2 | 7/2003 |
| WO | WO 2004/042027 A2 | 5/2004 |
| WO | WO 2004/064760 A2 | 8/2004 |
| WO | WO 2004/065600 A2 | 8/2004 |
| WO | WO 2004/065601 A2 | 8/2004 |
| WO | WO 2004/090105 A2 | 10/2004 |
| WO | WO 2005/019430 A2 | 3/2005 |
| WO | WO 2005/079533 A2 | 9/2005 |
| WO | WO 2005/097992 A2 | 10/2005 |
| WO | WO 2006/007372 A2 | 1/2006 |
| WO | WO 2006/019430 A2 | 2/2006 |
| WO | WO 2006/039656 A2 | 4/2006 |
| WO | WO 2006/065601 A2 | 6/2006 |
| WO | WO 2006/113679 A2 | 10/2006 |
| WO | WO 2006/128141 A2 | 11/2006 |
| WO | WO 2007/030167 A1 | 3/2007 |
| WO | WO 2007/044362 A2 | 4/2007 |
| WO | WO 2007/050643 A2 | 5/2007 |
| WO | WO 2007/069068 A2 | 6/2007 |
| WO | WO 2007/089607 A2 | 8/2007 |
| WO | WO 2008/036825 A2 | 3/2008 |
| WO | WO 2008/109353 A1 | 9/2008 |
| WO | WO 2009/005813 A1 | 1/2009 |
| WO | WO 2009/020344 A2 | 2/2009 |
| WO | WO 2009/029688 A3 | 3/2009 |
| WO | WO 2009/029690 A1 | 3/2009 |
| WO | WO 2009/044392 A2 | 4/2009 |
| WO | WO 2009/045457 A2 | 4/2009 |
| WO | WO 2009/078685 A2 | 6/2009 |
| WO | WO 2010/006237 A2 | 1/2010 |
| WO | WO 2010/027830 A2 | 3/2010 |
| WO | WO 2010/027831 A1 | 3/2010 |
| WO | WO 2010/027832 A1 | 3/2010 |
| WO | WO 2010/033246 A1 | 3/2010 |
| WO | WO 2010/042281 A2 | 4/2010 |
| WO | WO 2011/109698 A1 | 9/2011 |
| WO | WO 2011/119887 A1 | 9/2011 |

OTHER PUBLICATIONS

Aleckovic et al., RNAi at Oxford. J RNAi Gene Silencing. May 27, 2008;4(1):266-8.
Braasch et al., RNA Interference in Mammalian Cells by Chemically-Modified RNA. Biochem. 2003;42(26):7967-75.
Brown et al., Light at the end of the tunnel. J RNAi Gene Silencing. Jul. 28, 2006;2(2):175-7.
Cheng et al., Connective tissue growth factor is a biomarker and mediator of kidney allograft fibrosis. Am J Transplant. Oct. 2006;6(10):2292-306. Epub Aug. 4, 2006.
Chiu et al., siRNA function in RNAi: a chemical modification analysis. RNA. Sep. 2003;9(9):1034-48.
Choung et al. Chemical modification of siRNAs to improve serum stability without loss of efficacy. Biochem Biophys Res Commun. Apr. 14, 2006;342(3):919-27.
Chu et al., Potent RNAi by short RNA triggers. RNA. 2008;14:1714-9.
Cicha et al., Connective tissue growth factor is overexpressed in complicated atherosclerotic plaques and induces mononuclear cell chemotaxis in vitro. Arterioscler Thromb Vasc Biol. May 2005;25(5):1008-13. Epub Mar. 10, 2005.
Czauderna et al., Structural variations and stabilising modifications of synthetic siRNAs in mammalian cells. Nucleic Acids Res. Jun. 1, 2003;31(11):2705-16.
Daniels et al., Imatinib mesylate inhibits the profibrogenic activity of TGF-beta and prevents bleomycin-mediated lung fibrosis. J Clin Invest. Nov. 2004;114(9):1308-16.
Debart et al., Chemical modifications to improve the cellular uptake of oligonucleotides. Curr Top Med Chem. 2007;7(7):727-37.
Distler et al., Imatinib mesylate reduces production of extracellular matrix and prevents development of experimental dermal fibrosis. Arthritis Rheum. Jan. 2007;56(1):311-22.
Dranoff et al., Prevention of liver fibrosis by the purinoceptor antagonist pyridoxal-phosphate-6-2',4'-disulfonate (PPADS). In Vivo. 2007;21:957-66.
Dykxhoorn et al., The silent treatment: siRNAs as small molecule drugs. Gene Ther. Mar. 2006;13(6):541-52. Review.
Dziadzio et al., N-terminal connective tissue growth factor is a marker of the fibrotic phenotype in scleroderma. QJM. Jul. 2005;98(7):485-92. Epub Jun. 13, 2005.
Elbashir et al., Duplexes of 21-nucleotide RNAs mediate RNA interference in cultured mammalian cells. Nature. May 24, 2001;411(6836):494-8.
Elbashir et al., Functional anatomy of siRNAs for mediating efficient RNAi in Drosophila melanogaster embryo lysate. EMBO J. Dec. 3, 2001;20(23):6877-88.
Fedorov et al., Off-target effects by siRNA can induce toxic phenotype. RNA. Jul. 2006;12(7):1188-96. Epub May 8, 2006.
Gressner et al., Connective tissue growth factor in serum as a new candidate test for assessment of hepatic fibrosis. Clin Chem. Sep. 2006;52(9):1815-7. Epub Jul. 20, 2006.
Gressner et al., Connective tissue growth factor: a fibrogenic master switch in fibrotic liver diseases. Liver Int. Sep. 2008;28(8):1065-79. doi:10.1111/j.1478-3231.2008.01826.x.
Hinton et al., Novel growth factors involved in the pathogenesis of proliferative vitreoretinopathy. Eye (Lond). Jul. 2002;16(4):422-8.
Ito et al., Expression of connective tissue growth factor in human renal fibrosis. Kidney Int. Apr. 1998;53(4):853-61.
Ito et al., Kinetics of connective tissue growth factor expression during experimental proliferative glomerulonephritis. J Am Soc Nephrol. Mar. 2001;12(3):472-84.
Jackson et al., Position-specific chemical modification of siRNAs reduces "off-target" transcript silencing. RNA. Jul. 2006;12(7):1197-1205. Epub May 8, 2006.
Koitabashi et al., Plasma connective tissue growth factor is a novel potential biomarker of cardiac dysfunction in patients with chronic heart failure. Eur J Heart Fail. Apr. 2008;10(4):373-9. doi: 10.1016/j.ejheart.2008.02.011.
Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.
Kubo et al., Modified 27-nt dsRNAs with dramatically enhanced stability in serum and long-term RNAi activity. Oligonucleotides. 2007 Winter;17(4):445-64.
Layzer et al., In vivo activity of nuclease-resistant siRNAs. RNA. May 2004;10(5):766-71.

(56) References Cited

OTHER PUBLICATIONS

Leask et al., Connective tissue growth factor (CTGF, CCN2) gene regulation: a potent clinical bio-marker of fibroproliferative disease? J Cell Commun Signal. Jun. 2009;3(2):89-94. doi: 10.1007/s12079-009-0037-7. Epub Jan. 21, 2009.
Leask et al., Insights into the molecular mechanism of chronic fibrosis: the role of connective tissue growth factor in scleroderma. J Invest Dermatol. Jan. 2004;122(1):1-6.
Lee et al., Contributions of 3'-overhang to the dissociation of small interfering RNAs from the PAZ domain: molecular dynamics simulation study. J Mol Graph Model. Mar. 2007;25(6):784-93. Epub Jul. 11, 2006.
Leuschner et al., Cleavage of the siRNA passenger strand during RISC assembly in human cells. EMBO Rep. Mar. 2006;7(3):314-20. Epub Jan. 20, 2006.
Li et al., Inhibition of connective tissue growth factor by siRNA prevents liver fibrosis in rats. J Gene Med. Jul. 2006;8(7):889-900.
Liu et al., Role of connective tissue growth factor in experimental radiation nephropathy in rats. Chin Med J (Engl). Oct. 5, 2008;121(19):1925-31.
Luo et al., Inhibition of connective tissue growth factor by small interfering RNA prevents renal fibrosis in rats undergoing chronic allograft nephropathy. Transplant Proc. Sep. 2008;40(7):2365-9. doi:10.1016/j.transproceed.2008.07.100.
Manoharan et al., Chemical modifications to improve uptake and bioavailability of antisense oligonucleotides. Ann N Y Acad Sci. Oct. 28, 1992;660:306-9.
Mescalchin et al., Cellular uptake and intracellular release are major obstacles to the therapeutic application of siRNA: novel options by phosphorothioate-stimulated delivery. Expert Opin Biol Ther. Oct. 2007;7(10):1531-8. Review.
Overhoff et al., Phosphorothioate-stimulated uptake of short interfering RNA by human cells. EMBO Rep. Dec. 2005;6(12):1176-81.
Paradis et al., Expression of connective tissue growth factor in experimental rat and human liver fibrosis. Hepatology. Oct. 1999;30(4):968-76.
Pollio et al., Severe secondary postpartum hemorrhage 3 weeks after cesarean section: alternative etiologies of uterine scar non-union. J Obstet Gynaecol Res. Jun. 2007;33(3):360-2.
Rajeev et al., 2'-modified-2-thiothymidine oligonucleotides. Org Lett. Aug. 21, 2003;5(17):3005-8.
Sato et al., Serum levels of connective tissue growth factor are elevated in patients with systemic sclerosis: association with extent of skin sclerosis and severity of pulmonary fibrosis. J Rheumatol. Jan. 2000;27(1):149-54.
Shen, Advances in the development of siRNA-based therapeutics for cancer. IDrugs. Aug. 2008;11(8):572-8. Review.
Shi, Mammalian RNAi for the masses. Trends Genet. Jan. 2003;19(1):9-12.
Shi-Wen et al., Regulation and function of connective tissue growth factor/CCN2 in tissue repair, scarring and fibrosis. Cytokine Growth Factor Rev. Apr. 2008;19(2):133-44. doi: 10.1016/j.cytogfr.2008.01.002.
Sisco et al., Antisense inhibition of connective tissue growth factor (CTGF/CCN2) mRNA limits hypertrophic scarring without affecting wound healing in vivo. Wound Repair Regen. Sep.-Oct. 2008;16(5):661-73. doi:10.1111/j.1524-475X.2008.00416.x.
Soutschek et al., Therapeutic silencing of an endogenous gene by systemic administration of modified siRNAs. Nature. Nov. 11, 2004;432(7014):173-8.
Sun et al., Asymmetric RNA duplexes mediate RNA interference in mammalian cells. Nat Biotechnol. Dec. 2008;26(12):1379-82. doi: 10.1038/nbt.1512. Epub Nov. 23, 2008. Erratum in: Nat Biotechnol. Feb. 2009;27(2):205.
Uhlmann et al., Antisense oligonucleotides: a new therapeutic principle. Chem Rev. 1990;90(4):543-84.
Williams et al., Increased expression of connective tissue growth factor in fibrotic human liver and in activated hepatic stellate cells. J Hepatol. May 2000;32(5):754-61.
Wolfrum et al., Mechanisms and optimization of in vivo delivery of lipophilic siRNAs. Nat Biotechnol. Oct. 2007;25(10):1149-57. Epub Sep. 16, 2007.
Xiao et al., Effect of small interfering RNA on the expression of connective tissue growth factor and type I and III collagen in skin fibroblasts of patients with systemic sclerosis. Br J Dermatol. Dec. 2006;155(6):1145-53.
Alahari et al., Inhibition of expression of the multidrug resistance-associated P-glycoprotein of by phosphorothioate and 5' cholesterol-conjugated phosphorothioate antisense oligonucleotides. Mol Pharmacol. Oct. 1996;50(4):808-19.
Baigude et al., Design and creation of new nanomaterials for therapeutic RNAi. ACS Chem Biol. Apr. 24, 2007;2(4):237-41.
Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.
De Smidt et al., Association of antisense oligonucleotides with lipoproteins prolongs the plasma half-life and modifies the tissue distribution. Nucleic Acids Res. Sep. 11, 1991;19(17):4695-700.
Kim et al., Systemic and specific delivery of small interfering RNAs to the liver mediated by apolipoprotein A-I. Mol Ther. Jun. 2007;15(6):1145-52. Epub Apr. 17, 2007.
Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.
Li et al., Surface-modified LPD nanoparticles for tumor targeting. Ann N Y Acad Sci. Oct. 2006;1082:1-8.
Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.
Martins et al., Sterol side chain length and structure affect the clearance of chylomicron-like lipid emulsions in rats and mice. J Lipid Res. Feb. 1998;39(2):302-12.
Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.
Rump et al., Preparation of conjugates of oligodeoxynucleotides and lipid structures and their interaction with low-density lipoprotein. Bioconjug Chem. May-Jun. 1998;9(3):341-9.

Figure 10
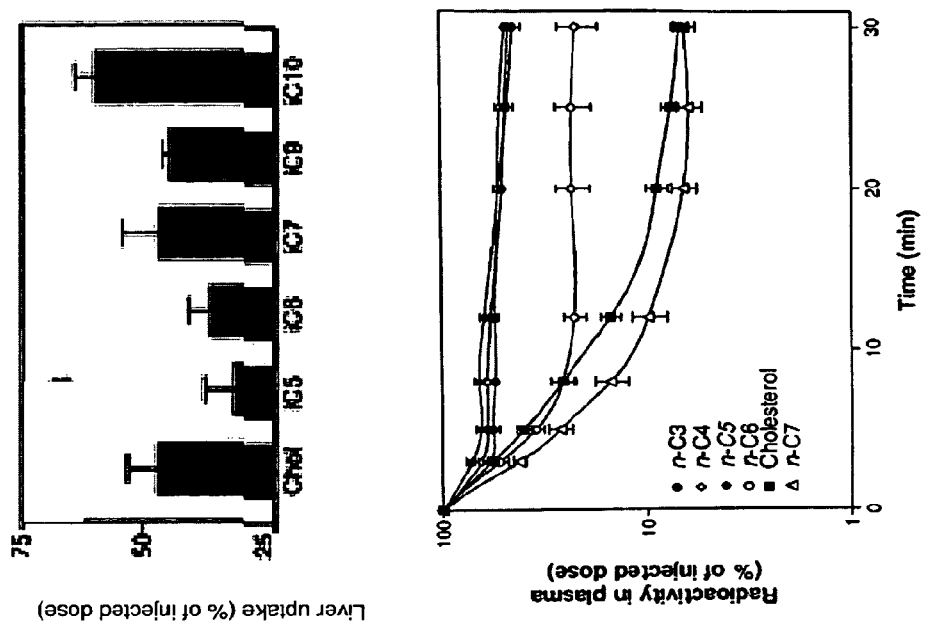
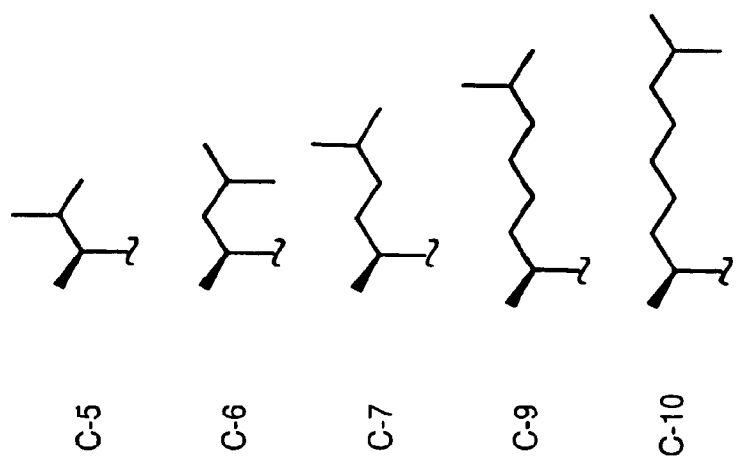
C-5
C-6
C-7
C-9
C-10

Structural Elucidation-MAP4K4

MAP4K4 Minimum Length RNAi Trigger

Structural Elucidation-SOD1

SOD1 Minimum Length RNAi Trigger

Figure 27
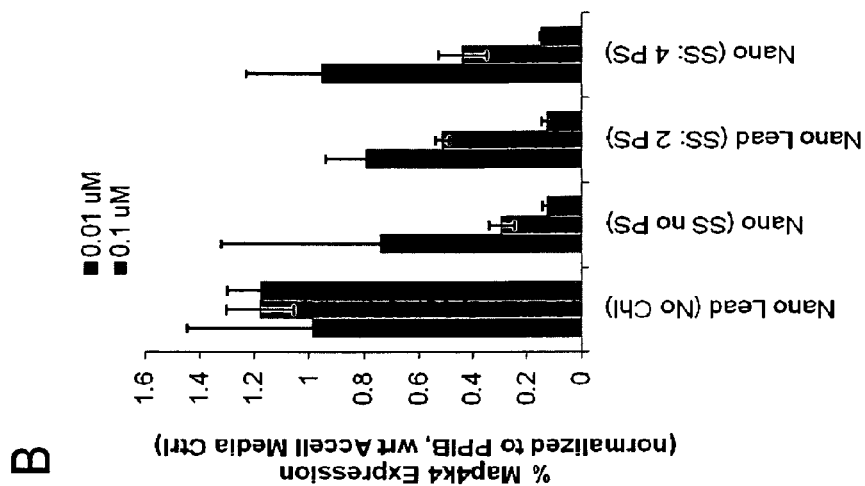
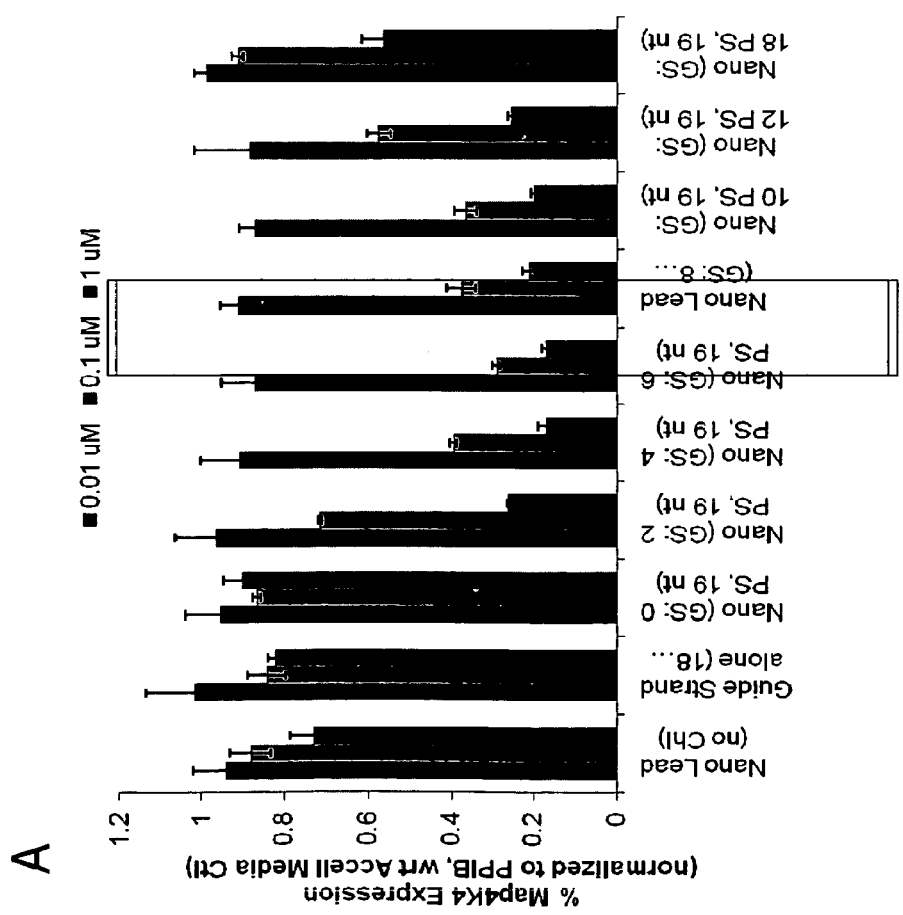

Chemical Modifications Screened for Optimization of sd-rxRNA nano (G1)

Figure 51 sd-rxRNA™: Spontaneous Cellular Uptake and Efficacy Without Delivery Vehicle

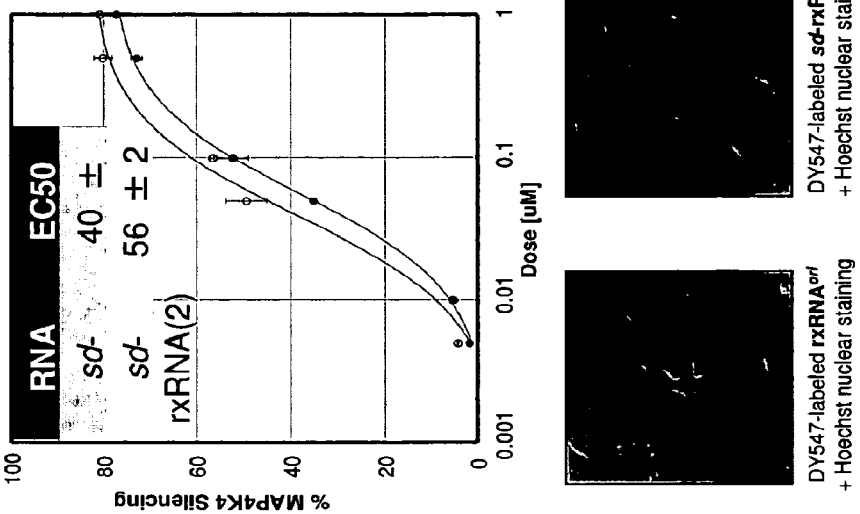

- Chemically modified bipartite RNAi molecules with self-delivering moiety(s)
- *Picomolar* activity after facilitated delivery(lipid-mediated transfection)
- *Nanomolar* activity in cell culture with NO transfection reagent (self-delivery)
- Efficient uptake (>95%) by most cell types in cell culture
- Stable (more then 3 days in 100% human serum)
- Results in distribution to tissues; reduced kidney clearance
- Compatible with SC administration
- Highly specific (little or no immune induction)

sd-rxRNA Delivery to RPE Cells With No Formulation

Silencing of MAP4K4 in RPE Cells Treated with sd-rxRNA*nano* sd-rxRNA™ Is Efficiently Delivered to Cytoplasm sd-rxRNA™ but not Competitor Molecules Are Internalized within Minutes

Figure 66
Local Delivery of sd-rxRNA™: Pilot Study
rxRNA*ori*
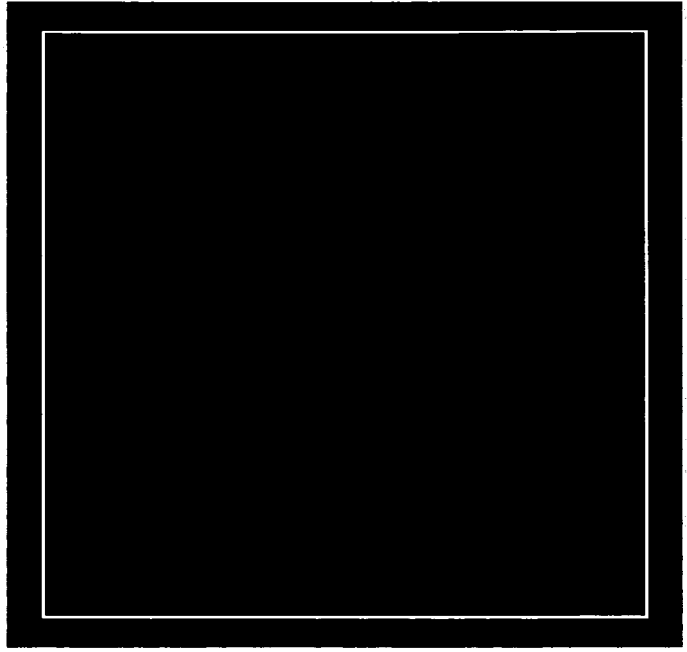
sd-rxRNA™
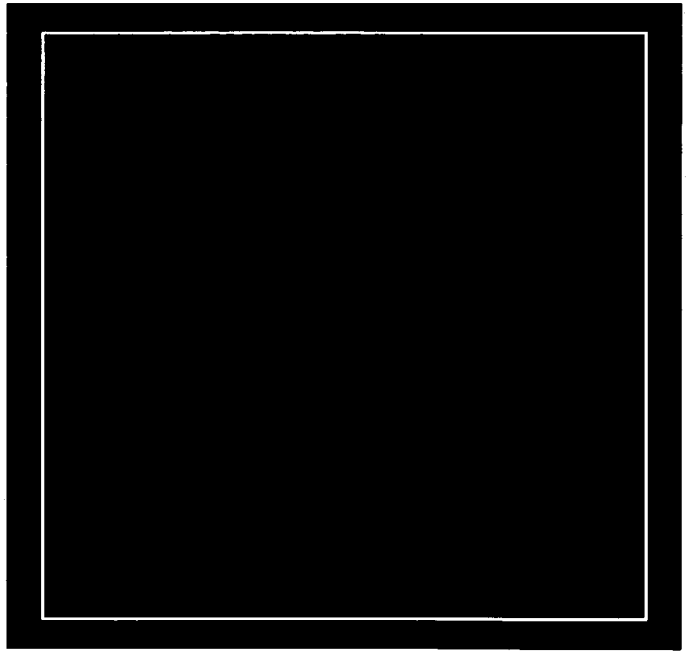
- 24 hours post delivery
- Hoechst and DY547

Figure 67
Local Delivery of sd-rxRNA™: Pilot Study
Competing conjugate* RNAs
*Soutschek et al (2004) Nature, 432:173
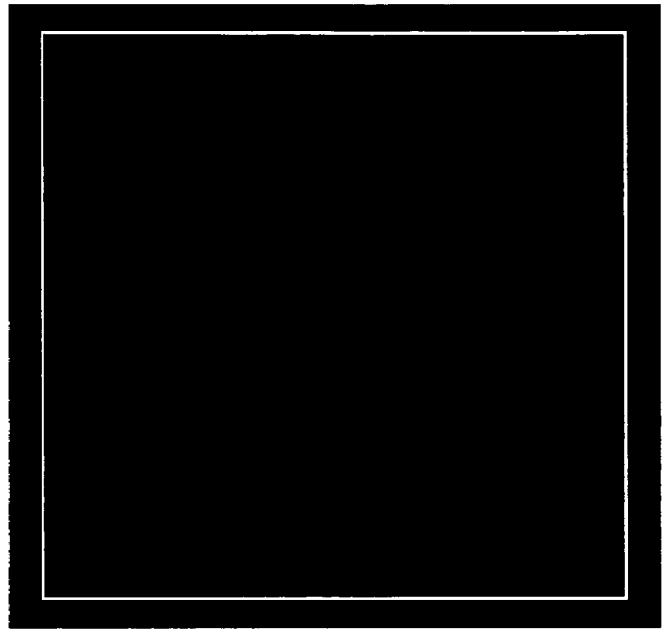
sd-rxRNA™
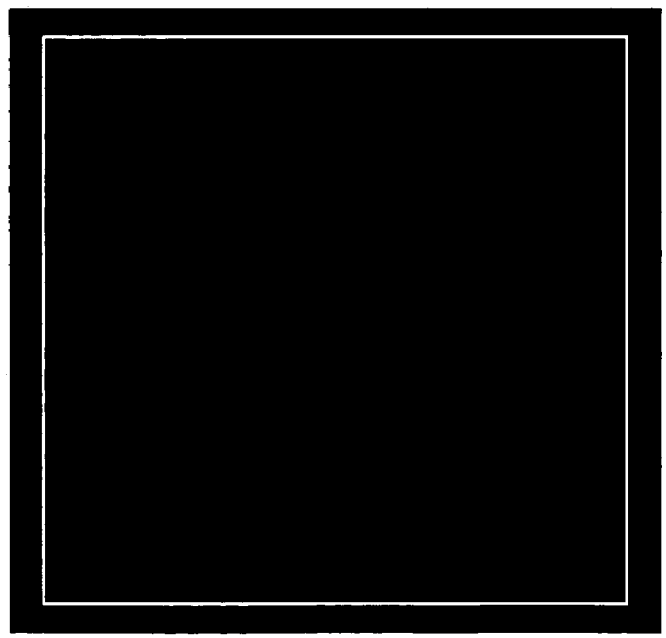
- 24 hours post delivery
- Hoechst and DY547

Incorporation of 5 Me C and/or ribothymidine in Guide Strand Reduces Efficacy

```
                         SEQUENCE LISTING

<160> NUMBER OF SEQ ID NOS: 821

<210> SEQ ID NO 1
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 1
auugguauuc agugugaug                                                    19

<210> SEQ ID NO 2
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 2
auucguauug agucugauc                                                    19

<210> SEQ ID NO 3
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 3
uagacuucca cagaacucu                                                    19

<210> SEQ ID NO 4
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 4
uagacuucca cagaacucu                                                    19

<210> SEQ ID NO 5
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 5
uagacuucca cagaacucu                                                    19
```

```
<210> SEQ ID NO 6
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 6
uagacuucca cagaacucu                                                      19

<210> SEQ ID NO 7
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 7
uagacuucca cagaacucu                                                      19

<210> SEQ ID NO 8
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 8
uagacuucca cagaacucu                                                      19

<210> SEQ ID NO 9
<211> LENGTH: 17
<212> TYPE: RNA
<213> ORGANISM: Artificial Sequence
<220> FEATURE:
<223> OTHER INFORMATION: synthetic oligonucleotide

<400> SEQUENCE: 9
uagacuucca cagaacu                                                        17

<210> SEQ ID NO 10
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 10
auugguauuc agugugauga c                                                   21

<210> SEQ ID NO 11
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 11
auucguauug agucugauca c                                                   21

<210> SEQ ID NO 12
<211> LENGTH: 19
<212> TYPE: RNA
<213> ORGANISM: Artificial Sequence
<220> FEATURE:
```

<223> OTHER INFORMATION: synthetic oligonucleotide

<400> SEQUENCE: 12
uagacuucca cagaacucu                                                    19

<210> SEQ ID NO 13
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 13
uagacuucca cagaacucu                                                    19

<210> SEQ ID NO 14
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 14
uagacuucca cagaacucu                                                    19

<210> SEQ ID NO 15
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 15
uagacuucca cagaacucuu c                                                 21

<210> SEQ ID NO 16
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 16
uagacuucca cagaacucuu c                                                 21

<210> SEQ ID NO 17
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 17
uagacuucca cagaacucuu caaag                                             25

<210> SEQ ID NO 18
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 18
auugguauuc agugugauga c                                                 21

```
<210> SEQ ID NO 19
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 19
auucguauug agucugauca c                                                    21

<210> SEQ ID NO 20
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 20
uagacuucca cagaacucu                                                       19

<210> SEQ ID NO 21
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 21
auugguauuc agugugauga c                                                    21

<210> SEQ ID NO 22
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 22
auucguauug agucugauca c                                                    21

<210> SEQ ID NO 23
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 23
uagacuucca cagaacucu                                                       19

<210> SEQ ID NO 24
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 24
uagacuucca cagaacucu                                                       19

<210> SEQ ID NO 25
<211> LENGTH: 19
<212> TYPE: RNA
<213> ORGANISM: Artificial Sequence
<220> FEATURE:
<223> OTHER INFORMATION: synthetic oligonucleotide
```

```
<400> SEQUENCE: 25
uagacuucca cagaacucu                                                   19

<210> SEQ ID NO 26
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 26
uagacuucca cagaacucu                                                   19

<210> SEQ ID NO 27
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 27
uagacuucca cagaacucu                                                   19

<210> SEQ ID NO 28
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 28
uagacuucca cagaacucu                                                   19

<210> SEQ ID NO 29
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 29
uagacuucca cagaacucu                                                   19

<210> SEQ ID NO 30
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 30
uagacuucca cagaacucu                                                   19

<210> SEQ ID NO 31
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 31
uagacuucca cagaacucu                                                   19

<210> SEQ ID NO 32
<211> LENGTH: 19
```

```
<212> TYPE: RNA
<213> ORGANISM: Artificial Sequence
<220> FEATURE:
<223> OTHER INFORMATION: synthetic oligonucleotide

<400> SEQUENCE: 32
uagacuucca cagaacucu                                                19

<210> SEQ ID NO 33
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 33
uagacuucca cagaacucu                                                19

<210> SEQ ID NO 34
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 34
uagacuucca cagaacucu                                                19

<210> SEQ ID NO 35
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 35
uagacuucca cagaacucu                                                19

<210> SEQ ID NO 36
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 36
uagacuucca cagaacucu                                                19

<210> SEQ ID NO 37
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 37
uagacuucca cagaacucu                                                19

<210> SEQ ID NO 38
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 38
```
uguuuuugua gccaaaucc                                              19

<210> SEQ ID NO 39
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 39
uacuuucuuc auuccacc                                               19

<210> SEQ ID NO 40
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 40
uucauuucca ccuuugccc                                              19

<210> SEQ ID NO 41
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 41
cuuuguacuu ucuucauuu                                              19

<210> SEQ ID NO 42
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 42
ucuuuguacu uucuucauu                                              19

<210> SEQ ID NO 43
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 43
ucagcaguca cauugccca                                              19

<210> SEQ ID NO 44
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 44
auugcccaag ucuccaaca                                              19

<210> SEQ ID NO 45
<211> LENGTH: 19
<212> TYPE: RNA
<213> ORGANISM: Artificial Sequence

```
<220> FEATURE:
<223> OTHER INFORMATION: synthetic oligonucleotide

<400> SEQUENCE: 45
uucugcucga aauugauga                                                    19

<210> SEQ ID NO 46
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 46
aaaucguauu ugucaauca                                                    19

<210> SEQ ID NO 47
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 47
aaaucguauu ugucaauca                                                    19

<210> SEQ ID NO 48
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 48
uagacuucca cagaacucu                                                    19

<210> SEQ ID NO 49
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 49
uagacuucca cagaacucu                                                    19

<210> SEQ ID NO 50
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 50
uagacauccu acacagcac                                                    19

<210> SEQ ID NO 51
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 51
uguuucucca gauccuugc                                                    19
```

```
<210> SEQ ID NO 52
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 52
uguuucucca gauccuugc                                                    19

<210> SEQ ID NO 53
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 53
uagcagauga guccauuug                                                    19

<210> SEQ ID NO 54
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 54
uagcagauga guccauuugg aga                                               23

<210> SEQ ID NO 55
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 55
uagcagauga guccauuug                                                    19

<210> SEQ ID NO 56
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 56
uagcagauga guccauuugg aga                                               23

<210> SEQ ID NO 57
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 57
auguuguuuc uccagaucc                                                    19

<210> SEQ ID NO 58
<211> LENGTH: 19
<212> TYPE: RNA
<213> ORGANISM: Artificial Sequence
<220> FEATURE:
<223> OTHER INFORMATION: synthetic oligonucleotide
```

```
<400> SEQUENCE: 58
auguuguuuc uccagaucc                                                19

<210> SEQ ID NO 59
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 59
uguuugaggg acucuguga                                                19

<210> SEQ ID NO 60
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 60
uguuugaggg acucuguga                                                19

<210> SEQ ID NO 61
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 61
auugguauuc agugugaug                                                19

<210> SEQ ID NO 62
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 62
auugguauuc agugugauga cac                                           23

<210> SEQ ID NO 63
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 63
auugguauuc agugugaug                                                19

<210> SEQ ID NO 64
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 64
auugguauuc agugugauga cac                                           23

<210> SEQ ID NO 65
```

```
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 65
uagacuucca cagaacucu                                               19

<210> SEQ ID NO 66
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 66
uacaucuucc uguaguaca                                               19

<210> SEQ ID NO 67
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 67
aggcgcucca cucuggu                                                 19

<210> SEQ ID NO 68
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 68
ugucuuccag ucgguaagc                                               19

<210> SEQ ID NO 69
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 69
gaacaggcgc uccacucug                                               19

<210> SEQ ID NO 70
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 70
caguuguaau ggcaggcac                                               19

<210> SEQ ID NO 71
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 71
```
agccagaaag cucaaacuu                                              19

<210> SEQ ID NO 72
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 72
caggcgcucc acucugugg                                              19

<210> SEQ ID NO 73
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 73
aacaggcgcu ccacucugu                                              19

<210> SEQ ID NO 74
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 74
agaaagcuca aacuugaua                                              19

<210> SEQ ID NO 75
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 75
aguuguaaug gcaggcaca                                              19

<210> SEQ ID NO 76
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 76
cgugucuucc agucgguaa                                              19

<210> SEQ ID NO 77
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 77
ggaccaggca guuggcucu                                              19

<210> SEQ ID NO 78
<211> LENGTH: 19
<212> TYPE: RNA

```
<213> ORGANISM: Artificial Sequence
<220> FEATURE:
<223> OTHER INFORMATION: synthetic oligonucleotide

<400> SEQUENCE: 78
caggcacagg ucuugauga                                               19

<210> SEQ ID NO 79
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 79
gcgcuccacu cuguggucu                                               19

<210> SEQ ID NO 80
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 80
ggucuggacc aggcaguug                                               19

<210> SEQ ID NO 81
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 81
acaguuguaa uggcaggca                                               19

<210> SEQ ID NO 82
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 82
guuguaaugg caggcacag                                               19

<210> SEQ ID NO 83
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 83
ggacaguugu aauggcagg                                               19

<210> SEQ ID NO 84
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 84
gacaguugua auggcaggc                                               19
```

<210> SEQ ID NO 85
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 85
ggcgcuccac ucugugguc                                                19

<210> SEQ ID NO 86
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 86
ucuuccaguc gguaagccg                                                19

<210> SEQ ID NO 87
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 87
ugucuccgua caucuuccu                                                19

<210> SEQ ID NO 88
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 88
agcuucgcaa ggccugacc                                                19

<210> SEQ ID NO 89
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 89
cacuccucgc agcauuucc                                                19

<210> SEQ ID NO 90
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 90
aaacuugaua ggcuuggag                                                19

<210> SEQ ID NO 91
<211> LENGTH: 19
<212> TYPE: RNA
<213> ORGANISM: Artificial Sequence
<220> FEATURE:

```
<223> OTHER INFORMATION: synthetic oligonucleotide

<400> SEQUENCE: 91
acuccacaga auuuagcuc                                                19

<210> SEQ ID NO 92
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 92
augucuccgu acaucuucc                                                19

<210> SEQ ID NO 93
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 93
aacuugauag gcuuggaga                                                19

<210> SEQ ID NO 94
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 94
aagcucaaac uugauaggc                                                19

<210> SEQ ID NO 95
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 95
acauacucca cagaauuua                                                19

<210> SEQ ID NO 96
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 96
cuccacagaa uuuagcucg                                                19

<210> SEQ ID NO 97
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 97
ugugcuacug aaaucauuu                                                19
```

```
<210> SEQ ID NO 98
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 98
aaagauguca uugucuccg                                                19

<210> SEQ ID NO 99
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 99
gugcacuggu acuugcagc                                                19

<210> SEQ ID NO 100
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 100
aaacgugucu uccagucgg                                                19

<210> SEQ ID NO 101
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 101
ucaaacuuga uaggcuugg                                                19

<210> SEQ ID NO 102
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 102
acagaauuua gcucgguau                                                19

<210> SEQ ID NO 103
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 103
uuacauucua ccuauggug                                                19

<210> SEQ ID NO 104
<211> LENGTH: 19
<212> TYPE: RNA
<213> ORGANISM: Artificial Sequence
<220> FEATURE:
<223> OTHER INFORMATION: synthetic oligonucleotide
```

```
<400> SEQUENCE: 104
aaacugauca gcuauauag                                                19

<210> SEQ ID NO 105
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 105
uaucugagca gaauuucca                                                19

<210> SEQ ID NO 106
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 106
uuaacuuaga uaacuguac                                                19

<210> SEQ ID NO 107
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 107
uauuacucgu auaagaugc                                                19

<210> SEQ ID NO 108
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 108
aagcugucca gucuaaucg                                                19

<210> SEQ ID NO 109
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 109
uaauaaaggc cauuuguuc                                                19

<210> SEQ ID NO 110
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 110
uuuagcucgg uaugucuuc                                                19

<210> SEQ ID NO 111
<211> LENGTH: 19
```

```
<212> TYPE: RNA
<213> ORGANISM: Artificial Sequence
<220> FEATURE:
<223> OTHER INFORMATION: synthetic oligonucleotide

<400> SEQUENCE: 111
acacucucaa caaauaaac                                              19

<210> SEQ ID NO 112
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 112
uagcucggua ugucuucau                                              19

<210> SEQ ID NO 113
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 113
uaaccuuucu gcugguacc                                              19

<210> SEQ ID NO 114
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 114
uuaaggaaca acuugacuc                                              19

<210> SEQ ID NO 115
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 115
uuacacuuca aauagcagg                                              19

<210> SEQ ID NO 116
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 116
uccaggucag cuucgcaag                                              19

<210> SEQ ID NO 117
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 117
```
cuucuucaug accucgccg                                                19

<210> SEQ ID NO 118
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 118
aaggccugac caugcacag                                                19

<210> SEQ ID NO 119
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 119
caaacguguc uuccagucg                                                19

<210> SEQ ID NO 120
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 120
cuucgcaagg ccugaccau                                                19

<210> SEQ ID NO 121
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 121
cuuccagucg guaagccgc                                                19

<210> SEQ ID NO 122
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 122
ccgaucuugc gguuggccg                                                19

<210> SEQ ID NO 123
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 123
uucgcaaggc cugaccaug                                                19

<210> SEQ ID NO 124
<211> LENGTH: 19
<212> TYPE: RNA
<213> ORGANISM: Artificial Sequence

```
<220> FEATURE:
<223> OTHER INFORMATION: synthetic oligonucleotide

<400> SEQUENCE: 124
agaauuuagc ucgguaugu                                                    19

<210> SEQ ID NO 125
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 125
cauacuccac agaauuuag                                                    19

<210> SEQ ID NO 126
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 126
ugccaugucu ccguacauc                                                    19

<210> SEQ ID NO 127
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 127
gaggcguugu cauugguaa                                                    19

<210> SEQ ID NO 128
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 128
ucuucaugac cucgccguc                                                    19

<210> SEQ ID NO 129
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 129
uccacagaau uuagcucgg                                                    19

<210> SEQ ID NO 130
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 130
aacgugucuu ccagucggu                                                    19
```

<210> SEQ ID NO 131
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 131
cuccguacau cuuccugua                                                    19

<210> SEQ ID NO 132
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 132
aggcguuguc auugguaac                                                    19

<210> SEQ ID NO 133
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 133
ucaugaccuc gccgucagg                                                    19

<210> SEQ ID NO 134
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 134
ggccaaacgu gucuuccag                                                    19

<210> SEQ ID NO 135
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 135
gccaugucuc cguacaucu                                                    19

<210> SEQ ID NO 136
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 136
ucgcaaggcc ugaccaugc                                                    19

<210> SEQ ID NO 137
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 137
aggucagcuu cgcaaggcc                                             19

<210> SEQ ID NO 138
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 138
ccguacaucu uccuguagu                                             19

<210> SEQ ID NO 139
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 139
gagccgaagu cacagaaga                                             19

<210> SEQ ID NO 140
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 140
ggagccgaag ucacagaag                                             19

<210> SEQ ID NO 141
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 141
caaggccuga ccaugcaca                                             19

<210> SEQ ID NO 142
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 142
agcucaaacu ugauaggcu                                             19

<210> SEQ ID NO 143
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 143
cugcaguucu ggccgacgg                                             19

<210> SEQ ID NO 144

```
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 144
gguacauacu ccacagaau                                                    19

<210> SEQ ID NO 145
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 145
cugcuucucu agccugcag                                                    19

<210> SEQ ID NO 146
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 146
gcaaggccug accaugcac                                                    19

<210> SEQ ID NO 147
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 147
cagaauuuag cucgguaug                                                    19

<210> SEQ ID NO 148
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 148
ccaaacgugu cuuccaguc                                                    19

<210> SEQ ID NO 149
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 149
cuucaugacc ucgccguca                                                    19

<210> SEQ ID NO 150
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 150
```

```
gcuucgcaag gccugacca                                              19

<210> SEQ ID NO 151
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 151
ucagcuucgc aaggccuga                                              19

<210> SEQ ID NO 152
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 152
gucuuccagu cgguaagcc                                              19

<210> SEQ ID NO 153
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 153
caaacuugau aggcuugga                                              19

<210> SEQ ID NO 154
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 154
aggucuugga acaggcgcu                                              19

<210> SEQ ID NO 155
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 155
caggucagcu ucgcaaggc                                              19

<210> SEQ ID NO 156
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 156
gucagcuucg caaggccug                                              19

<210> SEQ ID NO 157
<211> LENGTH: 19
<212> TYPE: RNA
```

```
<213> ORGANISM: Artificial Sequence
<220> FEATURE:
<223> OTHER INFORMATION: synthetic oligonucleotide

<400> SEQUENCE: 157
ggcguuguca uugguaacc                                                    19

<210> SEQ ID NO 158
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 158
cgugcacugg uacuugcag                                                    19

<210> SEQ ID NO 159
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 159
gucuuggaac aggcgcucc                                                    19

<210> SEQ ID NO 160
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 160
ccaugucucc guacaucuu                                                    19

<210> SEQ ID NO 161
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 161
ggucagcuuc gcaaggccu                                                    19

<210> SEQ ID NO 162
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 162
cagcuucgca aggccugac                                                    19

<210> SEQ ID NO 163
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 163
gccgaaguca cagaagagg                                                    19
```

```
<210> SEQ ID NO 164
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 164
cacagaauuu agcucggua                                              19

<210> SEQ ID NO 165
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 165
ccacagaauu uagcucggu                                              19

<210> SEQ ID NO 166
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 166
gccaaacgug ucuuccagu                                              19

<210> SEQ ID NO 167
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 167
gccgaucuug cgguuggcc                                              19

<210> SEQ ID NO 168
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 168
cucaaacuug auaggcuug                                              19

<210> SEQ ID NO 169
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 169
ccaggucagc uucgcaagg                                              19

<210> SEQ ID NO 170
<211> LENGTH: 19
<212> TYPE: RNA
<213> ORGANISM: Artificial Sequence
<220> FEATURE:
```

```
<223> OTHER INFORMATION: synthetic oligonucleotide

<400> SEQUENCE: 170
uuugacuaaa ugcaaagug                                                    19

<210> SEQ ID NO 171
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 171
uguuuuugua gccaaaucc                                                    19

<210> SEQ ID NO 172
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 172
uguuuuugua gccaaaucc                                                    19

<210> SEQ ID NO 173
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 173
uguuuuugua gccaaaucc                                                    19

<210> SEQ ID NO 174
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 174
aaaucguauu ugucaauca                                                    19

<210> SEQ ID NO 175
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 175
aaaucguauu ugucaauca                                                    19

<210> SEQ ID NO 176
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 176
gucaucacac ugaauaccaa u                                                 21
```

```
<210> SEQ ID NO 177
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 177
gugaucagac ucaauacgaa u                                             21

<210> SEQ ID NO 178
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 178
cuguggaagu cua                                                      13

<210> SEQ ID NO 179
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 179
cuguggaagu cua                                                      13

<210> SEQ ID NO 180
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 180
cuguggaagu cua                                                      13

<210> SEQ ID NO 181
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 181
cuguggaagu cua                                                      13

<210> SEQ ID NO 182
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 182
cuguggaagu cua                                                      13

<210> SEQ ID NO 183
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 183
cuguggaagu cua                                                      13

<210> SEQ ID NO 184
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 184
cuguggaagu cua                                                      13

<210> SEQ ID NO 185
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 185
cuguggaagu cua                                                      13

<210> SEQ ID NO 186
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 186
cuguggaagu cua                                                      13

<210> SEQ ID NO 187
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 187
cuguggaagu cua                                                      13

<210> SEQ ID NO 188
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 188
gucaucacac ugaauaccaa u                                             21

<210> SEQ ID NO 189
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 189
gugaucagac ucaauacgaa u                                             21

<210> SEQ ID NO 190
<211> LENGTH: 13
```

```
<212> TYPE: RNA
<213> ORGANISM: Artificial Sequence
<220> FEATURE:
<223> OTHER INFORMATION: synthetic oligonucleotide

<400> SEQUENCE: 190
cuguggaagu cua                                                          13

<210> SEQ ID NO 191
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 191
cuguggaagu cua                                                          13

<210> SEQ ID NO 192
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 192
cuguggaagu cua                                                          13

<210> SEQ ID NO 193
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 193
cuguggaagu cua                                                          13

<210> SEQ ID NO 194
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 194
cuguggaagu cua                                                          13

<210> SEQ ID NO 195
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 195
cuguggaagu cua                                                          13

<210> SEQ ID NO 196
<211> LENGTH: 27
<212> TYPE: RNA
<213> ORGANISM: Artificial Sequence
<220> FEATURE:
<223> OTHER INFORMATION: synthetic oligonucleotide

<400> SEQUENCE: 196
``` ucauaggu aa ccucugguug aaaguga                          27

<210> SEQ ID NO 197
<211> LENGTH: 27
<212> TYPE: RNA
<213> ORGANISM: Artificial Sequence
<220> FEATURE:
<223> OTHER INFORMATION: synthetic oligonucleotide

<400> SEQUENCE: 197
cggcuacagg ugcuuaugaa gaaagua                           27

<210> SEQ ID NO 198
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 198
gucaucacac ugaauaccaa u                                 21

<210> SEQ ID NO 199
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 199
gugaucagac ucaauacgaa u                                 21

<210> SEQ ID NO 200
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 200
cuguggaagu cua                                          13

<210> SEQ ID NO 201
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 201
gucaucacac ugaauaccaa u                                 21

<210> SEQ ID NO 202
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 202
gugaucagac ucaauacgaa u                                 21

<210> SEQ ID NO 203
<211> LENGTH: 13
<212> TYPE: RNA
<213> ORGANISM: Artificial Sequence

```
<220> FEATURE:
<223> OTHER INFORMATION: synthetic oligonucleotide

<400> SEQUENCE: 203
uguaggaugu cua                                                          13

<210> SEQ ID NO 204
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 204
cuguggaagu cua                                                          13

<210> SEQ ID NO 205
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 205
cuguggaagu cua                                                          13

<210> SEQ ID NO 206
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 206
acugaauacc aau                                                          13

<210> SEQ ID NO 207
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 207
cuguggaagu cua                                                          13

<210> SEQ ID NO 208
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 208
cuguggaagu cua                                                          13

<210> SEQ ID NO 209
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 209
cuguggaagu cua                                                          13
```

```
<210> SEQ ID NO 210
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 210
cuguggaagu cua                                                          13

<210> SEQ ID NO 211
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 211
cuguggaagu cua                                                          13

<210> SEQ ID NO 212
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 212
cuguggaagu cua                                                          13

<210> SEQ ID NO 213
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 213
cuguggaagu cua                                                          13

<210> SEQ ID NO 214
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 214
cuguggaagu cua                                                          13

<210> SEQ ID NO 215
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 215
cuguggaagu cua                                                          13

<210> SEQ ID NO 216
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 216
cuguggaagu cua                                                13

<210> SEQ ID NO 217
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 217
cuguggaagu cua                                                13

<210> SEQ ID NO 218
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 218
cuguggaagu cua                                                13

<210> SEQ ID NO 219
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 219
cuguggaagu cua                                                13

<210> SEQ ID NO 220
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 220
agaguucugu ggaagucua                                          19

<210> SEQ ID NO 221
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 221
agaguucugu ggaagucua                                          19

<210> SEQ ID NO 222
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 222
auuuggcuac aaa                                                13

<210> SEQ ID NO 223
```

```
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 223
acaaauacga uuu                                                          13

<210> SEQ ID NO 224
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 224
acaaauacga uuu                                                          13

<210> SEQ ID NO 225
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 225
cuguggaagu cua                                                          13

<210> SEQ ID NO 226
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 226
aaugaagaaa gua                                                          13

<210> SEQ ID NO 227
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 227
agguggaaau gaa                                                          13

<210> SEQ ID NO 228
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 228
agaaaguaca aag                                                          13

<210> SEQ ID NO 229
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 229
```
gaaaguacaa aga                                                    13

<210> SEQ ID NO 230
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 230
augugacugc uga                                                    13

<210> SEQ ID NO 231
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 231
agacuugggc aau                                                    13

<210> SEQ ID NO 232
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 232
auuucgagca gaa                                                    13

<210> SEQ ID NO 233
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 233
aucuggagaa aca                                                    13

<210> SEQ ID NO 234
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 234
ucagaacaag aaa                                                    13

<210> SEQ ID NO 235
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 235
gacucaucug cua                                                    13

<210> SEQ ID NO 236
<211> LENGTH: 13
<212> TYPE: RNA

```
<213> ORGANISM: Artificial Sequence
<220> FEATURE:
<223> OTHER INFORMATION: synthetic oligonucleotide

<400> SEQUENCE: 236
ggagaaacaa cau                                                    13

<210> SEQ ID NO 237
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 237
agucccucaa aca                                                    13

<210> SEQ ID NO 238
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 238
ggcuacaaaa aca                                                    13

<210> SEQ ID NO 239
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 239
agaucuggag aaaca                                                  15

<210> SEQ ID NO 240
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 240
uggacucauc ugcua                                                  15

<210> SEQ ID NO 241
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 241
cuggagaaac aacau                                                  15

<210> SEQ ID NO 242
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 242
agagucccuc aaaca                                                  15
```

<210> SEQ ID NO 243
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 243
acugaauacc aau                                                        13

<210> SEQ ID NO 244
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 244
acacugaaua ccaau                                                      15

<210> SEQ ID NO 245
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 245
aaugaagaaa gua                                                        13

<210> SEQ ID NO 246
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 246
agguggaaau gaa                                                        13

<210> SEQ ID NO 247
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 247
agaaaguaca aag                                                        13

<210> SEQ ID NO 248
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 248
gaaaguacaa aga                                                        13

<210> SEQ ID NO 249
<211> LENGTH: 13
<212> TYPE: RNA
<213> ORGANISM: Artificial Sequence
<220> FEATURE:

```
<223> OTHER INFORMATION: synthetic oligonucleotide

<400> SEQUENCE: 249
augugacugc uga                                                          13

<210> SEQ ID NO 250
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 250
agacuugggc aau                                                          13

<210> SEQ ID NO 251
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 251
auuucgagca gaa                                                          13

<210> SEQ ID NO 252
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 252
acaaauacga uuu                                                          13

<210> SEQ ID NO 253
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 253
acaaauacga uuu                                                          13

<210> SEQ ID NO 254
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 254
agaguucugu ggaagucua                                                    19

<210> SEQ ID NO 255
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 255
acaggaagau gua                                                          13
```

```
<210> SEQ ID NO 256
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 256
gaguggagcg ccu                                                          13

<210> SEQ ID NO 257
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 257
cgacuggaag aca                                                          13

<210> SEQ ID NO 258
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 258
ggagcgccug uuc                                                          13

<210> SEQ ID NO 259
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 259
gccauuacaa cug                                                          13

<210> SEQ ID NO 260
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 260
gagcuuucug gcu                                                          13

<210> SEQ ID NO 261
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 261
aguggagcgc cug                                                          13

<210> SEQ ID NO 262
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 262
uggagcgccu guu                                                        13

<210> SEQ ID NO 263
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 263
guuugagcuu ucu                                                        13

<210> SEQ ID NO 264
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 264
ugccauuaca acu                                                        13

<210> SEQ ID NO 265
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 265
acuggaagac acg                                                        13

<210> SEQ ID NO 266
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 266
aacugccugg ucc                                                        13

<210> SEQ ID NO 267
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 267
agaccugugc cug                                                        13

<210> SEQ ID NO 268
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 268
cagaguggag cgc                                                        13

<210> SEQ ID NO 269
<211> LENGTH: 13
```

```
<212> TYPE: RNA
<213> ORGANISM: Artificial Sequence
<220> FEATURE:
<223> OTHER INFORMATION: synthetic oligonucleotide

<400> SEQUENCE: 269
ccugguccag acc                                                              13

<210> SEQ ID NO 270
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 270
ccauuacaac ugu                                                              13

<210> SEQ ID NO 271
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 271
cugccauuac aac                                                              13

<210> SEQ ID NO 272
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 272
auuacaacug ucc                                                              13

<210> SEQ ID NO 273
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 273
cauuacaacu guc                                                              13

<210> SEQ ID NO 274
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 274
agaguggagc gcc                                                              13

<210> SEQ ID NO 275
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 275
```
accgacugga aga                                                    13

<210> SEQ ID NO 276
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 276
auguacggag aca                                                    13

<210> SEQ ID NO 277
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 277
gccuugcgaa gcu                                                    13

<210> SEQ ID NO 278
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 278
gcugcgagga gug                                                    13

<210> SEQ ID NO 279
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 279 gccaucaag uuu                                                     13

<210> SEQ ID NO 280
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 280
aauucugugg agu                                                    13

<210> SEQ ID NO 281
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 281
uguacggaga cau                                                    13

<210> SEQ ID NO 282
<211> LENGTH: 13
<212> TYPE: RNA
<213> ORGANISM: Artificial Sequence -continued

```
<220> FEATURE:
<223> OTHER INFORMATION: synthetic oligonucleotide

<400> SEQUENCE: 282
agccuaucaa guu                                                          13

<210> SEQ ID NO 283
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 283
caaguuugag cuu                                                          13

<210> SEQ ID NO 284
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 284
cuguggagua ugu                                                          13

<210> SEQ ID NO 285
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 285
aaauucugug gag                                                          13

<210> SEQ ID NO 286
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 286
uuucaguagc aca                                                          13

<210> SEQ ID NO 287
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 287
caaugacauc uuu                                                          13

<210> SEQ ID NO 288
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 288
aguaccagug cac                                                          13
```

```
<210> SEQ ID NO 289
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 289
ggaagacacg uuu                                                          13

<210> SEQ ID NO 290
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 290
cuaucaaguu uga                                                          13

<210> SEQ ID NO 291
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 291
agcuaaauuc ugu                                                          13

<210> SEQ ID NO 292
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 292
agguagaaug uaa                                                          13

<210> SEQ ID NO 293
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 293
agcugaucag uuu                                                          13

<210> SEQ ID NO 294
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 294
uucugcucag aua                                                          13

<210> SEQ ID NO 295
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 295
uuaucuaagu uaa                                                        13

<210> SEQ ID NO 296
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 296
uauacgagua aua                                                        13

<210> SEQ ID NO 297
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 297
gacuggacag cuu                                                        13

<210> SEQ ID NO 298
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 298
auggccuuua uua                                                        13

<210> SEQ ID NO 299
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 299
auaccgagcu aaa                                                        13

<210> SEQ ID NO 300
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 300
uuguugagag ugu                                                        13

<210> SEQ ID NO 301
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 301
acauaccgag cua                                                        13

<210> SEQ ID NO 302
```

```
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 302
agcagaaagg uua                                                          13

<210> SEQ ID NO 303
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 303
aguuguuccu uaa                                                          13

<210> SEQ ID NO 304
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 304
auuugaagug uaa                                                          13

<210> SEQ ID NO 305
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 305
aagcugaccu gga                                                          13

<210> SEQ ID NO 306
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 306
ggucaugaag aag                                                          13

<210> SEQ ID NO 307
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 307
auggucaggc cuu                                                          13

<210> SEQ ID NO 308
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 308
```
gaagacacgu uug                                                          13

<210> SEQ ID NO 309
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 309
aggccuugcg aag                                                          13

<210> SEQ ID NO 310
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 310
uaccgacugg aag                                                          13

<210> SEQ ID NO 311
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 311
accgcaagau cgg                                                          13

<210> SEQ ID NO 312
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 312
caggccuugc gaa                                                          13

<210> SEQ ID NO 313
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 313
cgagcuaaau ucu                                                          13

<210> SEQ ID NO 314
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 314
ucuguggagu aug                                                          13

<210> SEQ ID NO 315
<211> LENGTH: 13
<212> TYPE: RNA

```
<213> ORGANISM: Artificial Sequence
<220> FEATURE:
<223> OTHER INFORMATION: synthetic oligonucleotide

<400> SEQUENCE: 315
cggagacaug gca                                                            13

<210> SEQ ID NO 316
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 316
augacaacgc cuc                                                            13

<210> SEQ ID NO 317
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 317
gaggucauga aga                                                            13

<210> SEQ ID NO 318
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 318
uaaauucugu gga                                                            13

<210> SEQ ID NO 319
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 319
uggaagacac guu                                                            13

<210> SEQ ID NO 320
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 320
aagauguacg gag                                                            13

<210> SEQ ID NO 321
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 321
aaugacaacg ccu                                                            13
```

<210> SEQ ID NO 322
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 322
ggcgagguca uga                                                          13

<210> SEQ ID NO 323
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 323
gacacguuug gcc                                                          13

<210> SEQ ID NO 324
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 324
acggagacau ggc                                                          13

<210> SEQ ID NO 325
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 325
ucaggccuug cga                                                          13

<210> SEQ ID NO 326
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 326
gcgaagcuga ccu                                                          13

<210> SEQ ID NO 327
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 327
ggaagaugua cgg                                                          13

<210> SEQ ID NO 328
<211> LENGTH: 13
<212> TYPE: RNA
<213> ORGANISM: Artificial Sequence
<220> FEATURE:

<223> OTHER INFORMATION: synthetic oligonucleotide

<400> SEQUENCE: 328
gugacuucgg cuc					13

<210> SEQ ID NO 329
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 329
ugacuucggc ucc					13

<210> SEQ ID NO 330
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 330
uggucaggcc uug					13

<210> SEQ ID NO 331
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 331
ucaaguuuga gcu					13

<210> SEQ ID NO 332
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 332
gccagaacug cag					13

<210> SEQ ID NO 333
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 333
uggaguaugu acc					13

<210> SEQ ID NO 334
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 334
gcuagagaag cag					13

```
<210> SEQ ID NO 335
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 335
ggucaggccu ugc                                                         13

<210> SEQ ID NO 336
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 336
gagcuaaauu cug                                                         13

<210> SEQ ID NO 337
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 337
aagacacguu ugg                                                         13

<210> SEQ ID NO 338
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 338
cgaggucaug aag                                                         13

<210> SEQ ID NO 339
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 339
ggccuugcga agc                                                         13

<210> SEQ ID NO 340
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 340
cuugcgaagc uga                                                         13

<210> SEQ ID NO 341
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 341
ccgacuggaa gac                                                          13

<210> SEQ ID NO 342
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 342
ccuaucaagu uug                                                          13

<210> SEQ ID NO 343
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 343
uguuccaaga ccu                                                          13

<210> SEQ ID NO 344
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 344
cgaagcugac cug                                                          13

<210> SEQ ID NO 345
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 345
uugcgaagcu gac                                                          13

<210> SEQ ID NO 346
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 346
caaugacaac gcc                                                          13

<210> SEQ ID NO 347
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 347
guaccagugc acg                                                          13

<210> SEQ ID NO 348
<211> LENGTH: 13
```

```
<212> TYPE: RNA
<213> ORGANISM: Artificial Sequence
<220> FEATURE:
<223> OTHER INFORMATION: synthetic oligonucleotide

<400> SEQUENCE: 348
ccuguuccaa gac                                                           13

<210> SEQ ID NO 349
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 349
uacggagaca ugg                                                           13

<210> SEQ ID NO 350
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 350
ugcgaagcug acc                                                           13

<210> SEQ ID NO 351
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 351
ccuugcgaag cug                                                           13

<210> SEQ ID NO 352
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 352
cugugacuuc ggc                                                           13

<210> SEQ ID NO 353
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 353
gcuaaauucu gug                                                           13

<210> SEQ ID NO 354
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 354
```
cuaaauucug ugg                                          13

<210> SEQ ID NO 355
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 355
agacacguuu ggc                                          13

<210> SEQ ID NO 356
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 356
ccgcaagauc ggc                                          13

<210> SEQ ID NO 357
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 357
uaucaaguuu gag                                          13

<210> SEQ ID NO 358
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 358
gaagcugacc ugg                                          13

<210> SEQ ID NO 359
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 359
cucaugaauu aga                                          13

<210> SEQ ID NO 360
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 360
cugaggucaa uua                                          13

<210> SEQ ID NO 361
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 361
gaggucaauu aaa                                                          13

<210> SEQ ID NO 362
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 362 ucgagguca auu                                                           13

<210> SEQ ID NO 363
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 363
ugaggucaau uaa                                                          13

<210> SEQ ID NO 364
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 364
uucugagguc aau                                                          13

<210> SEQ ID NO 365
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 365
gucagcugga uga                                                          13

<210> SEQ ID NO 366
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 366
uucugaugaa ucu                                                          13

<210> SEQ ID NO 367
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 367
uggacugagg uca                                                          13

```
<210> SEQ ID NO 368
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 368
gagucucacc auu                                                        13

<210> SEQ ID NO 369
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 369
gacugagguc aaa                                                        13

<210> SEQ ID NO 370
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 370
ucacagccau gaa                                                        13

<210> SEQ ID NO 371
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 371
agucucacca uuc                                                        13

<210> SEQ ID NO 372
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 372
aagcggaaag cca                                                        13

<210> SEQ ID NO 373
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 373
agcggaaagc caa                                                        13

<210> SEQ ID NO 374
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 374
accacaugga uga                                                       13

<210> SEQ ID NO 375
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 375
gccaugacca cau                                                       13

<210> SEQ ID NO 376
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 376
aagccaugac cac                                                       13

<210> SEQ ID NO 377
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 377
gcggaaagcc aau                                                       13

<210> SEQ ID NO 378
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 378
aaauuucgua uuu                                                       13

<210> SEQ ID NO 379
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 379
auuucguauu ucu                                                       13

<210> SEQ ID NO 380
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 380
aaagccauga cca                                                       13

<210> SEQ ID NO 381
```

```
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 381
acauggauga uau                                                        13

<210> SEQ ID NO 382
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 382
gaaauuucgu auu                                                        13

<210> SEQ ID NO 383
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 383
gcgccuucug auu                                                        13

<210> SEQ ID NO 384
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 384
auuucucaug aau                                                        13

<210> SEQ ID NO 385
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 385
cucucaugaa uag                                                        13

<210> SEQ ID NO 386
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 386
aaguccaacg aaa                                                        13

<210> SEQ ID NO 387
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 387
```
augaugagag caa                                      13

<210> SEQ ID NO 388
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 388
gcgaggaguu gaa                                      13

<210> SEQ ID NO 389
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 389
ugauugauag uca                                      13

<210> SEQ ID NO 390
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 390
agauagugca ucu                                      13

<210> SEQ ID NO 391
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 391
auguguaucu auu                                      13

<210> SEQ ID NO 392
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 392
uucuauagaa gaa                                      13

<210> SEQ ID NO 393
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 393
uuguccagca auu                                      13

<210> SEQ ID NO 394
<211> LENGTH: 13
<212> TYPE: RNA

```
<213> ORGANISM: Artificial Sequence
<220> FEATURE:
<223> OTHER INFORMATION: synthetic oligonucleotide

<400> SEQUENCE: 394
acauggaaag cga                                                          13

<210> SEQ ID NO 395
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 395
gcaguccaga uua                                                          13

<210> SEQ ID NO 396
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 396
ugguugaaug ugu                                                          13

<210> SEQ ID NO 397
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 397
uuaugaaacg agu                                                          13

<210> SEQ ID NO 398
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 398
caguccagau uau                                                          13

<210> SEQ ID NO 399
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 399
auauaagcgg aaa                                                          13

<210> SEQ ID NO 400
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 400
uaccaguuaa aca                                                          13
```

<210> SEQ ID NO 401
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 401
uguucauucu aua                                                          13

<210> SEQ ID NO 402
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 402
ccgaccaagg aaa                                                          13

<210> SEQ ID NO 403
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 403
gaauggugca uac                                                          13

<210> SEQ ID NO 404
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 404
auaugauggc cga                                                          13

<210> SEQ ID NO 405
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 405
agcaguccag auu                                                          13

<210> SEQ ID NO 406
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 406
gcauuuaguc aaa                                                          13

<210> SEQ ID NO 407
<211> LENGTH: 13
<212> TYPE: RNA
<213> ORGANISM: Artificial Sequence
<220> FEATURE:

<223> OTHER INFORMATION: synthetic oligonucleotide

<400> SEQUENCE: 407
agcauuccga ugu                                                          13

<210> SEQ ID NO 408
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 408
uagucaggaa cuu                                                          13

<210> SEQ ID NO 409
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 409
ugcauuuagu caa                                                          13

<210> SEQ ID NO 410
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 410
gucugaugag ucu                                                          13

<210> SEQ ID NO 411
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 411
uagacacaua uga                                                          13

<210> SEQ ID NO 412
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 412
cagacgagga cau                                                          13

<210> SEQ ID NO 413
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 413
cagccgugaa uuc                                                          13

```
<210> SEQ ID NO 414
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 414
agucuggaaa uaa                                                        13

<210> SEQ ID NO 415
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 415
aguuuguggc uuc                                                        13

<210> SEQ ID NO 416
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 416
aguccaacga aag                                                        13

<210> SEQ ID NO 417
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 417
aaguuucgca gac                                                        13

<210> SEQ ID NO 418
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 418
agcaaugagc auu                                                        13

<210> SEQ ID NO 419
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 419
uuagauagug cau                                                        13

<210> SEQ ID NO 420
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 420
uggugcauac aag                                              13

<210> SEQ ID NO 421
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 421
augaaacgag uca                                              13

<210> SEQ ID NO 422
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 422
ccagagugcu gaa                                              13

<210> SEQ ID NO 423
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 423
cagccaugaa uuu                                              13

<210> SEQ ID NO 424
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 424
auugguugaa ugu                                              13

<210> SEQ ID NO 425
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 425
gguugaaugu gua                                              13

<210> SEQ ID NO 426
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 426
ggaaauaacu aau                                              13

<210> SEQ ID NO 427
<211> LENGTH: 13
```

```
<212> TYPE: RNA
<213> ORGANISM: Artificial Sequence
<220> FEATURE:
<223> OTHER INFORMATION: synthetic oligonucleotide

<400> SEQUENCE: 427
ucaugaauag aaa                                                          13

<210> SEQ ID NO 428
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 428
gccagcaacc gaa                                                          13

<210> SEQ ID NO 429
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 429
caccucacac aug                                                          13

<210> SEQ ID NO 430
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 430
aguugaaugg ugc                                                          13

<210> SEQ ID NO 431
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 431
agucagcugg aug                                                          13

<210> SEQ ID NO 432
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 432
uauaagcgga aag                                                          13

<210> SEQ ID NO 433
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 433
```

```
uuccgaugug auu                                                    13

<210> SEQ ID NO 434
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 434
auaacuaaug ugu                                                    13

<210> SEQ ID NO 435
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 435
ucauucuaua gaa                                                    13

<210> SEQ ID NO 436
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 436
aacuaucacu gua                                                    13

<210> SEQ ID NO 437
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 437
gucaauugcu uau                                                    13

<210> SEQ ID NO 438
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 438
agcaauuaau aaa                                                    13

<210> SEQ ID NO 439
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 439
acgacucuga uga                                                    13

<210> SEQ ID NO 440
<211> LENGTH: 13
<212> TYPE: RNA
<213> ORGANISM: Artificial Sequence
```

```
<220> FEATURE:
<223> OTHER INFORMATION: synthetic oligonucleotide

<400> SEQUENCE: 440 uaguggguu uau                                                           13

<210> SEQ ID NO 441
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 441
aagccaauga uga                                                          13

<210> SEQ ID NO 442
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 442
auagucagga acu                                                          13

<210> SEQ ID NO 443
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 443
agucagccgu gaa                                                          13

<210> SEQ ID NO 444
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 444
acuaccauga gaa                                                          13

<210> SEQ ID NO 445
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 445
aaacaggcug auu                                                          13

<210> SEQ ID NO 446
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 446
gagugcugaa acc                                                          13
```

```
<210> SEQ ID NO 447
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 447
ugagcauucc gau                                                            13

<210> SEQ ID NO 448
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 448
aauuccacag cca                                                            13

<210> SEQ ID NO 449
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 449
ugucaauugc uua                                                            13

<210> SEQ ID NO 450
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 450
accaugagaa uug                                                            13

<210> SEQ ID NO 451
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 451
ccaacgaaag cca                                                            13

<210> SEQ ID NO 452
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 452
cuggucacug auu                                                            13

<210> SEQ ID NO 453
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 453
ugguuuaugg acu                                                    13

<210> SEQ ID NO 454
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 454
gaccagagug cug                                                    13

<210> SEQ ID NO 455
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 455
gaugugauug aua                                                    13

<210> SEQ ID NO 456
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 456
gucagccgug aau                                                    13

<210> SEQ ID NO 457
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 457
aauguguauc uau                                                    13

<210> SEQ ID NO 458
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 458
uugagucugg aaa                                                    13

<210> SEQ ID NO 459
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 459
guccagcaau uaa                                                    13

<210> SEQ ID NO 460
```

```
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 460
ccagcaauua aua                                                          13

<210> SEQ ID NO 461
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 461
gacucgaacg acu                                                          13

<210> SEQ ID NO 462
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 462
accugccagc aac                                                          13

<210> SEQ ID NO 463
<211> LENGTH: 13
<212> TYPE: DNA
<213> ORGANISM: Artificial Sequence
<220> FEATURE:
<223> OTHER INFORMATION: synthetic oligonucleotide

<400> SEQUENCE: 463
actgaauacc aau                                                          13

<210> SEQ ID NO 464
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 464
acugaauacc aau                                                          13

<210> SEQ ID NO 465
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 465
cuguggaagu cua                                                          13

<210> SEQ ID NO 466
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 466
```

-continued ggcuacaaaa aca                                              13

<210> SEQ ID NO 467
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 467
uuggcuacaa aaaca                                            15

<210> SEQ ID NO 468
<211> LENGTH: 17
<212> TYPE: RNA
<213> ORGANISM: Artificial Sequence
<220> FEATURE:
<223> OTHER INFORMATION: synthetic oligonucleotide

<400> SEQUENCE: 468
auuuggcuac aaaaaca                                          17

<210> SEQ ID NO 469
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 469
uguaggaugu cua                                              13

<210> SEQ ID NO 470
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 470
aucuggagaa aca                                              13

<210> SEQ ID NO 471
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 471
agaucuggag aaaca                                            15

<210> SEQ ID NO 472
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 472
gacucaucug cua                                              13

<210> SEQ ID NO 473
<211> LENGTH: 13
<212> TYPE: RNA

```
<213> ORGANISM: Artificial Sequence
<220> FEATURE:
<223> OTHER INFORMATION: synthetic oligonucleotide

<400> SEQUENCE: 473
gacucaucug cua                                                        13

<210> SEQ ID NO 474
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 474
uggacucauc ugcua                                                      15

<210> SEQ ID NO 475
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 475
uggacucauc ugcua                                                      15

<210> SEQ ID NO 476
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 476
ggagaaacaa cau                                                        13

<210> SEQ ID NO 477
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 477
cuggagaaac aacau                                                      15

<210> SEQ ID NO 478
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 478
agucccucaa aca                                                        13

<210> SEQ ID NO 479
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 479
agagucccuc aaaca                                                      15
```

<210> SEQ ID NO 480
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 480
acugaauacc aau                                                          13

<210> SEQ ID NO 481
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 481
acugaauacc aau                                                          13

<210> SEQ ID NO 482
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 482
acacugaaua ccaau                                                        15

<210> SEQ ID NO 483
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 483
acacugaaua ccaau                                                        15

<210> SEQ ID NO 484
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 484
cuguggaagu cua                                                          13

<210> SEQ ID NO 485
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 485
acaggaagau gua                                                          13

<210> SEQ ID NO 486
<211> LENGTH: 13
<212> TYPE: RNA
<213> ORGANISM: Artificial Sequence
<220> FEATURE:

```
<223> OTHER INFORMATION: synthetic oligonucleotide

<400> SEQUENCE: 486
gaguggagcg ccu                                                          13

<210> SEQ ID NO 487
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 487
cgacuggaag aca                                                          13

<210> SEQ ID NO 488
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 488
ggagcgccug uuc                                                          13

<210> SEQ ID NO 489
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 489
gccauuacaa cug                                                          13

<210> SEQ ID NO 490
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 490
gagcuuucug gcu                                                          13

<210> SEQ ID NO 491
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 491
aguggagcgc cug                                                          13

<210> SEQ ID NO 492
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 492
uggagcgccu guu                                                          13
```

```
<210> SEQ ID NO 493
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 493
guuugagcuu ucu                                                          13

<210> SEQ ID NO 494
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 494
ugccauuaca acu                                                          13

<210> SEQ ID NO 495
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 495
acuggaagac acg                                                          13

<210> SEQ ID NO 496
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 496
aacugccugg ucc                                                          13

<210> SEQ ID NO 497
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 497
agaccugugc cug                                                          13

<210> SEQ ID NO 498
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 498
cagaguggag cgc                                                          13

<210> SEQ ID NO 499
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 499
ccugguccag acc                                                          13

<210> SEQ ID NO 500
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 500
ccauuacaac ugu                                                          13

<210> SEQ ID NO 501
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 501
cugccauuac aac                                                          13

<210> SEQ ID NO 502
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 502
auuacaacug ucc                                                          13

<210> SEQ ID NO 503
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 503
cauuacaacu guc                                                          13

<210> SEQ ID NO 504
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 504
agaguggagc gcc                                                          13

<210> SEQ ID NO 505
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 505
accgacugga aga                                                          13

<210> SEQ ID NO 506
<211> LENGTH: 13
```

```
<212> TYPE: RNA
<213> ORGANISM: Artificial Sequence
<220> FEATURE:
<223> OTHER INFORMATION: synthetic oligonucleotide

<400> SEQUENCE: 506
auguacggag aca                                                          13

<210> SEQ ID NO 507
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 507
gccuugcgaa gcu                                                          13

<210> SEQ ID NO 508
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 508
gcugcgagga gug                                                          13

<210> SEQ ID NO 509
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 509
gccuaucaag uuu                                                          13

<210> SEQ ID NO 510
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 510
aauucugugg agu                                                          13

<210> SEQ ID NO 511
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 511
uguacggaga cau                                                          13

<210> SEQ ID NO 512
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 512
```
agccuaucaa guu                                                          13

<210> SEQ ID NO 513
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 513
caaguuugag cuu                                                          13

<210> SEQ ID NO 514
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 514
cuguggagua ugu                                                          13

<210> SEQ ID NO 515
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 515
aaauucugug gag                                                          13

<210> SEQ ID NO 516
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 516
uuucaguagc aca                                                          13

<210> SEQ ID NO 517
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 517
caaugacauc uuu                                                          13

<210> SEQ ID NO 518
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 518
aguaccagug cac                                                          13

<210> SEQ ID NO 519
<211> LENGTH: 13
<212> TYPE: RNA
<213> ORGANISM: Artificial Sequence

```
<220> FEATURE:
<223> OTHER INFORMATION: synthetic oligonucleotide

<400> SEQUENCE: 519
ggaagacacg uuu                                                          13

<210> SEQ ID NO 520
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 520
cuaucaaguu uga                                                          13

<210> SEQ ID NO 521
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 521
agcuaaauuc ugu                                                          13

<210> SEQ ID NO 522
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 522
agguagaaug uaa                                                          13

<210> SEQ ID NO 523
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 523
agcugaucag uuu                                                          13

<210> SEQ ID NO 524
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 524
uucugcucag aua                                                          13

<210> SEQ ID NO 525
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 525
uuaucuaagu uaa                                                          13
```

```
<210> SEQ ID NO 526
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 526
uauacgagua aua                                                          13

<210> SEQ ID NO 527
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 527
gacuggacag cuu                                                          13

<210> SEQ ID NO 528
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 528
auggccuuua uua                                                          13

<210> SEQ ID NO 529
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 529
auaccgagcu aaa                                                          13

<210> SEQ ID NO 530
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 530
uuguugagag ugu                                                          13

<210> SEQ ID NO 531
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 531
acauaccgag cua                                                          13

<210> SEQ ID NO 532
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 532
agcagaaagg uua                                               13

<210> SEQ ID NO 533
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 533
aguuguuccu uaa                                               13

<210> SEQ ID NO 534
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 534
auuugaagug uaa                                               13

<210> SEQ ID NO 535
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 535
aagcugaccu gga                                               13

<210> SEQ ID NO 536
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 536
ggucaugaag aag                                               13

<210> SEQ ID NO 537
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 537
auggucaggc cuu                                               13

<210> SEQ ID NO 538
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 538
gaagacacgu uug                                               13

<210> SEQ ID NO 539
```

<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 539
aggccuugcg aag                                              13

<210> SEQ ID NO 540
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 540
uaccgacugg aag                                              13

<210> SEQ ID NO 541
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 541
accgcaagau cgg                                              13

<210> SEQ ID NO 542
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 542
caggccuugc gaa                                              13

<210> SEQ ID NO 543
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 543
cgagcuaaau ucu                                              13

<210> SEQ ID NO 544
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 544
ucuguggagu aug                                              13

<210> SEQ ID NO 545
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 545
cggagacaug gca                                              13

<210> SEQ ID NO 546
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 546
augacaacgc cuc                                              13

<210> SEQ ID NO 547
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 547
gaggucauga aga                                              13

<210> SEQ ID NO 548
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 548
uaaauucugu gga                                              13

<210> SEQ ID NO 549
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 549
uggaagacac guu                                              13

<210> SEQ ID NO 550
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 550
aagauguacg gag                                              13

<210> SEQ ID NO 551
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 551
aaugacaacg ccu                                              13

<210> SEQ ID NO 552
<211> LENGTH: 13
<212> TYPE: RNA

<213> ORGANISM: Artificial Sequence
<220> FEATURE:
<223> OTHER INFORMATION: synthetic oligonucleotide

<400> SEQUENCE: 552
ggcgagguca uga                                                            13

<210> SEQ ID NO 553
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 553
gacacguuug gcc                                                            13

<210> SEQ ID NO 554
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 554
acggagacau ggc                                                            13

<210> SEQ ID NO 555
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 555
ucaggccuug cga                                                            13

<210> SEQ ID NO 556
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 556
gcgaagcuga ccu                                                            13

<210> SEQ ID NO 557
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 557
ggaagaugua cgg                                                            13

<210> SEQ ID NO 558
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 558
gugacuucgg cuc                                                            13

```
<210> SEQ ID NO 559
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 559
ugacuucggc ucc                                                    13

<210> SEQ ID NO 560
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 560
uggucaggcc uug                                                    13

<210> SEQ ID NO 561
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 561
ucaaguuuga gcu                                                    13

<210> SEQ ID NO 562
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 562
gccagaacug cag                                                    13

<210> SEQ ID NO 563
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 563
uggaguaugu acc                                                    13

<210> SEQ ID NO 564
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 564
gcuagagaag cag                                                    13

<210> SEQ ID NO 565
<211> LENGTH: 13
<212> TYPE: RNA
<220> FEATURE:
<213> ORGANISM: Artificial Sequence
<220> FEATURE:
```

```
<223> OTHER INFORMATION: synthetic oligonucleotide

<400> SEQUENCE: 565
ggucaggccu ugc                                                            13

<210> SEQ ID NO 566
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 566
gagcuaaauu cug                                                            13

<210> SEQ ID NO 567
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 567
aagacacguu ugg                                                            13

<210> SEQ ID NO 568
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 568
cgaggucaug aag                                                            13

<210> SEQ ID NO 569
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 569
ggccuugcga agc                                                            13

<210> SEQ ID NO 570
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 570
cuugcgaagc uga                                                            13

<210> SEQ ID NO 571
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 571
ccgacuggaa gac                                                            13
```

```
<210> SEQ ID NO 572
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 572
ccuaucaagu uug                                                        13

<210> SEQ ID NO 573
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 573
uguuccaaga ccu                                                        13

<210> SEQ ID NO 574
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 574
cgaagcugac cug                                                        13

<210> SEQ ID NO 575
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 575
uugcgaagcu gac                                                        13

<210> SEQ ID NO 576
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 576
caaugacaac gcc                                                        13

<210> SEQ ID NO 577
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 577
guaccagugc acg                                                        13

<210> SEQ ID NO 578
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 578 ccguuccaa gac                                                        13

<210> SEQ ID NO 579
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 579
uacggagaca ugg                                                       13

<210> SEQ ID NO 580
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 580
ugcgaagcug acc                                                       13

<210> SEQ ID NO 581
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 581
ccuugcgaag cug                                                       13

<210> SEQ ID NO 582
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 582
cugugacuuc ggc                                                       13

<210> SEQ ID NO 583
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 583
gcuaaauucu gug                                                       13

<210> SEQ ID NO 584
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 584
cuaaauucug ugg                                                       13

<210> SEQ ID NO 585
<211> LENGTH: 13
```

```
<212> TYPE: RNA
<213> ORGANISM: Artificial Sequence
<220> FEATURE:
<223> OTHER INFORMATION: synthetic oligonucleotide

<400> SEQUENCE: 585
agacacguuu ggc                                                            13

<210> SEQ ID NO 586
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 586
ccgcaagauc ggc                                                            13

<210> SEQ ID NO 587
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 587
uaucaaguuu gag                                                            13

<210> SEQ ID NO 588
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 588
gaagcugacc ugg                                                            13

<210> SEQ ID NO 589
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 589
gcauuuaguc aaa                                                            13

<210> SEQ ID NO 590
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 590
ggcuacaaaa aca                                                            13

<210> SEQ ID NO 591
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 591
```

```
uuggcuacaa aaaca                                                  15

<210> SEQ ID NO 592
<211> LENGTH: 17
<212> TYPE: RNA
<213> ORGANISM: Artificial Sequence
<220> FEATURE:
<223> OTHER INFORMATION: synthetic oligonucleotide

<400> SEQUENCE: 592
auuuggcuac aaaaaca                                                17

<210> SEQ ID NO 593
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 593
acaaauacga uuu                                                    13

<210> SEQ ID NO 594
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 594
acaaauacga uuu                                                    13

<210> SEQ ID NO 595
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 595
cuuugaagag uucuguggaa gucua                                       25

<210> SEQ ID NO 596
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 596
acaaacacca uugucacacu cca                                         23

<210> SEQ ID NO 597
<211> LENGTH: 19
<212> TYPE: RNA
<213> ORGANISM: Artificial sequence
<220> FEATURE:
<223> OTHER INFORMATION: synthetic oligonucleotide

<400> SEQUENCE: 597
uagacuucca cagaacucu                                              19

<210> SEQ ID NO 598
<211> LENGTH: 13
<212> TYPE: RNA
<213> ORGANISM: Artificial sequence
```

```
<220> FEATURE:
<223> OTHER INFORMATION: synthetic oligonucleotide

<400> SEQUENCE: 598
cuguggaagu cua                                                      13

<210> SEQ ID NO 599
<211> LENGTH: 32
<212> TYPE: RNA
<213> ORGANISM: Artificial sequence
<220> FEATURE:
<223> OTHER INFORMATION: synthetic oligonuclotide

<400> SEQUENCE: 599
uagacuucca cagaacucug acaccuucag au                                 32

<210> SEQ ID NO 600
<211> LENGTH: 13
<212> TYPE: RNA
<213> ORGANISM: Artificial sequence
<220> FEATURE:
<223> OTHER INFORMATION: synthetic oligonucleotide

<400> SEQUENCE: 600
uagacuucca cag                                                      13

<210> SEQ ID NO 601
<211> LENGTH: 13
<212> TYPE: RNA
<213> ORGANISM: Artificial sequence
<220> FEATURE:
<223> OTHER INFORMATION: synthetic oligonucleotide

<400> SEQUENCE: 601
cuguggaagu cua                                                      13

<210> SEQ ID NO 602
<211> LENGTH: 31
<212> TYPE: RNA
<213> ORGANISM: Artificial sequence
<220> FEATURE:
<223> OTHER INFORMATION: synthetic oligonucleotide

<400> SEQUENCE: 602
uagacuucca cagaacucuu guggaagucu a                                  31

<210> SEQ ID NO 603
<211> LENGTH: 31
<212> TYPE: RNA
<213> ORGANISM: Artificial sequence
<220> FEATURE:
<223> OTHER INFORMATION: synthetic oligonucleotide

<400> SEQUENCE: 603
uagacuucca cagaacucuu guggaagucu a                                  31

<210> SEQ ID NO 604
<211> LENGTH: 25
<212> TYPE: RNA
<213> ORGANISM: Artificial sequence
<220> FEATURE:
<223> OTHER INFORMATION: synthetic oligonucleotide

<400> SEQUENCE: 604
cuuugaagag uucuguggaa gucua                                         25
```

```
<210> SEQ ID NO 605
<211> LENGTH: 25
<212> TYPE: RNA
<213> ORGANISM: Artificial sequence
<220> FEATURE:
<223> OTHER INFORMATION: synthetic oligonucleotide

<400> SEQUENCE: 605
uagacuucca cagaacucuu caaag                                     25

<210> SEQ ID NO 606
<211> LENGTH: 31
<212> TYPE: RNA
<213> ORGANISM: Artificial sequence
<220> FEATURE:
<223> OTHER INFORMATION: synthetic oligonucleotide

<400> SEQUENCE: 606
uagacuucca cagaacuucu guggaagucu a                              31

<210> SEQ ID NO 607
<211> LENGTH: 31
<212> TYPE: RNA
<213> ORGANISM: Artificial sequence
<220> FEATURE:
<223> OTHER INFORMATION: synthetic oligonucleotide

<400> SEQUENCE: 607
uagacuucca cagaacuucu guggaagucu a                              31

<210> SEQ ID NO 608
<211> LENGTH: 13
<212> TYPE: RNA
<213> ORGANISM: Artificial sequence
<220> FEATURE:
<223> OTHER INFORMATION: synthetoc oligonucleotide

<400> SEQUENCE: 608
uacuuucuuc auu                                                  13

<210> SEQ ID NO 609
<211> LENGTH: 13
<212> TYPE: RNA
<213> ORGANISM: Artificial sequence
<220> FEATURE:
<223> OTHER INFORMATION: synthetic oligonucleotide

<400> SEQUENCE: 609
aaugaagaaa gua                                                  13

<210> SEQ ID NO 610
<211> LENGTH: 32
<212> TYPE: RNA
<213> ORGANISM: Artificial sequence
<220> FEATURE:
<223> OTHER INFORMATION: synthetic oligonucleotide

<400> SEQUENCE: 610
uacuuucuuc auuccacca augaagaaag ua                              32

<210> SEQ ID NO 611
<211> LENGTH: 32
<212> TYPE: RNA
<213> ORGANISM: Artificial sequence
<220> FEATURE:
<223> OTHER INFORMATION: synthetic oligonucleotide
```

```
<400> SEQUENCE: 611
uacuuucuuc auuuccacca augaagaaag ua                              32

<210> SEQ ID NO 612
<211> LENGTH: 19
<212> TYPE: RNA
<213> ORGANISM: Artificial sequence
<220> FEATURE:
<223> OTHER INFORMATION: synthetic oligonucleotide

<400> SEQUENCE: 612
uacuuucuuc auuuccacc                                             19

<210> SEQ ID NO 613
<211> LENGTH: 13
<212> TYPE: RNA
<213> ORGANISM: Artificial sequence
<220> FEATURE:
<223> OTHER INFORMATION: synthetic oligonucleotide

<400> SEQUENCE: 613
aaugaagaaa gua                                                   13

<210> SEQ ID NO 614
<211> LENGTH: 25
<212> TYPE: RNA
<213> ORGANISM: Artificial sequence
<220> FEATURE:
<223> OTHER INFORMATION: synthetic oligonucleotide

<400> SEQUENCE: 614
uacuuucuuc auuuccaccu uugcc                                      25

<210> SEQ ID NO 615
<211> LENGTH: 25
<212> TYPE: RNA
<213> ORGANISM: Artificial sequence
<220> FEATURE:
<223> OTHER INFORMATION: synthetic oligonucleotide

<400> SEQUENCE: 615
ggcaaaggug gaaaugaaga aagua                                      25

<210> SEQ ID NO 616
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 616
ucuaauucau gagaaauac                                             19

<210> SEQ ID NO 617
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 617
uaauugaccu cagaagaug                                             19

<210> SEQ ID NO 618
```

<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 618
uuuaauugac cucagaaga                                                    19

<210> SEQ ID NO 619
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 619
aauugaccuc agaagaugc                                                    19

<210> SEQ ID NO 620
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 620
uuaauugacc ucagaagau                                                    19

<210> SEQ ID NO 621
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 621
auugaccuca gaagaugca                                                    19

<210> SEQ ID NO 622
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 622
ucauccagcu gacucguuu                                                    19

<210> SEQ ID NO 623
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 623
agauucauca gaaugguga                                                    19

<210> SEQ ID NO 624
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 624
ugaccucagu ccauaaacc					19

<210> SEQ ID NO 625
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 625
aauggugaga cucaucaga					19

<210> SEQ ID NO 626
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 626
uuugaccuca guccauaaa					19

<210> SEQ ID NO 627
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 627
uucauggcug ugaaauuca					19

<210> SEQ ID NO 628
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 628
gaauggugag acucaucag					19

<210> SEQ ID NO 629
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 629
uggcuuuccg cuuauauaa					19

<210> SEQ ID NO 630
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 630
uuggcuuucc gcuuauaua					19

<210> SEQ ID NO 631
<211> LENGTH: 19
<212> TYPE: RNA

```
<213> ORGANISM: Artificial Sequence
<220> FEATURE:
<223> OTHER INFORMATION: synthetic oligonucleotide

<400> SEQUENCE: 631
ucauccaugu ggucauggc                                               19

<210> SEQ ID NO 632
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 632
auguggucau ggcuuucgu                                               19

<210> SEQ ID NO 633
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 633
guggucaugg cuuucguug                                               19

<210> SEQ ID NO 634
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 634
auuggcuuuc cgcuuauau                                               19

<210> SEQ ID NO 635
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 635
aaauacgaaa uuucaggug                                               19

<210> SEQ ID NO 636
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 636 agaaaucga aauuucagg                                                19

<210> SEQ ID NO 637
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 637
uggucauggc uuucguugg                                               19
```

<210> SEQ ID NO 638
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 638
auaucaucca ugggucau                                            19

<210> SEQ ID NO 639
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 639
aauacgaaau uucaggugu                                           19

<210> SEQ ID NO 640
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 640
aaucagaagg cgcguucag                                           19

<210> SEQ ID NO 641
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 641
auucaugaga aauacgaaa                                           19

<210> SEQ ID NO 642
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 642
cuauucauga gagaauaac                                           19

<210> SEQ ID NO 643
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 643
uuucguugga cuuacuugg                                           19

<210> SEQ ID NO 644
<211> LENGTH: 19
<212> TYPE: RNA
<213> ORGANISM: Artificial Sequence
<220> FEATURE:

<223> OTHER INFORMATION: synthetic oligonucleotide

<400> SEQUENCE: 644
uugcucucau cauuggcuu                                                    19

<210> SEQ ID NO 645
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 645
uucaacuccu cgcuuucca                                                    19

<210> SEQ ID NO 646
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 646
ugacuaucaa ucacaucgg                                                    19

<210> SEQ ID NO 647
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 647
agaugcacua ucuaauuca                                                    19

<210> SEQ ID NO 648
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 648
aauagauaca cauucaacc                                                    19

<210> SEQ ID NO 649
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 649
uucuucuaua gaaugaaca                                                    19

<210> SEQ ID NO 650
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 650
aauugcugga caccgugg                                                     19

```
<210> SEQ ID NO 651
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 651
ucgcuuucca ugugugagg                                              19

<210> SEQ ID NO 652
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 652
uaaucuggac ugcuugugg                                              19

<210> SEQ ID NO 653
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 653
acacauucaa ccaauaaac                                              19

<210> SEQ ID NO 654
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 654
acucguuuca uaacugucc                                              19

<210> SEQ ID NO 655
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 655
auaaucugga cugcuugug                                              19

<210> SEQ ID NO 656
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 656
uuuccgcuua uauaaucug                                              19

<210> SEQ ID NO 657
<211> LENGTH: 19
<212> TYPE: RNA
<213> ORGANISM: Artificial Sequence
<220> FEATURE:
<223> OTHER INFORMATION: synthetic oligonucleotide
```

```
<400> SEQUENCE: 657
uguuuaacug guauggcac                                                    19

<210> SEQ ID NO 658
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 658
uauagaauga acauagaca                                                    19

<210> SEQ ID NO 659
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 659
uuuccuuggu cggcguuug                                                    19

<210> SEQ ID NO 660
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 660
guaugcacca uucaacucc                                                    19

<210> SEQ ID NO 661
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 661
ucggccauca uaugugucu                                                    19

<210> SEQ ID NO 662
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 662
aaucuggacu gcuuguggc                                                    19

<210> SEQ ID NO 663
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 663
acaucggaau gcucauugc                                                    19

<210> SEQ ID NO 664
<211> LENGTH: 19
```

```
-continued

<212> TYPE: RNA
<213> ORGANISM: Artificial Sequence
<220> FEATURE:
<223> OTHER INFORMATION: synthetic oligonucleotide

<400> SEQUENCE: 664
aaguuccuga cuaucaauc                                                  19

<210> SEQ ID NO 665
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 665
uugacuaaau gcaaaguga                                                  19

<210> SEQ ID NO 666
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 666
agacucauca gacugguga                                                  19

<210> SEQ ID NO 667
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 667
ucauaugugu cuacugugg                                                  19

<210> SEQ ID NO 668
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 668
auguccucgu cuguagcau                                                  19

<210> SEQ ID NO 669
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 669
gaauucacgg cugacuuug                                                  19

<210> SEQ ID NO 670
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 670
```
uuauuuccag acucaaaua                                                  19

<210> SEQ ID NO 671
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 671
gaagccacaa acuaaacua                                                  19

<210> SEQ ID NO 672
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 672
cuuucguugg acuuacuug                                                  19

<210> SEQ ID NO 673
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 673
gucugcgaaa cuucuuaga                                                  19

<210> SEQ ID NO 674
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 674
aaugcucauu gcucucauc                                                  19

<210> SEQ ID NO 675
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 675
augcacuauc uaauucaug                                                  19

<210> SEQ ID NO 676
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 676
cuuguaugca ccauucaac                                                  19

<210> SEQ ID NO 677
<211> LENGTH: 19
<212> TYPE: RNA
<213> ORGANISM: Artificial Sequence

```
<220> FEATURE:
<223> OTHER INFORMATION: synthetic oligonucleotide

<400> SEQUENCE: 677
ugacucguuu cauaacugu                                             19

<210> SEQ ID NO 678
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 678
uucagcacuc uggucaucc                                             19

<210> SEQ ID NO 679
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 679
aaauucaugg cuguggaau                                             19

<210> SEQ ID NO 680
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 680
acauucaacc aauaaacug                                             19

<210> SEQ ID NO 681
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 681
uacacauuca accaauaaa                                             19

<210> SEQ ID NO 682
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 682
auuaguuauu uccagacuc                                             19

<210> SEQ ID NO 683
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 683
uuucuauuca ugagagaau                                             19
```

```
<210> SEQ ID NO 684
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 684
uucgguugcu ggcaggucc                                              19

<210> SEQ ID NO 685
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 685
caugugugag gugaugucc                                              19

<210> SEQ ID NO 686
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 686
gcaccauuca acuccucgc                                              19

<210> SEQ ID NO 687
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 687
cauccagcug acucguuuc                                              19

<210> SEQ ID NO 688
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 688
cuuuccgcuu auauaaucu                                              19

<210> SEQ ID NO 689
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 689
aaucacaucg gaaugcuca                                              19

<210> SEQ ID NO 690
<211> LENGTH: 19
<212> TYPE: RNA
<213> ORGANISM: Artificial Sequence
<220> FEATURE:
<223> OTHER INFORMATION: synthetic oligonucleotide
```

```
<400> SEQUENCE: 690
acacauuagu uauuuccag                                            19

<210> SEQ ID NO 691
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 691
uucuauagaa ugaacauag                                            19

<210> SEQ ID NO 692
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 692
uacagugaua guuugcauu                                            19

<210> SEQ ID NO 693
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 693
auaagcaauu gacaccacc                                            19

<210> SEQ ID NO 694
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 694
uuuauuaauu gcuggacaa                                            19

<210> SEQ ID NO 695
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 695
ucaucagagu cguucgagu                                            19

<210> SEQ ID NO 696
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 696
auaaaccaca cuaucaccu                                            19

<210> SEQ ID NO 697
```

```
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 697
ucaucauugg cuuuccgcu                                                19

<210> SEQ ID NO 698
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 698
aguuccugac uaucaauca                                                19

<210> SEQ ID NO 699
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 699
uucacggcug acuuuggaa                                                19

<210> SEQ ID NO 700
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 700
uucucauggu agugaguuu                                                19

<210> SEQ ID NO 701
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 701
aaucagccug uuuaacugg                                                19

<210> SEQ ID NO 702
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 702
gguuucagca cucugguca                                                19

<210> SEQ ID NO 703
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 703
```
aucggaaugc ucauugcuc                                          19

<210> SEQ ID NO 704
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 704
uggcugugga auucacggc                                          19

<210> SEQ ID NO 705
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 705
uaagcaauug acaccacca                                          19

<210> SEQ ID NO 706
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 706
caauucucau gguagugag                                          19

<210> SEQ ID NO 707
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 707
uggcuuucgu uggacuuac                                          19

<210> SEQ ID NO 708
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 708
aaucagugac caguucauc                                          19

<210> SEQ ID NO 709
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 709
aguccauaaa ccacacuau                                          19

<210> SEQ ID NO 710
<211> LENGTH: 19
<212> TYPE: RNA

```
<213> ORGANISM: Artificial Sequence
<220> FEATURE:
<223> OTHER INFORMATION: synthetic oligonucleotide

<400> SEQUENCE: 710
cagcacucug gucauccag                                             19

<210> SEQ ID NO 711
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 711
uaucaaucac aucggaaug                                             19

<210> SEQ ID NO 712
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 712
auucacggcu gacuuugga                                             19

<210> SEQ ID NO 713
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 713
auagauacac auucaacca                                             19

<210> SEQ ID NO 714
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 714
uuuccagacu caaauagau                                             19

<210> SEQ ID NO 715
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 715
uuaauugcug gacaaccgu                                             19

<210> SEQ ID NO 716
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 716
uauuaauugc uggacaacc                                             19
```

```
<210> SEQ ID NO 717
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 717
agucguucga gucaaugga                                                    19

<210> SEQ ID NO 718
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 718
guugcuggca gguccgugg                                                    19

<210> SEQ ID NO 719
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 719
cucaugaauu aga                                                          13

<210> SEQ ID NO 720
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 720
cugaggucaa uua                                                          13

<210> SEQ ID NO 721
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 721
gaggucaauu aaa                                                          13

<210> SEQ ID NO 722
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 722
ucugagguca auu                                                          13

<210> SEQ ID NO 723
<211> LENGTH: 13
<212> TYPE: RNA
<213> ORGANISM: Artificial Sequence
<220> FEATURE:
```

<223> OTHER INFORMATION: synthetic oligonucleotide

<400> SEQUENCE: 723
ugaggucaau uaa                                                             13

<210> SEQ ID NO 724
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 724
uucugagguc aau                                                             13

<210> SEQ ID NO 725
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 725
gucagcugga uga                                                             13

<210> SEQ ID NO 726
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 726
uucugaugaa ucu                                                             13

<210> SEQ ID NO 727
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 727
uggacugagg uca                                                             13

<210> SEQ ID NO 728
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 728
gagucucacc auu                                                             13

<210> SEQ ID NO 729
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 729
gacugagguc aaa                                                             13

```
<210> SEQ ID NO 730
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 730
ucacagccau gaa                                                          13

<210> SEQ ID NO 731
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 731
agucucacca uuc                                                          13

<210> SEQ ID NO 732
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 732
aagcggaaag cca                                                          13

<210> SEQ ID NO 733
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 733
agcggaaagc caa                                                          13

<210> SEQ ID NO 734
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 734
accacaugga uga                                                          13

<210> SEQ ID NO 735
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 735
gccaugacca cau                                                          13

<210> SEQ ID NO 736
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 736
aagccaugac cac                                                        13

<210> SEQ ID NO 737
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 737
gcggaaagcc aau                                                        13

<210> SEQ ID NO 738
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 738
aaauuucgua uuu                                                        13

<210> SEQ ID NO 739
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 739
auuucguauu ucu                                                        13

<210> SEQ ID NO 740
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 740
aaagccauga cca                                                        13

<210> SEQ ID NO 741
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 741
acauggauga uau                                                        13

<210> SEQ ID NO 742
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 742
gaaauuucgu auu                                                        13

<210> SEQ ID NO 743
<211> LENGTH: 13
```

```
<212> TYPE: RNA
<213> ORGANISM: Artificial Sequence
<220> FEATURE:
<223> OTHER INFORMATION: synthetic oligonucleotide

<400> SEQUENCE: 743
gcgccuucug auu                                                      13

<210> SEQ ID NO 744
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 744
auuucucaug aau                                                      13

<210> SEQ ID NO 745
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 745
cucucaugaa uag                                                      13

<210> SEQ ID NO 746
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 746
aaguccaacg aaa                                                      13

<210> SEQ ID NO 747
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 747
augaugagag caa                                                      13

<210> SEQ ID NO 748
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 748
gcgaggaguu gaa                                                      13

<210> SEQ ID NO 749
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 749
```
ugauugauag uca                                                13

<210> SEQ ID NO 750
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 750
agauagugca ucu                                                13

<210> SEQ ID NO 751
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 751
auguguaucu auu                                                13

<210> SEQ ID NO 752
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 752
uucuauagaa gaa                                                13

<210> SEQ ID NO 753
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 753
uuguccagca auu                                                13

<210> SEQ ID NO 754
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 754
acauggaaag cga                                                13

<210> SEQ ID NO 755
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 755
gcaguccaga uua                                                13

<210> SEQ ID NO 756
<211> LENGTH: 13
<212> TYPE: RNA
<213> ORGANISM: Artificial Sequence

```
<220> FEATURE:
<223> OTHER INFORMATION: synthetic oligonucleotide

<400> SEQUENCE: 756
ugguugaaug ugu                                                          13

<210> SEQ ID NO 757
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 757
uuaugaaacg agu                                                          13

<210> SEQ ID NO 758
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 758
caguccagau uau                                                          13

<210> SEQ ID NO 759
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 759
auauaagcgg aaa                                                          13

<210> SEQ ID NO 760
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 760
uaccaguuaa aca                                                          13

<210> SEQ ID NO 761
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 761
uguucauucu aua                                                          13

<210> SEQ ID NO 762
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 762
ccgaccaagg aaa                                                          13
```

```
<210> SEQ ID NO 763
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 763
gaauggugca uac                                                          13

<210> SEQ ID NO 764
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 764
auaugauggc cga                                                          13

<210> SEQ ID NO 765
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 765
agcaguccag auu                                                          13

<210> SEQ ID NO 766
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 766
agcauuccga ugu                                                          13

<210> SEQ ID NO 767
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 767
uagucaggaa cuu                                                          13

<210> SEQ ID NO 768
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 768
ugcauuuagu caa                                                          13

<210> SEQ ID NO 769
<211> LENGTH: 13
<212> TYPE: RNA
<213> ORGANISM: Artificial Sequence
<220> FEATURE:
<223> OTHER INFORMATION: synthetic oligonucleotide
```

<400> SEQUENCE: 769
gucugaugag ucu                                                              13

<210> SEQ ID NO 770
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 770
uagacacaua uga                                                              13

<210> SEQ ID NO 771
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 771
cagacgagga cau                                                              13

<210> SEQ ID NO 772
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 772
cagccgugaa uuc                                                              13

<210> SEQ ID NO 773
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 773
agucuggaaa uaa                                                              13

<210> SEQ ID NO 774
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 774
aguuuguggc uuc                                                              13

<210> SEQ ID NO 775
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 775
aguccaacga aag                                                              13

<210> SEQ ID NO 776

```
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 776
aaguuucgca gac                                                          13

<210> SEQ ID NO 777
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 777
agcaaugagc auu                                                          13

<210> SEQ ID NO 778
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 778
uuagauagug cau                                                          13

<210> SEQ ID NO 779
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 779
uggugcauac aag                                                          13

<210> SEQ ID NO 780
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 780
augaaacgag uca                                                          13

<210> SEQ ID NO 781
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 781
ccagagugcu gaa                                                          13

<210> SEQ ID NO 782
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 782
```

```
cagccaugaa uuu                                                         13

<210> SEQ ID NO 783
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 783
auugguugaa ugu                                                         13

<210> SEQ ID NO 784
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 784
gguugaaugu gua                                                         13

<210> SEQ ID NO 785
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 785
ggaaauaacu aau                                                         13

<210> SEQ ID NO 786
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 786
ucaugaauag aaa                                                         13

<210> SEQ ID NO 787
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 787
gccagcaacc gaa                                                         13

<210> SEQ ID NO 788
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 788
caccucacac aug                                                         13

<210> SEQ ID NO 789
<211> LENGTH: 13
<212> TYPE: RNA
```

<213> ORGANISM: Artificial Sequence
<220> FEATURE:
<223> OTHER INFORMATION: synthetic oligonucleotide

<400> SEQUENCE: 789
aguugaaugg ugc                                                            13

<210> SEQ ID NO 790
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 790
agucagcugg aug                                                            13

<210> SEQ ID NO 791
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 791
uauaagcgga aag                                                            13

<210> SEQ ID NO 792
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 792
uuccgaugug auu                                                            13

<210> SEQ ID NO 793
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 793
auaacuaaug ugu                                                            13

<210> SEQ ID NO 794
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 794
ucauucuaua gaa                                                            13

<210> SEQ ID NO 795
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 795
aacuaucacu gua                                                            13

<210> SEQ ID NO 796
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 796
gucaauugcu uau                                                        13

<210> SEQ ID NO 797
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 797
agcaauuaau aaa                                                        13

<210> SEQ ID NO 798
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 798
acgacucuga uga                                                        13

<210> SEQ ID NO 799
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 799
uagugugguu uau                                                        13

<210> SEQ ID NO 800
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 800
aagccaauga uga                                                        13

<210> SEQ ID NO 801
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 801
auagucagga acu                                                        13

<210> SEQ ID NO 802
<211> LENGTH: 13
<212> TYPE: RNA
<213> ORGANISM: Artificial Sequence
<220> FEATURE:

<223> OTHER INFORMATION: synthetic oligonucleotide

<400> SEQUENCE: 802
agucagccgu gaa                                                          13

<210> SEQ ID NO 803
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 803
acuaccauga gaa                                                          13

<210> SEQ ID NO 804
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 804
aaacaggcug auu                                                          13

<210> SEQ ID NO 805
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 805
gagugcugaa acc                                                          13

<210> SEQ ID NO 806
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 806
ugagcauucc gau                                                          13

<210> SEQ ID NO 807
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 807
aauuccacag cca                                                          13

<210> SEQ ID NO 808
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 808
ugucaauugc uua                                                          13

```
<210> SEQ ID NO 809
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 809
accaugagaa uug                                                          13

<210> SEQ ID NO 810
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 810
ccaacgaaag cca                                                          13

<210> SEQ ID NO 811
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 811
cuggucacug auu                                                          13

<210> SEQ ID NO 812
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 812
ugguuuaugg acu                                                          13

<210> SEQ ID NO 813
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 813
gaccagagug cug                                                          13

<210> SEQ ID NO 814
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 814
gaugugauug aua                                                          13

<210> SEQ ID NO 815
<211> LENGTH: 13
<212> TYPE: RNA
<213> ORGANISM: Artificial Sequence
<220> FEATURE:
<223> OTHER INFORMATION: synthetic oligonucleotide
```

```
<400> SEQUENCE: 815
gucagccgug aau                                                      13

<210> SEQ ID NO 816
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 816
aauguguauc uau                                                      13

<210> SEQ ID NO 817
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 817
uugagucugg aaa                                                      13

<210> SEQ ID NO 818
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 818
guccagcaau uaa                                                      13

<210> SEQ ID NO 819
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 819
ccagcaauua aua                                                      13

<210> SEQ ID NO 820
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 820
gacucgaacg acu                                                      13

<210> SEQ ID NO 821
<211> LENGTH: 13
<212> TYPE: RNA
<213> ORGANISM: Artificial Sequence
<220> FEATURE:
<223> OTHER INFORMATION: synthetic oligonucleotide

<400> SEQUENCE: 821
accugccagc aac                                                      13
```

RNA INTERFERENCE IN SKIN INDICATIONS

RELATED APPLICATIONS

This application is a continuation of U.S. application Ser. No. 13/120,315, filed Mar. 22, 2011 which is a national stage filing under 35 U.S.C. §371 of international application PCT/US2009/005246, filed Sep. 22, 2009, which was published under PCT Article 21(2) in English, and claims the benefit of 35 U.S.C. §119(e) of U.S. provisional application Ser. No. 61/192,954, entitled "Chemically Modified Polynucleotides and Methods of Using the Same," filed on Sep. 22, 2008, U.S. 61/149,946, entitled "Minimum Length Triggeres of RNA Interference," filed on Feb. 4, 2009, and U.S. 61/224,031, entitled "Minimum Length Triggers of RNA Interference," filed on Jul. 8, 2009, the disclsoure of each of which is incorporated by reference herein in its entirety.

FIELD OF INVENTION

The invention pertains to the field of RNA interference (RNAi). The invention more specifically relates to nucleic acid molecules with improved in vivo delivery properties without the use of a delivering agent and their use in efficient gene silencing.

BACKGROUND OF INVENTION

Complementary oligonucleotide sequences are promising therapeutic agents and useful research tools in elucidating gene functions. However, prior art oligonucleotide molecules suffer from several problems that may impede their clinical development, and frequently make it difficult to achieve intended efficient inhibition of gene expression (including protein synthesis) using such compositions in vivo.

A major problem has been the delivery of these compounds to cells and tissues. Conventional double-stranded RNAi compounds, 19-29 bases long, form a highly negatively-charged rigid helix of approximately 1.5 by 10-15 nm in size. This rod type molecule cannot get through the cell-membrane and as a result has very limited efficacy both in vitro and in vivo. As a result, all conventional RNAi compounds require some kind of a delivery vehicle to promote their tissue distribution and cellular uptake. This is considered to be a major limitation of the RNAi technology.

There have been previous attempts to apply chemical modifications to oligonucleotides to improve their cellular uptake properties. One such modification was the attachment of a cholesterol molecule to the oligonucleotide. A first report on this approach was by Letsinger et al., in 1989. Subsequently, ISIS Pharmaceuticals, Inc. (Carlsbad, Calif.) reported on more advanced techniques in attaching the cholesterol molecule to the oilgonucleotide (Manoharan, 1992).

With the discovery of siRNAs in the late nineties, similar types of modifications were attempted on these molecules to enhance their delivery profiles. Cholesterol molecules conjugated to slightly modified (Soutschek, 2004) and heavily modified (Wolfrum, 2007) siRNAs appeared in the literature. Yamada et al., 2008 also reported on the use of advanced linker chemistries which further improved cholesterol mediated uptake of siRNAs. In spite of all this effort, the uptake of these types of compounds appears to be inhibited in the presence of biological fluids resulting in highly limited efficacy in gene silencing in vivo, limiting the applicability of these compounds in a clinical setting.

Therefore, it would be of great benefit to improve upon the prior art oligonucleotides by designing oligonucleotides that have improved delivery properties in vivo and are clinically meaningful.

SUMMARY OF INVENTION

Described herein are asymmetric chemically modified nucleic acid molecules with minimal double stranded regions, and the use of such molecules in gene silencing. RNAi molecules associated with the invention contain single stranded regions and double stranded regions, and can contain a variety of chemical modifications within both the single stranded and double stranded regions of the molecule. Additionally, the RNAi molecules can be attached to a hydrophobic conjugate such as a conventional and advanced sterol-type molecule. This new class of RNAi molecules has superior efficacy both in vitro and in vivo than previously described RNAi molecules.

In some aspects the invention is a method involving administering a double stranded nucleic acid molecule selected from the nucleic acid molecules contained in Tables 1-3 such that an antisense and a sense strand make up the double stranded nucleic acid molecule, to a subject, wherein the nucleic acid molecule is administered on the skin of the subject.

In other aspects the invention is a method involving administering a double stranded nucleic acid molecule selected from the nucleic acid molecules contained in Tables 1-3 such that an antisense and a sense strand make up the double stranded nucleic acid molecule, to a subject, wherein the nucleic acid molecule is administered via intradermal injection.

A method for treating compromised skin is provided according to other aspects of the invention. The method involves administering to a subject a therapeutically effective amount for treating compromised skin of a double stranded nucleic acid molecule comprising a guide strand, with a minimal length of 16 nucleotides, and a passenger strand forming a double stranded nucleic acid, having a double stranded region and a single stranded region, the double stranded region having 8-15 nucleotides in length, the single stranded region having 4-12 nucleotides in length, wherein position 1 of the guide strand is 5' phosphorylated or has a 2' O-methyl modification, wherein the passenger strand is linked to a lipophilic group, wherein at least 40% of the nucleotides of the double stranded nucleic acid are modified, and wherein the double stranded nucleic acid molecule has one end that is blunt or includes a one nucleotide overhang.

In another aspect the invention is a method for delivering a nucleic acid to a subject by administering to a subject prior to or simultaneously with a medical procedure a therapeutically effective amount for treating compromised skin of a double stranded nucleic acid molecule comprising a guide strand, with a minimal length of 16 nucleotides, and a passenger strand forming a double stranded nucleic acid, having a double stranded region and a single stranded region, the double stranded region having 8-15 nucleotides in length, the single stranded region having 4-12 nucleotides in length, wherein position 1 of the guide strand is 5' phosphorylated or has a 2' O-methyl modification, wherein the passenger strand is linked to a lipophilic group, wherein at least 40% of the nucleotides of the double stranded nucleic acid are modified, and wherein the double stranded nucleic acid molecule has one end that is blunt or includes a one nucleotide overhang. In one embodiment the medical procedure is surgery. Optionally the surgery is elective.

A method for promoting wound healing is provided in another aspect. The method involves administering a therapeutically effective amount for promoting wound healing of a double stranded nucleic acid molecule comprising a guide strand, with a minimal length of 16 nucleotides, and a passenger strand forming a double stranded nucleic acid, having a double stranded region and a single stranded region, the double stranded region having 8-15 nucleotides in length, the single stranded region having 4-12 nucleotides in length, wherein position 1 of the guide strand is 5' phosphorylated or has a 2' O-methyl modification, wherein the passenger strand is linked to a lipophilic group, wherein at least 40% of the nucleotides of the double stranded nucleic acid are modified, and wherein the double stranded nucleic acid molecule has one end that is blunt or includes a one nucleotide overhang.

In some embodiments the subject has a wound, such as a chronic wound. The wound may be a result of elective surgery. In some embodiments the wound is external. In other embodiments the wound is internal.

The nucleic acid molecule may in some embodiments be administered before or after an injury. For example the nucleic acid molecule may be administered before or after the injury via intradermal injection or locally to the skin.

In some embodiments the nucleic acid molecule is administered before a surgery. The surgery may be for instance epithelial grafting or skin grafting.

In some embodiments the nucleic acid molecule is administered to a graft donor site. In other embodiments the nucleic acid molecule is administered to a graft recipient site. In yet other embodiments the nucleic acid molecule is administered after burn injury.

Optionally the nucleic acid molecule may be administered prior to injury or surgery.

The double stranded nucleic acid molecule is directed against a gene encoding for a protein selected from the group consisting of: Transforming growth factor β (TGFβ1, TGFβ2), Osteopontin, Connective tissue growth factor (CTGF), Platelet-derived growth factor (PDGF), Hypoxia inducible factor-1α (HIF1α), Collagen I and/or III, Prolyl 4-hydroxylase (P4H), Procollagen C-protease (PCP), Matrix metalloproteinase 2, 9 (MMP2, 9), Integrins, Connexin, Histamine H1 receptor, Tissue transglutaminase, Mammalian target of rapamycin (mTOR), HoxB13, VEGF, IL-6, SMAD proteins, Ribosomal protein S6 kinases (RSP6) and Cyclooxygenase-2 (COX-2) in some embodiments.

In one embodiment the double stranded nucleic acid molecule is administered on the skin of the subject in need thereof. It may be in the form of a cream or ointment. In other embodiments the nucleic acid molecule is administered by local injection.

A composition of a double stranded nucleic acid molecule selected from the nucleic acid molecules contained in Tables 1-3 such that an antisense and a sense strand make up the double stranded nucleic acid molecule formulated for delivery to the skin is provided according to another aspect of the invention.

In another aspect the invention is a composition of a double stranded nucleic acid molecule comprising a guide strand, with a minimal length of 16 nucleotides, and a passenger strand forming a double stranded nucleic acid, having a double stranded region and a single stranded region, the double stranded region having 8-15 nucleotides in length, the single stranded region having 4-12 nucleotides in length, wherein position 1 of the guide strand is 5' phosphorylated or has a 2' O-methyl modification, wherein the passenger strand is linked to a lipophilic group, wherein at least 40% of the nucleotides of the double stranded nucleic acid are modified, and wherein the double stranded nucleic acid molecule has one end that is blunt or includes a one nucleotide overhang formulated for delivery to the skin. In one embodiment the nucleic acid molecule is in the form of a cream or ointment.

In some aspects the invention is methods for inhibiting scar tissue formation or for promoting epithelial regeneration. The methods involve administering a therapeutically effective amount for inhibiting scar tissue formation of a double stranded nucleic acid molecule selected from the nucleic acid molecules listed in Tables 1-3, to a subject in need thereof, to a subject in need thereof, to a subject in need thereof.

Alternatively the methods for inhibiting scar tissue formation or for promoting epithelial regeneration involve contacting epithelial cells with an effective amount for promoting epithelial regeneration of a double stranded nucleic acid molecule comprising a guide strand and a passenger strand, wherein the region of the molecule that is double stranded is from 8-14 nucleotides long, wherein the guide strand contains a single stranded region that is 4-12 nucleotides long, and wherein the single stranded region of the guide strand contains 2-12 phosphorothioate modifications, to a subject in need thereof.

Alternatively the methods for inhibiting scar tissue formation or for promoting epithelial regeneration involve administering to skin of a subject a therapeutically effective amount for inhibiting scar tissue formation or for promoting epithelial regeneration of a double stranded nucleic acid molecule comprising a guide strand, with a minimal length of 16 nucleotides, and a passenger strand forming a double stranded nucleic acid, having a double stranded region and a single stranded region, the double stranded region having 8-15 nucleotides in length, the single stranded region having 4-12 nucleotides in length, wherein position 1 of the guide strand is 5' phosphorylated and/or has a 2' O-methyl modification, wherein the passenger strand is linked to a lipophilic group, wherein at least 40% of the nucleotides of the double stranded nucleic acid are modified, and wherein the double stranded nucleic acid molecule has one end that is blunt or includes a one or two nucleotide overhang.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A depicts adsRNA with extended guide or passenger strands; FIG. 1B depicts adsRNA with length variations of a cell penetrating polynucleotide; FIG. 1C depicts adsRNA with 3' and 5' conjugates; FIG. 1D depicts adsRNAs with mismatches.

FIG. 7A depicts an adsRNA molecule; FIG. 7B depicts an siRNA molecule of approximately 17-30 bp long; FIG. 7C depicts a RISC entering strand; FIG. 7D depicts a substrate analog strand. Chemical modification patterns, as depicted in FIG. 7, can be optimized to promote desired function.

FIG. 10 presents schematics and graphs demonstrating that the percentage of liver uptake and plasma clearance of lipid emulsions containing sterol type molecules is directly affected by the size of the polycarbon chain attached at position 17. This figure is adapted from Martins et al, Journal of Lipid Research (1998).

FIG. 11A depicts a polynucleotide with a hydrophobic conjugate; FIG. 11B depicts linoleic acid; FIG. 11C depicts a micelle formed from a mixture of polynucleotides containing hydrophobic conjugates combined with fatty acids.

FIG. 27 is a graph demonstrating the importance of phosphorothioate content for un-assisted delivery. FIG. 27A demonstrates the results of a systematic screen that revealed that the presence of at least 2-12 phosphorothioates in the guide strand significantly improves uptake; in some embodiments, 4-8 phosphorothioate modifications were found to be preferred. FIG. 27B reveals that the presence or absence of phosphorothioate modifications in the sense strand did not alter efficacy.

FIG. 51 presents a graph indicating EC50 values for MAP4K4 silencing in the presence of sd-rxRNA, and images depicting localization of DY547-labeled rxRNA$^{ori}$ and DY547-labeled sd-rxRNA.

FIG. 65A,B compare uptake in RPE cells, FIG. 65C,D compare uptake upon local administration to skin and FIG. 65E,F compare uptake by the liver upon systemic administration. The level of uptake is at least an order of magnitude higher for the sd-rxRNA compounds relative to the regular siRNA-cholesterol compounds.

FIG. 66 presents images depicting localization of rxRNA$^{ori}$ and sd-rxRNA following local delivery.

FIG. 67 presents images depicting localization of sd-rxRNA and other conjugate RNAs following local delivery.

DETAILED DESCRIPTION

Figure 1:
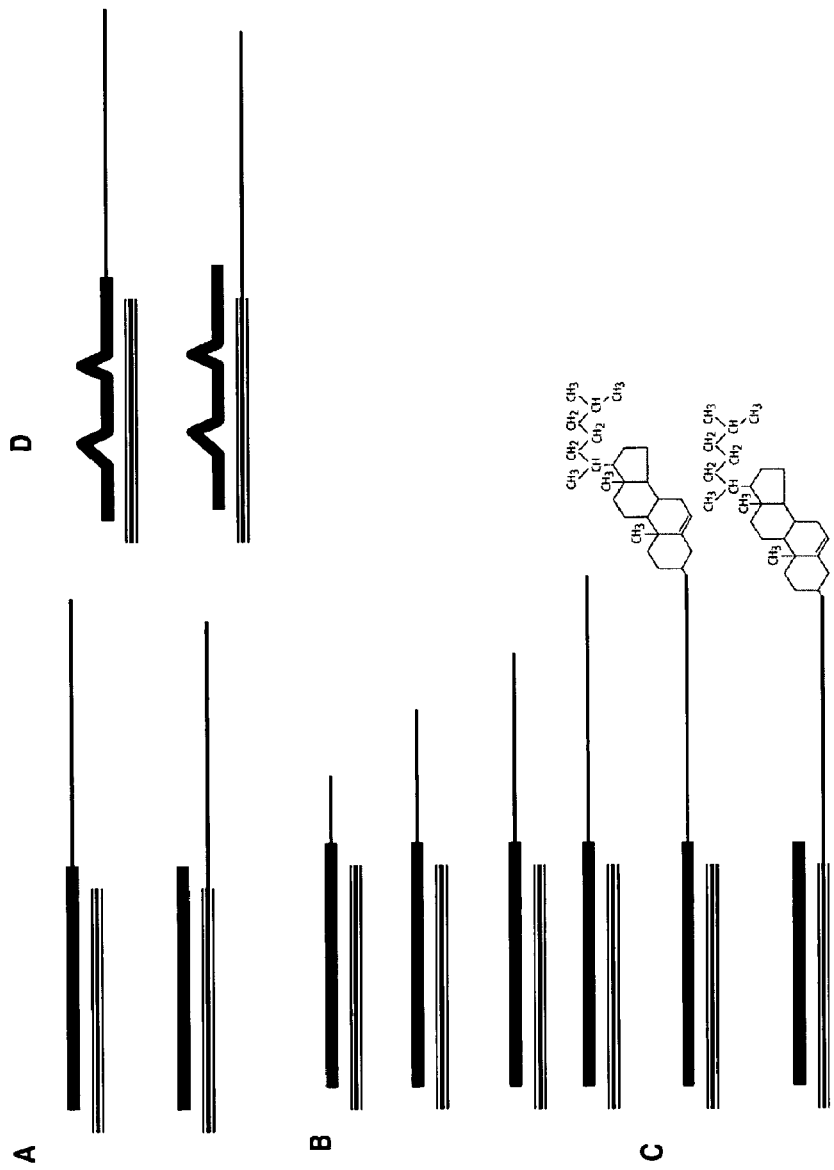
FIG. 1 is a schematic depicting proposed structures of asymmetric double stranded RNA molecules (adsRNA). Bold lines represent sequences carrying modification patterns compatible with RISC loading. Striped lines represent polynucleotides carrying modifications compatible with passenger strands. Plain lines represent a single stranded polynucleotide with modification patterns optimized for cell interaction and uptake.

Aspects of the invention relate to methods and compositions involved in gene silencing. The invention is based at least in part on the surprising discovery that asymmetric nucleic acid molecules with a double stranded region of a minimal length such as 8-14 nucleotides, are effective in silencing gene expression. Molecules with such a short double stranded region have not previously been demonstrated to be effective in mediating RNA interference. It had previously been assumed that that there must be a double stranded region of 19 nucleotides or greater. The molecules described herein are optimized through chemical modification, and in some instances through attachment of hydrophobic conjugates.

The invention is based at least in part on another surprising discovery that asymmetric nucleic acid molecules with reduced double stranded regions are much more effectively taken up by cells compared to conventional siRNAs. These molecules are highly efficient in silencing of target gene expression and offer significant advantages over previously described RNAi molecules including high activity in the presence of serum, efficient self delivery, compatibility with a wide variety of linkers, and reduced presence or complete absence of chemical modifications that are associated with toxicity.

In contrast to single-stranded polynucleotides, duplex polynucleotides have been difficult to deliver to a cell as they have rigid structures and a large number of negative charges which makes membrane transfer difficult. Unexpectedly, it was found that the polynucleotides of the present invention, although partially double-stranded, are recognized in vivo as single-stranded and, as such, are capable of efficiently being delivered across cell membranes. As a result the polynucleotides of the invention are capable in many instances of self delivery. Thus, the polynucleotides of the invention may be formulated in a manner similar to conventional RNAi agents or they may be delivered to the cell or subject alone (or with non-delivery type carriers) and allowed to self deliver. In one embodiment of the present invention, self delivering asymmetric double-stranded RNA molecules are provided in which one portion of the molecule resembles a conventional RNA duplex and a second portion of the molecule is single stranded.

The polynucleotides of the invention are referred to herein as isolated double stranded or duplex nucleic acids, oligonucleotides or polynucleotides, nano molecules, nano RNA, sd-rxRNA$^{nano}$, sd-rxRNA or RNA molecules of the invention.

The oligonucleotides of the invention in some aspects have a combination of asymmetric structures including a double stranded region and a single stranded region of 5 nucleotides or longer, specific chemical modification patterns and are conjugated to lipophilic or hydrophobic molecules. This new class of RNAi like compounds have superior efficacy in vitro and in vivo. Based on the data described herein it is believed that the reduction in the size of the rigid duplex region in combination with phosphorothioate modifications applied to a single stranded region are new and important for achieving the observed superior efficacy. Thus, the RNA molecules described herein are different in both structure and composition as well as in vitro and in vivo activity.

In a preferred embodiment the RNAi compounds of the invention comprise an asymmetric compound comprising a duplex region (required for efficient RISC entry of 10-15 bases long) and single stranded region of 4-12 nucleotides long; with a 13 nucleotide duplex. A 6 nucleotide single stranded region is preferred in some embodiments. The single stranded region of the new RNAi compounds also comprises 2-12 phosphorothioate internucleotide linkages (referred to as phosphorothioate modifications). 6-8 phosphorothioate internucleotide linkages are preferred in some embodiments. Additionally, the RNAi compounds of the invention also include a unique chemical modification pattern, which provides stability and is compatible with RISC entry. The combination of these elements has resulted in unexpected properties which are highly useful for delivery of RNAi reagents in vitro and in vivo.

The chemically modification pattern, which provides stability and is compatible with RISC entry includes modifications to the sense, or passenger, strand as well as the antisense, or guide, strand. For instance the passenger strand can be modified with any chemical entities which confirm stability and do not interfere with activity. Such modifications include 2' ribo modifications (O-methyl, 2' F, 2 deoxy and others) and backbone modification like phosphorothioate modifications. A preferred chemical modification pattern in the passenger strand includes Omethyl modification of C and U nucleotides within the passenger strand or alternatively the passenger strand may be completely Omethyl modified.

The guide strand, for example, may also be modified by any chemical modification which confirms stability without interfering with RISC entry. A preferred chemical modification pattern in the guide strand includes the majority of C and U nucleotides being 2' F modified and the 5' end being phosphorylated. Another preferred chemical modification pattern in the guide strand includes 2'Omethyl modification of position 1 and C/U in positions 11-18 and 5' end chemical phosphorylation. Yet another preferred chemical modification pattern in the guide strand includes 2'Omethyl modification of position 1 and C/U in positions 11-18 and 5' end chemical phosphorylation and 2'F modification of C/U in positions 2-10.

It was surprisingly discovered according to the invention that the above-described chemical modification patterns of the oligonucleotides of the invention are well tolerated and actually improved efficacy of asymmetric RNAi compounds. See, for instance, FIG. 22.

Figure 23:
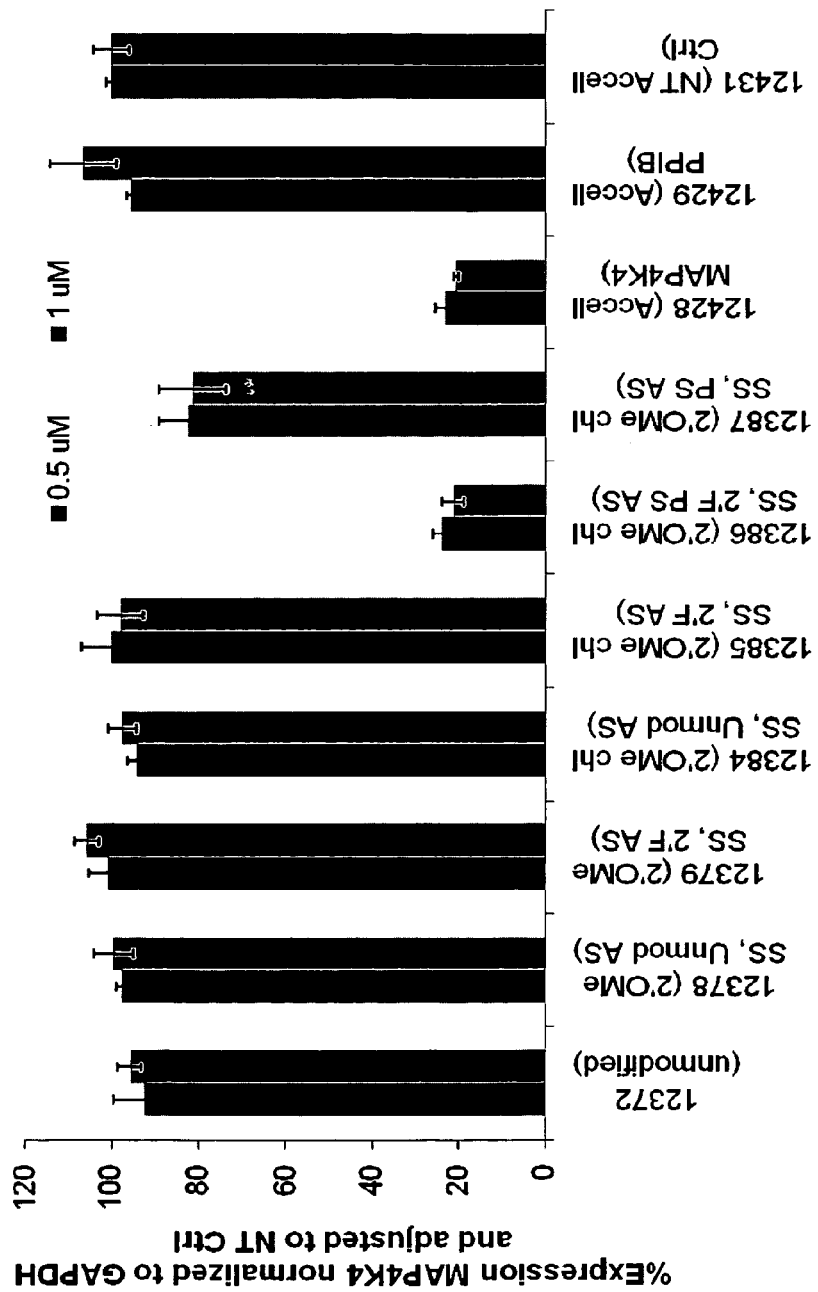
FIG. 23 demonstrates that the chemical modifications described herein significantly increase in vitro efficacy in un-assisted delivery of RNAi molecules in HeLa cells. The structure and sequence of the compounds were not altered; only the chemical modification patterns of the molecules were modified. Compounds lacking 2' F, 2'O-me, phosphorothioate modification, or cholesterol conjugates were completely inactive in passive uptake. A combination of all 4 of these types of modifications produced the highest levels of activity (compound 12386).

It was also demonstrated experimentally herein that the combination of modifications to RNAi when used together in a polynucleotide results in the achievement of optimal efficacy in passive uptake of the RNAi. Elimination of any of the described components (Guide strand stabilization, phosphorothioate stretch, sense strand stabilization and hydrophobic conjugate) or increase in size results in sub-optimal efficacy and in some instances complete lost of efficacy. The combination of elements results in development of compound, which is fully active following passive delivery to cells such as HeLa cells. (FIG. 23). The degree to which the combination of elements results in efficient self delivery of RNAi molecules was completely unexpected.

Figure 26:
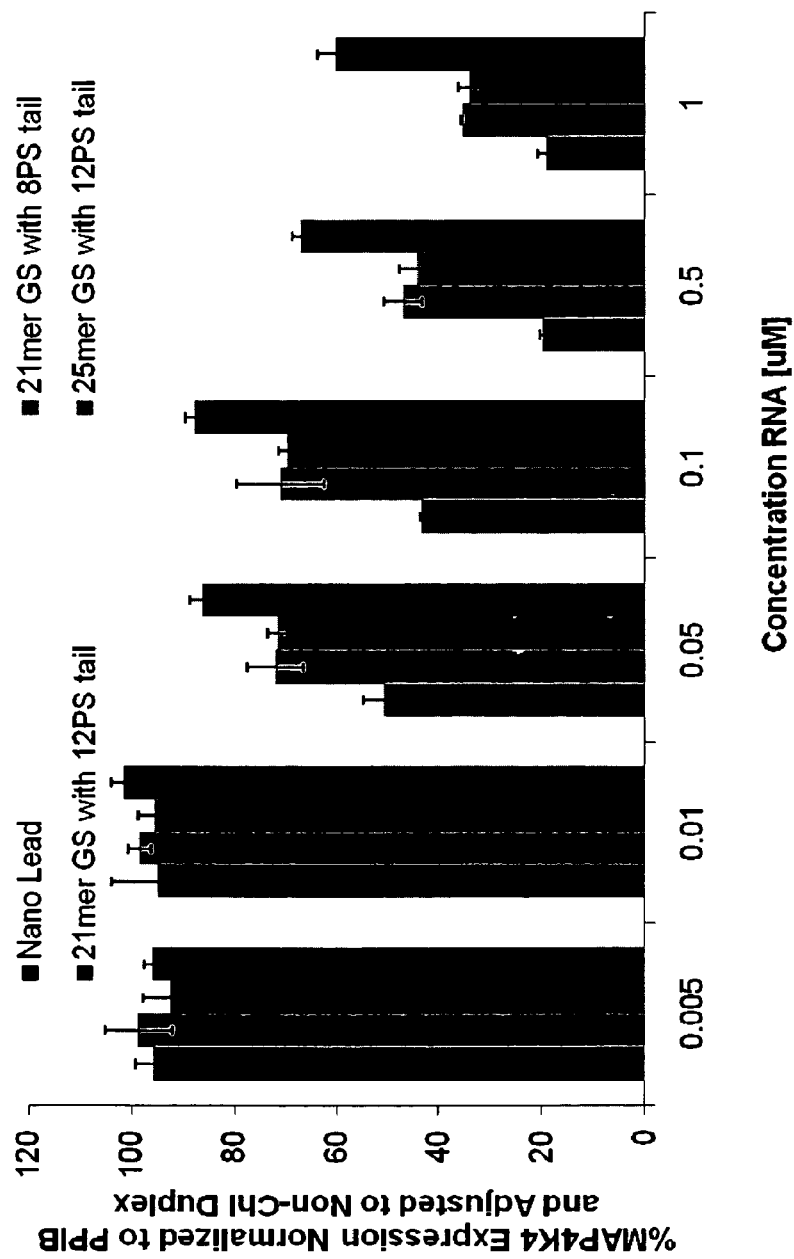
FIG. 26 is a graph demonstrating that reduction in oligonucleotide content increases the efficacy of unassisted uptake. Similar chemical modifications were applied to asymmetric compounds, traditional siRNA compounds and 25 mer RNAi compounds. The asymmetric small compounds demonstrated the most significant efficacy.
Figure 43:
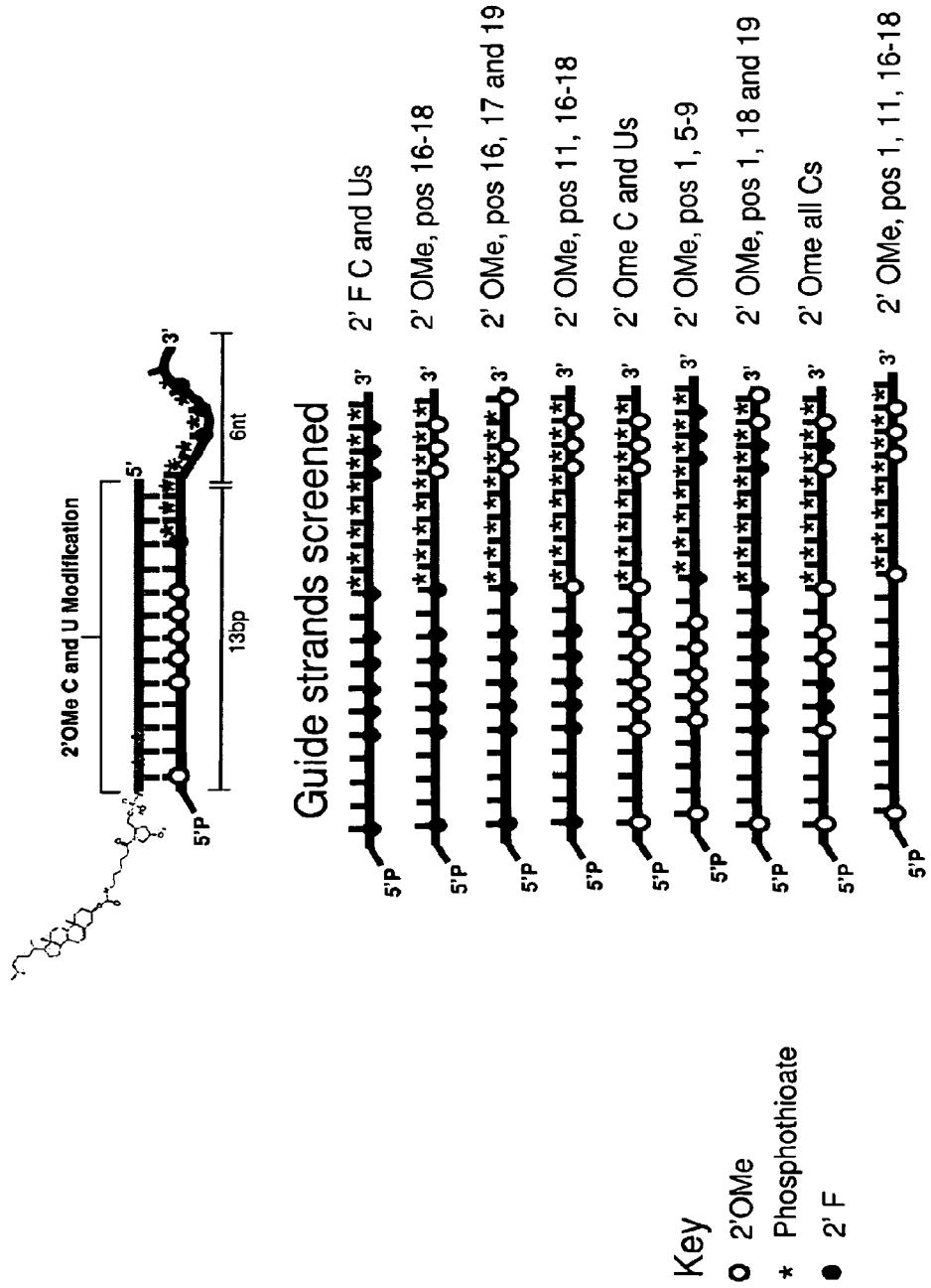
FIG. 43 is a schematic depicting guide strand chemical modifications that were screened for optimization.

The data shown in FIGS. 26, 27 and 43 demonstrated the importance of the various modifications to the RNAi in achieving stabilization and activity. For instance, FIG. 26 demonstrates that use off asymmetric configuration is important in getting efficacy in passive uptake. When the same chemical composition is applied to compounds of traditional configurations (19-21 bases duplex and 25 mer duplex) the efficacy was drastically decreased in a length dependent manner. FIG. 27 demonstrated a systematic screen of the impact of phosphorothioate chemical modifications on activity. The sequence, structure, stabilization chemical modifications, hydrophobic conjugate were kept constant and compound phosphorothioate content was varied (from 0 to 18 PS bond). Both compounds having no phosphorothioate linkages and having 18 phosphorothioate linkages were completely inactive in passive uptake. Compounds having 2-16 phosphorothioate linkages were active, with compounds having 4-10 phosphorothioate being the most active compounds.

Figure 65:
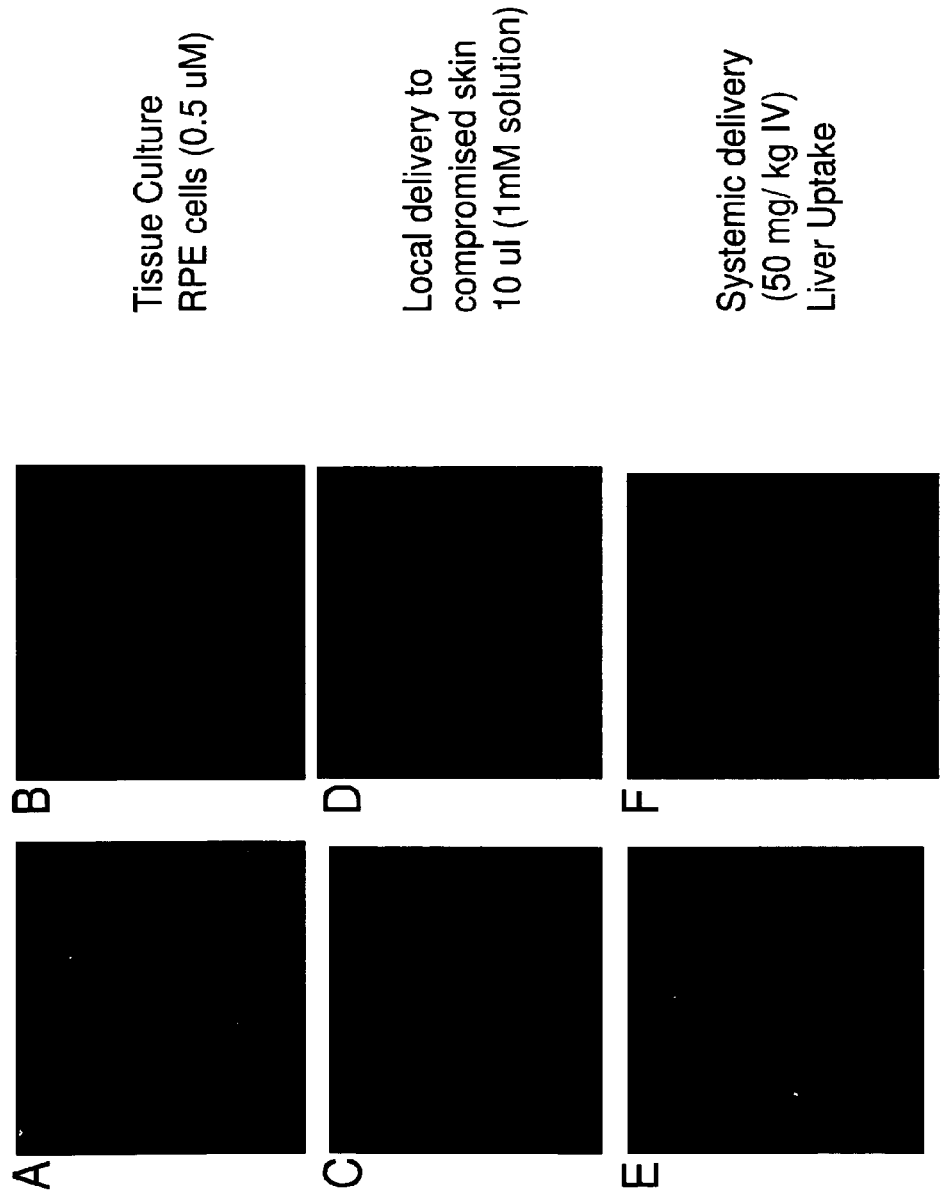
FIG. 65 presents images demonstrating that sd-rxRNA compounds have drastically better cellular and tissue uptake characteristics when compared to conventional cholesterol conjugated siRNAs (such as those published by Soucheck et al).
Figure 68:
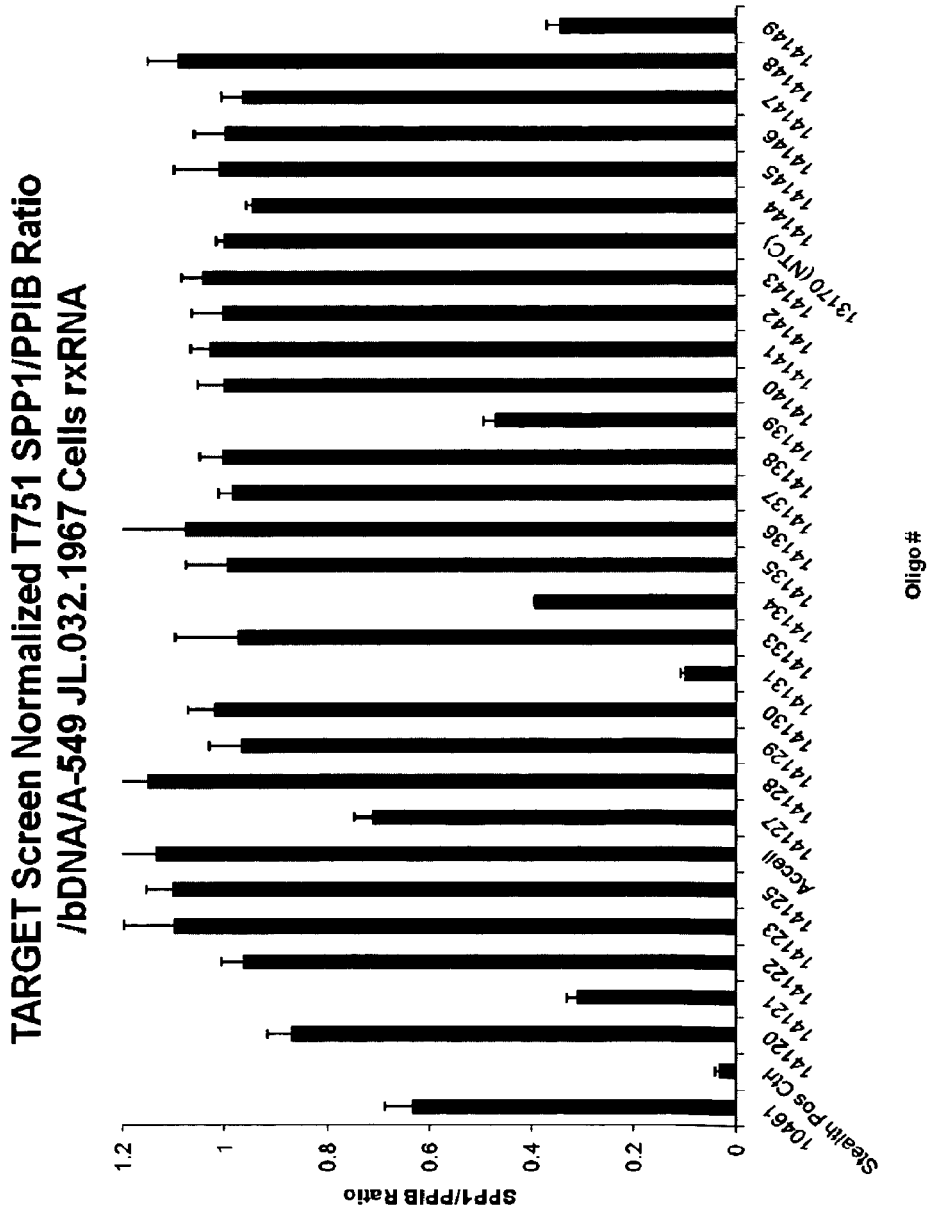
FIG. 68 presents a graph revealing the results of a screen performed with sd-rxRNAGII chemistry to identify functional compounds targeting the SPP1 gene. Multiple effective compounds were identified, with 14131 being the most effective. The compounds were added to A-549 cells and the level of the ratio of SPP1/PPIB was determined by B-DNA after 48 hours.

The data in the Examples presented below demonstrates high efficacy of the oligonucleotides of the invention both in vitro in variety of cell types (supporting data) and in vivo upon local and systemic administration. For instance, the data compares the ability of several competitive RNAi molecules having different chemistries to silence a gene. Comparison of sd-rxRNA (oligonucleotides of the invention) with RNAs described in Soucheck et al. and Wolfrum at al., as applied to the same targeting region, demonstrated that only sd-rxRNA chemistry showed a significant functionality in passive uptake. The composition of the invention achieved EC50 values of 10-50 pM. This level of efficacy is un-attainable with conventional chemistries like those described in Sauthceck at al and Accell. Similar comparisons were made in other systems, such as in vitro (RPE cell line), in vivo upon local administration (wounded skin) and systemic (50 mg/kg) as well as other genes (FIGS. 65 and 68). In each case the oligonucleotides of the invention achieved better results. FIG.

Figure 70:
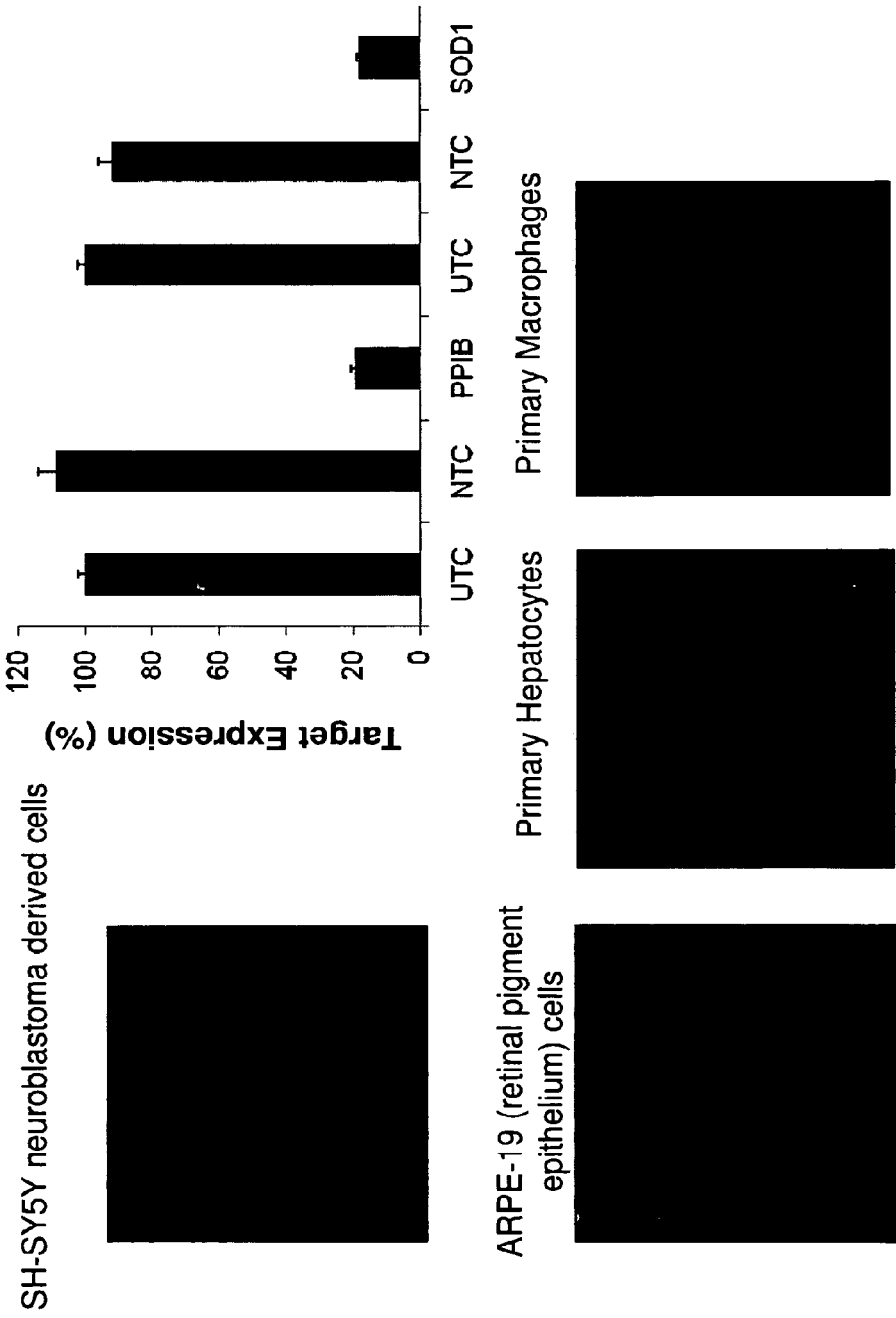
FIG. 70 presents a graph and several images demonstrating efficient uptake and silencing of sd-rxRNA compounds in multiple cell types with multiple sequences. In each case silencing was confirmed by looking at target gene expression using a Branched DNA assay.
Figure 71:
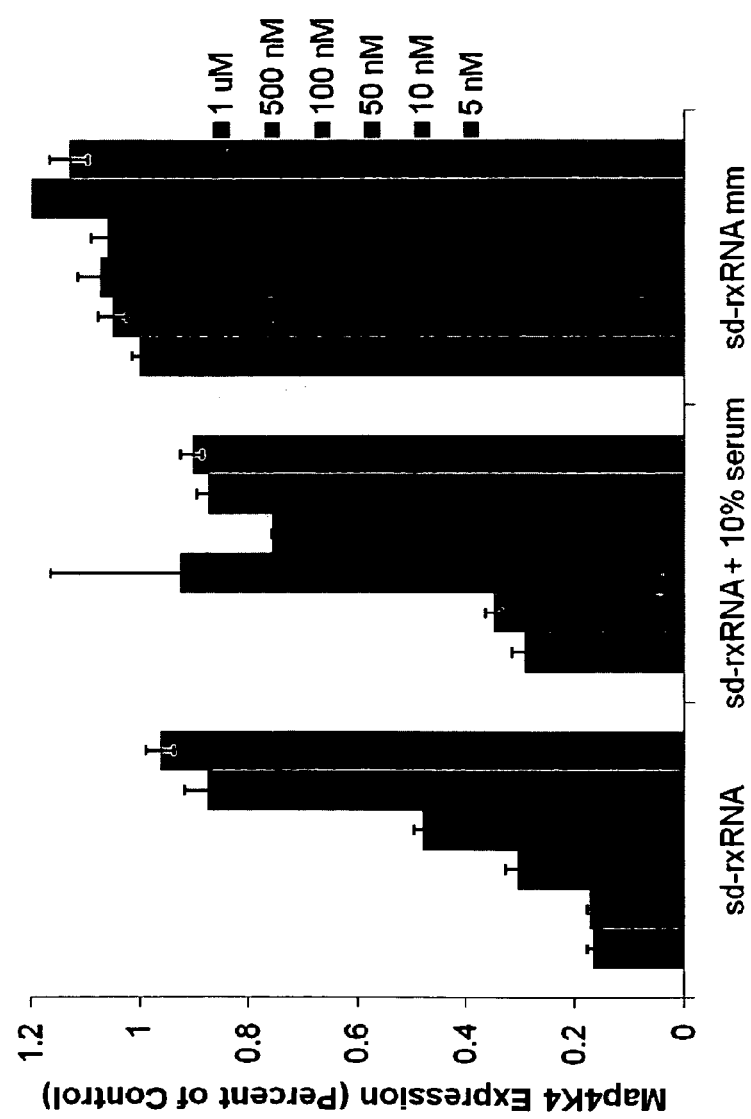
FIG. 71 presents a graph revealing that sd-rxRNA is active in the presence and absence of serum. A slight reduction in efficacy (2-5 fold) was observed in the presence of serum. This minimal reduction in efficacy in the presence of serum differentiates the sd-rxRNA compounds described herein from previously described RNAi compounds, which had a greater reduction in efficacy, and thus creates a foundation for in vivo efficacy of the sd-rxRNA molecules described herein.

64 includes data demonstrating efficient cellular uptake and resulting silencing by sd-rxRNA compounds only after 1 minute of exposure. Such an efficacy is unique to this composition and have not been seen with other types of molecules in this class. FIG. 70 demonstrates efficient uptake and silencing of sd-rxRNA compounds in multiple cell types with multiple sequences. The sd-rxRNA compounds are also active in cells in presence and absence of serum and other biological liquids. FIG. 71 demonstrates only a slight reduction in activity in the presence of serum. This ability to function in biologically aggressive environment effectively further differentiates sd-rxRNA compounds from other compounds described previously in this group, like Accell and Soucheck et al, in which uptake is drastically inhibited in a presence of serum.

Figure 72:
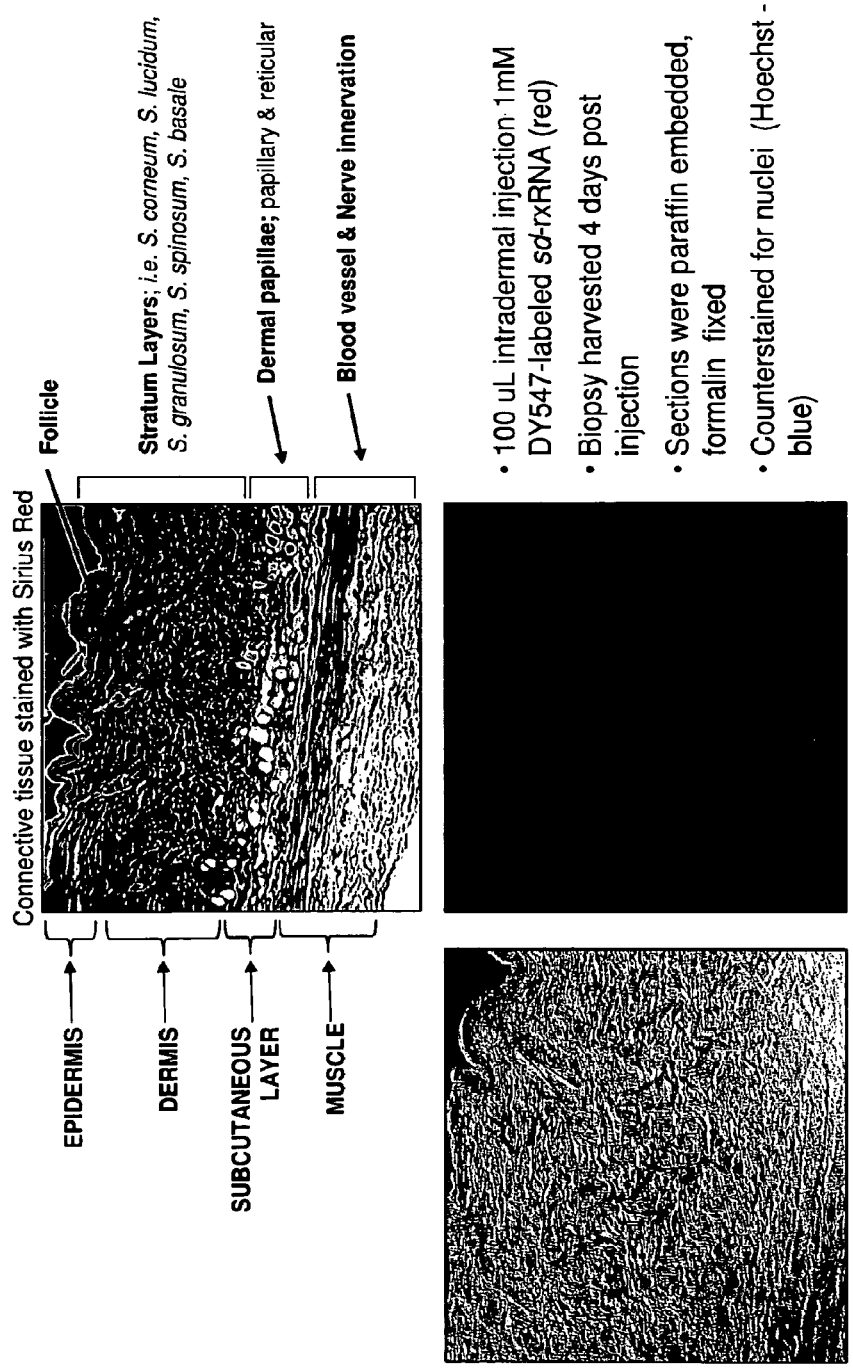
FIG. 72 presents images demonstrating efficient tissue penetration and cellular uptake upon single intradermal injection of sd-rxRNA compounds described herein. This represents a model for local delivery of sd-rxRNA compounds as well as an effective demonstration of delivery of sd-rxRNA compounds and silencing of genes in dermatological applications.
Figure 73:
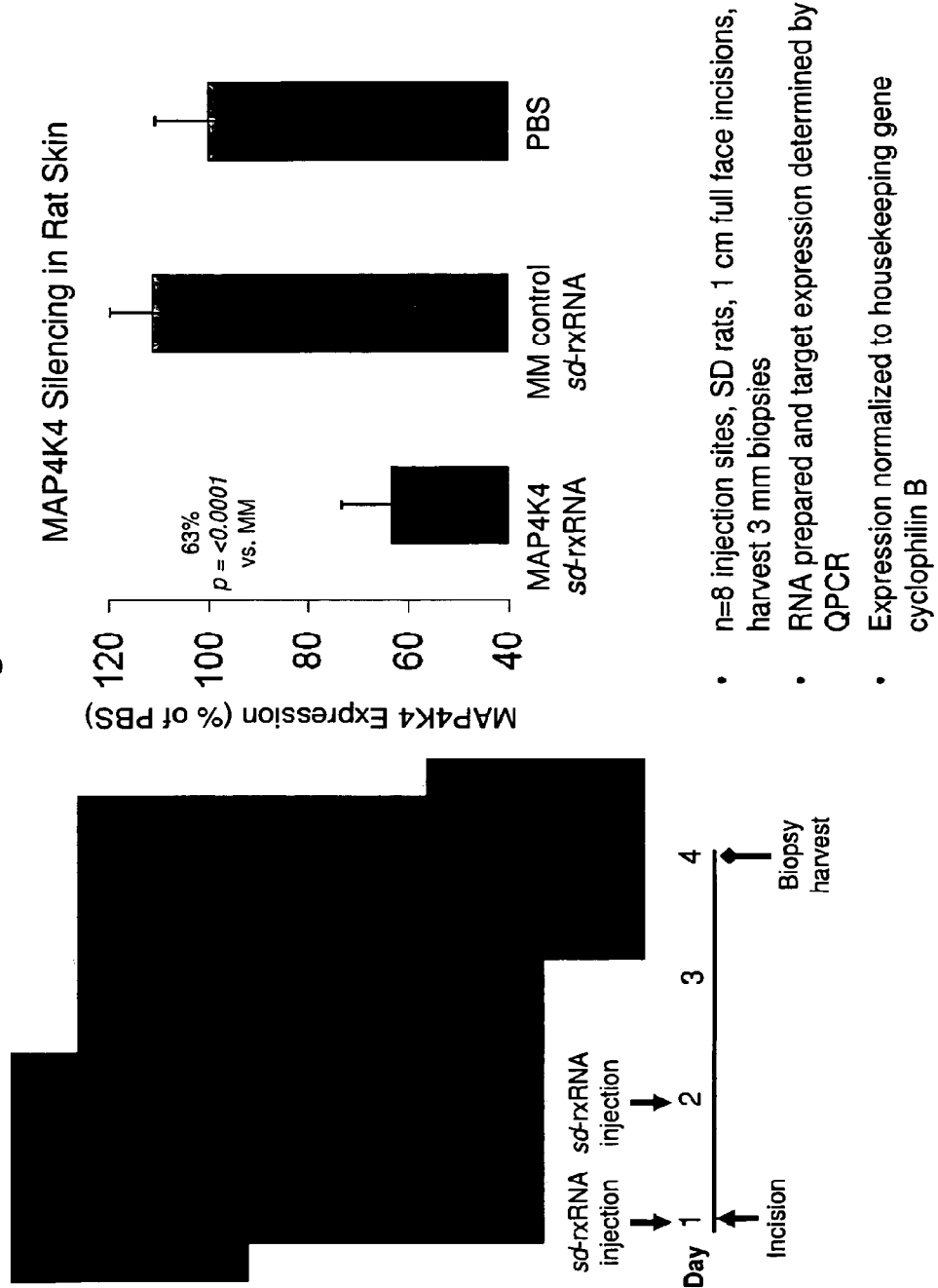
FIG. 73 presents images and a graph demonstrating efficient cellular uptake and in vivo silencing with sd-rxRNA following intradermal injection.

Significant amounts of data also demonstrate the in vivo efficacy of the compounds of the invention. For instance FIGS. 72-74 involve multiple routes of in vivo delivery of the compounds of the invention resulting in significant activity. FIG. 72, for example, demonstrates efficient tissue penetration and cellular uptake upon single intradermal injection. This is a model for local delivery of sd-rxRNA compounds as well as an effective delivery mode for sd-rxRNA compounds and silencing genes in any dermatology applications. FIG. 73 demonstrated efficient tissue penetration, cellular uptake and silencing upon local in vivo intradermal injection of sd-rxRNA compounds. The data of FIG. 74 demonstrate that sd-rxRNA compounds result in highly effective liver uptake upon IV administration. Comparison to Souicheck at al molecule showed that the level of liver uptake at identical dose level was quite surprisingly, at least 50 fold higher with the sd-rxRNA compound than the Souicheck at al molecule.

The sd-rxRNA can be further improved in some instances by improving the hydrophobicity of compounds using of novel types of chemistries. For example one chemistry is related to use of hydrophobic base modifications. Any base in any position might be modified, as long as modification results in an increase of the partition coefficient of the base. The preferred locations for modification chemistries are positions 4 and 5 of the pyrimidines. The major advantage of these positions is (a) ease of synthesis and (b) lack of interference with base-pairing and A form helix formation, which are essential for RISC complex loading and target recognition. Examples of these chemistries is shown in FIGS. 75-83. A version of sd-rxRNA compounds where multiple deoxy Uridines are present without interfering with overall compound efficacy was used. In addition major improvement in tissue distribution and cellular uptake might be obtained by optimizing the structure of the hydrophobic conjugate. In some of the preferred embodiment the structure of sterol is modified to alter (increase/decrease) C17 attached chain. This type of modification results in significant increase in cellular uptake and improvement of tissue uptake prosperities in vivo.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Thus, aspects of the invention relate to isolated double stranded nucleic acid molecules comprising a guide (antisense) strand and a passenger (sense) strand. As used herein, the term "double-stranded" refers to one or more nucleic acid molecules in which at least a portion of the nucleomonomers are complementary and hydrogen bond to form a double-stranded region. In some embodiments, the length of the guide strand ranges from 16-29 nucleotides long. In certain embodiments, the guide strand is 16, 17, 18, 19, 20, 21, 22, 23, 24, 25, 26, 27, 28, or 29 nucleotides long. The guide strand has complementarity to a target gene. Complementarity between the guide strand and the target gene may exist over any portion of the guide strand. Complementarity as used herein may be perfect complementarity or less than perfect complementarity as long as the guide strand is sufficiently complementary to the target that it mediates RNAi. In some embodiments complementarity refers to less than 25%, 20%, 15%, 10%, 5%, 4%, 3%, 2%, or 1% mismatch between the guide strand and the target. Perfect complementarity refers to 100% complementarity. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Moreover, not all positions of a siRNA contribute equally to target recognition. Mismatches in the center of the siRNA are most critical and essentially abolish target RNA cleavage. Mismatches upstream of the center or upstream of the cleavage site referencing the antisense strand are tolerated but significantly reduce target RNA cleavage. Mismatches downstream of the center or cleavage site referencing the antisense strand, preferably located near the 3' end of the antisense strand, e.g. 1, 2, 3, 4, 5 or 6 nucleotides from the 3' end of the antisense strand, are tolerated and reduce target RNA cleavage only slightly.

While not wishing to be bound by any particular theory, in some embodiments, the guide strand is at least 16 nucleotides in length and anchors the Argonaute protein in RISC. In some embodiments, when the guide strand loads into RISC it has a defined seed region and target mRNA cleavage takes place across from position 10-11 of the guide strand. In some embodiments, the 5' end of the guide strand is or is able to be phosphorylated. The nucleic acid molecules described herein may be referred to as minimum trigger RNA.

In some embodiments, the length of the passenger strand ranges from 8-14 nucleotides long. In certain embodiments, the passenger strand is 8, 9, 10, 11, 12, 13 or 14 nucleotides long. The passenger strand has complementarity to the guide strand. Complementarity between the passenger strand and the guide strand can exist over any portion of the passenger or guide strand. In some embodiments, there is 100% complementarity between the guide and passenger strands within the double stranded region of the molecule.

Aspects of the invention relate to double stranded nucleic acid molecules with minimal double stranded regions. In some embodiments the region of the molecule that is double stranded ranges from 8-14 nucleotides long. In certain embodiments, the region of the molecule that is double stranded is 8, 9, 10, 11, 12, 13 or 14 nucleotides long. In certain embodiments the double stranded region is 13 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. For example the single stranded region can be 4, 5, 6, 7, 8, 9, 10, 11 or 12 nucleotides long. However, in certain embodiments, the single stranded region can also be less than 4 or greater than 12 nucleotides long. In certain embodiments, the single stranded region is 6 nucleotides long.

RNAi constructs associated with the invention can have a thermodynamic stability (ΔG) of less than −13 kkal/mol. In some embodiments, the thermodynamic stability (ΔG) is less than −20 kkal/mol. In some embodiments there is a loss of efficacy when (ΔG) goes below −21 kkal/mol. In some embodiments a (ΔG) value higher than −13 kkal/mol is compatible with aspects of the invention. Without wishing to be bound by any theory, in some embodiments a molecule with a relatively higher (ΔG) value may become active at a relatively higher concentration, while a molecule with a relatively lower (ΔG) value may become active at a relatively lower concentration. In some embodiments, the (ΔG) value may be higher than −9 kkcal/mol. The gene silencing effects mediated by the RNAi constructs associated with the invention, containing minimal double stranded regions, are unexpected because molecules of almost identical design but lower thermodynamic stability have been demonstrated to be inactive (Rana et al. 2004).

Without wishing to be bound by any theory, results described herein suggest that a stretch of 8-10 bp of dsRNA or dsDNA will be structurally recognized by protein components of RISC or co-factors of RISC. Additionally, there is a free energy requirement for the triggering compound that it may be either sensed by the protein components and/or stable enough to interact with such components so that it may be loaded into the Argonaute protein. If optimal thermodynamics are present and there is a double stranded portion that is preferably at least 8 nucleotides then the duplex will be recognized and loaded into the RNAi machinery.

In some embodiments, thermodynamic stability is increased through the use of LNA bases. In some embodiments, additional chemical modifications are introduced. Several non-limiting examples of chemical modifications include: 5' Phosphate, 2'-O-methyl, 2'-O-ethyl, 2'-fluoro, ribothymidine, C-5 propynyl-dC (pdC) and C-5 propynyl-dU (pdU); C-5 propynyl-C (pC) and C-5 propynyl-U (pU); 5-methyl C, 5-methyl U, 5-methyl dC, 5-methyl dU methoxy, (2,6-diaminopurine), 5'-Dimethoxytrityl-N4-ethyl-2'-deoxy-Cytidine and MGB (minor groove binder). It should be appreciated that more than one chemical modification can be combined within the same molecule.

Molecules associated with the invention are optimized for increased potency and/or reduced toxicity. For example, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-O-methyl (2'OMe) modifications can in some aspects influence toxicity of the molecule. Specifically, reduction in 2'F content of a molecule is predicted to reduce toxicity of the molecule. The Examples section presents molecules in which 2'F modifications have been eliminated, offering an advantage over previously described RNAi compounds due to a predicted reduction in toxicity. Furthermore, the number of phosphorothioate modifications in an RNA molecule can influence the uptake of the molecule into a cell, for example the efficiency of passive uptake of the molecule into a cell. Preferred embodiments of molecules described herein have no 2'F modification and yet are characterized by equal efficacy in cellular uptake and tissue penetration. Such molecules represent a significant improvement over prior art, such as molecules described by Accell and Wolfrum, which are heavily modified with extensive use of 2'F.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contains 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2' OMe modified. For example, C and U nucleotides in positions 11-18 of a 19 nt guide strand (or corresponding positions in a guide strand of a different length) can be 2' OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

In some aspects, an optimal passenger strand is approximately 11-14 nucleotides in length. The passenger strand may contain modifications that confer increased stability. One or more nucleotides in the passenger strand can be 2' OMe modified. In some embodiments, one or more of the C and/or U nucleotides in the passenger strand is 2'OMe modified, or all of the C and U nucleotides in the passenger strand are 2'OMe modified. In certain embodiments, all of the nucleotides in the passenger strand are 2' OMe modified. One or more of the nucleotides on the passenger strand can also be phosphate-modified such as phosphorothioate modified. The passenger strand can also contain 2' ribo, 2'F and 2 deoxy modifications or any combination of the above. As demonstrated in the Examples, chemical modification patterns on both the guide and passenger strand are well tolerated and a combination of chemical modifications is shown herein to lead to increased efficacy and self-delivery of RNA molecules.

Aspects of the invention relate to RNAi constructs that have extended single-stranded regions relative to double stranded regions, as compared to molecules that have been used previously for RNAi. The single stranded region of the molecules may be modified to promote cellular uptake or gene silencing. In some embodiments, phosphorothioate modification of the single stranded region influences cellular uptake and/or gene silencing. The region of the guide strand that is phosphorothioate modified can include nucleotides within both the single stranded and double stranded regions of the molecule. In some embodiments, the single stranded region includes 2-12 phosphorothioate modifications. For example, the single stranded region can include 2, 3, 4, 5, 6, 7, 8, 9, 10, 11, or 12 phosphorothioate modifications. In some instances, the single stranded region contains 6-8 phosphorothioate modifications.

Molecules associated with the invention are also optimized for cellular uptake. In RNA molecules described herein, the guide and/or passenger strands can be attached to a conjugate. In certain embodiments the conjugate is hydrophobic. The hydrophobic conjugate can be a small molecule with a partition coefficient that is higher than 10. The conjugate can be a sterol-type molecule such as cholesterol, or a molecule with an increased length polycarbon chain attached to C17, and the presence of a conjugate can influence the ability of an RNA molecule to be taken into a cell with or without a lipid transfection reagent. The conjugate can be attached to the passenger or guide strand through a hydrophobic linker. In some embodiments, a hydrophobic linker is 5-12C in length, and/or is hydroxypyrrolidine-based. In some embodiments, a hydrophobic conjugate is attached to the passenger strand and the CU residues of either the passenger and/or guide strand are modified. In some embodiments, at least 50%, 55%, 60%, 65%, 70%, 75%, 80%, 85%, 90% or 95% of the CU residues on the passenger strand and/or the guide strand are modified. In some aspects, molecules associated with the invention are self-delivering (sd). As used herein, "self-delivery" refers to the ability of a molecule to be delivered into a cell without the need for an additional delivery vehicle such as a transfection reagent.

Aspects of the invention relate to selecting molecules for use in RNAi. Based on the data described herein, molecules that have a double stranded region of 8-14 nucleotides can be selected for use in RNAi. In some embodiments, molecules are selected based on their thermodynamic stability ($\Delta G$). In some embodiments, molecules will be selected that have a ($\Delta G$) of less than −13 kkal/mol. For example, the ($\Delta G$) value may be −13, −14, −15, −16, −17, −18, −19, −21, −22 or less than −22 kkal/mol. In other embodiments, the ($\Delta G$) value may be higher than −13 kkal/mol. For example, the ($\Delta G$) value may be −12, −11, −10, −9, −8, −7 or more than −7 kkal/mol. It should be appreciated that $\Delta G$ can be calculated using any method known in the art. In some embodiments $\Delta G$ is calculated using Mfold, available through the Mfold internet site (http://mfold.bioinfo.rpi.edu/cgi-bin/rna-form1.cgi). Methods for calculating $\Delta G$ are described in, and are incorporated by reference from, the following references: Zuker, M. (2003) Nucleic Acids Res., 31(13):3406-15; Mathews, D. H., Sabina, J., Zuker, M. and Turner, D. H. (1999) J. Mol. Biol. 288:911-940; Mathews, D. H., Disney, M. D., Childs, J. L., Schroeder, S. J., Zuker, M., and Turner, D. H. (2004) Proc. Natl. Acad. Sci. 101:7287-7292; Duan, S., Mathews, D. H., and Turner, D. H. (2006) Biochemistry 45:9819-9832; Wuchty, S., Fontana, W., Hofacker, I. L., and Schuster, P. (1999) Biopolymers 49:145-165.

Aspects of the invention relate to using nucleic acid molecules described herein, with minimal double stranded regions and/or with a ($\Delta G$) of less than −13 kkal/mol, for gene silencing. RNAi molecules can be administered in vivo or in vitro, and gene silencing effects can be achieved in vivo or in vitro.

In certain embodiments, the polynucleotide contains 5'- and/or 3'-end overhangs. The number and/or sequence of nucleotides overhang on one end of the polynucleotide may be the same or different from the other end of the polynucleotide. In certain embodiments, one or more of the overhang nucleotides may contain chemical modification(s), such as phosphorothioate or 2'-OMe modification.

In certain embodiments, the polynucleotide is unmodified. In other embodiments, at least one nucleotide is modified. In further embodiments, the modification includes a 2'-H or 2'-modified ribose sugar at the 2nd nucleotide from the 5'-end of the guide sequence. The "2nd nucleotide" is defined as the second nucleotide from the 5'-end of the polynucleotide.

As used herein, "2'-modified ribose sugar" includes those ribose sugars that do not have a 2'-OH group. "2'-modified ribose sugar" does not include 2'-deoxyribose (found in unmodified canonical DNA nucleotides). For example, the 2'-modified ribose sugar may be 2'-O-alkyl nucleotides, 2'-deoxy-2'-fluoro nucleotides, 2'-deoxy nucleotides, or combination thereof.

In certain embodiments, the 2'-modified nucleotides are pyrimidine nucleotides (e.g., C/U). Examples of 2'-O-alkyl nucleotides include 2'-O-methyl nucleotides, or 2'-O-allyl nucleotides.

In certain embodiments, the miniRNA polynucleotide of the invention with the above-referenced 5'-end modification exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the RNAi reagent or therapeutics.

As used herein, "off-target" gene silencing refers to unintended gene silencing due to, for example, spurious sequence homology between the antisense (guide) sequence and the unintended target mRNA sequence.

According to this aspect of the invention, certain guide strand modifications further increase nuclease stability, and/or lower interferon induction, without significantly decreasing RNAi activity (or no decrease in RNAi activity at all).

In some embodiments, wherein the RNAi construct involves a hairpin, the 5'-stem sequence may comprise a 2'-modified ribose sugar, such as 2'-O-methyl modified nucleotide, at the $2^{nd}$ nucleotide on the 5'-end of the polynucleotide and, in some embodiments, no other modified nucleotides. The hairpin structure having such modification may have enhanced target specificity or reduced off-target silencing compared to a similar construct without the 2'-O-methyl modification at said position.

Certain combinations of specific 5'-stem sequence and 3'-stem sequence modifications may result in further unexpected advantages, as partly manifested by enhanced ability to inhibit target gene expression, enhanced serum stability, and/or increased target specificity, etc.

In certain embodiments, the guide strand comprises a 2'-O-methyl modified nucleotide at the $2^{nd}$ nucleotide on the 5'-end of the guide strand and no other modified nucleotides.

In other aspects, the miniRNA structures of the present invention mediates sequence-dependent gene silencing by a microRNA mechanism. As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

microRNAs are involved in down-regulating target genes in critical pathways, such as development and cancer, in mice, worms and mammals. Gene silencing through a microRNA mechanism is achieved by specific yet imperfect base-pairing of the miRNA and its target messenger RNA (mRNA). Various mechanisms may be used in microRNA-mediated down-regulation of target mRNA expression.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNAs are expressed by endogenous genes in vivo and are processed from a hairpin or stem-loop precursor (pre-miRNA or pri-miRNAs) by Dicer or other RNAses. miRNAs can exist transiently in vivo as a double-stranded duplex but only one strand is taken up by the RISC complex to direct gene silencing.

In some embodiments a version of sd-rxRNA compounds, which are effective in cellular uptake and inhibiting of miRNA activity are described. Essentially the compounds are similar to RISC entering version but large strand chemical modification patterns are optimized in the way to block cleavage and act as an effective inhibitor of the RISC action. For example, the compound might be completely or mostly Omethyl modified with the PS content described previously. For these types of compounds the 5' phosphorilation is not necessary. The presence of double stranded region is preferred as it is promotes cellular uptake and efficient RISC loading.

Another pathway that uses small RNAs as sequence-specific regulators is the RNA interference (RNAi) pathway, which is an evolutionarily conserved response to the presence of double-stranded RNA (dsRNA) in the cell. The dsRNAs are cleaved into ~20-base pair (bp) duplexes of small-interfering RNAs (siRNAs) by Dicer. These small RNAs get assembled into multiprotein effector complexes called RNA-induced silencing complexes (RISCs). The siRNAs then guide the cleavage of target mRNAs with perfect complementarity.

Some aspects of biogenesis, protein complexes, and function are shared between the siRNA pathway and the miRNA pathway. The subject single-stranded polynucleotides may mimic the dsRNA in the siRNA mechanism, or the microRNA in the miRNA mechanism.

In certain embodiments, the modified RNAi constructs may have improved stability in serum and/or cerebral spinal fluid compared to an unmodified RNAi constructs having the same sequence.

In certain embodiments, the structure of the RNAi construct does not induce interferon response in primary cells, such as mammalian primary cells, including primary cells from human, mouse and other rodents, and other non-human mammals. In certain embodiments, the RNAi construct may also be used to inhibit expression of a target gene in an invertebrate organism.

To further increase the stability of the subject constructs in vivo, the 3'-end of the hairpin structure may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

The RNAi constructs of the invention are capable of inhibiting the synthesis of any target protein encoded by target gene(s). The invention includes methods to inhibit expression of a target gene either in a cell in vitro, or in vivo. As such, the RNAi constructs of the invention are useful for treating a patient with a disease characterized by the overexpression of a target gene.

The target gene can be endogenous or exogenous (e.g., introduced into a cell by a virus or using recombinant DNA technology) to a cell. Such methods may include introduction of RNA into a cell in an amount sufficient to inhibit expression of the target gene. By way of example, such an RNA molecule may have a guide strand that is complementary to the nucleotide sequence of the target gene, such that the composition inhibits expression of the target gene.

The invention also relates to vectors expressing the subject hairpin constructs, and cells comprising such vectors or the subject hairpin constructs. The cell may be a mammalian cell in vivo or in culture, such as a human cell.

The invention further relates to compositions comprising the subject RNAi constructs, and a pharmaceutically acceptable carrier or diluent.

Another aspect of the invention provides a method for inhibiting the expression of a target gene in a mammalian cell, comprising contacting the mammalian cell with any of the subject RNAi constructs.

The method may be carried out in vitro, ex vivo, or in vivo, in, for example, mammalian cells in culture, such as a human cell in culture.

The target cells (e.g., mammalian cell) may be contacted in the presence of a delivery reagent, such as a lipid (e.g., a cationic lipid) or a liposome.

Another aspect of the invention provides a method for inhibiting the expression of a target gene in a mammalian cell, comprising contacting the mammalian cell with a vector expressing the subject RNAi constructs.

In one aspect of the invention, a longer duplex polynucleotide is provided, including a first polynucleotide that ranges in size from about 16 to about 30 nucleotides; a second polynucleotide that ranges in size from about 26 to about 46 nucleotides, wherein the first polynucleotide (the antisense strand) is complementary to both the second polynucleotide (the sense strand) and a target gene, and wherein both polynucleotides form a duplex and wherein the first polynucleotide contains a single stranded region longer than 6 bases in length and is modified with alternative chemical modification pattern, and/or includes a conjugate moiety that facilitates cellular delivery. In this embodiment, between about 40% to about 90% of the nucleotides of the passenger strand between about 40% to about 90% of the nucleotides of the guide strand, and between about 40% to about 90% of the nucleotides of the single stranded region of the first polynucleotide are chemically modified nucleotides.

In an embodiment, the chemically modified nucleotide in the polynucleotide duplex may be any chemically modified nucleotide known in the art, such as those discussed in detail above. In a particular embodiment, the chemically modified nucleotide is selected from the group consisting of 2' F modified nucleotides, 2'-O-methyl modified and 2'deoxy nucleotides. In another particular embodiment, the chemically modified nucleotides results from "hydrophobic modifications" of the nucleotide base. In another particular embodiment, the chemically modified nucleotides are phosphorothioates. In an additional particular embodiment, chemically modified nucleotides are combination of phosphorothioates, 2'-O-methyl, 2'deoxy, hydrophobic modifications and phosphorothioates. As these groups of modifications refer to modification of the ribose ring, back bone and nucleotide, it is feasible that some modified nucleotides will carry a combination of all three modification types.

In another embodiment, the chemical modification is not the same across the various regions of the duplex. In a particular embodiment, the first polynucleotide (the passenger strand), has a large number of diverse chemical modifications in various positions. For this polynucleotide up to 90% of nucleotides might be chemically modified and/or have mismatches introduced. In another embodiment, chemical modifications of the first or second polynucleotide include, but not limited to, 5' position modification of Uridine and Cytosine (4-pyridyl, 2-pyridyl, indolyl, phenyl ($C_6H_5OH$); tryptophanyl (C8H6N)CH2CH(NH2)CO), isobutyl, butyl, aminobenzyl; phenyl; naphthyl, etc), where the chemical modification might alter base pairing capabilities of a nucleotide. For the guide strand an important feature of this aspect of the invention is the position of the chemical modification relative to the 5' end of the antisense and sequence. For example, chemical phosphorylation of the 5' end of the guide strand is usually beneficial for efficacy. O-methyl modifications in the seed region of the sense strand (position 2-7 relative to the 5' end) are not generally well tolerated, whereas 2'F and deoxy are well tolerated. The mid part of the guide strand and the 3' end of the guide strand are more permissive in a type of chemical modifications applied. Deoxy modifications are not tolerated at the 3' end of the guide strand.

A unique feature of this aspect of the invention involves the use of hydrophobic modification on the bases. In one embodiment, the hydrophobic modifications are preferably positioned near the 5' end of the guide strand, in other embodiments, they localized in the middle of the guides strand, in other embodiment they localized at the 3' end of the guide strand and yet in another embodiment they are distributed thought the whole length of the polynucleotide. The same type of patterns is applicable to the passenger strand of the duplex.

The other part of the molecule is a single stranded region. The single stranded region is expected to range from 7 to 40 nucleotides.

In one embodiment, the single stranded region of the first polynucleotide contains modifications selected from the group consisting of between 40% and 90% hydrophobic base modifications, between 40%-90% phosphorothioates, between 40%-90% modification of the ribose moiety, and any combination of the preceding.

Efficiency of guide strand (first polynucleotide) loading into the RISC complex might be altered for heavily modified polynucleotides, so in one embodiment, the duplex polynucleotide includes a mismatch between nucleotide 9, 11, 12, 13, or 14 on the guide strand (first polynucleotide) and the opposite nucleotide on the sense strand (second polynucleotide) to promote efficient guide strand loading.

More detailed aspects of the invention are described in the sections below.

Duplex Characteristics

Double-stranded oligonucleotides of the invention may be formed by two separate complementary nucleic acid strands. Duplex formation can occur either inside or outside the cell containing the target gene.

As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14, or 15 mismatches.

Modifications

The nucleotides of the invention may be modified at various locations, including the sugar moiety, the phosphodiester linkage, and/or the base.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2'-O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a non-naturally occurring base (instead of a naturally occurring base), such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alxoxy (or OR), R or alkyl, halogen, SH, SR, amino (such as $NH_2$, NHR, $NR_2$), or CN group, wherein R is lower alkyl, alkenyl, or alkynyl.

Modified ribonucleotides may also have the phosphodiester group connecting to adjacent ribonucleotides replaced by a modified group, e.g., of phosphorothioate group. More generally, the various nucleotide modifications may be combined.

Although the antisense (guide) strand may be substantially identical to at least a portion of the target gene (or genes), at least with respect to the base pairing properties, the sequence need not be perfectly identical to be useful, e.g., to inhibit expression of a target gene's phenotype. Generally, higher homology can be used to compensate for the use of a shorter antisense gene. In some cases, the antisense strand generally will be substantially identical (although in antisense orientation) to the target gene.

The use of 2'-O-methyl modified RNA may also be beneficial in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy (—OCH$_2$CH═CH$_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulffiydryl, alkylthio, arylthio, thiocarboxylate, sulfates, alkylsulfmyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "hydrophobic modifications' include bases modified in a fashion, where (1) overall hydrophobicity of the base is significantly increases, (2) the base is still capable of forming close to regular Watson-Crick interaction. Some, of the examples of base modifications include but are not limited to 5-position uridine and cytidine modifications like phenyl, 4-pyridyl, 2-pyridyl, indolyl, and isobutyl, phenyl (C6H5OH); tryptophanyl (C8H6N)CH2CH(NH2)CO), Isobutyl, butyl, aminobenzyl; phenyl; naphthyl, For purposes of the present invention, the term "overhang" refers to terminal non-base pairing nucleotide(s) resulting from one strand or region extending beyond the terminus of the complementary strand to which the first strand or region forms a duplex. One or more polynucleotides that are capable of forming a duplex through hydrogen bonding can have overhangs. The overhand length generally doesn't exceed 5 bases in length.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O⁻ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-2}R'$, $(CR'R'')_{0-3}O(CR'R'')_{0-3}H$, $(CR'R'')_{0-3}COR'$, $(CR'R'')_{0-3}CO_2R'$, or $(CR'R'')_{0-3}OR'$ groups; wherein each R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl)cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligonucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$ Ed., Wiley-Interscience, New York, 1999).

The term "nucleotide" includes nucleosides which further comprise a phosphate group or a phosphate analog.

As used herein, the term "linkage" includes a naturally occurring, unmodified phosphodiester moiety (—O—$(PO^{2-})$—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothioate linkages.

In certain embodiments, oligonucleotides of the invention comprise hydrophobicly modified nucleotides or "hydrophobic modifications." As used herein "hydrophobic modifications" refers to bases that are modified such that (1) overall hydrophobicity of the base is significantly increased, and/or (2) the base is still capable of forming close to regular Watson-Crick interaction. Several non-limiting examples of base modifications include 5-position uridine and cytidine modifications such as phenyl, 4-pyridyl, 2-pyridyl, indolyl, and isobutyl, phenyl (C6H5OH); tryptophanyl (C8H6N)CH2CH (NH2)CO), Isobutyl, butyl, aminobenzyl; phenyl; and naphthyl.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849, 902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a internucleotide linkage. For example, the alkyloxy radical can be methoxy, ethoxy, or isopropoxy, and preferably, ethoxy. Optionally, the 3'→3' linked nucleotide at the 3' terminus can be linked by a substitute linkage. To reduce nuclease degradation, the 5' most 3'→5' linkage can be a modified linkage, e.g., a phosphorothioate or a P-alkyloxy-phosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxy-phosphate.

Another type of conjugates that can be attached to the end (3' or 5' end), the loop region, or any other parts of the miniRNA might include a sterol, sterol type molecule, peptide, small molecule, protein, etc. In some embodiments, a miniRNA may contain more than one conjugates (same or different chemical nature). In some embodiments, the conjugate is cholesterol.

Another way to increase target gene specificity, or to reduce off-target silencing effect, is to introduce a 2'-modification (such as the 2'-O methyl modification) at a position corresponding to the second 5'-end nucleotide of the guide sequence. This allows the positioning of this 2'-modification in the Dicer-resistant hairpin structure, thus enabling one to design better RNAi constructs with less or no off-target silencing.

In one embodiment, a hairpin polynucleotide of the invention can comprise one nucleic acid portion which is DNA and one nucleic acid portion which is RNA. Antisense (guide) sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

In one embodiment, at least a portion of the contiguous polynucleotides are linked by a substitute linkage, e.g., a phosphorothioate linkage.

In certain embodiments, most or all of the nucleotides beyond the guide sequence (2'-modified or not) are linked by phosphorothioate linkages. Such constructs tend to have improved pharmacokinetics due to their higher affinity for serum proteins. The phosphorothioate linkages in the non-guide sequence portion of the polynucleotide generally do not interfere with guide strand activity, once the latter is loaded into RISC.

Antisense (guide) sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

The chemical modifications described herein are believed, based on the data described herein, to promote single stranded polynucleotide loading into the RISC. Single stranded polynucleotides have been shown to be active in loading into RISC and inducing gene silencing. However, the level of activity for single stranded polynucleotides appears to be 2 to 4 orders of magnitude lower when compared to a duplex polynucleotide.

Figure 5:
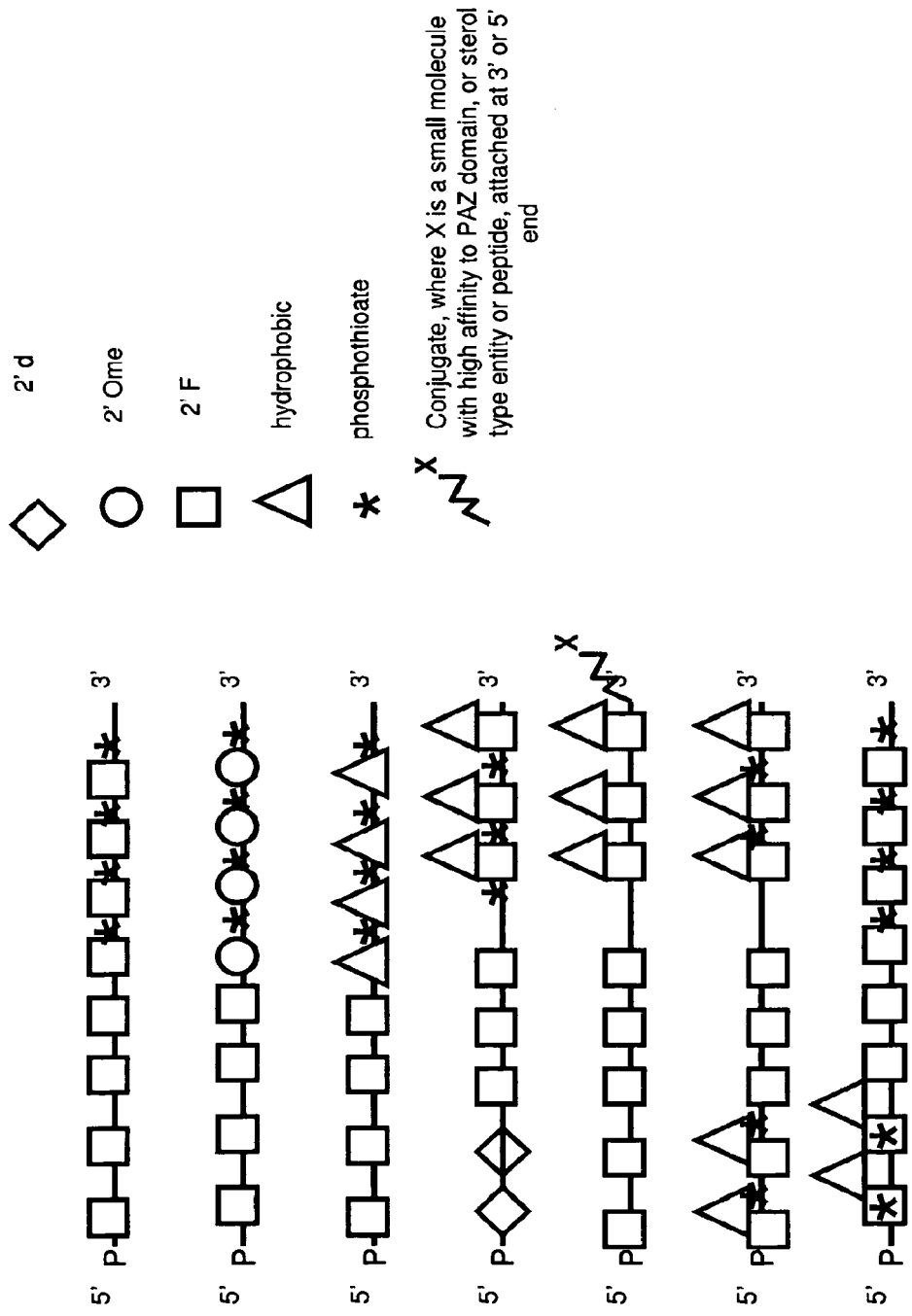
FIG. 5 is a schematic depicting examples of structural and chemical compositions of single stranded RISC entering polynucleotides. The combination of one or more modifications including 2'd, 2'Ome, 2'F, hydrophobic and phosphothioate modifications can be used to optimize single strand entry into the RISC.

The present invention provides a description of the chemical modification patterns, which may (a) significantly increase stability of the single stranded polynucleotide (b) promote efficient loading of the polynucleotide into the RISC complex and (c) improve uptake of the single stranded nucleotide by the cell. FIG. 5 provides some non-limiting examples of the chemical modification patterns which may be beneficial for achieving single stranded polynucleotide efficacy inside the cell. The chemical modification patterns may include combination of ribose, backbone, hydrophobic nucleoside and conjugate type of modifications. In addition, in some of the embodiments, the 5' end of the single polynucleotide may be chemically phosphorylated.

In yet another embodiment, the present invention provides a description of the chemical modifications patterns, which improve functionality of RISC inhibiting polynucleotides.

Figure 6:
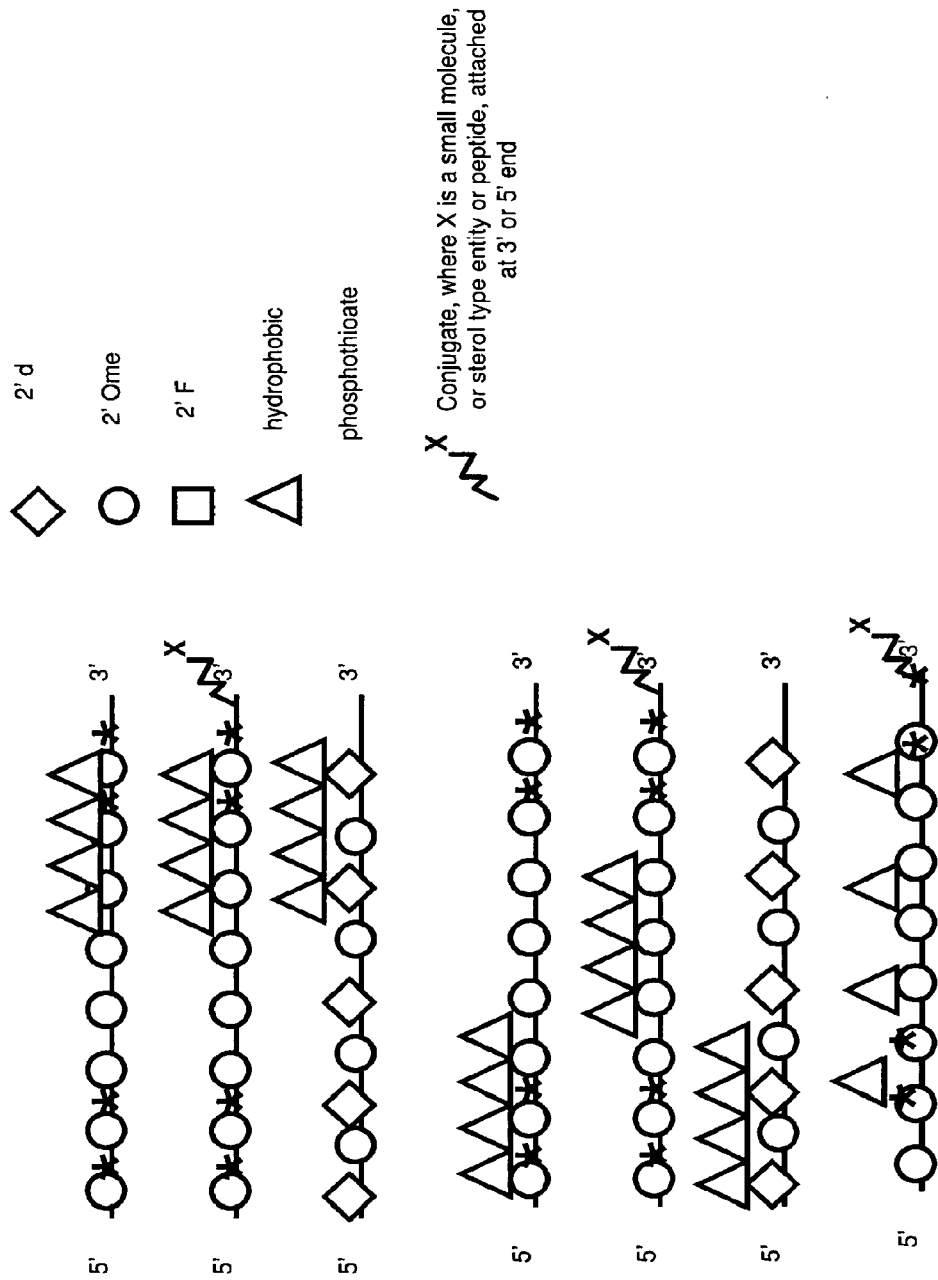
FIG. 6 is a schematic depicting examples of structural and chemical composition of RISC substrate inhibitors. Combinations of one or more chemical modifications can be used to mediate efficient uptake and efficient binding to preloaded RISC complex.

Single stranded polynucleotides have been shown to inhibit activity of a preloaded RISC complex through the substrate competition mechanism. For these types of molecules, conventionally called antagomers, the activity usually requires high concentration and in vivo delivery is not very effective. The present invention provides a description of the chemical modification patterns, which may (a) significantly increase stability of the single stranded polynucleotide (b) promote efficient recognition of the polynucleotide by the RISC as a substrate and/or (c) improve uptake of the single stranded nucleotide by the cell. FIG. 6 provides some non-limiting examples of the chemical modification patterns that may be beneficial for achieving single stranded polynucleotide efficacy inside the cell. The chemical modification patterns may include combination of ribose, backbone, hydrophobic nucleoside and conjugate type of modifications.

The modifications provided by the present invention are applicable to all polynucleotides. This includes single stranded RISC entering polynucleotides, single stranded RISC inhibiting polynucleotides, conventional duplexed polynucleotides of variable length (15-40 bp), asymmetric duplexed polynucleotides, and the like. Polynucleotides may be modified with wide variety of chemical modification patterns, including 5' end, ribose, backbone and hydrophobic nucleoside modifications.

Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J. Org. Chem.* 50:3908; Stec et al. *J. Chromatog.* 1985. 326:263; LaPlanche et al. 1986. *Nucl. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. No. 5,013,830; U.S. Pat. No. 5,214,135; U.S. Pat. No. 5,525,719; Kawasaki et al. 1993. *J. Med. Chem.* 36:831; WO 92/03568; U.S. Pat. No. 5,276,019; and U.S. Pat. No. 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (D N Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

Delivery/Carrier

Uptake of Oligonucleotides by Cells

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research.* 21:3567). Enhanced delivery of oligonucleotides can also be mediated by the use of vectors (See e.g., Shi, Y. 2003. Trends Genet 2003 Jan. 19:9; Reichhart J M et al. Genesis. 2002. 34(1-2):1604, Yu et al. 2002. Proc. Natl. Acad Sci. USA 99:6047; Sui et al. 2002. Proc. Natl. Acad Sci. USA 99:5515) viruses, polyamine or polycation conjugates using compounds such as polylysine, protamine, or Ni, N12-bis(ethyl) spermine (see, e.g., Bartzatt, R. et al. 1989. *Biotechnol. Appl. Biochem.* 11:133; Wagner E. et al. 1992. *Proc. Natl. Acad. Sci.* 88:4255).

In certain embodiments, the miniRNA of the invention may be delivered by using various beta-glucan containing particles, such as those described in US 2005/0281781 A1, WO 2006/007372, and WO 2007/050643 (all incorporated herein by reference). In certain embodiments, the beta-glucan particle is derived from yeast. In certain embodiments, the payload trapping molecule is a polymer, such as those with a molecular weight of at least about 1000 Da, 10,000 Da, 50,000 Da, 100 kDa, 500 kDa, etc. Preferred polymers include (without limitation) cationic polymers, chitosans, or PEI (polyethylenimine), etc.

Such beta-glucan based delivery system may be formulated for oral delivery, where the orally delivered beta-glucan/miniRNA constructs may be engulfed by macrophages or other related phagocytic cells, which may in turn release the miniRNA constructs in selected in vivo sites. Alternatively or in addition, the miniRNA may changes the expression of certain macrophage target genes.

The optimal protocol for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown.

Encapsulating Agents

Encapsulating agents entrap oligonucleotides within vesicles. In another embodiment of the invention, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotides pharmacokinetic or toxicological properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a lipid delivery vehicle originally designed as a research tool, such as Lipofectin or LIPO-FECTAMINE™2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

In some aspects, formulations associated with the invention might be selected for a class of naturally occurring or chemically synthesized or modified saturated and unsaturated fatty acid residues. Fatty acids might exist in a form of triglycerides, diglycerides or individual fatty acids. In another embodiment, the use of well-validated mixtures of fatty acids and/or fat emulsions currently used in pharmacology for parenteral nutrition may be utilized.

Liposome based formulations are widely used for oligonucleotide delivery. However, most of commercially available lipid or liposome formulations contain at least one positively charged lipid (cationic lipids). The presence of this positively charged lipid is believed to be essential for obtaining a high degree of oligonucleotide loading and for enhancing liposome fusogenic properties. Several methods have been performed and published to identify optimal positively charged lipid chemistries. However, the commercially available liposome formulations containing cationic lipids are characterized by a high level of toxicity. In vivo limited therapeutic indexes have revealed that liposome formulations containing positive charged lipids are associated with toxicity (i.e. elevation in liver enzymes) at concentrations only slightly higher than concentration required to achieve RNA silencing.

New liposome formulations, lacking the toxicity of the prior art liposomes have been developed according to the invention. These new liposome formulations are neutral fat-based formulations for the efficient delivery of oligonucleotides, and in particular for the delivery of the RNA molecules of the invention. The compositions are referred to as neutral nanotransporters because they enable quantitative oligonucleotide incorporation into non-charged lipids mixtures. The lack of toxic levels of cationic lipids in the neutral nanotransporter compositions of the invention is an important feature.

The neutral nanotransporters compositions enable efficient loading of oligonucleotide into neutral fat formulation. The composition includes an oligonucleotide that is modified in a manner such that the hydrophobicity of the molecule is increased (for example a hydrophobic molecule is attached (covalently or no-covalently) to a hydrophobic molecule on the oligonucleotide terminus or a non-terminal nucleotide, base, sugar, or backbone), the modified oligonucleotide being mixed with a neutral fat formulation (for example containing at least 25% of cholesterol and 25% of DOPC or analogs thereof). A cargo molecule, such as another lipid can also be included in the composition. This composition, where part of the formulation is build into the oligonucleotide itself, enables efficient encapsulation of oligonucleotide in neutral lipid particles.

One of several unexpected observations associated with the invention was that the oligonucleotides of the invention could effectively be incorporated in a lipid mixture that was free of cationic lipids and that such a composition could effectively deliver the therapeutic oligonucleotide to a cell in a manner that it is functional. Another unexpected observation was the high level of activity observed when the fatty mixture is composed of a phosphatidylcholine base fatty acid and a sterol such as a cholesterol. For instance, one preferred formulation of neutral fatty mixture is composed of at least 20% of DOPC or DSPC and at least 20% of sterol such as cholesterol. Even as low as 1:5 lipid to oligonucleotide ratio was shown to be sufficient to get complete encapsulation of the oligonucleotide in a non charged formulation. The prior art demonstrated only a 1-5% oligonucleotide encapsulation with non-charged formulations, which is not sufficient to get to a desired amount of in vivo efficacy. Compared to the prior art using neutral lipids the level of oligonucleotide delivery to a cell was quite unexpected.

Stable particles ranging in size from 50 to 140 nm were formed upon complexing of hydrophobic oligonucleotides with preferred formulations. It is interesting to mention that the formulation by itself typically does not form small particles, but rather, forms agglomerates, which are transformed into stable 50-120 nm particles upon addition of the hydrophobic modified oligonucleotide.

The neutral nanotransporter compositions of the invention include a hydrophobic modified polynucleotide, a neutral fatty mixture, and optionally a cargo molecule. A "hydrophobic modified polynucleotide" as used herein is a polynucleotide of the invention (i.e. sd-rxRNA) that has at least one modification that renders the polynucleotide more hydrophobic than the polynucleotide was prior to modification. The modification may be achieved by attaching (covalently or non-covalently) a hydrophobic molecule to the polynucleotide. In some instances the hydrophobic molecule is or includes a lipophilic group.

The term "lipophilic group" means a group that has a higher affinity for lipids than its affinity for water. Examples of lipophilic groups include, but are not limited to, cholesterol, a cholesteryl or modified cholesteryl residue, adamantine, dihydrotesterone, long chain alkyl, long chain alkenyl, long chain alkynyl, olely-lithocholic, cholenic, oleoyl-cholenic, palmityl, heptadecyl, myrisityl, bile acids, cholic acid or taurocholic acid, deoxycholate, oleyl litocholic acid, oleoyl cholenic acid, glycolipids, phospholipids, sphingolipids, isoprenoids, such as steroids, vitamins, such as vitamin E, fatty acids either saturated or unsaturated, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. The cholesterol moiety may be reduced (e.g. as in cholestan) or may be substituted (e.g. by halogen). A combination of different lipophilic groups in one molecule is also possible.

The hydrophobic molecule may be attached at various positions of the polynucleotide. As described above, the hydrophobic molecule may be linked to the terminal residue of the polynucleotide such as the 3' of 5'-end of the polynucleotide. Alternatively, it may be linked to an internal nucleotide or a nucleotide on a branch of the polynucleotide. The hydrophobic molecule may be attached, for instance to a 2'-position of the nucleotide. The hydrophobic molecule may also be linked to the heterocyclic base, the sugar or the backbone of a nucleotide of the polynucleotide.

The hydrophobic molecule may be connected to the polynucleotide by a linker moiety. Optionally the linker moiety is a non-nucleotidic linker moiety. Non-nucleotidic linkers are e.g. abasic residues (dSpacer), oligoethyleneglycol, such as triethyleneglycol (spacer 9) or hexaethylenegylcol (spacer 18), or alkane-diol, such as butanediol. The spacer units are preferably linked by phosphodiester or phosphorothioate bonds. The linker units may appear just once in the molecule or may be incorporated several times, e.g. via phosphodiester, phosphorothioate, methylphosphonate, or amide linkages.

Typical conjugation protocols involve the synthesis of polynucleotides bearing an aminolinker at one or more positions of the sequence, however, a linker is not required. The amino group is then reacted with the molecule being conjugated using appropriate coupling or activating reagents. The conjugation reaction may be performed either with the polynucleotide still bound to a solid support or following cleavage of the polynucleotide in solution phase. Purification of the modified polynucleotide by HPLC typically results in a pure material.

In some embodiments the hydrophobic molecule is a sterol type conjugate, a PhytoSterol conjugate, cholesterol conjugate, sterol type conjugate with altered side chain length, fatty acid conjugate, any other hydrophobic group conjugate, and/or hydrophobic modifications of the internal nucleoside, which provide sufficient hydrophobicity to be incorporated into micelles.

For purposes of the present invention, the term "sterols", refers or steroid alcohols are a subgroup of steroids with a hydroxyl group at the 3-position of the A-ring. They are amphipathic lipids synthesized from acetyl-coenzyme A via the HMG-CoA reductase pathway. The overall molecule is quite flat. The hydroxyl group on the A ring is polar. The rest of the aliphatic chain is non-polar. Usually sterols are considered to have an 8 carbon chain at position 17.

For purposes of the present invention, the term "sterol type molecules", refers to steroid alcohols, which are similar in structure to sterols. The main difference is the structure of the ring and number of carbons in a position 21 attached side chain.

For purposes of the present invention, the term "PhytoSterols" (also called plant sterols) are a group of steroid alcohols, phytochemicals naturally occurring in plants. There are more then 200 different known PhytoSterols For purposes of the present invention, the term "Sterol side chain" refers to a chemical composition of a side chain attached at the position 17 of sterol-type molecule. In a standard definition sterols are limited to a 4 ring structure carrying a 8 carbon chain at position 17. In this invention, the sterol type molecules with side chain longer and shorter than conventional are described. The side chain may branched or contain double back bones.

Figure 9:
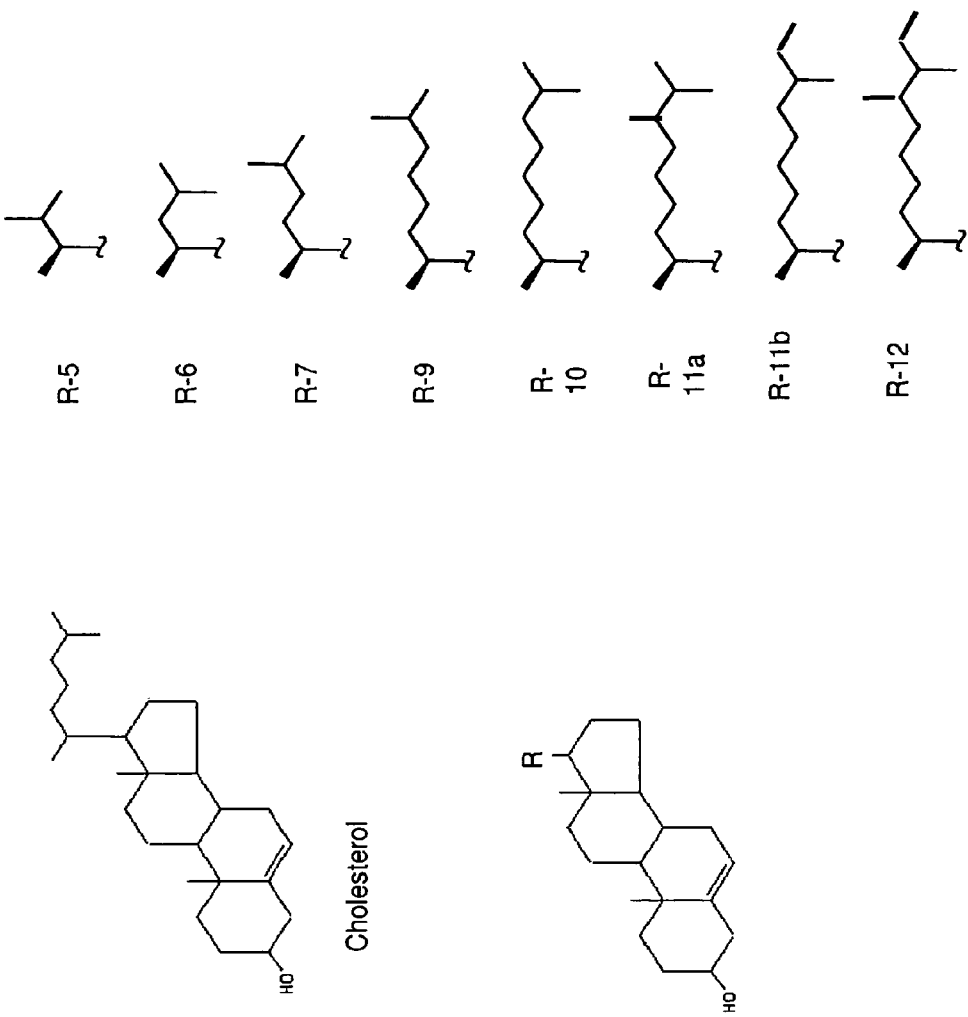
FIG. 9 is a schematic depicting examples of sterol-like structures, with variations in the size of the polycarbon chains attached at position 17.

Thus, sterols useful in the invention, for example, include cholesterols, as well as unique sterols in which position 17 has attached side chain of 2-7 or longer then 9 carbons. In a particular embodiment, the length of the polycarbon tail is varied between 5 and 9 carbons. FIG. 9 demonstrates that there is a correlation between plasma clearance, liver uptake and the length of the polycarbon chain. Such conjugates may have significantly better in vivo efficacy, in particular delivery to liver. These types of molecules are expected to work at concentrations 5 to 9 fold lower then oligonucleotides conjugated to conventional cholesterols.

Alternatively the polynucleotide may be bound to a protein, peptide or positively charged chemical that functions as the hydrophobic molecule. The proteins may be selected from the group consisting of protamine, dsRNA binding domain, and arginine rich peptides. Exemplary positively charged chemicals include spermine, spermidine, cadaverine, and putrescine.

In another embodiment hydrophobic molecule conjugates may demonstrate even higher efficacy when it is combined with optimal chemical modification patterns of the polynucleotide (as described herein in detail), containing but not limited to hydrophobic modifications, phosphorothioate modifications, and 2' ribo modifications.

Figure 8:
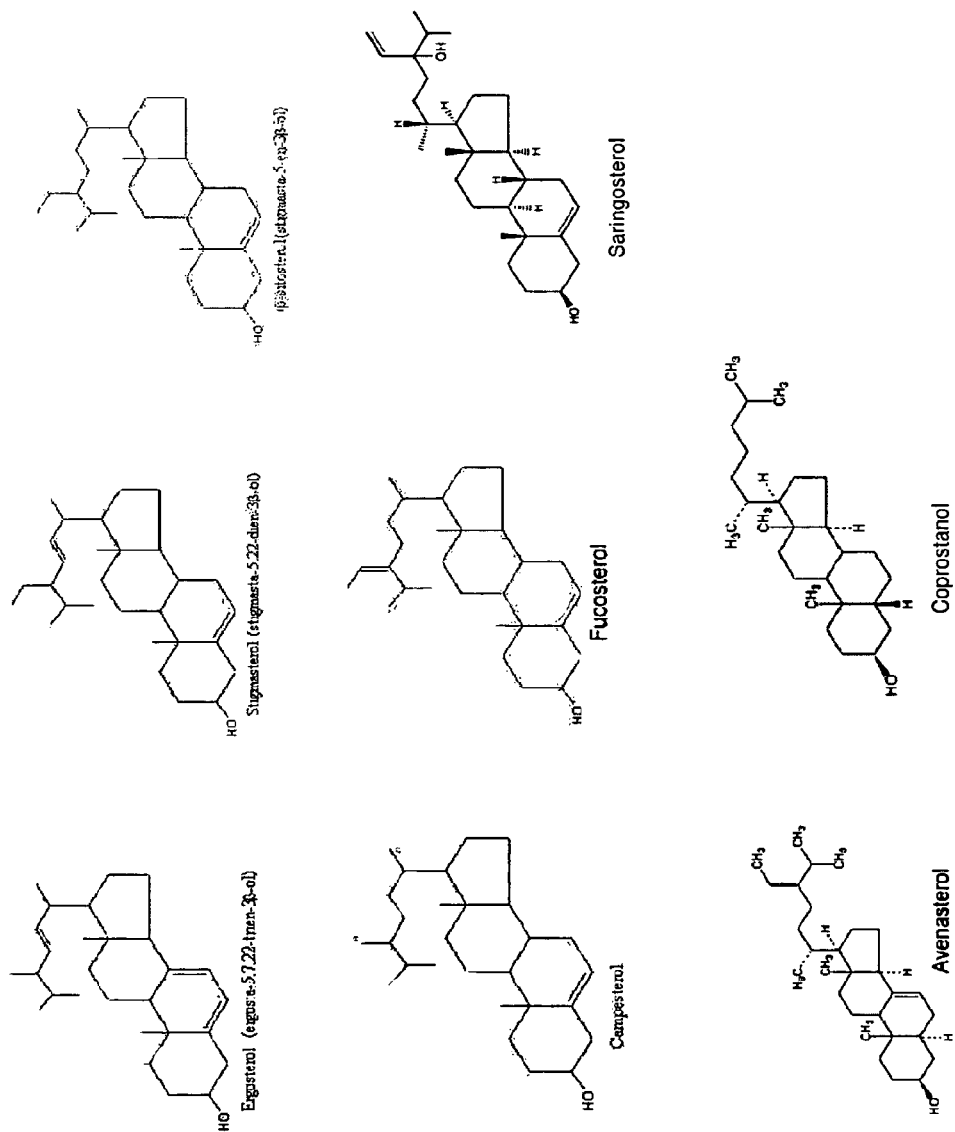
FIG. 8 is a schematic depicting examples of naturally occurring phytosterols with a polycarbon chain that is longer than 8, attached at position 17. More than 250 different types of phytosterols are known.

In another embodiment the sterol type molecule may be a naturally occurring PhytoSterols such as those shown in FIG. 8. The polycarbon chain may be longer than 9 and may be linear, branched and/or contain double bonds. Some PhytoSterol containing polynucleotide conjugates may be significantly more potent and active in delivery of polynucleotides to various tissues. Some PhytoSterols may demonstrate tissue preference and thus be used as a way to delivery RNAi specifically to particular tissues.

The hydrophobic modified polynucleotide is mixed with a neutral fatty mixture to form a micelle. The neutral fatty acid mixture is a mixture of fats that has a net neutral or slightly net negative charge at or around physiological pH that can form a micelle with the hydrophobic modified polynucleotide. For purposes of the present invention, the term "micelle" refers to a small nanoparticle formed by a mixture of non charged fatty acids and phospholipids. The neutral fatty mixture may include cationic lipids as long as they are present in an amount that does not cause toxicity. In preferred embodiments the neutral fatty mixture is free of cationic lipids. A mixture that is free of cationic lipids is one that has less than 1% and preferably 0% of the total lipid being cationic lipid. The term "cationic lipid" includes lipids and synthetic lipids having a net positive charge at or around physiological pH. The term "anionic lipid" includes lipids and synthetic lipids having a net negative charge at or around physiological pH.

The neutral fats bind to the oligonucleotides of the invention by a strong but non-covalent attraction (e.g., an electrostatic, van der Waals, pi-stacking, etc. interaction).

The neutral fat mixture may include formulations selected from a class of naturally occurring or chemically synthesized or modified saturated and unsaturated fatty acid residues. Fatty acids might exist in a form of triglycerides, diglycerides or individual fatty acids. In another embodiment the use of well-validated mixtures of fatty acids and/or fat emulsions currently used in pharmacology for parenteral nutrition may be utilized.

The neutral fatty mixture is preferably a mixture of a choline based fatty acid and a sterol. Choline based fatty acids include for instance, synthetic phosphocholine derivatives such as DDPC, DLPC, DMPC, DPPC, DSPC, DOPC, POPC, and DEPC. DOPC (chemical registry number 4235-95-4) is dioleoylphosphatidylcholine (also known as dielaidoylphosphatidylcholine, dioleoyl-PC, dioleoylphosphocholine, dioleoyl-sn-glycero-3-phosphocholine, dioleylphosphatidylcholine). DSPC (chemical registry number 816-94-4) is distearoylphosphatidylcholine (also known as 1,2-Distearoyl-sn-Glycero-3-phosphocholine).

The sterol in the neutral fatty mixture may be for instance cholesterol. The neutral fatty mixture may be made up completely of a choline based fatty acid and a sterol or it may optionally include a cargo molecule. For instance, the neutral fatty mixture may have at least 20% or 25% fatty acid and 20% or 25% sterol.

For purposes of the present invention, the term "Fatty acids" relates to conventional description of fatty acid. They may exist as individual entities or in a form of two- and triglycerides. For purposes of the present invention, the term "fat emulsions" refers to safe fat formulations given intravenously to subjects who are unable to get enough fat in their diet. It is an emulsion of soy bean oil (or other naturally occurring oils) and egg phospholipids. Fat emulsions are being used for formulation of some insoluble anesthetics. In this disclosure, fat emulsions might be part of commercially available preparations like Intralipid, Liposyn, Nutrilipid, modified commercial preparations, where they are enriched with particular fatty acids or fully de novo-formulated combinations of fatty acids and phospholipids.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

50%-60% of the formulation can optionally be any other lipid or molecule. Such a lipid or molecule is referred to herein as a cargo lipid or cargo molecule. Cargo molecules include but are not limited to intralipid, small molecules, fusogenic peptides or lipids or other small molecules might be added to alter cellular uptake, endosomal release or tissue distribution properties. The ability to tolerate cargo molecules is important for modulation of properties of these particles, if such properties are desirable. For instance the presence of some tissue specific metabolites might drastically alter tissue distribution profiles. For example use of Intralipid type formulation enriched in shorter or longer fatty chains with various degrees of saturation affects tissue distribution profiles of these type of formulations (and their loads).

An example of a cargo lipid useful according to the invention is a fusogenic lipid. For instance, the zwiterionic lipid DOPE (chemical registry number 4004-5-1, 1,2-Dioleoyl-sn-Glycero-3-phosphoethanolamine) is a preferred cargo lipid.

Intralipid may be comprised of the following composition: 1 000 mL contain: purified soybean oil 90 g, purified egg phospholipids 12 g, glycerol anhydrous 22 g, water for injection q.s. ad 1 000 mL. pH is adjusted with sodium hydroxide to pH approximately 8. Energy content/L: 4.6 MJ (190 kcal). Osmolality (approx.): 300 mOsm/kg water. In another embodiment fat emulsion is Liposyn that contains 5% safflower oil, 5% soybean oil, up to 1.2% egg phosphatides added as an emulsifier and 2.5% glycerin in water for injection. It may also contain sodium hydroxide for pH adjustment. pH 8.0 (6.0-9.0). Liposyn has an osmolarity of 276 m Osmol/liter (actual).

Figure 21:
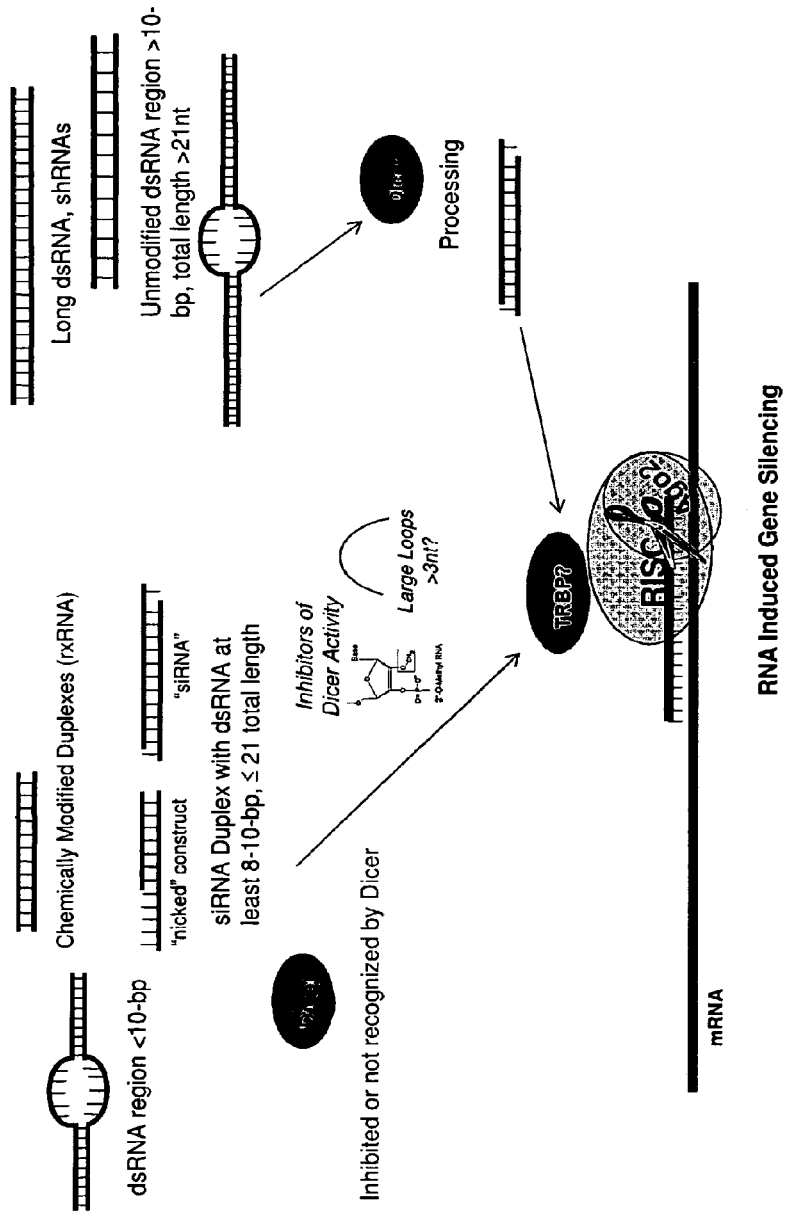
FIG. 21 is a schematic revealing a hypothetical RNAi model for RNA induced gene silencing.
Figure 22:
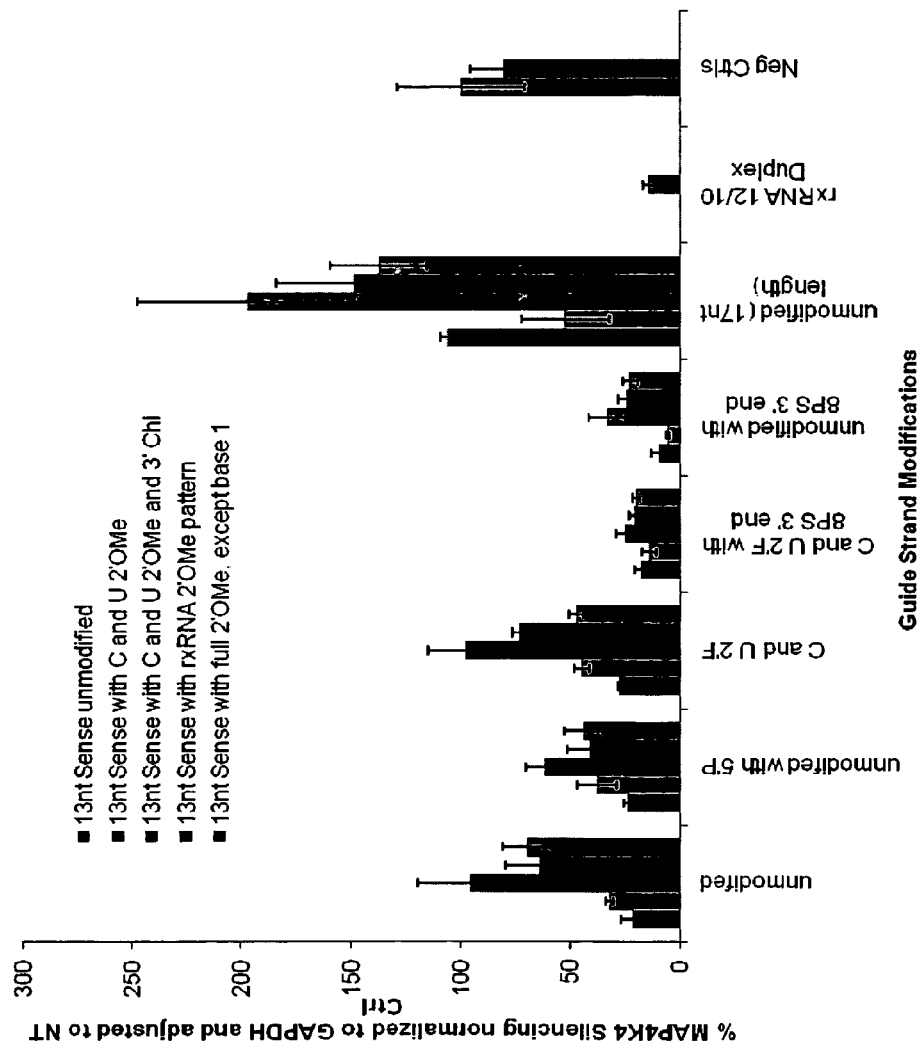
FIG. 22 is a graph showing chemical optimization of asymmetric RNAi compounds. The presence of chemical modifications, in particular 2'F UC, phosphorothioate modifications on the guide strand, and complete CU 2'OMe modification of the passenger strands results in development of functional compounds. Silencing of MAP4K4 following lipid-mediated transfection is shown using RNAi molecules with specific modifications. RNAi molecules tested had sense strands that were 13 nucleotides long and contained the following modifications: unmodified; C and U 2'OMe; C and U 2'OMe and 3' Chl; rxRNA 2'OMe pattern; or full 2'OMe, except base 1. Additionally, the guide (anti-sense) strands of the RNAi molecules tested contained the following modifications: unmodified; unmodified with 5'P; C and U 2'F; C and U 2'F with 8 PS 3' end; and unmodified (17 nt length). Results for rxRNA 12/10 Duplex and negative controls are also shown.

Variation in the identity, amounts and ratios of cargo lipids affects the cellular uptake and tissue distribution characteristics of these compounds. For example, the length of lipid tails and level of saturability will affect differential uptake to liver, lung, fat and cardiomyocytes. Addition of special hydrophobic molecules like vitamins or different forms of sterols can favor distribution to special tissues which are involved in the metabolism of particular compounds. Complexes are formed at different oligonucleotide concentrations, with higher concentrations favoring more efficient complex formation (FIGS. 21-22).

In another embodiment, the fat emulsion is based on a mixture of lipids. Such lipids may include natural compounds, chemically synthesized compounds, purified fatty acids or any other lipids. In yet another embodiment the composition of fat emulsion is entirely artificial. In a particular embodiment, the fat emulsion is more then 70% linoleic acid. In yet another particular embodiment the fat emulsion is at least 1% of cardiolipin. Linoleic acid (LA) is an unsaturated omega-6 fatty acid. It is a colorless liquid made of a carboxylic acid with an 18-carbon chain and two cis double bonds.

Figure 12:
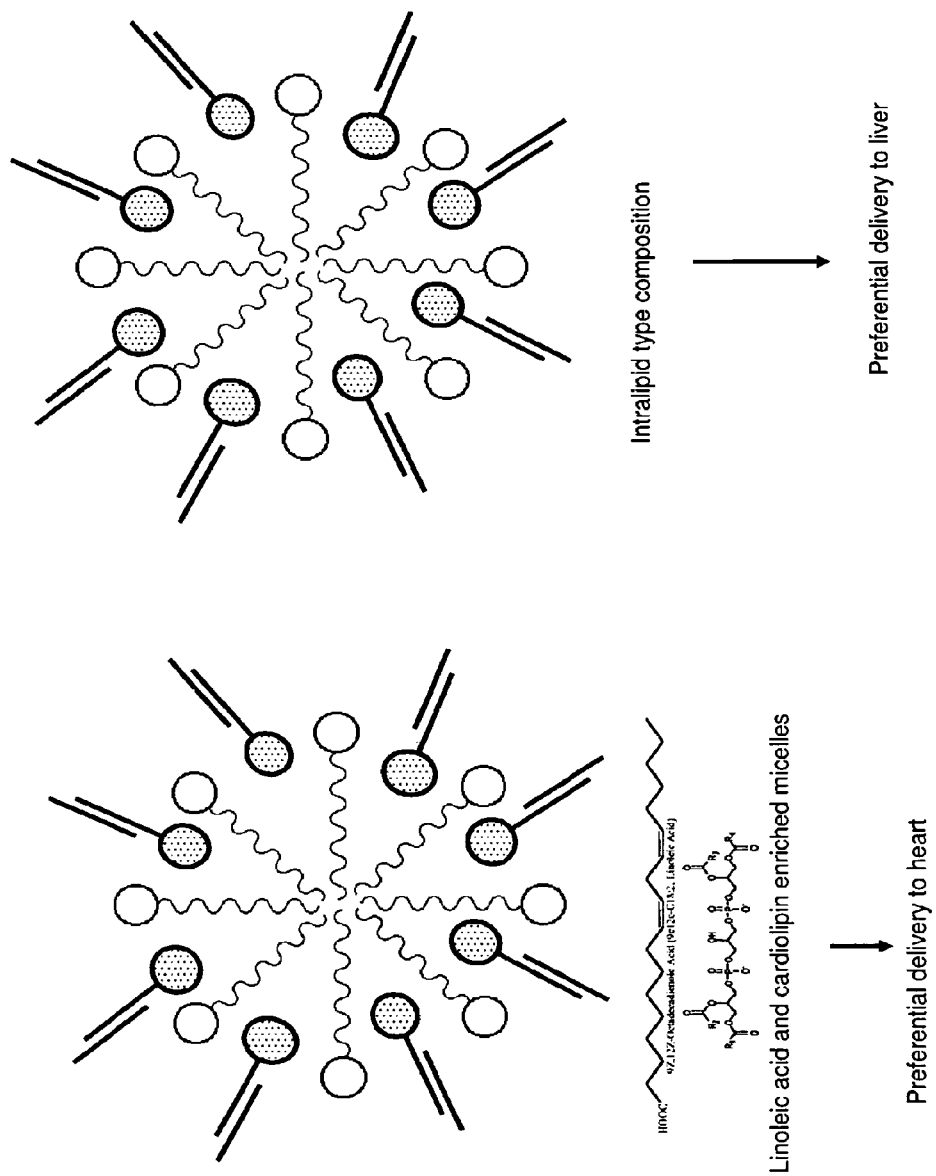
FIG. 12 is a schematic depicting how alteration in lipid composition can affect pharmacokinetic behavior and tissue distribution of hydrophobically modified and/or hydrophobically conjugated polynucleotides. In particular, use of lipid mixtures enriched in linoleic acid and cardiolipin results in preferential uptake by cardiomyocites.

In yet another embodiment of the present invention, the alteration of the composition of the fat emulsion is used as a way to alter tissue distribution of hydrophobicly modified polynucleotides. This methodology provides for the specific delivery of the polynucleotides to particular tissues (FIG. 12).

In another embodiment the fat emulsions of the cargo molecule contain more then 70% of Linoleic acid ($C18H32O2$) and/or cardiolipin are used for specifically delivering RNAi to heart muscle.

Fat emulsions, like intralipid have been used before as a delivery formulation for some non-water soluble drugs (such as Propofol, re-formulated as Diprivan). Unique features of the present invention include (a) the concept of combining modified polynucleotides with the hydrophobic compound(s), so it can be incorporated in the fat micelles and (b) mixing it with the fat emulsions to provide a reversible carrier. After injection into a blood stream, micelles usually bind to serum proteins, including albumin, HDL, LDL and other. This binding is reversible and eventually the fat is absorbed by cells. The polynucleotide, incorporated as a part of the micelle will then be delivered closely to the surface of the cells. After that cellular uptake might be happening though variable mechanisms, including but not limited to sterol type delivery.

Complexing Agents

Complexing agents bind to the oligonucleotides of the invention by a strong but non-covalent attraction (e.g., an electrostatic, van der Waals, pi-stacking, etc. interaction). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells. However, as discussed above, formulations free in cationic lipids are preferred in some embodiments.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., $Cl^-$, $Br^-$, $I^-$, $F^-$, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane) carbamoyl]cholesterol (DC-Chol), 2,3,-dioleyloxy-N-[2 (sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphorothioate oligonucleotide. (Vlassov et al., 1994, Biochimica et Biophysica Acta 1197:95-108). Oligonucleotides can also be complexed with, e.g., poly(L-lysine) or avidin and lipids may, or may not, be included in this mixture, e.g., steryl-poly(L-lysine).

Cationic lipids have been used in the art to deliver oligonucleotides to cells (see, e.g., U.S. Pat. Nos. 5,855,910; 5,851, 548; 5,830,430; 5,780,053; U.S. Pat. No. 5,767,099; Lewis et al. 1996. *Proc. Natl. Acad. Sci. USA* 93:3176; Hope et al. 1998. *Molecular Membrane Biology* 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. No. 4,235,871; U.S. Pat. Nos. 4,501,728; 4,837, 028; 4,737,323.

In one embodiment lipid compositions can further comprise agents, e.g., viral proteins to enhance lipid-mediated transfections of oligonucleotides (Kamata, et al., 1994. *Nucl. Acids. Res.* 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to optimize uptake of oligonucleotides. Peptoids have been used to create cationic lipid-like compounds for transfection (Murphy, et al., 1998. *Proc. Natl. Acad. Sci.* 95:1517). Peptoids can be synthesized using standard methods (e.g., Zuckermann, R. N., et al. 1992. *J. Am. Chem. Soc.* 114:10646; Zuckermann, R. N., et al. 1992. *Int. J. Peptide Protein Res.* 40:497). Combinations of cationic lipids and peptoids, liptoids, can also be used to optimize uptake of the subject oligonucleotides (Hunag, et al., 1998. *Chemistry and Biology.* 5:345). Liptoids can be synthesized by elaborating peptoid oligonucleotides and coupling the amino terminal submonomer to a lipid via its amino group (Hunag, et al., 1998. *Chemistry and Biology.* 5:345).

It is known in the art that positively charged amino acids can be used for creating highly active cationic lipids (Lewis et al. 1996. *Proc. Natl. Acad. Sci. U.S.A.* 93:3176). In one embodiment, a composition for delivering oligonucleotides of the invention comprises a number of arginine, lysine, histidine or ornithine residues linked to a lipophilic moiety (see e.g., U.S. Pat. No. 5,777,153).

In another embodiment, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used.

In one embodiment, a composition for delivering oligonucleotides of the invention comprises a natural or synthetic polypeptide having one or more gamma carboxyglutamic acid residues, or γ-Gla residues. These gamma carboxyglutamic acid residues may enable the polypeptide to bind to each other and to membrane surfaces. In other words, a polypeptide having a series of γ-Gla may be used as a general delivery modality that helps an RNAi construct to stick to whatever membrane to which it comes in contact. This may at least slow RNAi constructs from being cleared from the blood stream and enhance their chance of homing to the target.

The gamma carboxyglutamic acid residues may exist in natural proteins (for example, prothrombin has 10 γ-Gla residues). Alternatively, they can be introduced into the purified, recombinantly produced, or chemically synthesized polypeptides by carboxylation using, for example, a vitamin K-dependent carboxylase. The gamma carboxyglutamic acid residues may be consecutive or non-consecutive, and the total number and location of such gamma carboxyglutamic acid residues in the polypeptide can be regulated/fine tuned to achieve different levels of "stickiness" of the polypeptide.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment, the incubation of the cells with the mixture comprising a lipid and an oligonucleotide composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. Cell 88:223).

Oligonucleotides can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the β turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. *J Cell Biol.* 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S, O, NH, etc.). Other exemplary linkers include bifunctional crosslinking agents such as sulfosuccinimidyl-4-(maleimidophenyl)-butyrate (SMPB) (see, e.g., Smith et al. Biochem J 1991. 276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559, and the references cited therein).

Targeting Agents

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197:95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eucaryotic cells. Mannosylated glycoprotein conjugated to poly(L-lysine) in aveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target oligonucleotides to cancerous cells. For example, when folic acid is linked to poly(L-lysine) enhanced oligonucleotide uptake is seen in promyelocytic leukaemia (HL-60) cells and human melanoma (M-14) cells. Ginobbi et al. 1997. *Anticancer Res.* 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes naturally accumulate in the liver, spleen, and reticuloendothelial system (so-called, passive targeting). By coupling liposomes to various ligands such as antibodies are protein A, they can be actively targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. *Biochimica et Biophysica Acta* 1197:95-108).

Other in vitro and/or in vivo delivery of RNAi reagents are known in the art, and can be used to deliver the subject RNAi constructs. See, for example, U.S. patent application publications 20080152661, 20080112916, 20080107694, 20080038296, 20070231392, 20060240093, 20060178327, 20060008910, 20050265957, 20050064595, 20050042227, 20050037496, 20050026286, 20040162235, 20040072785, 20040063654, 20030107030, WO 2008/036825, WO04/065601, and AU2004206255B2, just to name a few (all incorporated by reference).

Administration

The optimal course of administration or delivery of the oligonucleotides may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

Moreover, the present invention provides for administering the subject oligonucleotides with an osmotic pump providing continuous infusion of such oligonucleotides, for example, as described in Rataiczak et al. (1992 *Proc. Natl. Acad. Sci. USA* 89:11823-11827). Such osmotic pumps are commercially available, e.g., from Alzet Inc. (Palo Alto, Calif.). Topical administration and parenteral administration in a cationic lipid carrier are preferred.

With respect to in vivo applications, the formulations of the present invention can be administered to a patient in a variety of forms adapted to the chosen route of administration, e.g., parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

Pharmaceutical preparations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations for oral administration include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligonucleotides are formulated into conventional oral administration forms such as capsules, tablets, and tonics. For topical administration, the oligonucleotides of the invention are formulated into ointments, salves, gels, or creams as known in the art.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described oligonucleotides may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified oligonucleotide into the cell.

The chosen method of delivery will result in entry into cells. Preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogeneous systems of one liquid dispersed in another in the form of droplets usually exceeding 0.1 µm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

In an embodiment, the present invention employs various penetration enhancers to affect the efficient delivery of nucleic acids, particularly oligonucleotides, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants. Other agents may be utilized to enhance the penetration of the administered oligonucleotides include: glycols such as ethylene glycol and propylene glycol, pyrrols such as 2-15 pyrrol, azones, and terpenes such as limonene, and menthone.

The oligonucleotides, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a lipid formulation may be specifically bound to the surface of the device. Such binding techniques are described, for example, in K. Ishihara et al., Journal of Biomedical Materials Research, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regime may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

Physical methods of introducing nucleic acids include injection of a solution containing the nucleic acid, bombardment by particles covered by the nucleic acid, soaking the cell or organism in a solution of the nucleic acid, or electroporation of cell membranes in the presence of the nucleic acid. A viral construct packaged into a viral particle would accomplish both efficient introduction of an expression construct into the cell and transcription of nucleic acid encoded by the expression construct. Other methods known in the art for introducing nucleic acids to cells may be used, such as lipid-mediated carrier transport, chemical-mediated transport, such as calcium phosphate, and the like. Thus the nucleic acid may be introduced along with components that perform one or more of the following activities: enhance nucleic acid uptake by the cell, inhibit annealing of single strands, stabilize the single strands, or other-wise increase inhibition of the target gene.

Nucleic acid may be directly introduced into the cell (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals.

Alternatively, vectors, e.g., transgenes encoding a siRNA of the invention can be engineered into a host cell or transgenic animal using art recognized techniques.

A further preferred use for the agents of the present invention (or vectors or transgenes encoding same) is a functional analysis to be carried out in eukaryotic cells, or eukaryotic non-human organisms, preferably mammalian cells or organisms and most preferably human cells, e.g. cell lines such as HeLa or 293 or rodents, e.g. rats and mice. By administering a suitable priming agent/RNAi agent which is sufficiently complementary to a target mRNA sequence to direct target-specific RNA interference, a specific knockout or knockdown phenotype can be obtained in a target cell, e.g. in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogenous target gene wherein said cell or organism is transfected with at least one vector comprising DNA encoding an RNAi agent capable of inhibiting the expression of the target gene. It should be noted that the present invention allows a target-specific knockout or knockdown of several different endogenous genes due to the specificity of the RNAi agent.

Gene-specific knockout or knockdown phenotypes of cells or non-human organisms, particularly of human cells or non-human mammals may be used in analytic to procedures, e.g. in the functional and/or phenotypical analysis of complex physiological processes such as analysis of gene expression profiles and/or proteomes. Preferably the analysis is carried out by high throughput methods using oligonucleotide based chips.

Assays of Oligonucleotide Stability

In some embodiments, the oligonucleotides of the invention are stabilized, i.e., substantially resistant to endonuclease and exonuclease degradation. An oligonucleotide is defined as being substantially resistant to nucleases when it is at least about 3-fold more resistant to attack by an endogenous cellular nuclease, and is highly nuclease resistant when it is at least about 6-fold more resistant than a corresponding oligonucleotide. This can be demonstrated by showing that the oligonucleotides of the invention are substantially resistant to nucleases using techniques which are known in the art.

One way in which substantial stability can be demonstrated is by showing that the oligonucleotides of the invention function when delivered to a cell, e.g., that they reduce transcription or translation of target nucleic acid molecules, e.g., by measuring protein levels or by measuring cleavage of mRNA. Assays which measure the stability of target RNA can be performed at about 24 hours post-transfection (e.g., using Northern blot techniques, RNase Protection Assays, or QC-PCR assays as known in the art). Alternatively, levels of the target protein can be measured. Preferably, in addition to testing the RNA or protein levels of interest, the RNA or protein levels of a control, non-targeted gene will be measured (e.g., actin, or preferably a control with sequence similarity to the target) as a specificity control. RNA or protein measurements can be made using any art-recognized technique. Preferably, measurements will be made beginning at about 16-24 hours post transfection. (M. Y. Chiang, et al. 1991. J Biol Chem. 266:18162-71; T. Fisher, et al. 1993. Nucleic Acids Research. 21 3857).

The ability of an oligonucleotide composition of the invention to inhibit protein synthesis can be measured using techniques which are known in the art, for example, by detecting an inhibition in gene transcription or protein synthesis. For example, Nuclease Si mapping can be performed. In another example, Northern blot analysis can be used to measure the presence of RNA encoding a particular protein. For example, total RNA can be prepared over a cesium chloride cushion (see, e.g., Ausebel et al., 1987. Current Protocols in Molecular Biology (Greene & Wiley, New York)). Northern blots can then be made using the RNA and probed (see, e.g., Id.). In another example, the level of the specific mRNA produced by the target protein can be measured, e.g., using PCR. In yet another example, Western blots can be used to measure the amount of target protein present. In still another embodiment, a phenotype influenced by the amount of the protein can be detected. Techniques for performing Western blots are well known in the art, see, e.g., Chen et al. J. Biol. Chem. 271: 28259.

In another example, the promoter sequence of a target gene can be linked to a reporter gene and reporter gene transcription (e.g., as described in more detail below) can be monitored. Alternatively, oligonucleotide compositions that do not target a promoter can be identified by fusing a portion of the target nucleic acid molecule with a reporter gene so that the reporter gene is transcribed. By monitoring a change in the expression of the reporter gene in the presence of the oligonucleotide composition, it is possible to determine the effectiveness of the oligonucleotide composition in inhibiting the expression of the reporter gene. For example, in one embodiment, an effective oligonucleotide composition will reduce the expression of the reporter gene.

A "reporter gene" is a nucleic acid that expresses a detectable gene product, which may be RNA or protein. Detection of mRNA expression may be accomplished by Northern blotting and detection of protein may be accomplished by staining with antibodies specific to the protein. Preferred reporter genes produce a readily detectable product. A reporter gene may be operably linked with a regulatory DNA sequence such that detection of the reporter gene product provides a measure of the transcriptional to activity of the regulatory sequence. In preferred embodiments, the gene product of the reporter gene is detected by an intrinsic activity associated with that product. For instance, the reporter gene may encode a gene product that, by enzymatic activity, gives rise to a detectable signal based on color, fluorescence, or luminescence. Examples of reporter genes include, but are not limited to, those coding for chloramphenicol acetyl transferase (CAT), luciferase, beta-galactosidase, and alkaline phosphatase.

One skilled in the art would readily recognize numerous reporter genes suitable for use in the present invention. These include, but are not limited to, chloramphenicol acetyltransferase (CAT), luciferase, human growth hormone (hGH), and beta-galactosidase. Examples of such reporter genes can be found in F. A. Ausubel et al., Eds., Current Protocols in Molecular Biology, John Wiley & Sons, New York, (1989). Any gene that encodes a detectable product, e.g., any product having detectable enzymatic activity or against which a specific antibody can be raised, can be used as a reporter gene in the present methods.

One reporter gene system is the firefly luciferase reporter system. (Gould, S. J., and Subramani, S. 1988. Anal. Biochem., 7:404-408 incorporated herein by reference). The luciferase assay is fast and sensitive. In this assay, a lysate of the test cell is prepared and combined with ATP and the substrate luciferin. The encoded enzyme luciferase catalyzes a rapid, ATP dependent oxidation of the substrate to generate a light-emitting product. The total light output is measured and is proportional to the amount of luciferase present over a wide range of enzyme concentrations.

CAT is another frequently used reporter gene system; a major advantage of this system is that it has been an extensively validated and is widely accepted as a measure of promoter activity. (Gorman C. M., Moffat, L. F., and Howard, B. H. 1982. Mol. Cell. Biol., 2:1044-1051). In this system, test cells are transfected with CAT expression vectors and incubated with the candidate substance within 2-3 days of the initial transfection. Thereafter, cell extracts are prepared. The extracts are incubated with acetyl CoA and radioactive chloramphenicol. Following the incubation, acetylated chloramphenicol is separated from nonacetylated form by thin layer chromatography. In this assay, the degree of acetylation reflects the CAT gene activity with the particular promoter.

Another suitable reporter gene system is based on immunologic detection of hGH. This system is also quick and easy to use. (Selden, R., Burke-Howie, K. Rowe, M. E., Goodman, H. M., and Moore, D. D. (1986), Mol. Cell, Biol., 6:3173-3179 incorporated herein by reference). The hGH system is advantageous in that the expressed hGH polypeptide is assayed in the media, rather than in a cell extract. Thus, this system does not require the destruction of the test cells. It will be appreciated that the principle of this reporter gene system is not limited to hGH but rather adapted for use with any polypeptide for which an antibody of acceptable specificity is available or can be prepared.

In one embodiment, nuclease stability of a double-stranded oligonucleotide of the invention is measured and compared to a control, e.g., an RNAi molecule typically used in the art (e.g., a duplex oligonucleotide of less than 25 nucleotides in length and comprising 2 nucleotide base overhangs) or an unmodified RNA duplex with blunt ends.

The target RNA cleavage reaction achieved using the siRNAs of the invention is highly sequence specific. Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10. Greater than 90% sequence identity, e.g., 91%, 92%, 93%, 94%, 95%, 96%, 97%, 98%, 99% or even 100% sequence identity, between the siRNA and the portion of the target gene is preferred. Alternatively, the siRNA may be defined functionally as a nucleotide sequence (or oligonucleotide sequence) that is capable of hybridizing with a portion of the target gene transcript. Examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Therapeutic Use

By inhibiting the expression of a gene, the oligonucleotide compositions of the present invention can be used to treat any disease involving the expression of a protein. Examples of diseases that can be treated by oligonucleotide compositions, just to illustrate, include: cancer, retinopathies, autoimmune diseases, inflammatory diseases (i.e., ICAM-1 related disorders, Psoriasis, Ulcerative Colitus, Crohn's disease), viral diseases (i.e., HIV, Hepatitis C), miRNA disorders, and cardiovascular diseases.

In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. There are numerous medical conditions for which antisense therapy is reported to be suitable (see, e.g., U.S. Pat. No. 5,830,653) as well as respiratory syncytial virus infection (WO 95/22,553) influenza virus (WO 94/23,028), and malignancies (WO 94/08,003). Other examples of clinical uses of antisense sequences are reviewed, e.g., in Glaser. 1996. *Genetic Engineering News* 16:1. Exemplary targets for cleavage by oligonucleotides include, e.g., protein kinase Ca, ICAM-1, c-raf kinase, p53, c-myb, and the bcr/abl fusion gene found in chronic myelogenous leukemia.

The subject nucleic acids can be used in RNAi-based therapy in any animal having RNAi pathway, such as human, non-human primate, non-human mammal, non-human vertebrates, rodents (mice, rats, hamsters, rabbits, etc.), domestic livestock animals, pets (cats, dogs, etc.), *Xenopus*, fish, insects (*Drosophila*, etc.), and worms (*C. elegans*), etc.

The invention provides methods for preventing in a subject, a disease or condition associated with an aberrant or unwanted target gene expression or activity, by administering to the subject a therapeutic agent (e.g., a RNAi agent or vector or transgene encoding same). If appropriate, subjects are first treated with a priming agent so as to be more responsive to the subsequent RNAi therapy. Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject.

In another aspect, the invention pertains to methods of modulating target gene expression, protein expression or activity for therapeutic purposes. Accordingly, in an exemplary embodiment, the modulatory method of the invention involves contacting a cell capable of expressing target gene with a therapeutic agent of the invention that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent), in vivo (e.g., by administering the agent to a subject), or ex vivo. Typically, subjects are first treated with a priming agent so as to be more responsive to the subsequent RNAi therapy. As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

The therapeutic agents of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent. Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10-11): 983-985 and Linder, M. W. et al. (1997) Clin. Chem. 43(2):254-266

RNAi in Skin Indications

Nucleic acid molecules, or compositions comprising nucleic acid molecules, described herein may in some embodiments be administered to pre-treat, treat or prevent compromised skin. As used herein "compromised skin" refers to skin which exhibits characteristics distinct from normal skin. Compromised skin may occur in association with a dermatological condition. Several non-limiting examples of dermatological conditions include rosacea, common acne, seborrheic dermatitis, perioral dermatitis, acneform rashes, transient acantholytic dermatosis, and acne necrotica miliaris. In some instances, compromised skin may comprise a wound and/or scar tissue. In some instances, methods and compositions associated with the invention may be used to promote wound healing, prevention, reduction or inhibition of scarring, and/or promotion of re-epithelialisation of wounds.

A subject can be pre-treated or treated prophylactically with a molecule associated with the invention, prior to the skin of the subject becoming compromised. As used herein "pre-treatment" or "prophylactic treatment" refers to administering a nucleic acid to the skin prior to the skin becoming compromised. For example, a subject could be pre-treated 15 minutes, 30 minutes, 1 hour, 2 hours, 3 hours, 4 hours, 5 hours, 6 hours, 7 hours, 8 hours, 9 hours, 10 hours, 11 hours, 12 hours, 24 hours, 48 hours, or more than 48 hours prior to the skin becoming compromised. In other embodiments, a subject can be treated with a molecule associated with the invention immediately before the skin becomes compromised and/or simultaneous to the skin becoming compromised and/or after the skin has been compromised. In some embodiments, the skin is compromised through a medical procedure such as surgery, including elective surgery. In certain embodiments methods and compositions may be applied to areas of the skin that are believed to be at risk of becoming compromised. It should be appreciated that one of ordinary skill in the art would be able to optimize timing of administration using no more than routine experimentation.

In some aspects, methods associated with the invention can be applied to promote healing of compromised skin. Administration can occur at any time up until the compromised skin has healed, even if the compromised skin has already partially healed. The timing of administration can depend on several factors including the nature of the compromised skin, the degree of damage within the compromised skin, and the size of the compromised area. In some embodiments administration may occur immediately after the skin is compromised, or 30 minutes, 1 hour, 2 hours, 4 hours, 6 hours, 8 hours, 12 hours, 24 hours, 48 hours, or more than 48 hours after the skin has been compromised. Methods and compositions of the invention may be administered one or more times as necessary. For example, in some embodiments, compositions may be administered daily or twice daily. In some instances, compositions may be administered both before and after formation of compromised skin.

Compositions associated with the invention may be administered by any suitable route. In some embodiments, administration occurs locally at an area of compromised skin. For example, compositions may be administered by intradermal injection. Compositions for intradermal injection may include injectable solutions. Intradermal injection may in some embodiments occur around the are of compromised skin or at a site where the skin is likely to become compromised. In some embodiments, compositions may also be administered in a topical form, such as in a cream or ointment. In some embodiments, administration of compositions described herein comprises part of an initial treatment or pre-treatment of compromised skin, while in other embodiments, administration of such compositions comprises follow-up care for an area of compromised skin.

The appropriate amount of a composition or medicament to be applied can depend on many different factors and can be determined by one of ordinary skill in the art through routine experimentation. Several non-limiting factors that might be considered include biological activity and bioavailability of the agent, nature of the agent, mode of administration, half-life, and characteristics of the subject to be treated.

In some aspects, nucleic acid molecules associated with the invention may also be used in treatment and/or prevention of fibrotic disorders, including pulmonary fibrosis, liver cirrhosis, scleroderma and glomerulonephritis, lung fibrosis, liver fibrosis, skin fibrosis, muscle fibrosis, radiation fibrosis, kidney fibrosis, proliferative vitreoretinopathy and uterine fibrosis.

A therapeutically effective amount of a nucleic acid molecule described herein may in some embodiments be an amount sufficient to prevent the formation of compromised skin and/or improve the condition of compromised skin. In some embodiments, improvement of the condition of compromised skin may correspond to promotion of wound healing and/or inhibition of scarring and/or promotion of epithelial regeneration. The extent of prevention of formation of compromised skin and/or improvement to the condition of compromised skin may in some instances be determined by, for example, a doctor or clinician.

The ability of nucleic acid molecules associated with the invention to prevent the formation of compromised skin and/or improve the condition of compromised skin may in some instances be measured with reference to properties exhibited by the skin. In some instances, these properties may include rate of epithelialisation and/or decreased size of an area of compromised skin compared to control skin at comparable time points.

As used herein, prevention of formation of compromised skin, for example prior to a surgical procedure, and/or improvement of the condition of compromised skin, for example after a surgical procedure, can encompass any increase in the rate of healing in the compromised skin as compared with the rate of healing occurring in a control sample. In some instances, the condition of compromised skin may be assessed with respect to either comparison of the rate of re-epithelialisation achieved in treated and control skin, or comparison of the relative areas of treated and control areas of compromised skin at comparable time points. In some aspects, a molecule that prevents formation of compromised skin or promotes healing of compromised skin may be a molecule that, upon administration, causes the area of compromised skin to exhibit an increased rate of re-epithelialisation and/or a reduction of the size of compromised skin compared to a control at comparable time points. In some embodiments, the healing of compromised skin may give rise to a rate of healing that is 5%, 10%, 20%, 30%, 40%, 50%, 60%, 70%, 80%, 90% or 100% greater than the rate occurring in controls.

In some aspects, subjects to be treated by methods and compositions associated with the invention may be subjects who will undergo, are undergoing or have undergone a medical procedure such as a surgery. In some embodiments, the subject may be prone to defective, delayed or otherwise impaired re-epithelialisation, such as dermal wounds in the aged. Other non-limiting examples of conditions or disorders in which wound healing is associated with delayed or otherwise impaired re-epithelialisation include patients suffering from diabetes, patients with polypharmacy, post-menopausal women, patients susceptible to pressure injuries, patients with venous disease, clinically obese patients, patients receiving chemotherapy, patients receiving radiotherapy, patients receiving steroid treatment, and immuno-compromised patients. In some instances, defective re-epithelialisation response can contributes to infections at the wound site, and to the formation of chronic wounds such as ulcers.

In some embodiments, methods associated with the invention may promote the re-epithelialisation of compromised skin in chronic wounds, such as ulcers, and may also inhibit scarring associated with wound healing. In other embodiments, methods associated with the invention are applied to prevention or treatment of compromised skin in acute wounds in patients predisposed to impaired wound healing developing into chronic wounds. In other aspects, methods associated with the invention are applied to promote accelerated healing of compromised skin while preventing, reducing or inhibiting scarring for use in general clinical contexts. In some aspects, this can involve the treatment of surgical incisions and application of such methods may result in the prevention, reduction or inhibition of scarring that may otherwise occur on such healing. Such treatment may result in the scars being less noticeable and exhibiting regeneration of a more normal skin structure. In other embodiments, the compromised skin that is treated is not compromised skin that is caused by a surgical incision. The compromised skin may be subject to continued care and continued application of medicaments to encourage re-epithelialisation and healing.

In some aspects, methods associated with the invention may also be used in the treatment of compromised skin associated with grafting procedures. This can involve treatment at a graft donor site and/or at a graft recipient site. Grafts can in some embodiments involve skin, artificial skin, or skin substitutes. Methods associated with the invention can also be used for promoting epithelial regeneration. As used herein, promotion of epithelial regeneration encompasses any increase in the rate of epithelial regeneration as compared to the regeneration occurring in a control-treated or untreated epithelium. The rate of epithelial regeneration attained can in some instances be compared with that taking place in control-treated or untreated epithelia using any suitable model of epithelial regeneration known in the art. Promotion of epithelial regeneration may be of use to induce effective re-epithelialisation in contexts in which the re-epithelialisation response is impaired, inhibited, retarded or otherwise defective. Promotion of epithelial regeneration may be also effected to accelerate the rate of defective or normal epithelial regeneration responses in patients suffering from epithelial damage.

Some instances where re-epithelialisation response may be defective include conditions such as pemphigus, Hailey-Hailey disease (familial benign pemphigus), toxic epidermal necrolysis (TEN)/Lyell's syndrome, epidermolysis bullosa, cutaneous leishmaniasis and actinic keratosis. Defective re-epithelialisation of the lungs may be associated with idiopathic pulmonary fibrosis (IPF) or interstitial lung disease. Defective re-epithelialisation of the eye may be associated with conditions such as partial limbal stem cell deficiency or corneal erosions. Defective re-epithelialisation of the gastrointestinal tract or colon may be associated with conditions such as chronic anal fissures (fissure in ano), ulcerative colitis or Crohn's disease, and other inflammatory bowel disorders.

In some aspects, methods associated with the invention are used to prevent, reduce or otherwise inhibit compromised skin associated with scarring. This can be applied to any site within the body and any tissue or organ, including the skin, eye, nerves, tendons, ligaments, muscle, and oral cavity (including the lips and palate), as well as internal organs (such as the liver, heart, brain, abdominal cavity, pelvic cavity, thoracic cavity, guts and reproductive tissue). In the skin, treatment may change the morphology and organization of collagen fibers and may result in making the scars less visible and blend in with the surrounding skin. As used herein, prevention, reduction or inhibition of scarring encompasses any degree of prevention, reduction or inhibition in scarring as compared to the level of scarring occurring in a control-treated or untreated wound.

Prevention, reduction or inhibition of compromised skin, such as compromised skin associated with dermal scarring, can be assessed and/or measured with reference to microscopic and/or macroscopic characteristics. Macroscopic characteristics may include color, height, surface texture and stiffness of the skin. In some instances, prevention, reduction or inhibition of compromised skin may be demonstrated when the color, height, surface texture and stiffness of the skin resembles that of normal skin more closely after treatment than does a control that is untreated. Microscopic assessment of compromised skin may involve examining characteristics such as thickness and/or orientation and/or composition of the extracellular matrix (ECM) fibers, and cellularity of the compromised skin. In some instances, prevention, reduction or inhibition of compromised skin may be demonstrated when the thickness and/or orientation and/or composition of the extracellular matrix (ECM) fibers, and/or cellularity of the compromised skin resembles that of normal skin more closely after treatment than does a control that is untreated.

In some aspects, methods associated with the invention are used for cosmetic purposes, at least in part to contribute to improving the cosmetic appearance of compromised skin. In some embodiments, methods associated with the invention may be used to prevent, reduce or inhibit compromised skin such as scarring of wounds covering joints of the body. In other embodiments, methods associated with the invention may be used to promote accelerated wound healing and/or prevent, reduce or inhibit scarring of wounds at increased risk of forming a contractile scar, and/or of wounds located at sites of high skin tension.

In some embodiments, methods associated with the invention can be applied to promoting healing of compromised skin in instances where there is an increased risk of pathological scar formation, such as hypertrophic scars and keloids, which may have more pronounced deleterious effects than normal scarring. In some embodiments, methods described herein for promoting accelerated healing of compromised skin and/or preventing, reducing or inhibiting scarring are applied to compromised skin produced by surgical revision of pathological scars.

Aspects of the invention can be applied to compromised skin caused by burn injuries. Healing in response to burn injuries can lead to adverse scarring, including the formation of hypertrophic scars. Methods associated with the invention can be applied to treatment of all injuries involving damage to an epithelial layer, such as injuries to the skin in which the epidermis is damaged. Other non-limiting examples of injuries to epithelial tissue include injuries involving the respiratory epithelia, digestive epithelia or epithelia surrounding internal tissues or organs.

Target Genes

It should be appreciated that based on the RNAi molecules designed and disclosed herein, one of ordinary skill in the art would be able to design such RNAi molecules to target a variety of different genes depending on the context and intended use. For purposes of pre-treating, treating, or preventing compromised skin and/or promoting wound healing and/or preventing, reducing or inhibiting scarring, one of ordinary skill in the art would appreciate that a variety of suitable target genes could be identified based at least in part on the known or predicted functions of the genes, and/or the known or predicted expression patterns of the genes. Several non-limiting examples of genes that could be targeted by RNAi molecules for pre-treating, treating, or preventing compromised skin and/or promoting wound healing and/or preventing, reducing or inhibiting scarring include genes that encode for the following proteins: Transforming growth factor β (TGFβ1, TGFβ2, TGFβ3), Osteopontin, Connective tissue growth factor (CTGF), Platelet-derived growth factor (PDGF), Hypoxia inducible factor-1α (HIF1α), Collagen I and/or III, Prolyl 4-hydroxylase (P4H), Procollagen C-protease (PCP), Matrix metalloproteinase 2, 9 (MMP2, 9), Integrins, Connexin, Histamine H1 receptor, Tissue transglutaminase, Mammalian target of rapamycin (mTOR), HoxB13, VEGF, IL-6, SMAD proteins, Ribosomal protein S6 kinases (RSP6) and Cyclooxygenase-2 (COX-2).

Transforming growth factor β proteins, for which three isoforms exist in mammals (TGFβ1, TGFβ2, TGFβ3), are secreted proteins belonging to a superfamily of growth factors involved in the regulation of many cellular processes including proliferation, migration, apoptosis, adhesion, differentiation, inflammation, immuno-suppression and expression of extracellular proteins. These proteins are produced by a wide range of cell types including epithelial, endothelial, hematopoietic, neuronal, and connective tissue cells. Representative Genbank accession numbers providing DNA and protein sequence information for human TGFβ1, TGFβ2 and TGFβ3 are BT007245, BC096235, and X14149, respectively. Within the TGFβ family, TGFβ1 and TGFβ2 but not TGFβ3 represent suitable targets. The alteration in the ratio of TGFβ variants will promote better wound healing and will prevent excessive scar formation. Osteopontin (OPN), also known as Secreted phosphoprotein 1 (SPP1), Bone Sinaloprotein 1 (BSP-1), and early T-lymphocyte activation (ETA-1) is a secreted glycoprotein protein that binds to hydroxyapatite. OPN has been implicated in a variety of biological processes including bone remodeling, immune functions, chemotaxis, cell activation and apoptosis. Osteopontin is produced by a variety of cell types including fibroblasts, preosteoblasts, osteoblasts, osteocytes, odontoblasts, bone marrow cells, hypertrophic chondrocytes, dendritic cells, macrophages, smooth muscle, skeletal muscle myoblasts, endothelial cells, and extraosseous (non-bone) cells in the inner ear, brain, kidney, deciduum, and placenta. Representative Genbank accession number providing DNA and protein sequence information for human Osteopontin are NM_000582.2 and X13694.

Connective tissue growth factor (CTGF), also known as Hypertrophic chondrocyte-specific protein 24, is a secreted heparin-binding protein that has been implicated in wound healing and scleroderma. Connective tissue growth factor is active in many cell types including fibroblasts, myofibroblasts, endothelial and epithelial cells. Representative Genbank accession number providing DNA and protein sequence information for human CTGF are NM_001901.2 and M92934.

The Platelet-derived growth factor (PDGF) family of proteins, including several isoforms, are secreted mitogens. PDGF proteins are implicated in wound healing, at least in part, because they are released from platelets following wounding. Representative Genbank accession numbers providing DNA and protein sequence information for human PDGF genes and proteins include X03795 (PDGFA), X02811 (PDGFB), AF091434 (PDGFC), AB033832 (PDGFD).

Hypoxia inducible factor-1α (HIF1α), is a transcription factor involved in cellular response to hypoxia. HIF1α is implicated in cellular processes such as embryonic vascularization, tumor angiogenesis and pathophysiology of ischemic disease. A representative Genbank accession number providing DNA and protein sequence information for human HIF1α is U22431.

Collagen proteins are the most abundant mammalian proteins and are found in tissues such as skin, tendon, vascular, ligature, organs, and bone. Collagen I proteins (such as COL1A1 and COL1A2) are detected in scar tissue during wound healing, and are expressed in the skin. Collagen III proteins (including COL3A1) are detected in connective tissue in wounds (granulation tissue), and are also expressed in skin. Representative Genbank accession numbers providing DNA and protein sequence information for human Collagen proteins include: Z74615 (COL1A1), J03464 (COL1A2) and X14420 (COL3A1).

Prolyl 4-hydroxylase (P4H), is involved in production of collagen and in oxygen sensing. A representative Genbank accession number providing DNA and protein sequence information for human P4H is AY198406.

Procollagen C-protease (PCP) is another target.

Matrix metalloproteinase 2, 9 (MMP2, 9) belong to the metzincin metalloproteinase superfamily and are zinc-dependent endopeptidases. These proteins are implicated in a variety of cellular processes including tissue repair. Representative Genbank accession numbers providing DNA and protein sequence information for human MMP proteins are M55593 (MMP2) and J05070 (MMP9).

Integrins are a family of proteins involved in interaction and communication between a cell and the extracellular matrix. Vertebrates contain a variety of integrins including $\alpha_1\beta_1$, $\alpha_2\beta_1$, $\alpha_4\beta_1$, $\alpha_5\beta_1$, $\alpha_6\beta_1$, $\alpha_L\beta_2$, $\alpha_M\beta_2$, $\alpha_{IIb}\beta_3$, $\alpha_v\beta_3$, $\alpha_v\beta_5$, $\alpha_v\beta_6$, $\alpha_6\beta_4$.

Connexins are a family of vertebrate transmembrane proteins that form gap junctions. Several examples of Connexins, with the accompanying gene name shown in brackets, include Cx23 (GJE1), Cx25 (GJB7), Cx26 (GJB2), Cx29 (GJE1), Cx30 (GJB6), Cx30.2 (GJC3), Cx30.3 (GJB4), Cx31 (GJB3), Cx31.1 (GJB5), Cx31.9 (GJC1/GJD3), Cx32 (GJB1), Cx33 (GJA6), Cx36 (GJD2/GJA9), Cx37 (GJA4), Cx39 (GJD4), Cx40 (GJA5), Cx40.1 (GJD4), Cx43 (GJA1), Cx45 (GJC1/GJA7), Cx46 (GJA3), Cx47 (GJC2/GJA12), Cx50 (GJA8), Cx59 (GJA10), and Cx62 (GJA10).

Histamine H1 receptor (HRH1) is a metabotropic G-protein-coupled receptor involved in the phospholipase C and phosphatidylinositol (PIP2) signaling pathways. A representative Genbank accession number providing DNA and protein sequence information for human HRH1 is Z34897.

Tissue transglutaminase, also called Protein-glutamine gamma-glutamyltransferase 2, is involved in protein crosslinking and is implicated is biological processes such as apoptosis, cellular differentiation and matrix stabilization. A representative Genbank accession number providing DNA and protein sequence information for human Tissue transglutaminase is M55153.

Mammalian target of rapamycin (mTOR), also known as Serine/threonine-protein kinase mTOR and FK506 binding protein 12-rapamycin associated protein 1 (FRAP1), is involved in regulating cell growth and survival, cell motility, transcription and translation. A representative Genbank accession number providing DNA and protein sequence information for human mTOR is L34075.

HoxB13 belongs to the family of Homeobox proteins and has been linked to functions such as cutaneous regeneration and fetal skin development. A representative Genbank accession number providing DNA and protein sequence information for human HoxB13 is U57052.

Vascular endothelial growth factor (VEGF) proteins are growth factors that bind to tyrosine kinase receptors and are implicated in multiple disorders such as cancer, age-related macular degeneration, rheumatoid arthritis and diabetic retinopathy. Members of this protein family include VEGF-A, VEGF-B, VEGF-C and VEGF-D. Representative Genbank accession numbers providing DNA and protein sequence information for human VEGF proteins are M32977 (VEGF-A), U43368 (VEGF-B), X94216 (VEGF-C), and D89630 (VEGF-D).

Interleukin-6 (IL-6) is a cytokine involved in stimulating immune response to tissue damage. A representative Genbank accession number providing DNA and protein sequence information for human IL-6 is X04430.

SMAD proteins (SMAD1-7, 9) are a family of transcription factors involved in regulation of TGFβ3 signaling. Representative Genbank accession numbers providing DNA and protein sequence information for human SMAD proteins are U59912 (SMAD1), U59911 (SMAD2), U68019 (SMAD3), U44378 (SMAD4), U59913 (SMAD5), U59914 (SMAD6), AF015261 (SMAD7), and BC011559 (SMAD9).

Ribosomal protein S6 kinases (RSK6) represent a family of serine/threonine kinases involved in activation of the transcription factor CREB. A representative Genbank accession number providing DNA and protein sequence information for human Ribosomal protein S6 kinase alpha-6 is AF184965.

Cyclooxygenase-2 (COX-2), also called Prostaglandin G/H synthase 2 (PTGS2), is involved in lipid metabolism and biosynthesis of prostanoids and is implicated in inflammatory disorders such as rheumatoid arthritis. A representative Genbank accession number providing DNA and protein sequence information for human COX-2 is AY462100.

EXAMPLES

Example 1

Inhibition of Gene Expression Using Minimum Length Trigger RNAs

Transfection of Minimum Length Trigger (mlt) RNA mltRNA constructs were chemically synthesized (Integrated DNA Technologies, Coralville, Iowa) and transfected into HEK293 cells (ATCC, Manassas, Va.) using the Lipofectamine RNAiMAX (Invitrogen, Carlsbad, Calif.) reagent according to manufacturer's instructions. In brief, RNA was diluted to a 12× concentration and then combined with a 12× concentration of Lipofectamine RNAiMAX to complex. The RNA and transfection reagent were allowed to complex at room temperature for 20 minutes and make a 6× concentration. While complexing, HEK293 cells were washed, trypsinized and counted. The cells were diluted to a concentration recommended by the manufacturer and previously described conditions which was at $1 \times 10^5$ cells/ml. When RNA had completed complexing with the RNAiMAX transfection reagent, 20 ul of the complexes were added to the appropriate well of the 96-well plate in triplicate. Cells were added to each well (100 ul volume) to make the final cell count per well at $1 \times 10^4$ cells/well. The volume of cells diluted the 6× concentration of complex to 1× which was equal to a concentration noted (between 10-0.05 nM). Cells were incubated for 24 or 48 hours under normal growth conditions.

After 24 or 48 hour incubation cells were lysed and gene silencing activity was measured using the QuantiGene assay (Panomics, Freemont, Calif.) which employs bDNA hybridization technology. The assay was carried out according to manufacturer's instructions.

ΔG Calculation

ΔG was calculated using Mfold, available through the Mfold internet site (http://mfold.bioinfospi.edu/cgi-bin/rna-form1.cgi). Methods for calculating ΔG are described in, and are incorporated by reference from, the following references: Zuker, M. (2003) Nucleic Acids Res., 31(13):3406-15; Mathews, D. H., Sabina, J., Zuker, M. and Turner, D. H. (1999) J. Mol. Biol. 288:911-940; Mathews, D. H., Disney, M. D., Childs, J. L., Schroeder, S. J., Zuker, M., and Turner, D. H. (2004) Proc. Natl. Acad. Sci. 101:7287-7292; Duan, S., Mathews, D. H., and Turner, D. H. (2006) Biochemistry 45:9819-9832; Wuchty, S., Fontana, W., Hofacker, I. L., and Schuster, P. (1999) Biopolymers 49:145-165.

Example 2

Optimization of sd-rxRNA$^{nano}$ Molecules for Gene Silencing

Asymmetric double stranded RNAi molecules, with minimal double stranded regions, were developed herein and are highly effective at gene silencing. These molecules can contain a variety of chemical modifications on the sense and/or anti-sense strands, and can be conjugated to sterol-like compounds such as cholesterol.

Figure 2:
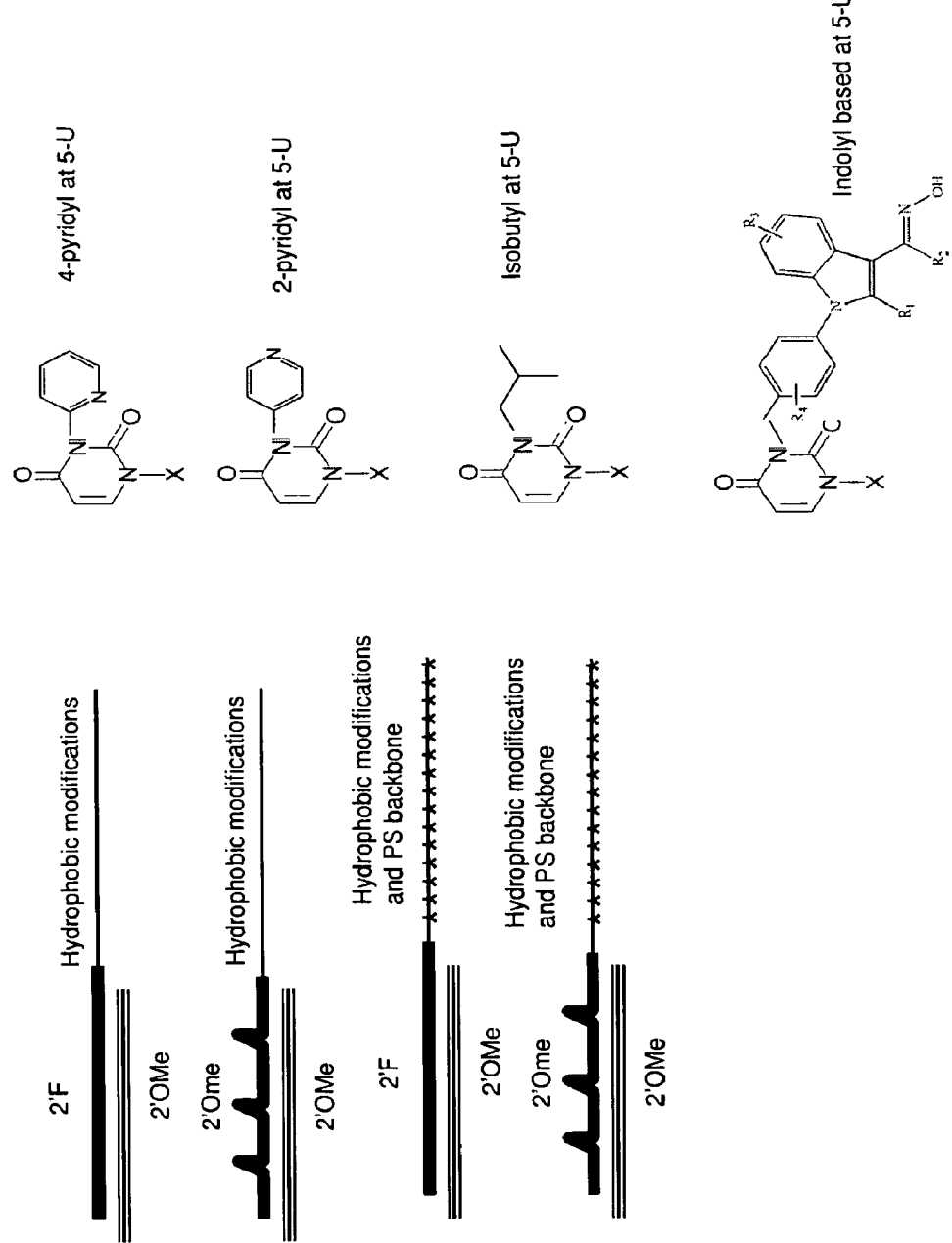
FIG. 2 is a schematic depicting asymmetric dsRNA molecules with different chemical modification patterns. Several examples of chemical modifications that might be used to increase hydrophobicity are shown including 4-pyridyl, 2-pyridyl, isobutyl and indolyl based position 5 uridine modifications.
Figure 3:
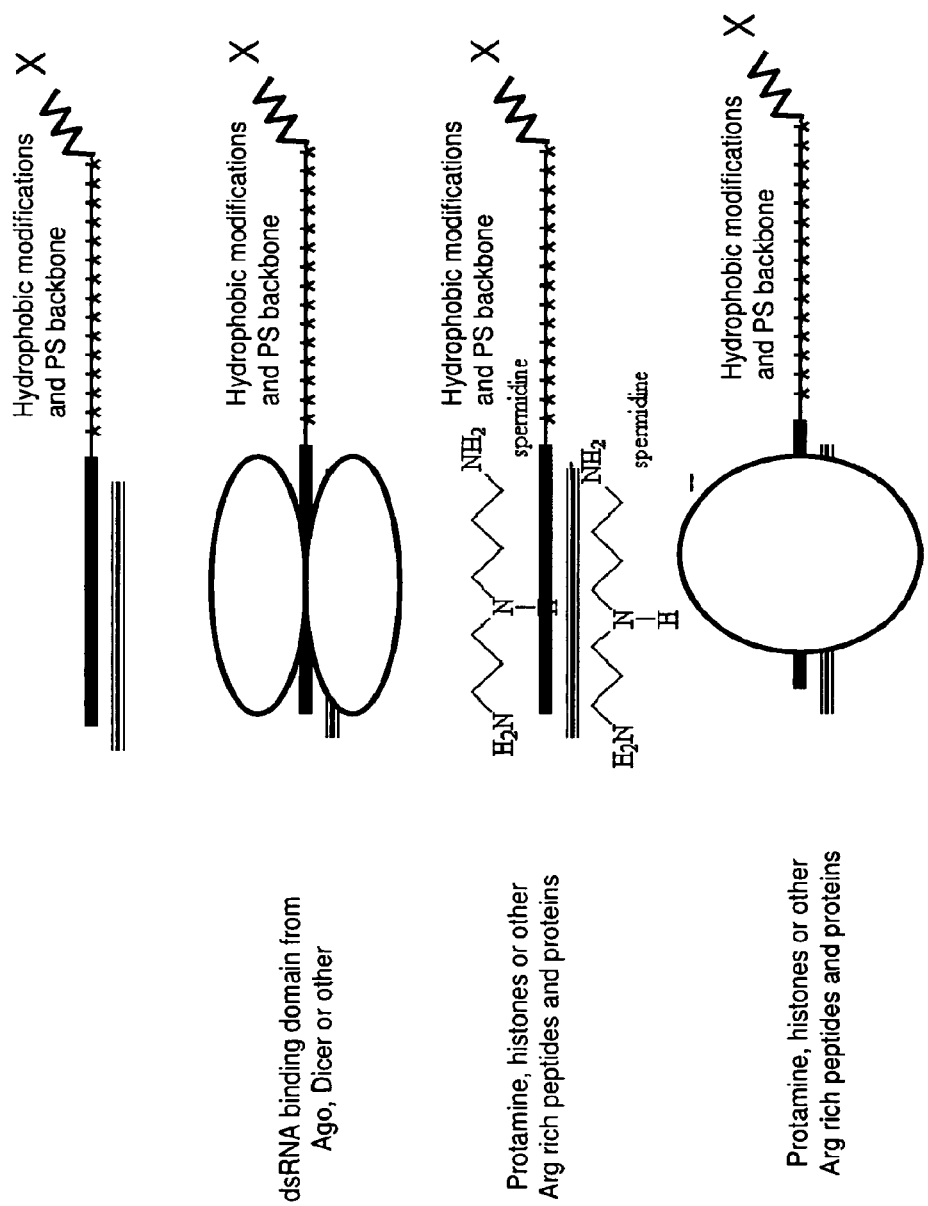
FIG. 3 is a schematic depicting the use of dsRNA binding domains, protamine (or other Arg rich peptides), spermidine or similar chemical structures to block duplex charge to facilitate cellular entry.
Figure 4:
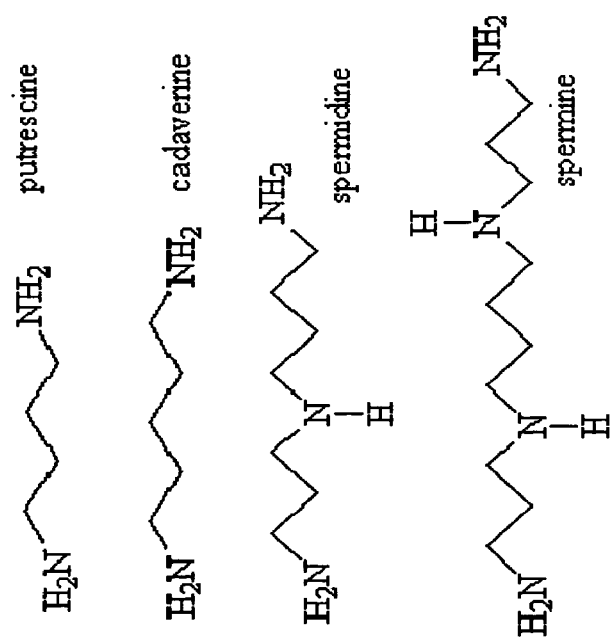
FIG. 4 is a schematic depicting positively charged chemicals that might be used for polynucleotide charge blockage.

FIGS. 1-3 present schematics of RNAi molecules associated with the invention. In the asymmetric molecules, which contain a sense and anti-sense strand, either of the strands can be the longer strand. Either strand can also contain a single-stranded region. There can also be mismatches between the sense and anti-sense strand, as indicated in FIG. 1D. Preferably, one end of the double-stranded molecule is either blunt-ended or contains a short overhang such as an overhang of one nucleotide. FIG. 2 indicates types of chemical modifications applied to the sense and anti-sense strands including 2'F, 2'OMe, hydrophobic modifications and phosphorothioate modifications. Preferably, the single stranded region of the molecule contains multiple phosphorothioate modifications. Hydrophobicity of molecules can be increased using such compounds as 4-pyridyl at 5-U, 2-pyridyl at 5-U, isobutyl at 5-U and indolyl at 5-U (FIG. 2). Proteins or peptides such as protamine (or other Arg rich peptides), spermidine or other similar chemical structures can also be used to block duplex charge and facilitate cellular entry (FIG. 3). Increased hydrophobicity can be achieved through either covalent or non-covalent modifications. Several positively charged chemicals, which might be used for polynucleotide charge blockage are depicted in FIG. 4.

Chemical modifications of polynucleotides, such as the guide strand in a duplex molecule, can facilitate RISC entry. FIG. 5 depicts single stranded polynucleotides, representing a guide strand in a duplex molecule, with a variety of chemical modifications including 2'd, 2'OMe, 2'F, hydrophobic modifications, phosphorothioate modifications, and attachment of conjugates such as "X" in FIG. 5, where X can be a small molecule with high affinity to a PAZ domain, or sterol-type entity. Similarly, FIG. 6 depicts single stranded polynucleotides, representing a passenger strand in a duplex molecule, with proposed structural and chemical compositions of RISC substrate inhibitors. Combinations of chemical modifications can ensure efficient uptake and efficient binding to preloaded RISC complexes.

Figure 7:
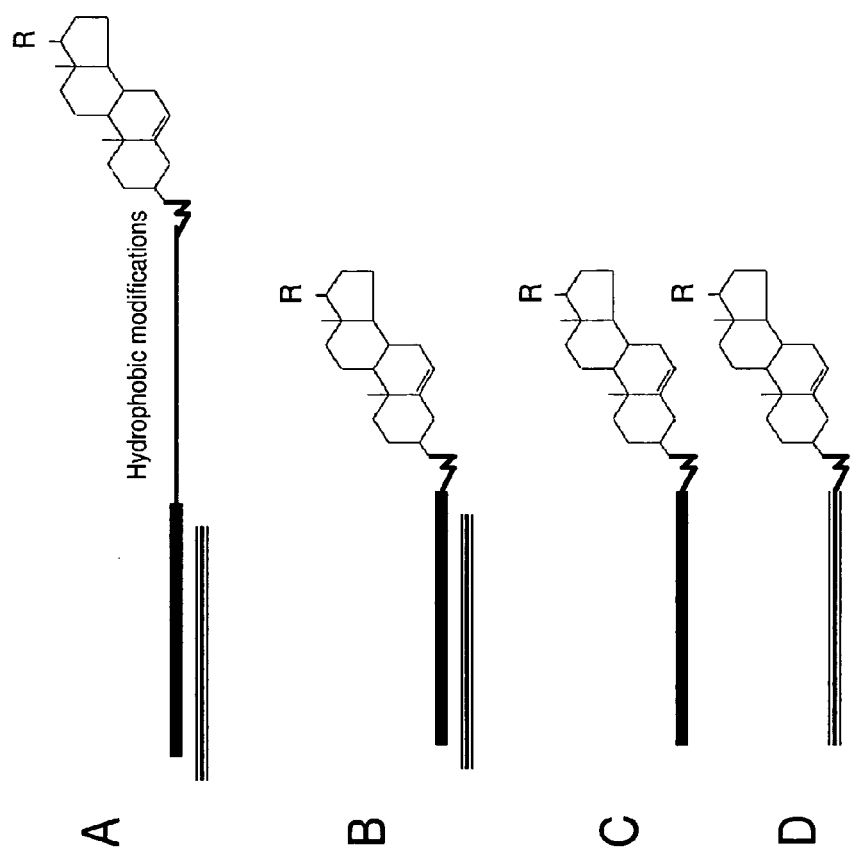
FIG. 7 is a schematic depicting structures of polynucleotides with sterol type molecules attached, where R represent a polycarbonic tail of 9 carbons or longer.
Figure 11:
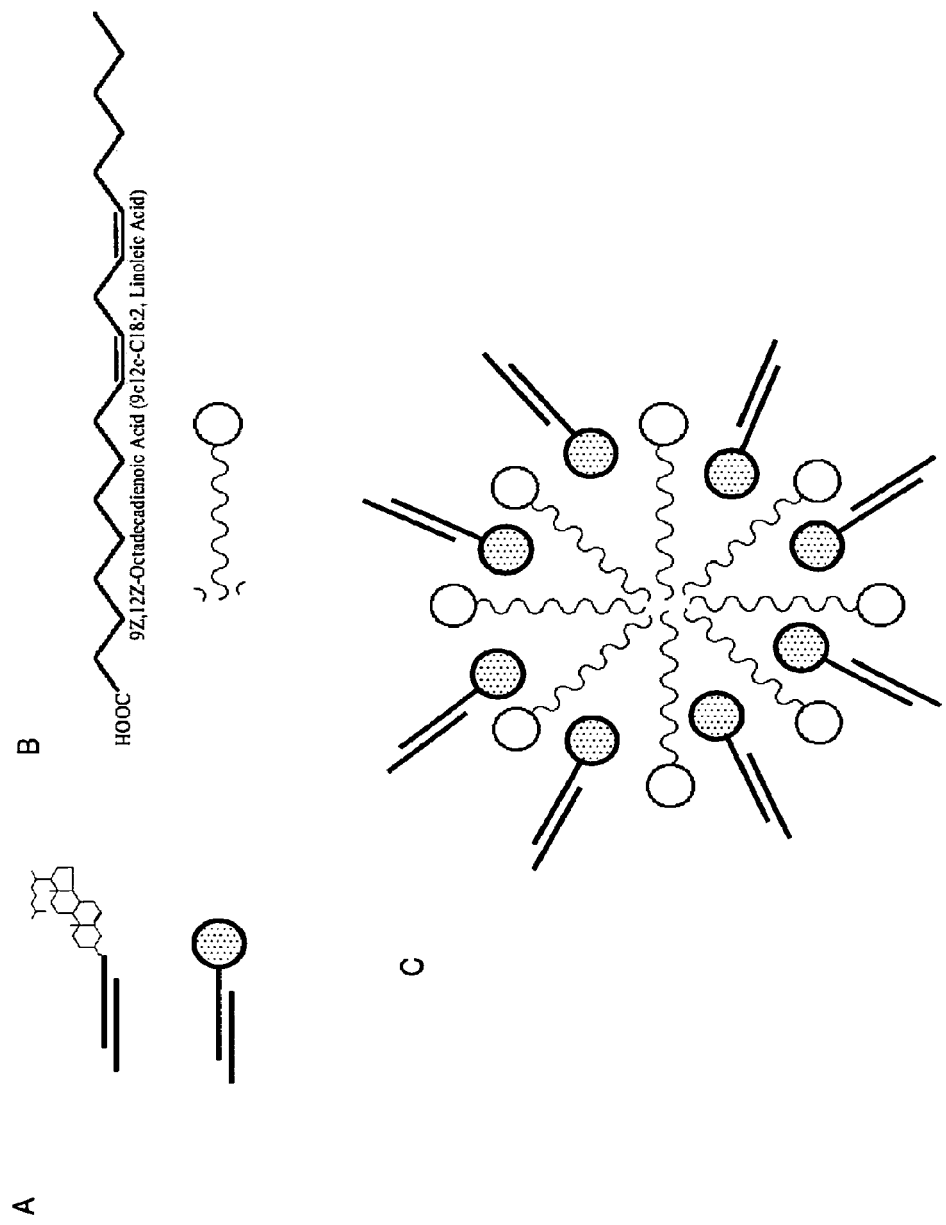
FIG. 11 is a schematic depicting micelle formation.
Figure 91:
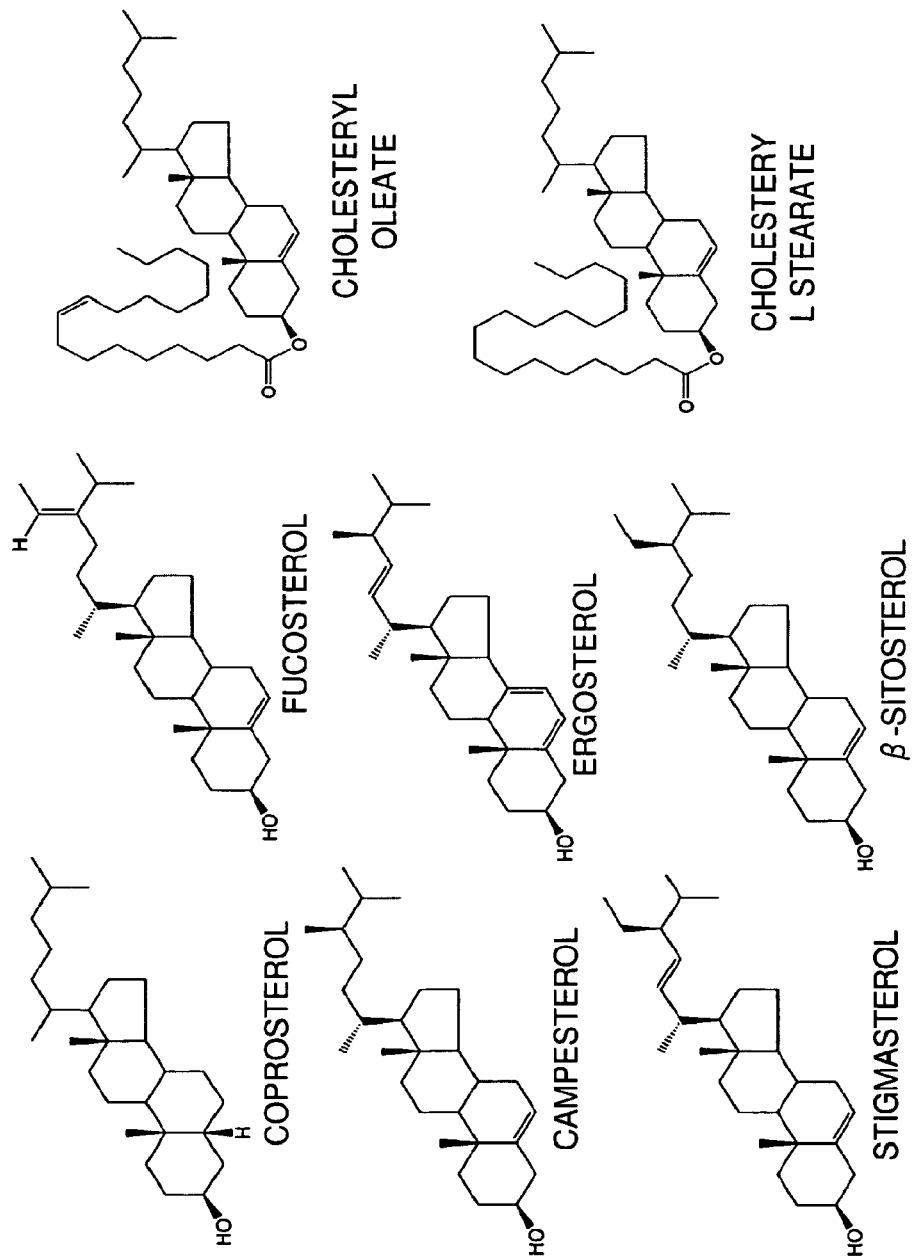
FIG. 91 is a schematic depicting a panel of sterol-type molecules which can be used as a hydrophobic entity in place of cholesterol. In some instances, the use of sterol-type molecules comprising longer chains results in generation of sd-rxRNA compounds with significantly better cellular uptake and tissue distribution properties.
Figure 92:
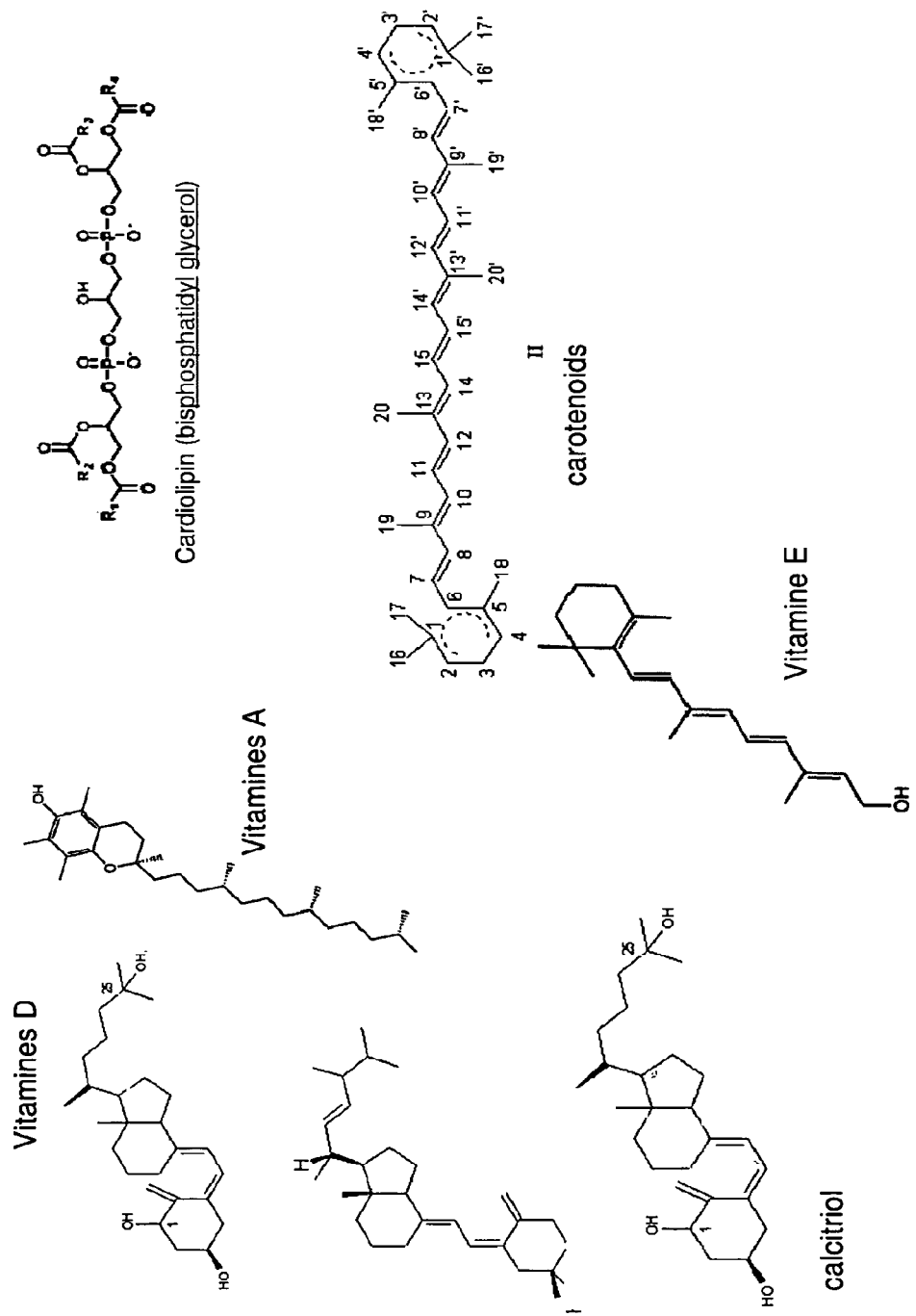
FIG. 92 presents schematics depicting a panel of hydrophobic molecules which might be used as a hydrophobic entity in place of cholesterol. These list just provides representative examples; any small molecule with substantial hydrophobicity can be used.

FIG. 7 depicts structures of polynucleotides with sterol-type molecules attached, where R represents a polycarbonic tail of 9 carbons or longer. FIG. 8 presents examples of naturally occurring phytosterols with a polycarbon chain longer than 8 attached at position 17. More than 250 different types of phytosterols are known. FIG. 9 presents examples of sterol-like structures with variations in the sizes of the polycarbon chains attached at position 17. FIG. 91 presents further examples of sterol-type molecules that can be used as a hydrophobic entity in place of cholesterol. FIG. 92 presents further examples of hydrophobic molecules that might be used as hydrophobic entities in place of cholesterol. Optimization of such characteristics can improve uptake properties of the RNAi molecules. FIG. 10 presents data adapted from Martins et al. (J Lipid Research), showing that the percentage of liver uptake and plasma clearance of lipid emulsions containing sterol-type molecules is directly affected by the size of the attached polycarbon chain at position 17. FIG. 11 depicts a micelle formed from a mixture of polynucleotides attached to hydrophobic conjugates and fatty acids. FIG. 12 describes how alteration in lipid composition can affect pharmacokinetic behavior and tissue distribution of hydrophobically modified and/or hydrophobically conjugated polynucleotides. In particular, the use of lipid mixtures that are enriched in linoleic acid and cardiolipin results in preferential uptake by cardiomyocytes.

Figure 13:
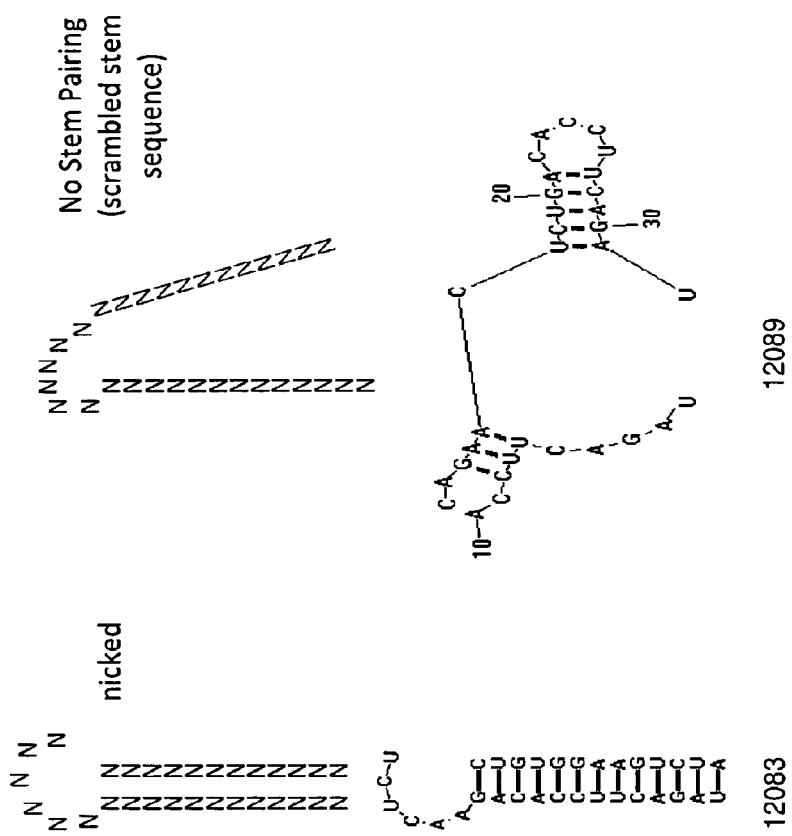
FIG. 13 is a schematic showing examples of RNAi constructs and controls used to target MAP4K4 expression. RNAi construct 12083 corresponds to SEQ ID NOs:597 and 598. RNAi construct 12089 corresponds to SEQ ID NO:599.
Figure 14:
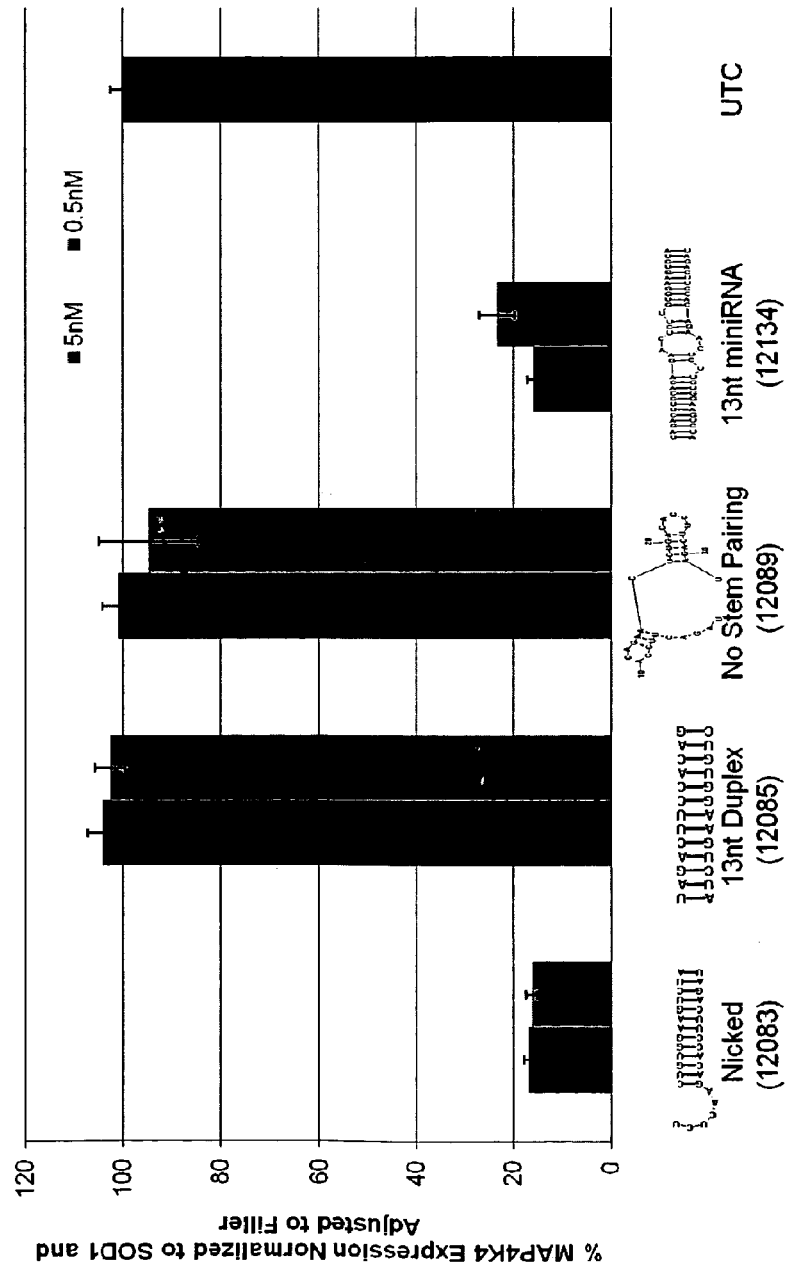
FIG. 14 is a graph showing MAP4K4 expression following transfection with RNAi constructs associated with the invention. RNAi constructs tested were: 12083 (Nicked), 12085 (13 nt Duplex), 12089 (No Stem Pairing) and 12134 (13 nt miniRNA). Results of transfection were compared to an untransfected control sample. RNAi construct 12083 corresponds to SEQ ID NOs:597 and 598. RNAi construct 12085 corresponds to SEQ ID NOs:600 and 601. RNAi construct 12089 corresponds to SEQ ID NO:599. RNAi construct 12134 corresponds to SEQ ID NOs:602 and 603.
Figure 15:
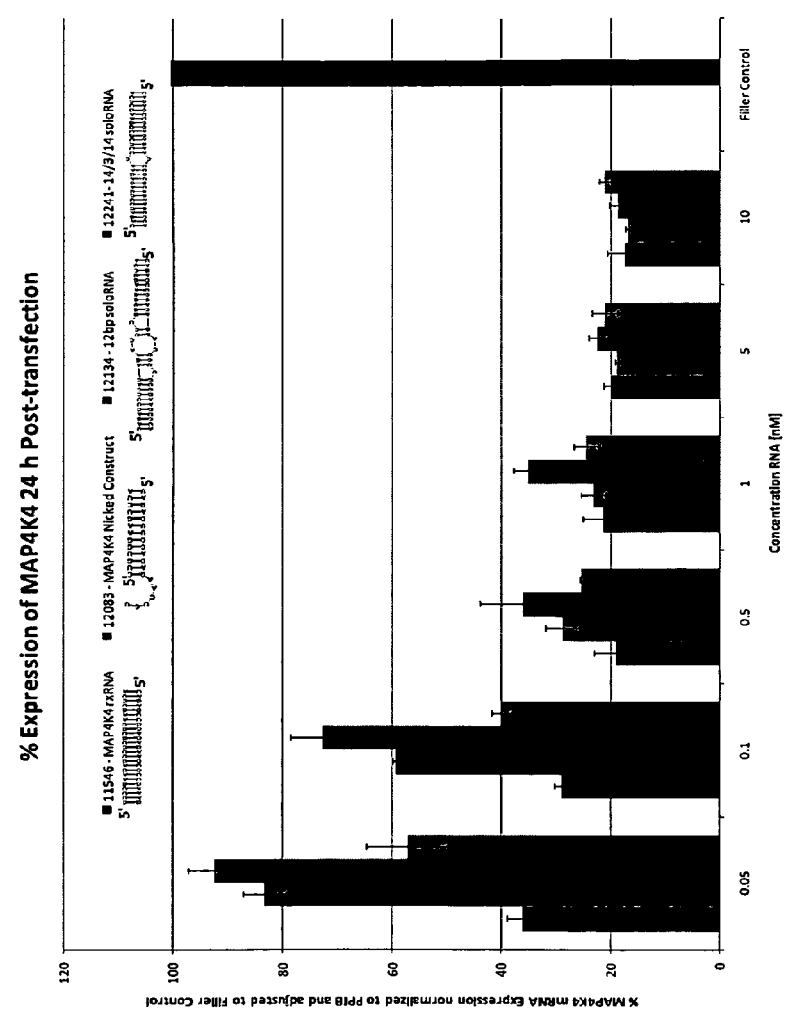
FIG. 15 is a graph showing expression of MAP4K4 24 hours post-transfection with RNAi constructs associated with the invention. RNAi constructs tested were: 11546 (MAP4K4 rxRNA), 12083 (MAP4K4 Nicked Construct), 12134 (12 bp soloRNA) and 12241 (14/3/14 soloRNA). Results of transfection were compared to a filler control sample. RNAi construct 11546 corresponds to SEQ ID NOs:604 and 605. RNAi construct 12083 corresponds to SEQ ID NOs:597 and 598. RNAi construct 12134 corresponds to SEQ ID NOs:602 and 603. RNAi construct 12241 corresponds to SEQ ID NOs:606 and 607.
Figure 16:
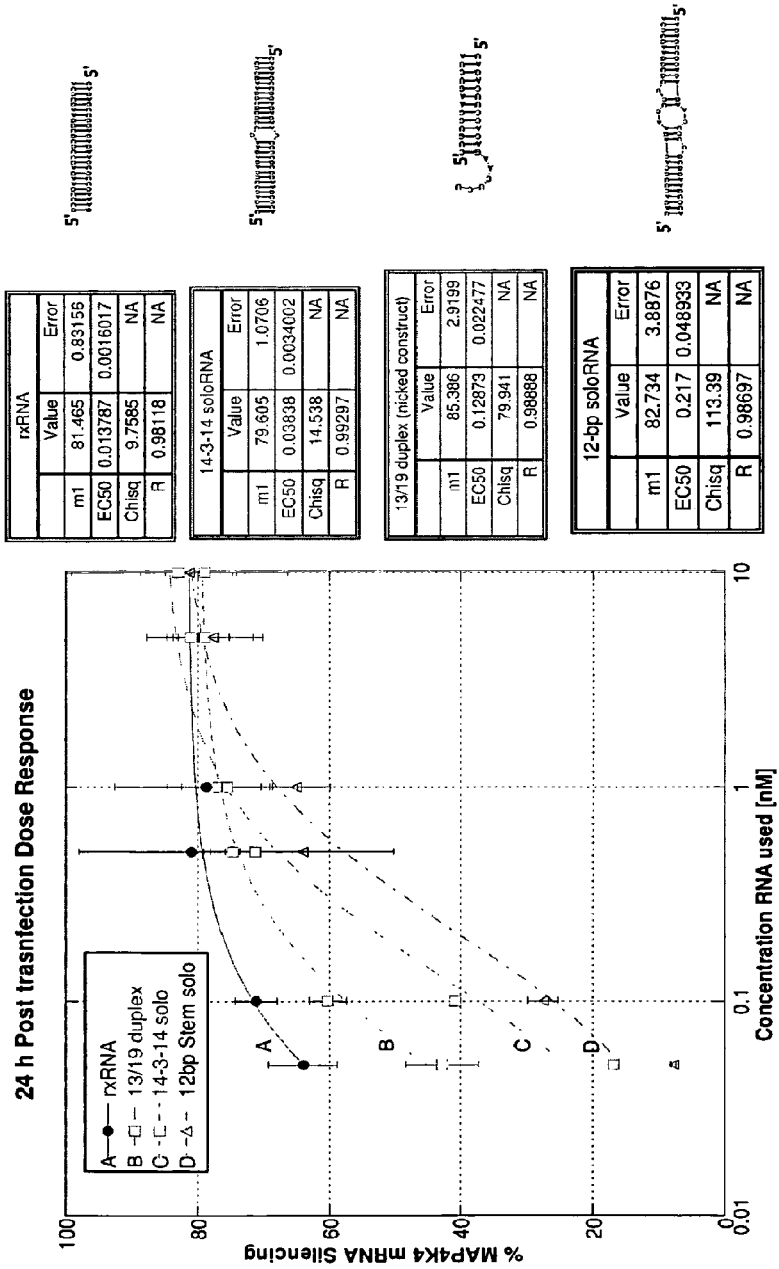
FIG. 16 presents a graph and several tables comparing parameters associated with silencing of MAP4K4 expression following transfection with RNAi constructs associated with the invention. The rxRNA construct corresponds to SEQ ID NOs:604 and 605. The 14-3-14 soloRNA construct corresponds to SEQ ID NOs:606 and 607. The 13/19 duplex (nicked construct) corresponds to SEQ ID NOs:597 and 598. The 12-bp soloRNA construct corresponds to SEQ ID NOs: 602 and 603.
Figure 17:
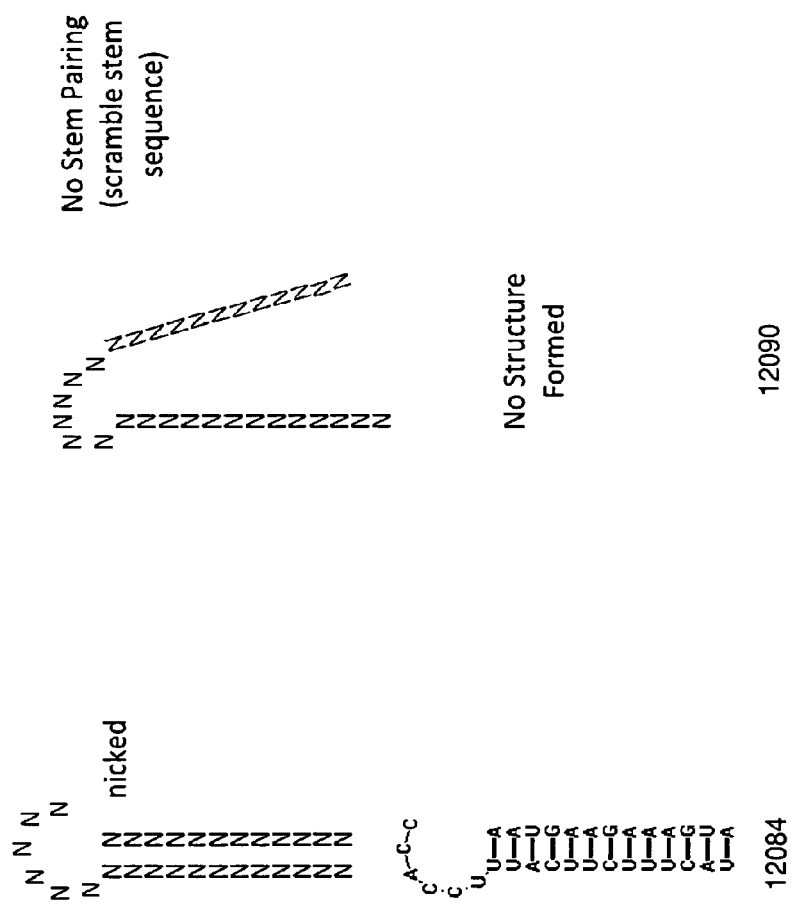
FIG. 17 is a schematic showing examples of RNAi constructs and controls used to target SOD1 expression. The 12084 RNAi construct corresponds to SEQ ID NOs:612 and 613.
Figure 18:
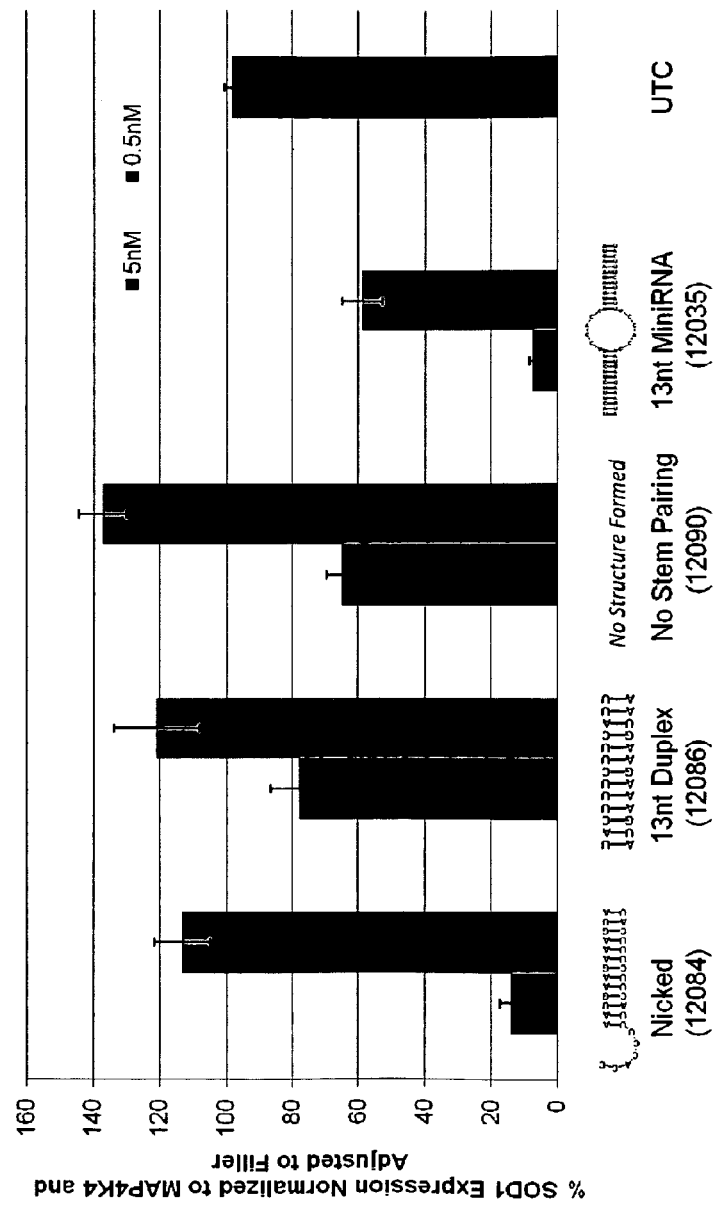
FIG. 18 is a graph showing SOD1 expression following transfection with RNAi constructs associated with the invention. RNAi constructs tested were: 12084 (Nicked), 12086 (13 nt Duplex), 12090 (No Stem Pairing) and 12035 (13 nt MiniRNA). Results of transfection were compared to an untransfected control sample. The 12084 RNAi construct corresponds to SEQ ID NOs:612 and 613. The 12086 RNAi construct corresponds to SEQ ID NOs:608 and 609. The 12035 RNAi construct corresponds to SEQ ID NOs:610 and 611.
Figure 19:
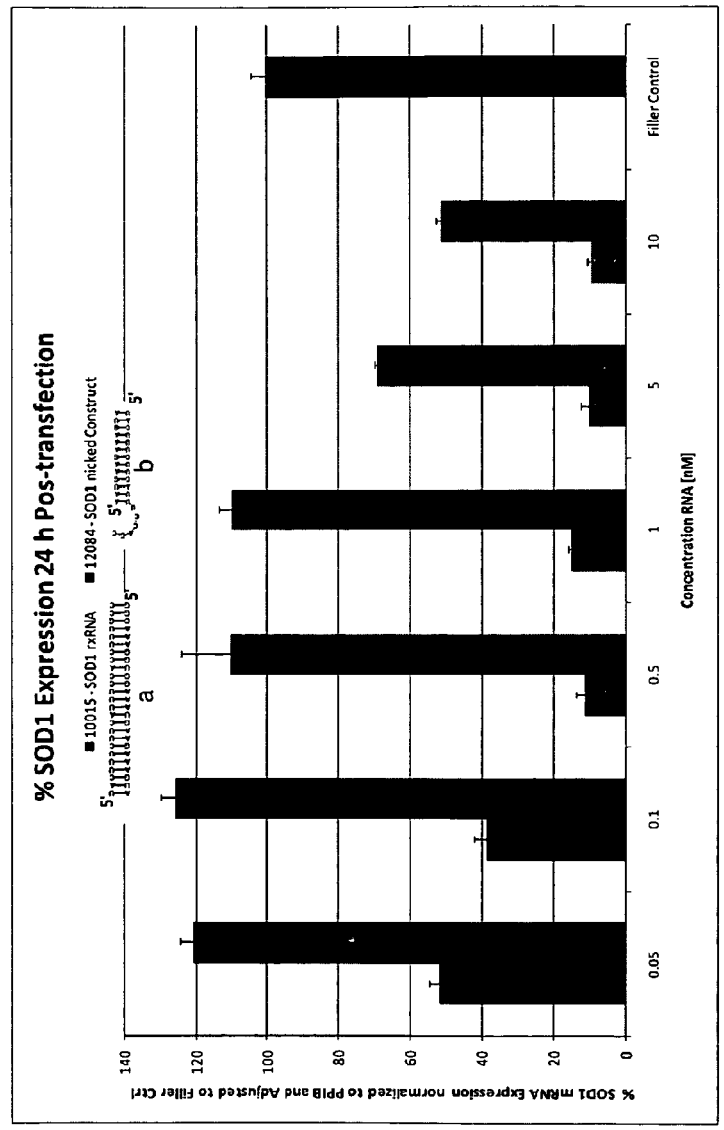
FIG. 19 is a graph showing expression of SOD1 24 hours post-transfection with RNAi constructs associated with the invention. RNAi constructs tested were: 10015 (SOD1 rxRNA) and 12084 (SOD1 Nicked Construct). Results of transfection were compared to a filler control sample. The 10015 RNAi construct corresponds to SEQ ID NOs:614 and 615. The 12084 RNAi construct corresponds to SEQ ID NOs: 612 and 613.
Figure 20:
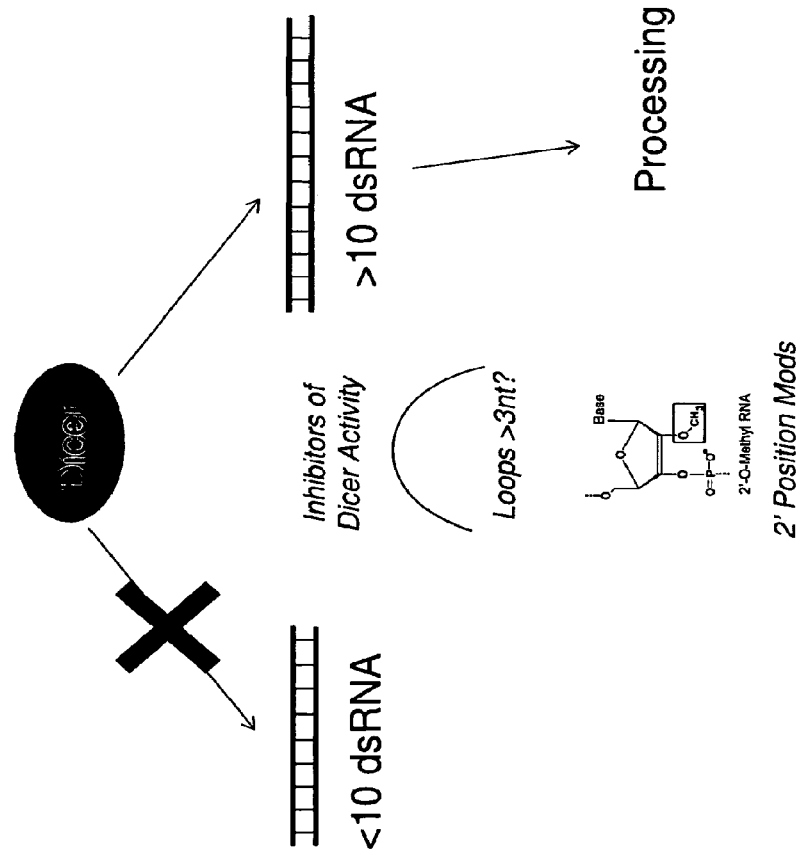
FIG. 20 is a schematic indicating that RNA molecules with double stranded regions that are less than 10 nucleotides are not cleaved by Dicer.

FIG. 13 depicts examples of RNAi constructs and controls designed to target MAP4K4 expression. FIGS. 14 and 15 reveal that RNAi constructs with minimal duplex regions (such as duplex regions of approximately 13 nucleotides) are effective in mediating RNA silencing in cell culture. Parameters associated with these RNA molecules are shown in FIG. 16. FIG. 17 depicts examples of RNAi constructs and controls designed to target SOD1 expression. FIGS. 18 and 19 reveal the results of gene silencing experiments using these RNAi molecules to target SOD1 in cells. FIG. 20 presents a schematic indicating that RNA molecules with double stranded regions that are less than 10 nucleotides are not cleaved by Dicer, and FIG. 21 presents a schematic of a hypothetical RNAi model for RNA induced gene silencing.

The RNA molecules described herein were subject to a variety of chemical modifications on the sense and antisense strands, and the effects of such modifications were observed. RNAi molecules were synthesized and optimized through testing of a variety of modifications. In first generation optimization, the sense (passenger) and anti-sense (guide) strands of the sd-rxRNA$^{nano}$ molecules were modified for example through incorporation of C and U 2'OMe modifications, 2'F modifications, phosphorothioate modifications, phosphorylation, and conjugation of cholesterol. Molecules were tested for inhibition of MAP4K4 expression in cells including HeLa, primary mouse hepatocytes and primary human hepatocytes through both lipid-mediated and passive uptake transfection.

Figure 24:
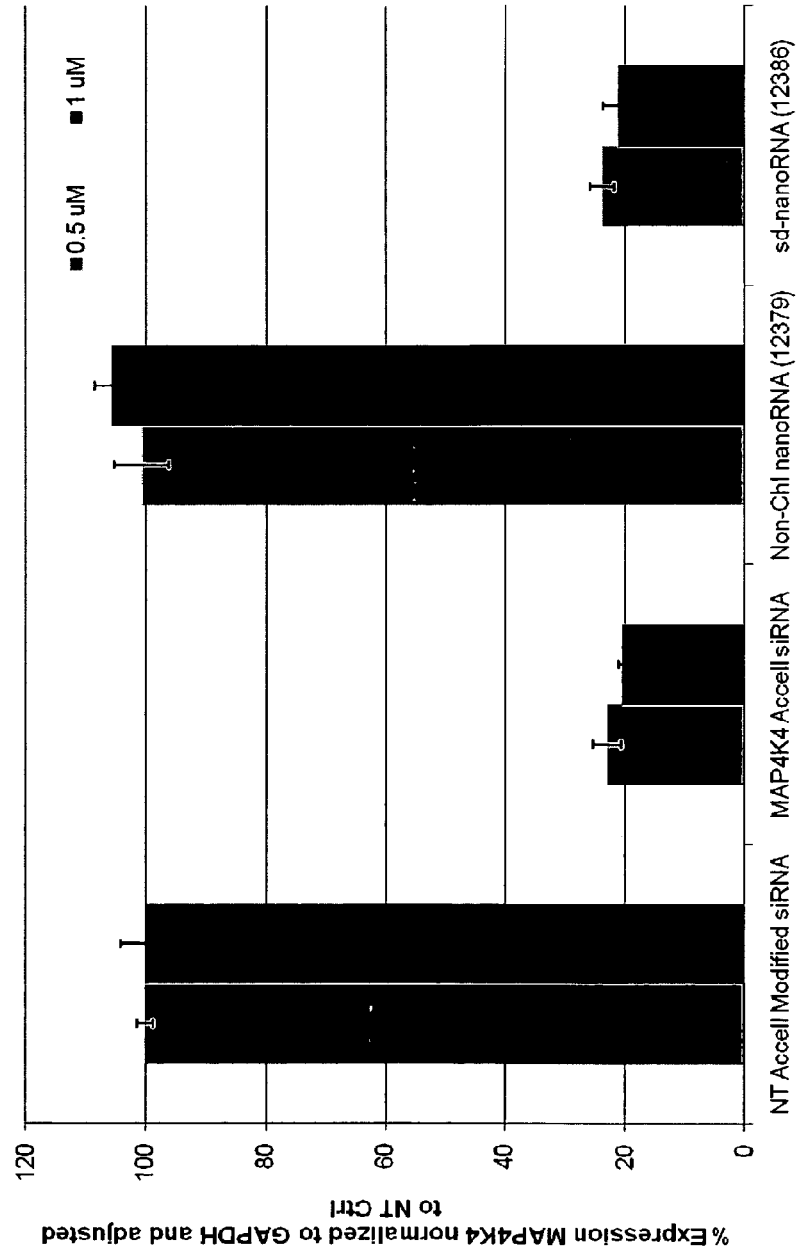
FIG. 24 is a graph showing MAP4K4 expression in Hela cells following passive uptake transfection of: NT Accell modified siRNA, MAP4K4 Accell siRNA, Non-Chl nanoRNA (12379) and sd-nanoRNA (12386).

FIG. 22 reveals that chemical modifications can enhance gene silencing. In particular, modifying the guide strand with 2'F UC modifications, and with a stretch of phosphorothioate modifications, combined with complete CU O'Me modification of the passenger strands, resulted in molecules that were highly effective in gene silencing. The effect of chemical modification on in vitro efficacy in un-assisted delivery in HeLa cells was also examined. FIG. 23 reveals that compounds lacking any of 2'F, 2'OMe, a stretch of phosphorothioate modifications, or cholesterol conjugates, were completely inactive in passive uptake. A combination of all 4 types of chemical modifications, for example in compound 12386, was found to be highly effective in gene silencing. FIG. 24 also shows the effectiveness of compound 12386 in gene silencing.

Figure 25:
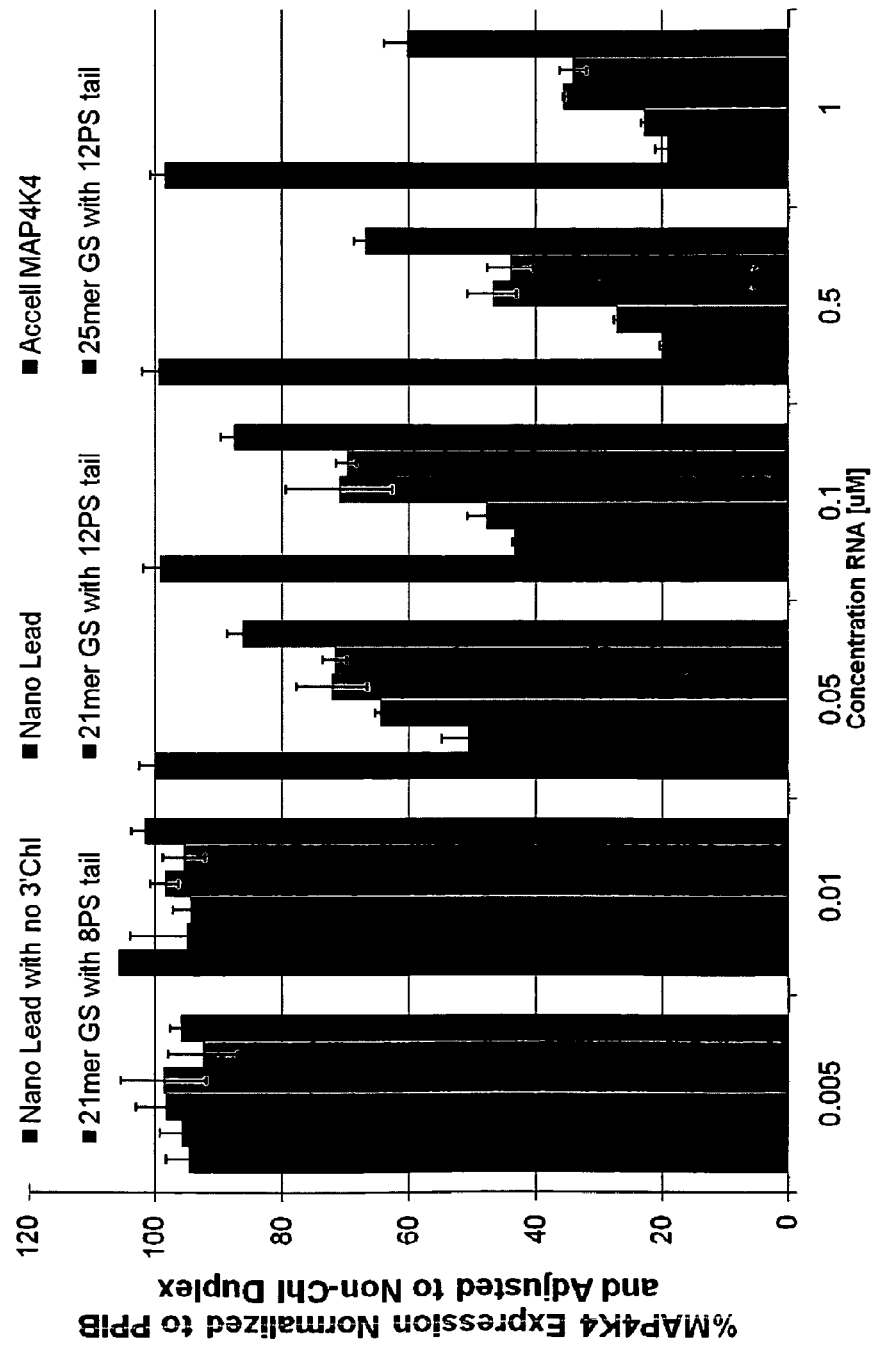
FIG. 25 is a graph showing expression of MAP4K4 in HeLa cells following passive uptake transfection of various concentrations of RNA molecules containing the following parameters: Nano Lead with no 3'Chl; Nano Lead; Accell MAP4K4; 21 mer GS with 8 PS tail; 21 mer GS with 12 PS tail; and 25 mer GS with 12 PS tail.
Figure 88:
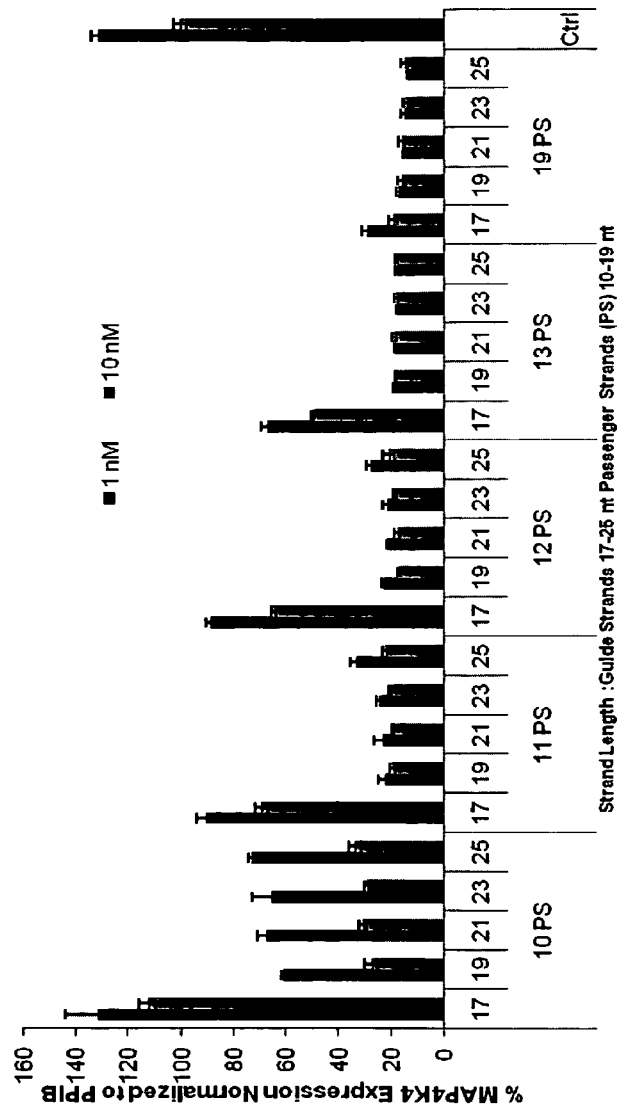
FIG. 88 demonstrates a systematic screen identifying the minimal length of the asymmetric compounds. The passenger strand of 10-19 bases was hybridized to a guide strand of 17-25 bases. In this assay, compounds with duplex regions as short as 10 bases were found to be effective in inducing.
Figure 89:
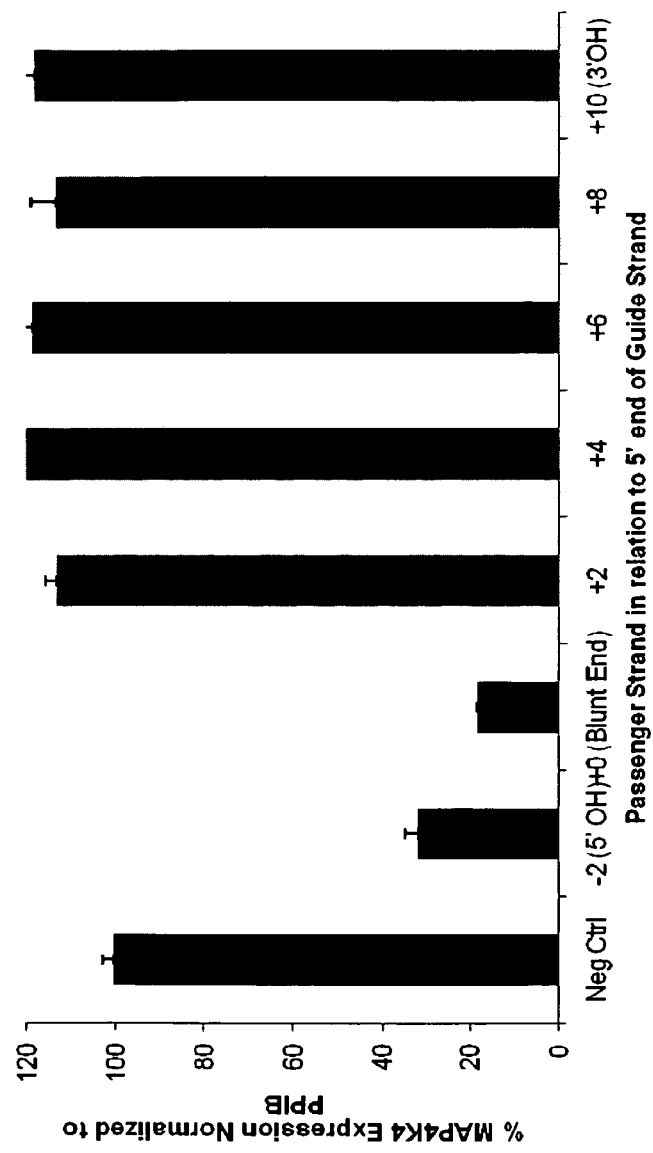
FIG. 89 demonstrates that positioning of the sense strand relative to the guide strand is critical for RNAi Activity. In this assay, a blunt end was found to be optimal, a 3' overhang was tolerated, and a 5' overhang resulted in complete loss of functionality.
Figure 90:
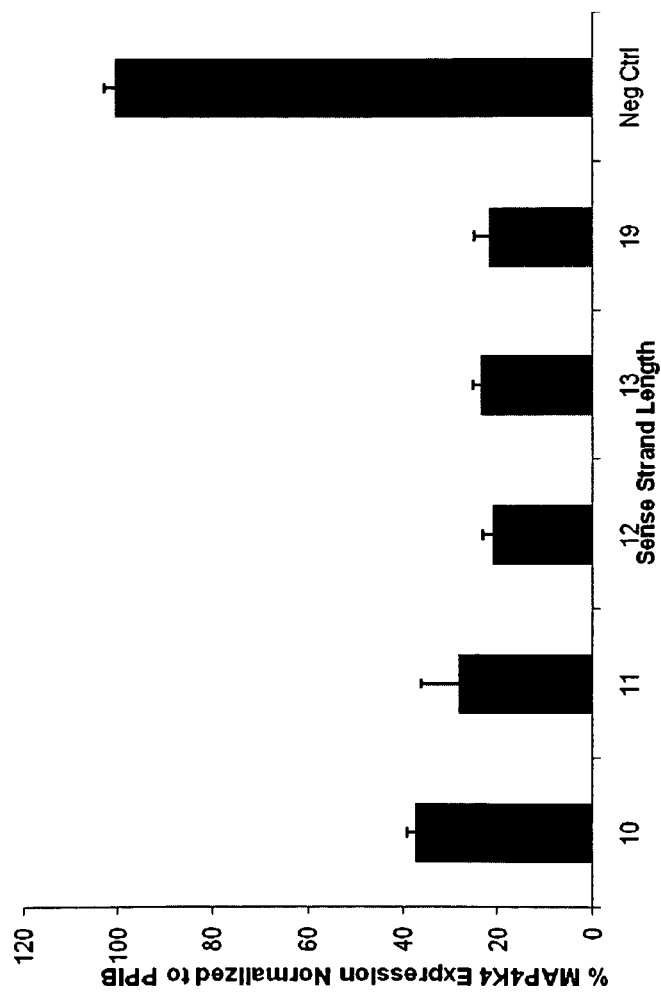
FIG. 90 demonstrates that the guide strand, which has homology to the target only at nucleotides 2-17, resulted in effective RNAi when hybridized with sense strands of different lengths. The compounds were introduced into HeLa cells via lipid mediated transfection.

Optimization of the length of the oligonucleotide was also investigated. FIGS. 25 and 26 reveal that oligonucleotides with a length of 21 nucleotides were more effective than oligonucleotides with a length of 25 nucleotides, indicating that reduction in the size of an RNA molecule can improve efficiency, potentially by assisting in its uptake. Screening was also conducted to optimize the size of the duplex region of double stranded RNA molecules. FIG. 88 reveals that compounds with duplexes of 10 nucleotides were effective in inducing gene silencing. Positioning of the sense strand relative to the guide strand can also be critical for silencing gene expression (FIG. 89). In this assay, a blunt end was found to be most effective. 3' overhangs were tolerated, but 5' overhangs resulted in a complete loss of functionality. The guide strand can be effective in gene silencing when hybridized to a sense strand of varying lengths (FIG. 90). In this assay presented in FIG. 90, the compounds were introduced into HeLa cells via lipid mediated transfection.

The importance of phosphorothioate content of the RNA molecule for unassisted delivery was also investigated. FIG. 27 presents the results of a systematic screen that identified that the presence of at least 2-12 phosphorothioates in the guide strand as being highly advantageous for achieving uptake, with 4-8 being the preferred number. FIG. 27 also shows that presence or absence of phosphorothioate modifications in the sense strand did not alter efficacy.

Figure 28:
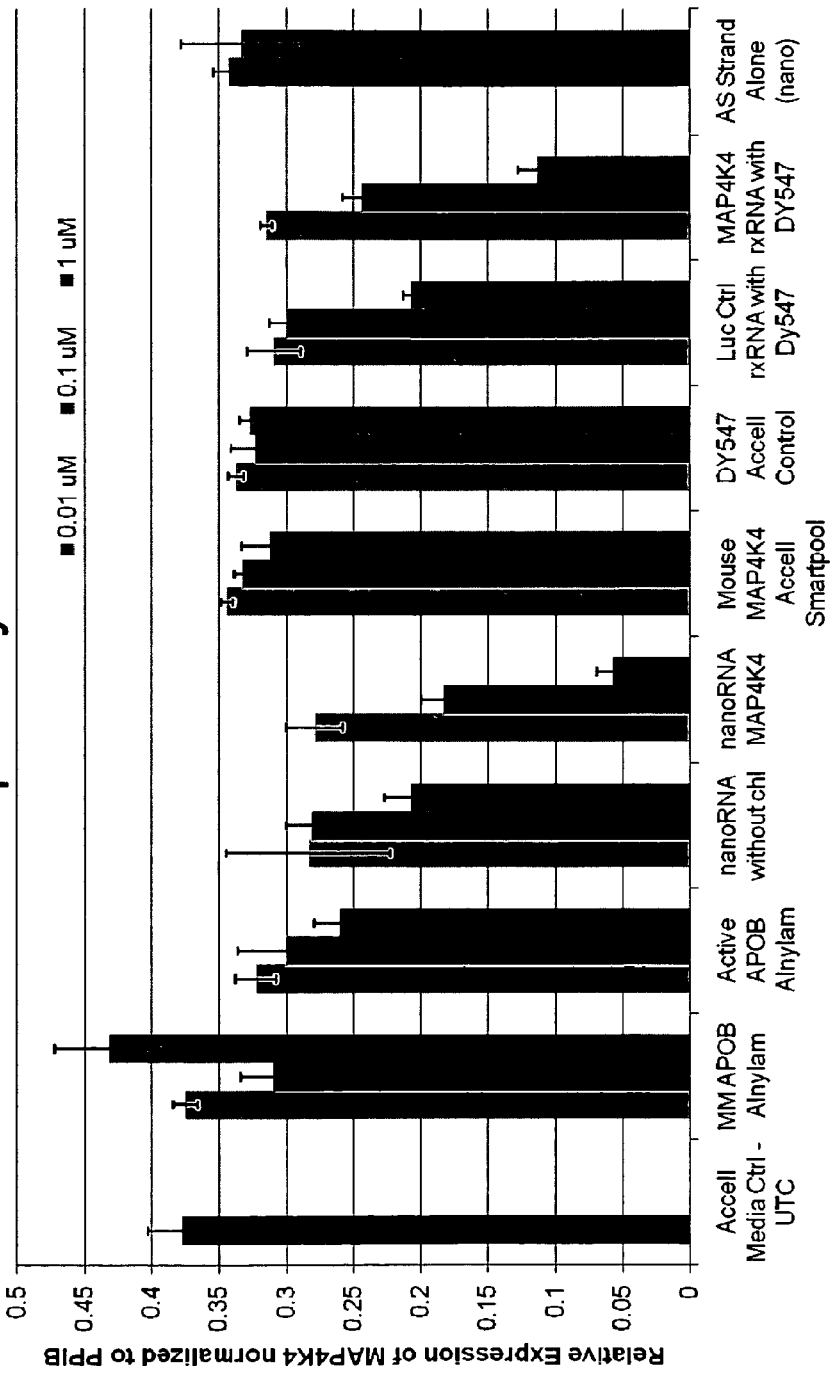
FIG. 28 is a graph showing expression of MAP4K4 in primary mouse hepatocytes following passive uptake transfection of: Accell Media-Ctrl-UTC; MM APOB Alnylam; Active APOB Alnylam; nanoRNA without chl; nanoRNA MAP4K4; Mouse MAP4K4 Accell Smartpool; DY547 Accell Control; Luc Ctrl rxRNA with Dy547; MAP4K4 rxRNA with DY547; and AS Strand Alone (nano).
Figure 29:
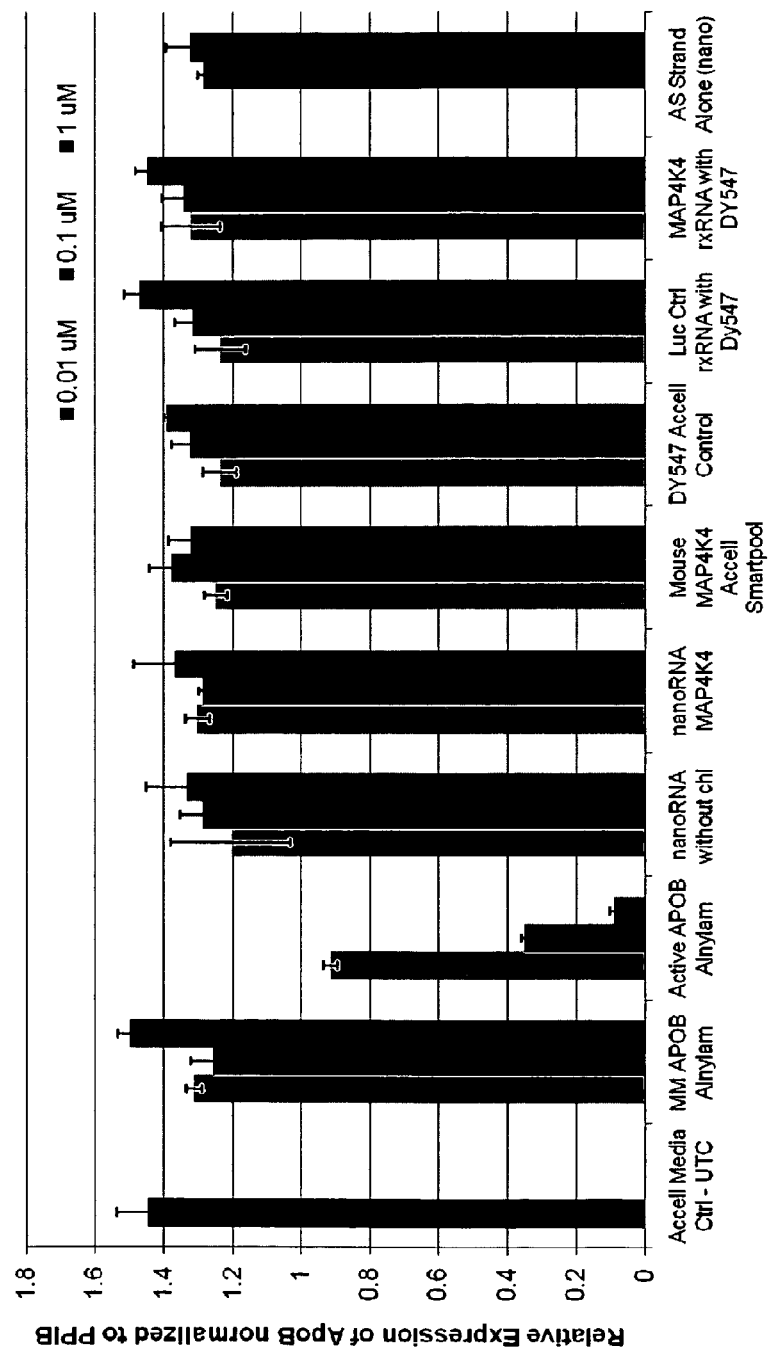
FIG. 29 is a graph showing expression of ApoB in mouse primary hepatocytes following passive uptake transfection of: Accell Media-Ctrl-UTC; MM APOB Alnylam; Active APOB Alnylam; nanoRNA without chl; nanoRNA MAP4K4; Mouse MAP4K4 Accell Smartpool; DY547 Accell Control; Luc Ctrl rxRNA with Dy547; MAP4K4 rxRNA with DY547; and AS Strand Alone (nano).
Figure 30:
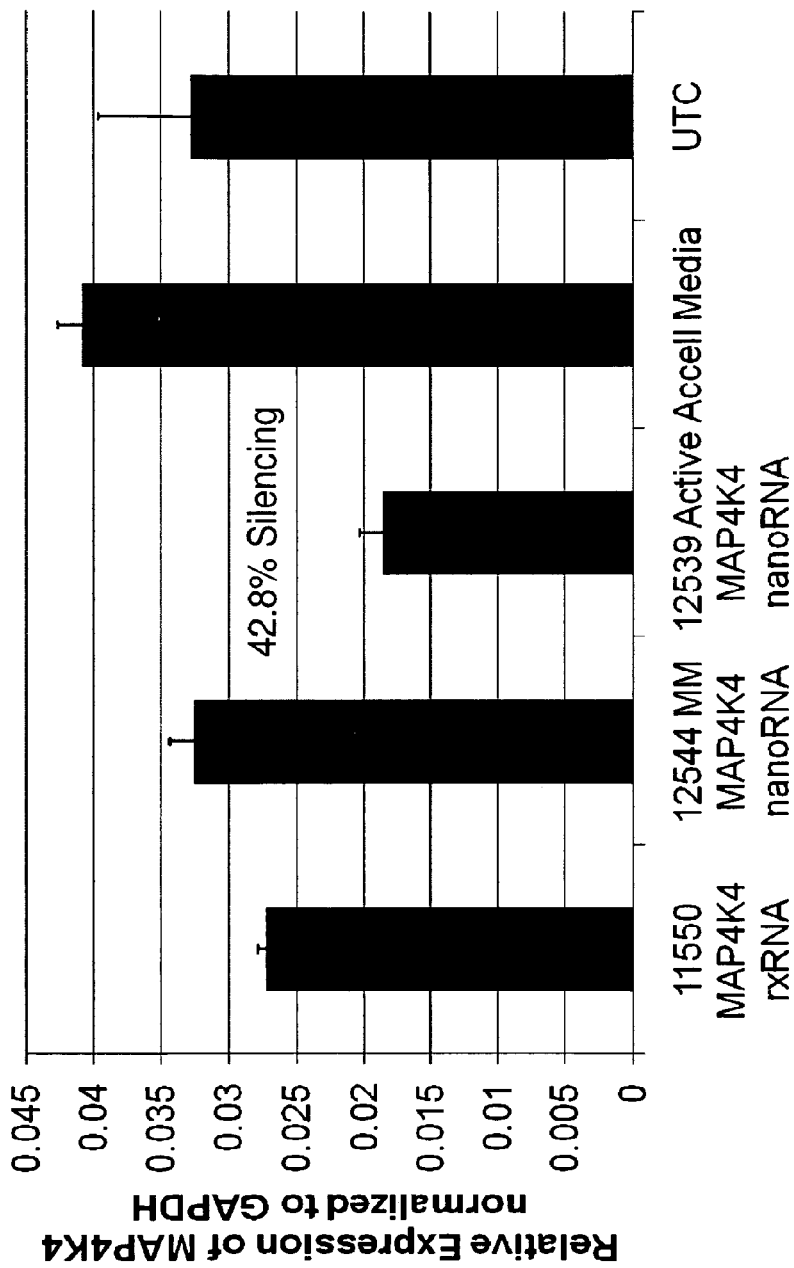
FIG. 30 is a graph showing expression of MAP4K4 in primary human hepatocytes following passive uptake transfection of: 11550 MAP4K4 rxRNA; 12544 MM MAP4K4 nanoRNA; 12539 Active MAP4K4 nanoRNA; Accell Media; and UTC.
Figure 31:
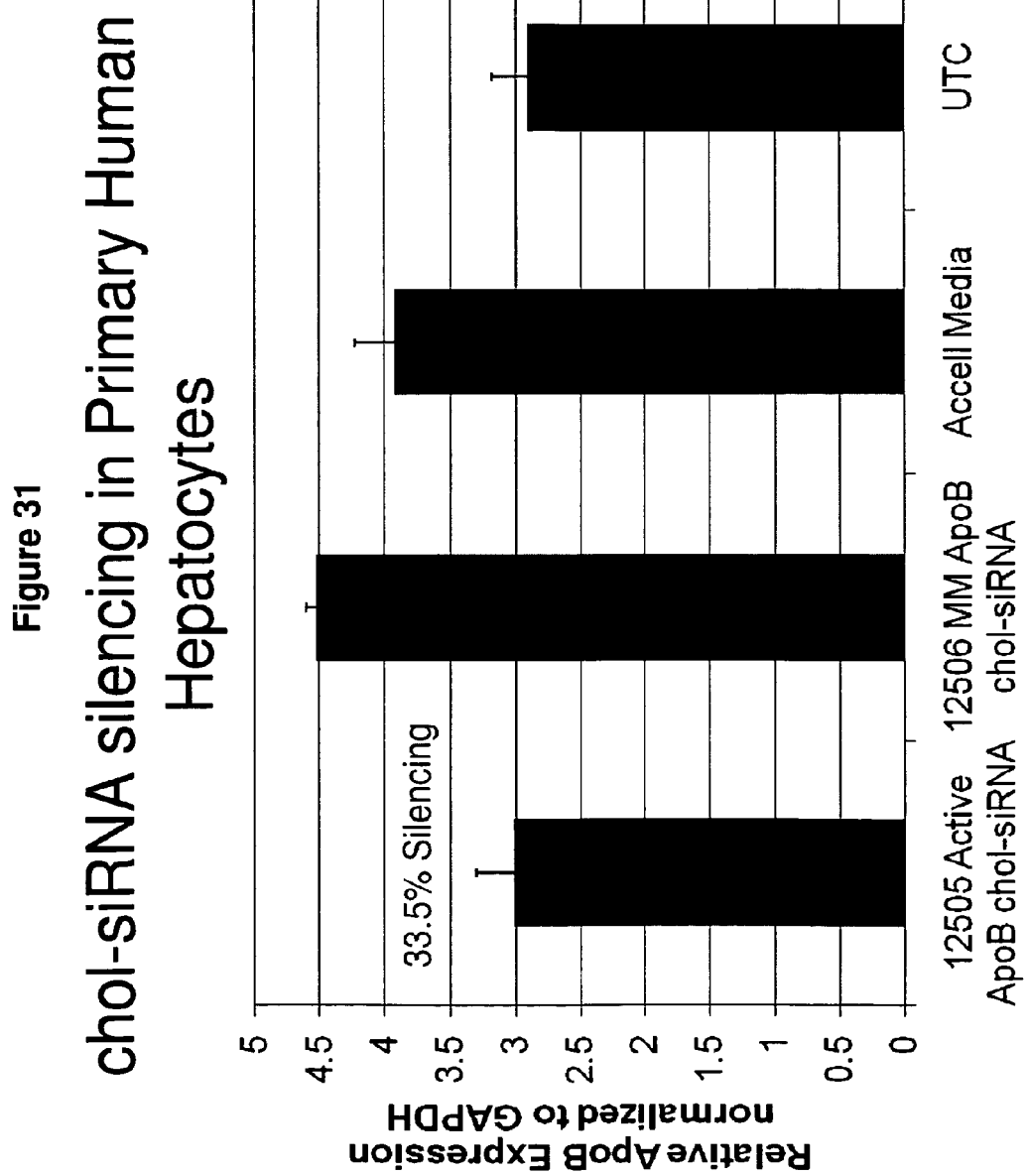
FIG. 31 is a graph showing ApoB expression in primary human hepatoctyes following passive uptake transfection of: 12505 Active ApoB chol-siRNA; 12506 MM ApoB chol-siRNA; Accell Media; and UTC.
Figure 32:
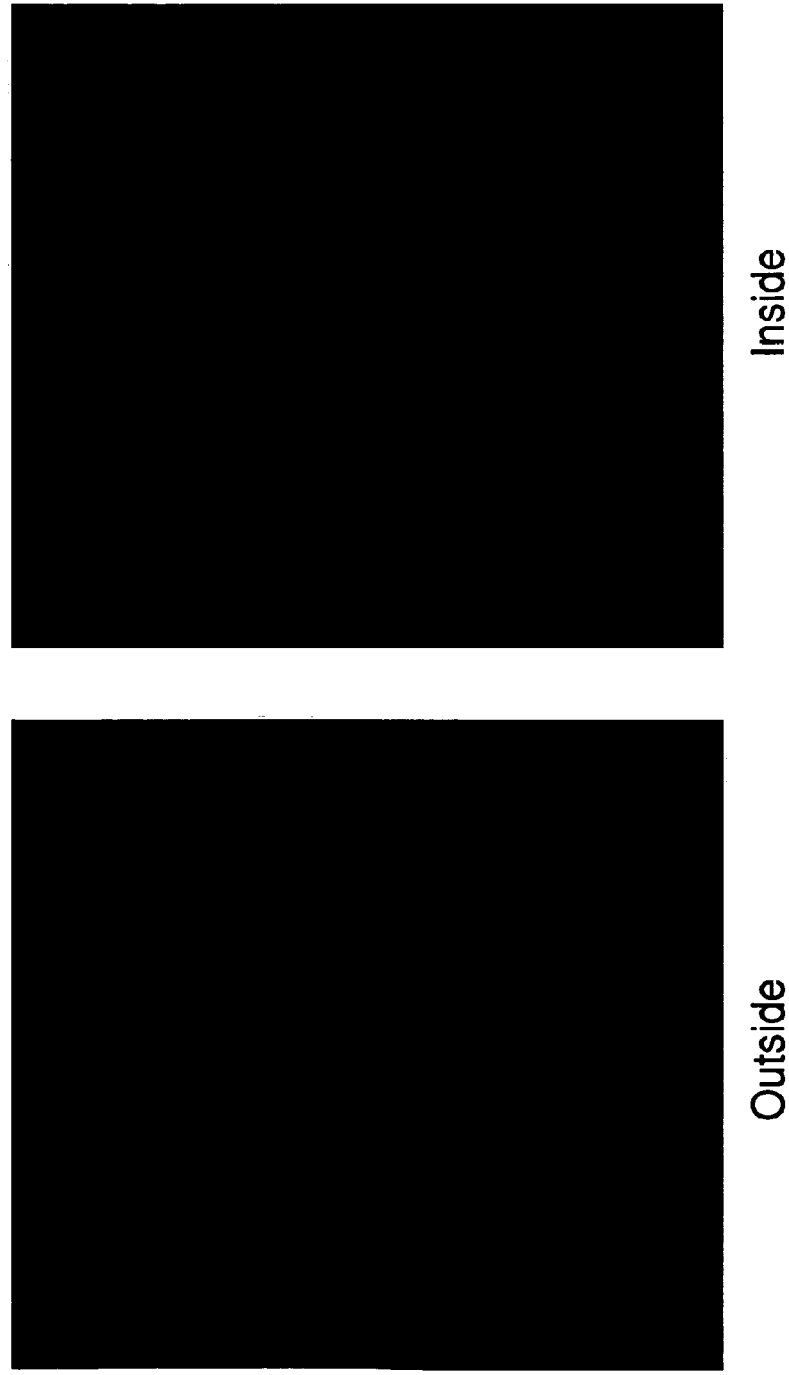
FIG. 32 is an image depicting localization of sd-rxRNA$^{nano}$ localization.
Figure 33:
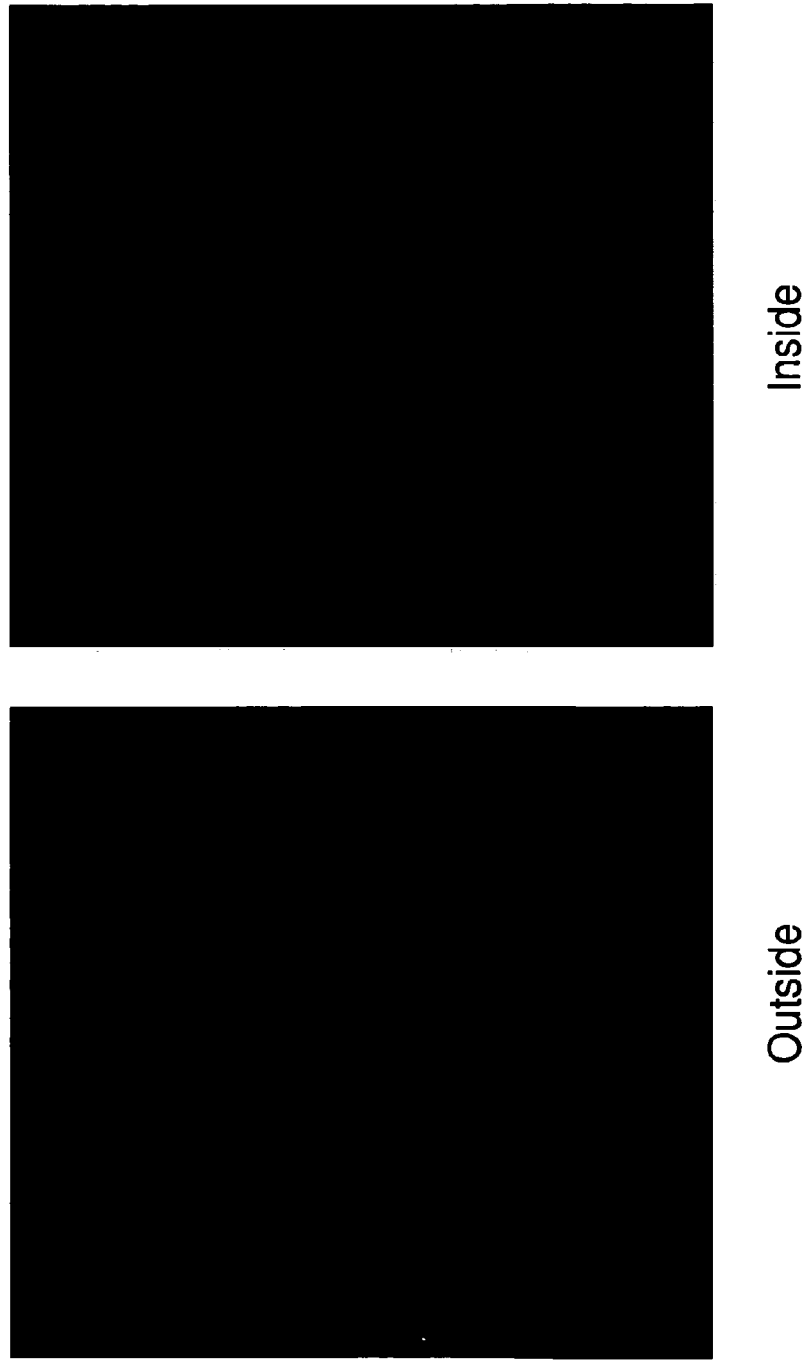
FIG. 33 is an image depicting localization of Chol-siRNA (Alnylam).
Figure 34:
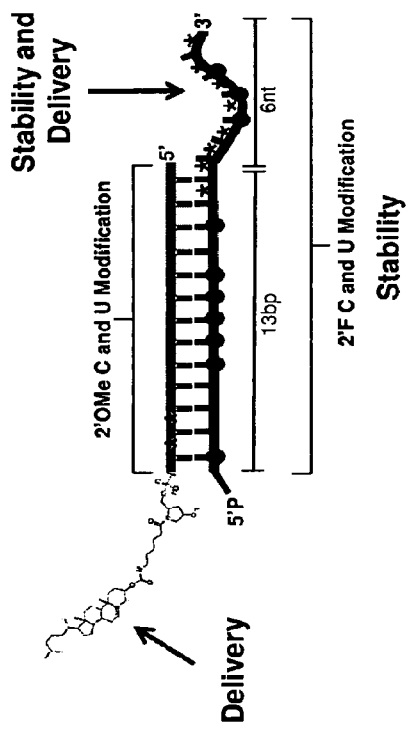
FIG. 34 is a schematic of $1^{st}$ generation (G1) sd-rxRNA$^{nano}$ molecules associated with the invention indicating regions that are targeted for modification, and functions associated with different regions of the molecules.

FIGS. 28-29 reveal the effects of passive uptake of RNA compounds on gene silencing in primary mouse hepatocytes. nanoRNA molecules were found to be highly effective, especially at a concentration of μM (FIG. 28). FIGS. 30 and 31 reveal that the RNA compounds associated with the invention were also effective in gene silencing following passive uptake in primary human hepatocytes. The cellular localization of the RNA molecules associated with the invention was examined and compared to the localization of Chol-siRNA (Alnylam) molecules, as shown in FIGS. 32 and 33.

Figure 35:
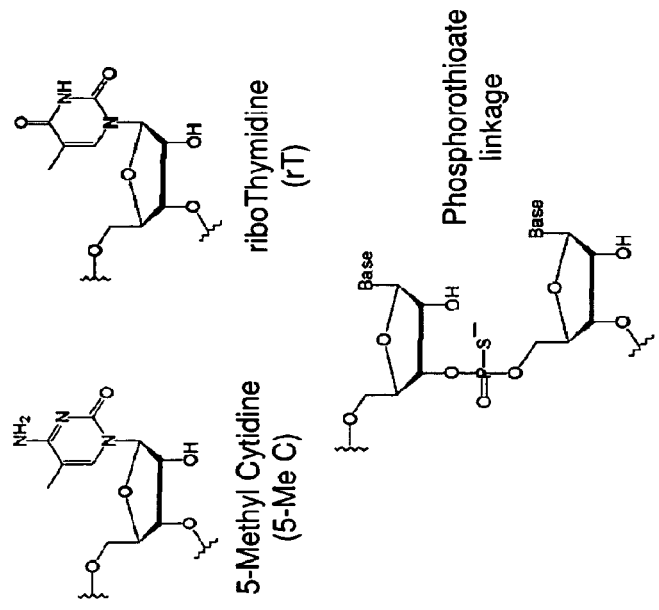
FIG. 35 depicts modification patterns that were screened for optimization of sd-rxRNA$^{nano}$ (G1). The modifications that were screened included, on the guide strand, lengths of 19, 21 and 25 nucleotides, phosphorothioate modifications of 0-18 nucleotides, and replacement of 2'F modifications with 2'OMe, 5 Methyl C and/or ribo Thymidine modifications. Modifications on the sense strand that were screened included nucleotide lengths of 11, 13 and 19 nucleotides, phosphorothiote modifications of 0-4 nucleotides and 2'OMe modifications.
Figure 36:
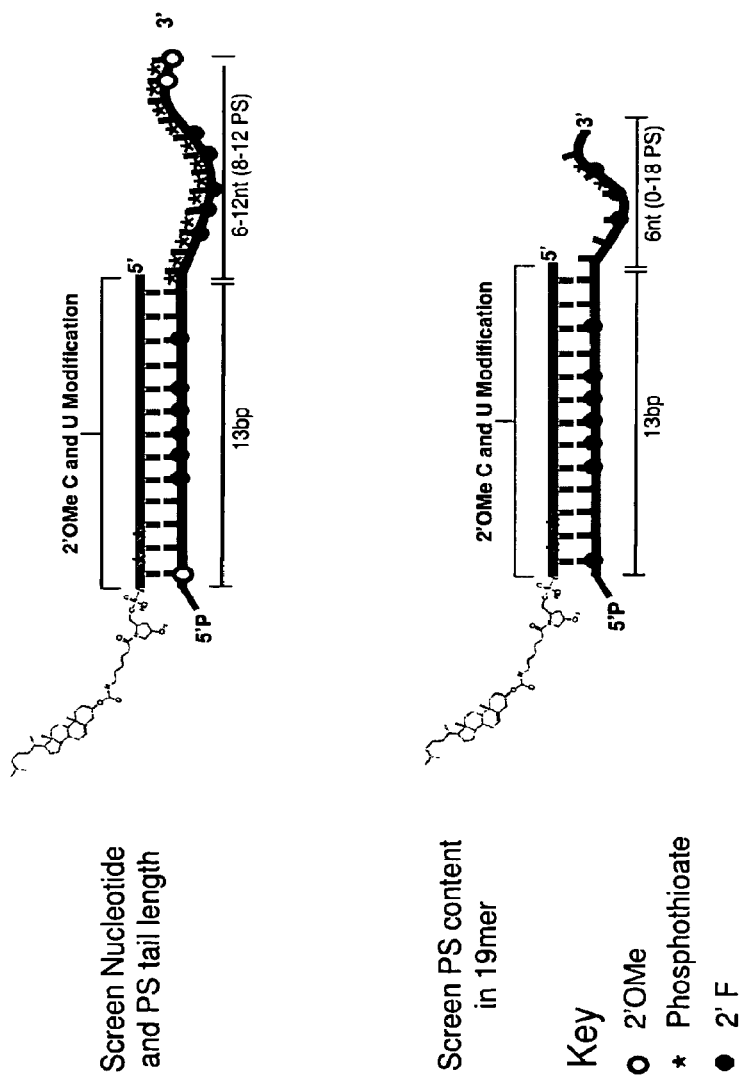
FIG. 36 is a schematic depicting modifications of sd-rxRNA$^{nano}$ that were screened for optimization.
Figure 37:
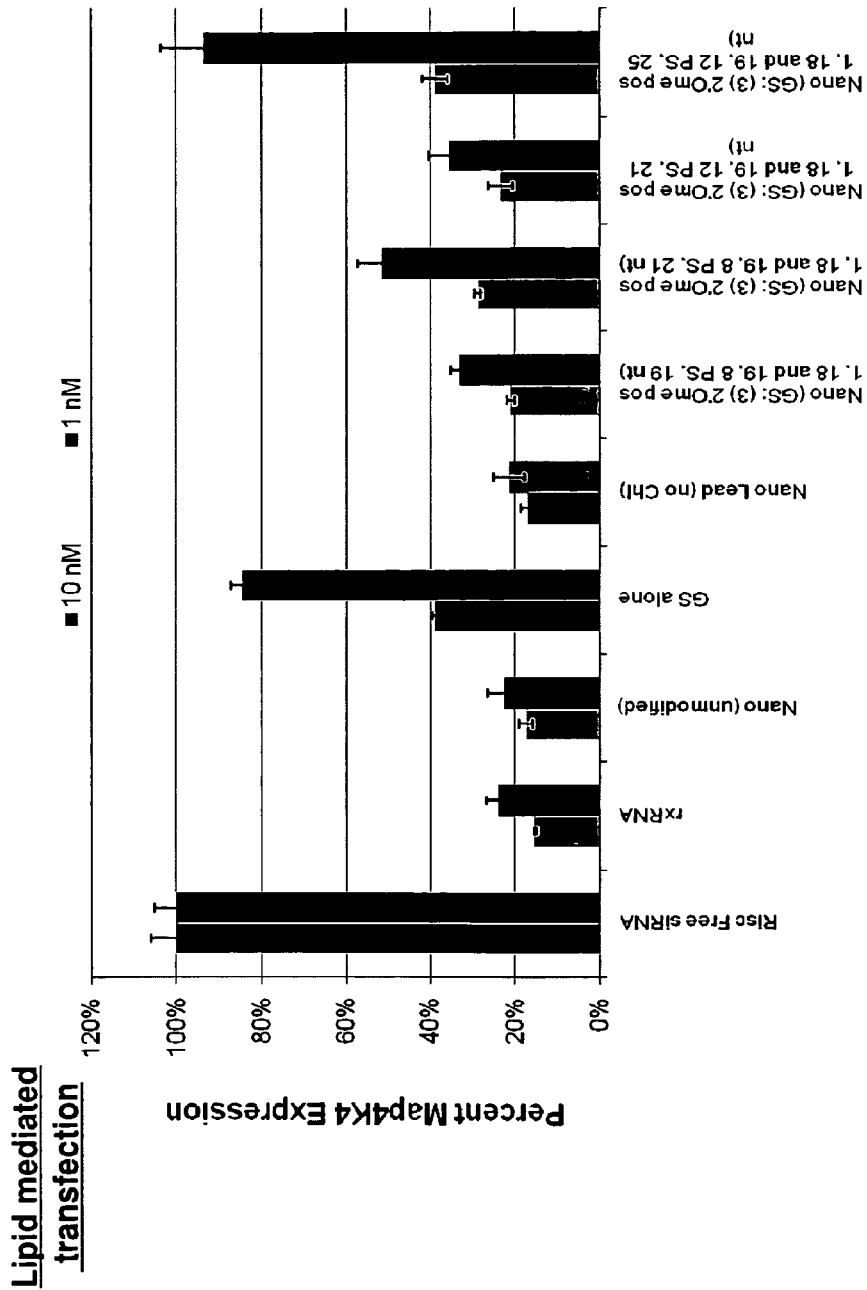
FIG. 37 is a graph showing percent MAP4K4 expression in Hek293 cells following transfection of: Risc Free siRNA; rxRNA; Nano (unmodified); GS alone; Nano Lead (no Chl); Nano (GS: (3) 2'OMe at positions 1, 18, and 19, 8 PS, 19 nt); Nano (GS: (3) 2'OMe at positions 1, 18, and 19, 8 PS, 21 nt); Nano (GS: (3) 2'OMe at positions 1, 18, and 19, 12 PS, 21 nt); and Nano (GS: (3) 2'OMe at positions 1, 18, and 19, 12 PS, 25 nt)
Figure 38:
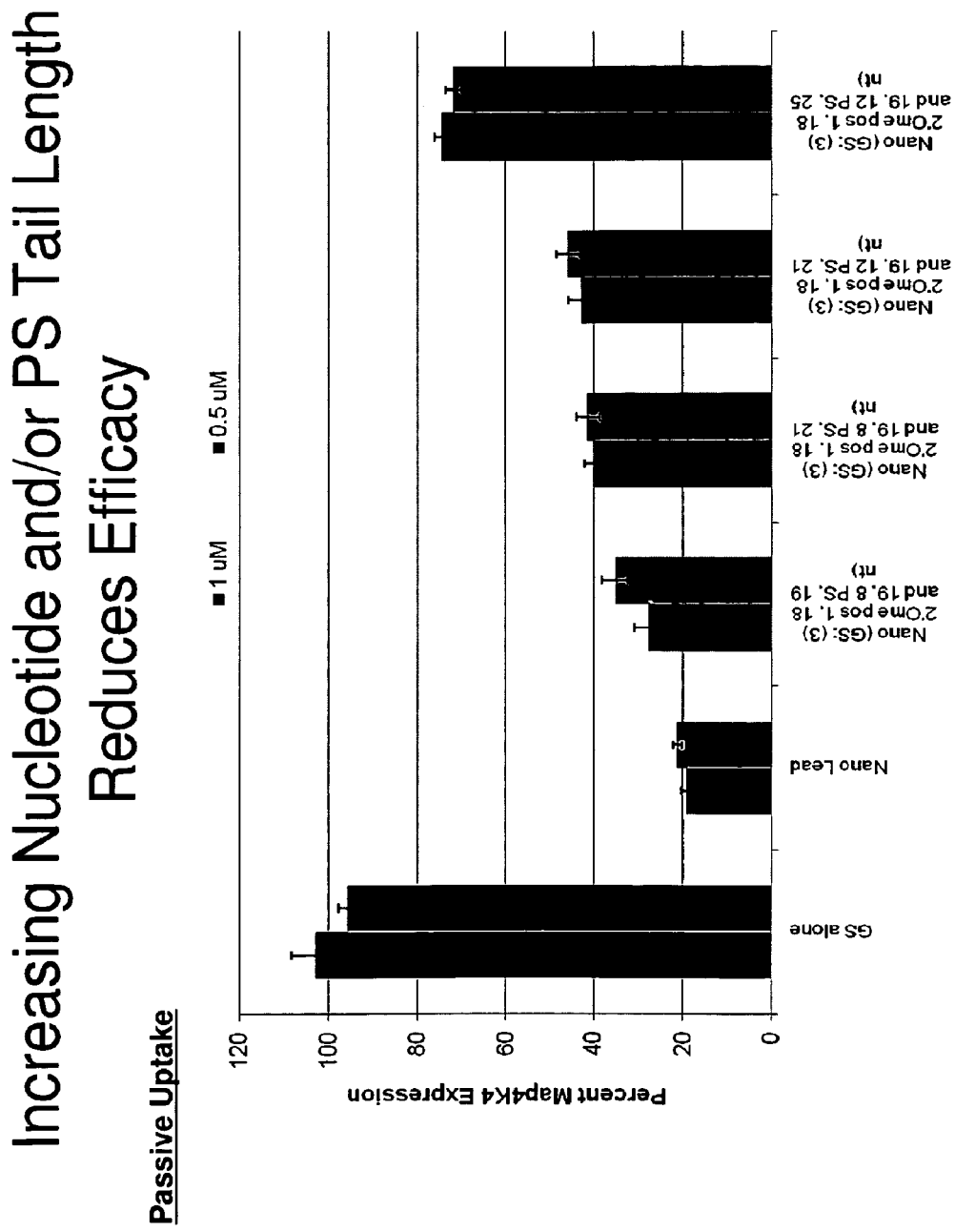
FIG. 38 is a graph showing percent MAP4K4 expression in HeLa cells following passive uptake transfection of: GS alone; Nano Lead; Nano (GS: (3) 2'OMe at positions 1, 18, and 19, 8 PS, 19 nt); Nano (GS: (3) 2'OMe at positions 1, 18, and 19, 8 PS, 21 nt); Nano (GS: (3) 2'OMe at positions 1, 18, and 19, 12 PS, 21 nt); Nano (GS: (3) 2'OMe at positions 1, 18, and 19, 12 PS, 25 nt).
Figure 39:
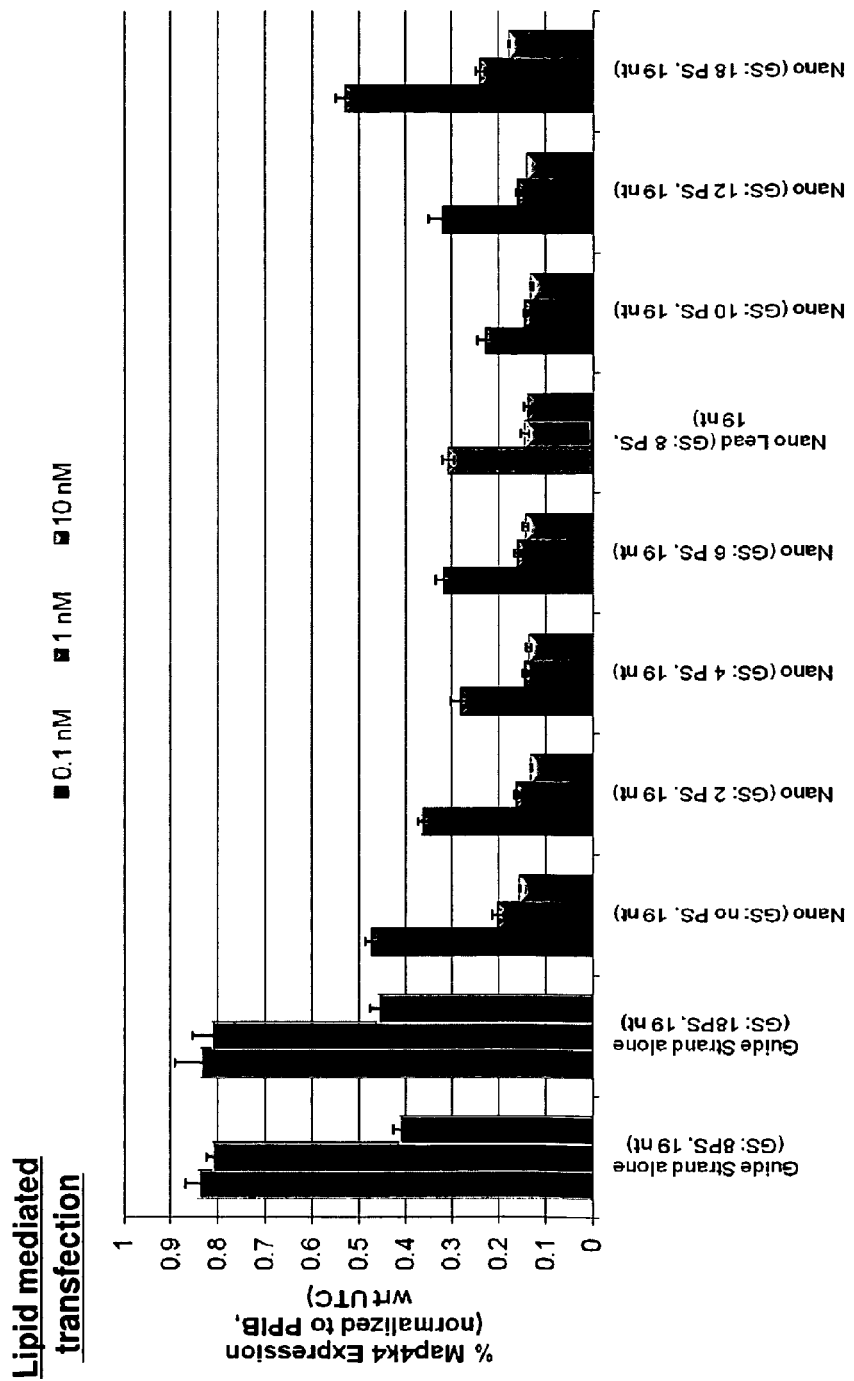
FIG. 39 is a graph showing percent MAP4K4 expression in Hek293 cells following lipid mediated transfection of: Guide Strand alone (GS: 8PS, 19 nt); Guide Strand alone (GS: 18PS, 19 nt); Nano (GS: no PS, 19 nt); Nano (GS: 2 PS, 19 nt); Nano (GS: 4 PS, 19 nt); Nano (GS: 6 PS, 19 nt); Nano Lead (GS: 8 PS, 19 nt); Nano (GS: 10 PS, 19 nt); Nano (GS: 12 PS, 19 nt); and Nano (GS: 18 PS, 19 nt).
Figure 40:
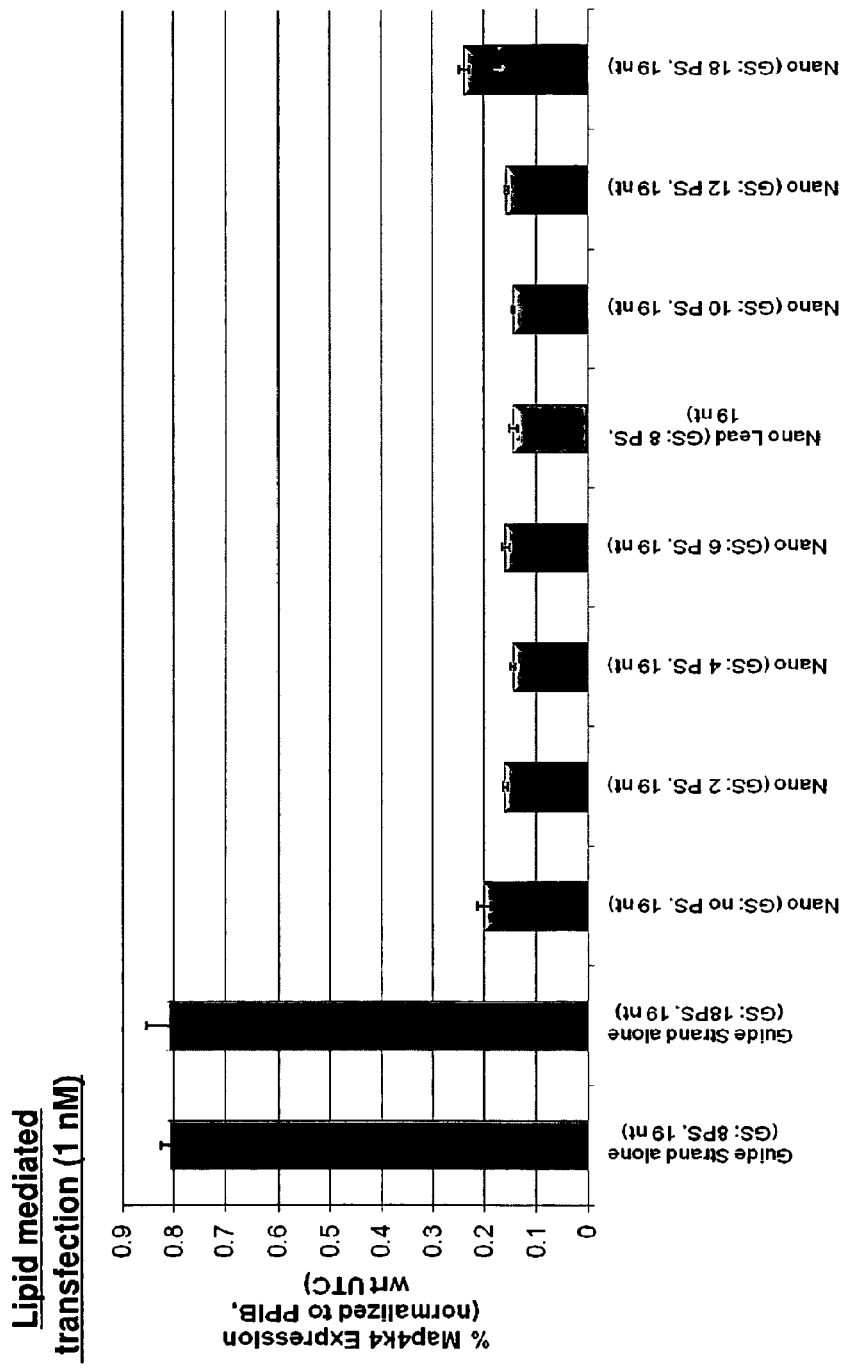
FIG. 40 is a graph showing percent MAP4K4 expression in Hek293 cells following lipid mediated transfection of: Guide Strand alone (GS: 8PS, 19 nt); Guide Strand alone (GS: 18PS, 19 nt); Nano (GS: no PS, 19 nt); Nano (GS: 2 PS, 19 nt); Nano (GS: 4 PS, 19 nt); Nano (GS: 6 PS, 19 nt); Nano Lead (GS: 8 PS, 19 nt); Nano (GS: 10 PS, 19 nt); Nano (GS: 12 PS, 19 nt); and Nano (GS: 18 PS, 19 nt).
Figure 41:
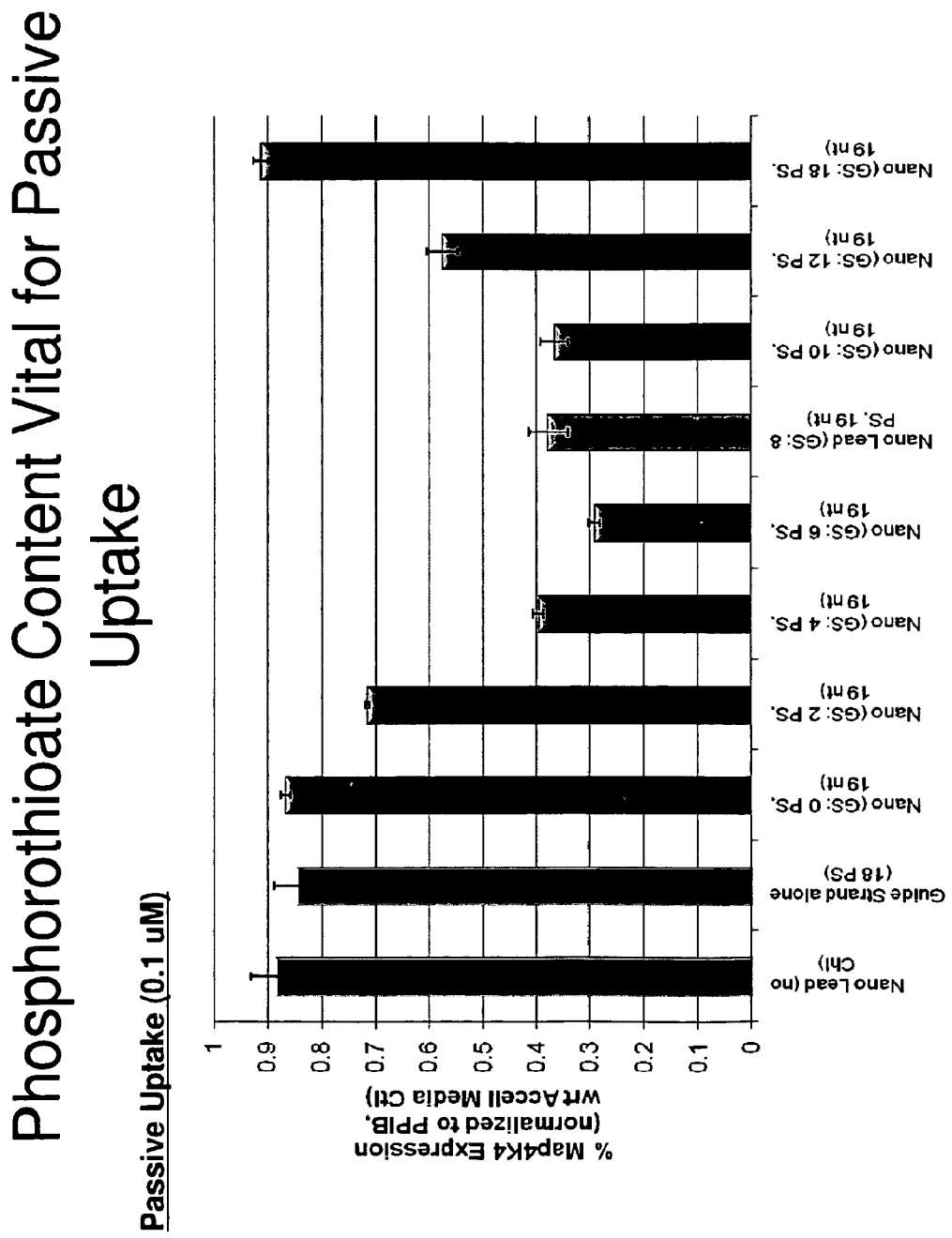
FIG. 41 is a graph showing percent MAP4K4 expression in HeLa cells following passive uptake transfection of: Nano Lead (no Chl); Guide Strand alone (18 PS); Nano (GS: 0 PS, 19 nt); Nano (GS: 2 PS, 19 nt); Nano (GS: 4 PS, 19 nt); Nano (GS: 6 PS, 19 nt); Nano Lead (GS: 8 PS, 19 nt); Nano (GS: 10 PS, 19 nt); Nano (GS: 12 PS, 19 nt); and Nano (GS: 18 PS, 19 nt).
Figure 42:
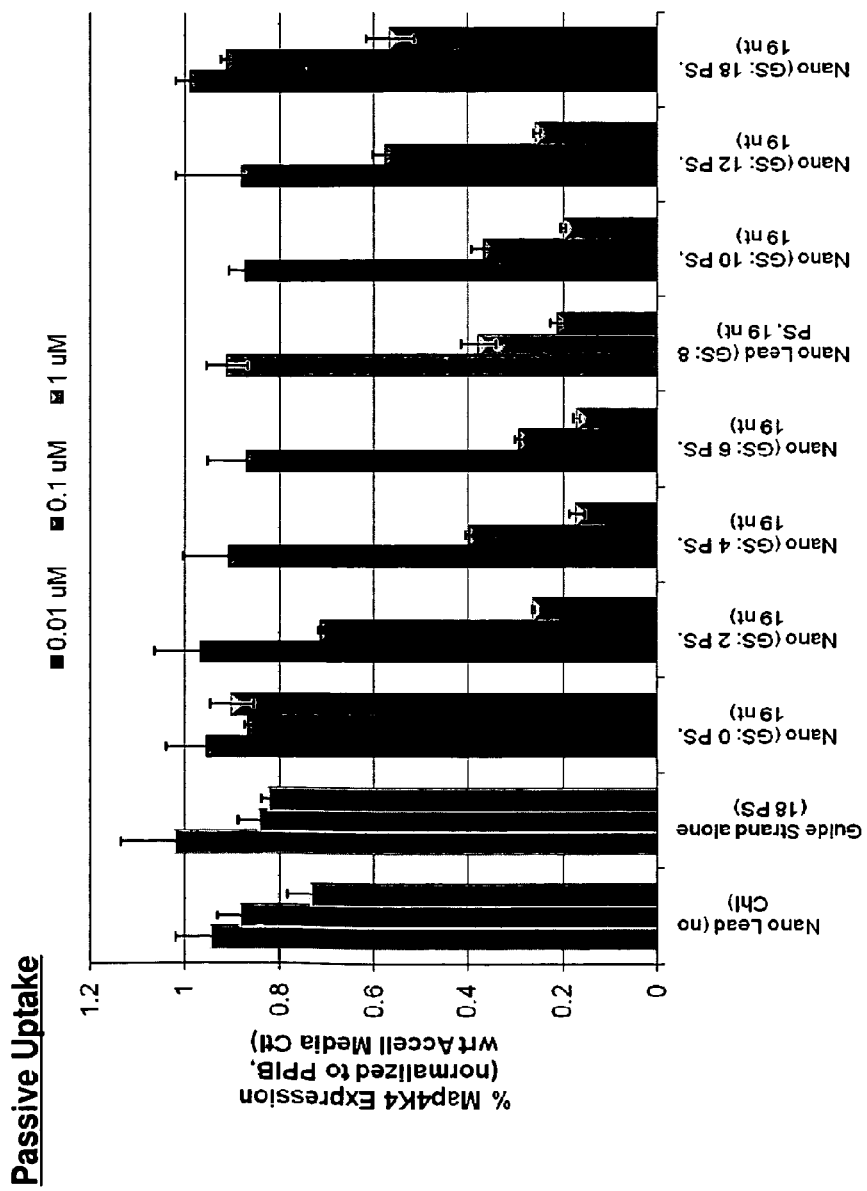
FIG. 42 is a graph showing percent MAP4K4 expression in HeLa cells following passive uptake transfection of: Nano Lead (no Chl); Guide Strand alone (18 PS); Nano (GS: 0 PS, 19 nt); Nano (GS: 2 PS, 19 nt); Nano (GS: 4 PS, 19 nt); Nano (GS: 6 PS, 19 nt); Nano Lead (GS: 8 PS, 19 nt); Nano (GS: 10 PS, 19 nt); Nano (GS: 12 PS, 19 nt); and Nano (GS: 18 PS, 19 nt).

A summary of 1$^{st}$ generation sd-rxRNA molecules is presented in FIG. 21. Chemical modifications were introduced into the RNA molecules, at least in part, to increase potency, such as through optimization of nucleotide length and phosphorothioate content, to reduce toxicity, such as through replacing 2'F modifications on the guide strand with other modifications, to improve delivery such as by adding or conjugating the RNA molecules to linker and sterol modalities, and to improve the ease of manufacturing the RNA molecules. FIG. 35 presents schematic depictions of some of the chemical modifications that were screened in 1$^{st}$ generation molecules. Parameters that were optimized for the guide strand included nucleotide length (e.g., 19, 21 and 25 nucleotides), phosphorothioate content (e.g., 0-18 phosphorothioate linkages) and replacement of 2'F groups with 2'OMe and 5 Me C or riboThymidine. Parameters that were optimized for the sense strand included nucleotide length (e.g., 11, 13 and 19 nucleotides), phosphorothioate content (e.g., 0-4 phosphorothioate linkages), and 2'OMe modifications. FIG. 36 summarizes parameters that were screened. For example, the nucleotide length and the phosphorothioate tail length were modified and screened for optimization, as were the additions of 2'OMe C and U modifications. Guide strand length and the length of the phosphorothioate modified stretch of nucleotides were found to influence efficacy (FIGS. 37-38). Phosphorothioate modifications were tolerated in the guide strand and were found to influence passive uptake (FIGS. 39-42).

Figure 44:
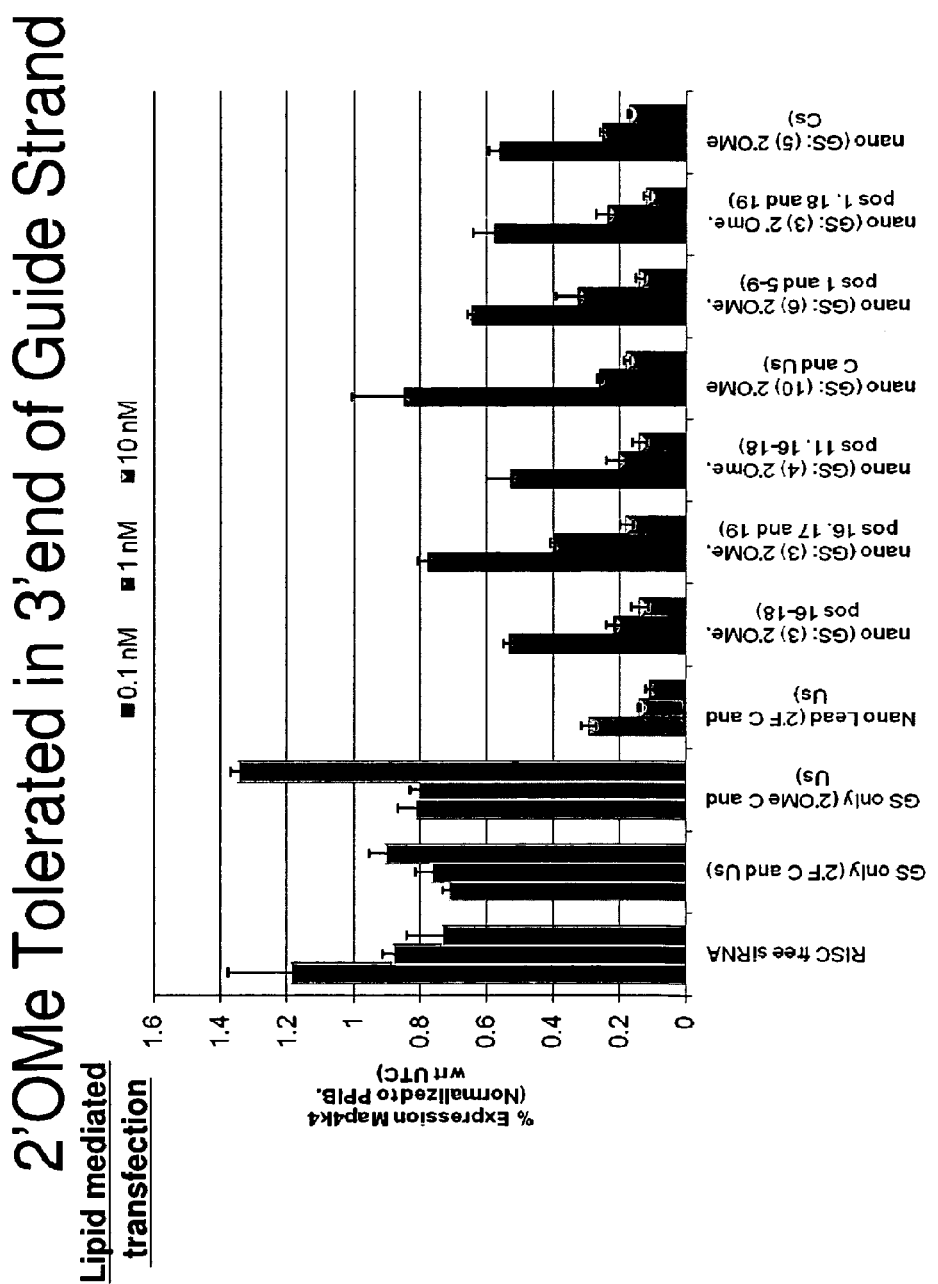
FIG. 44 is a graph showing percent MAP4K4 expression in Hek293 cells following reverse transfection of: RISC free siRNA; GS only (2'F C and Us); GS only (2'OMe C and Us); Nano Lead (2'F C and Us); nano (GS: (3) 2'OMe, positions 16-18); nano (GS: (3) 2'OMe, positions 16, 17 and 19); nano (GS: (4) 2'OMe, positions 11, 16-18); nano (GS: (10) 2'OMe, C and Us); nano (GS: (6) 2'OMe, positions 1 and 5-9); nano (GS: (3) 2'OMe, positions 1, 18 and 19); and nano (GS: (5) 2'OMe Cs).
Figure 45:
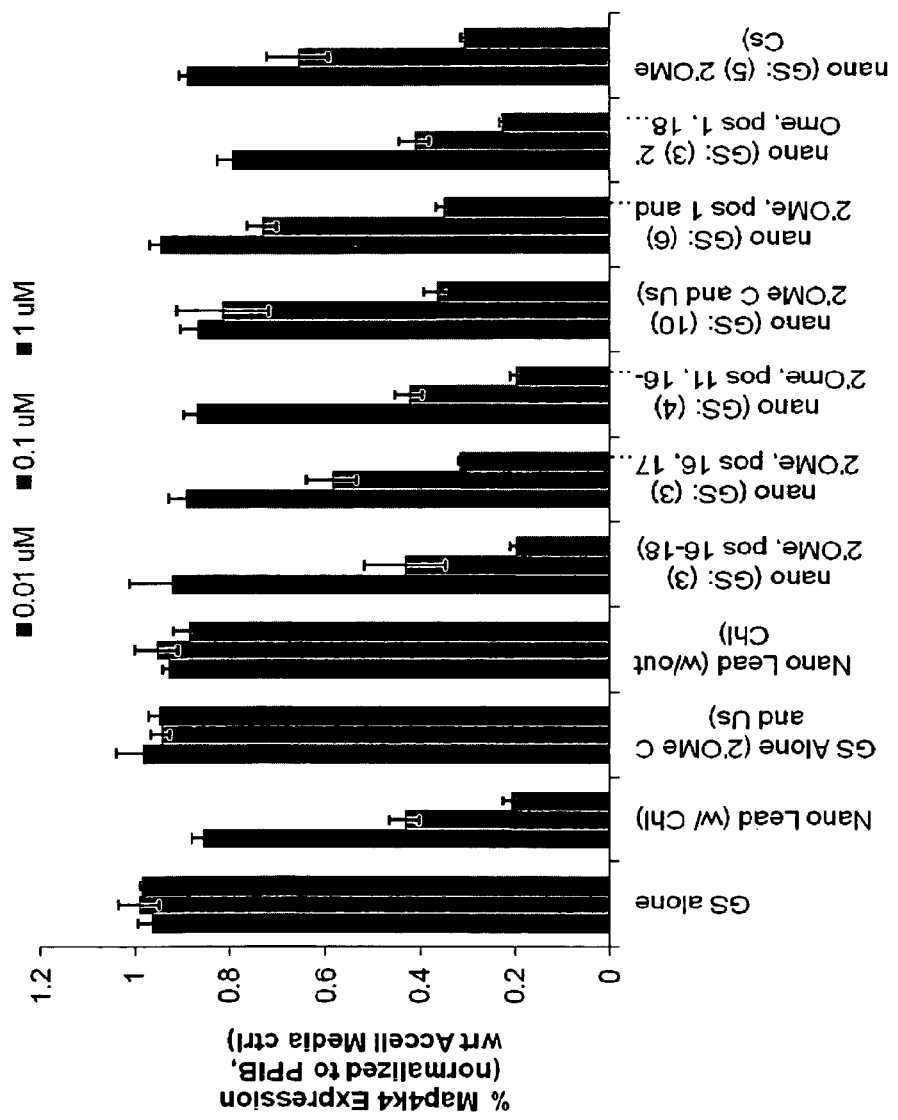
FIG. 45 is a graph demonstrating efficacy of various chemical modification patterns. In particular, 2-OMe modification in positions 1 and 11-18 was well tolerated. 2'OMe modifications in the seed area resulted in a slight reduction of efficacy (but were still highly efficient). Ribo-modifications in the seed were well tolerated. This data enabled the generation of self delivering compounds with reduced or no 2'F modifications. This is significant because 2'F modifications may be associated with toxicity in vivo.

FIG. 43 presents a schematic revealing guide strand chemical modifications that were screened. FIGS. 44 and 45 reveal that 2'OMe modifications were tolerated in the 3' end of the guide strand. In particular, 2'OMe modifications in positions 1 and 11-18 were well tolerated. The 2'OMe modifications in the seed area were tolerated but resulted in slight reduction of efficacy. Ribo-modifications in the seed were also well tolerated. These data indicate that the molecules associated with the invention offer the significant advantage of having reduced or no 2'F modification content. This is advantageous because 2'F modifications are thought to generate toxicity in vivo. In some instances, a complete substitution of 2'F modifications with 2'OMe was found to lead to some reduction in potency. However, the 2' OMe substituted molecules were still very active. A molecule with 50% reduction in 2'F content (including at positions 11, 16-18 which were changed to 2'OMe modifications), was found to have comparable efficacy to a compound with complete 2'F C and U modification. 2'OMe modification in position was found in some instances to reduce efficacy, although this can be at least partially compensated by 2'OMe modification in position 1 (with chemical phosphate). In some instances, 5 Me C and/or ribothymidine substitution for 2'F modifications led to a reduction in passive uptake efficacy, but increased potency in lipid mediated transfections compared to 2'F modifications. Optimization results for lipid mediated transfection were not necessarily the same as for passive uptake.

Figure 46:
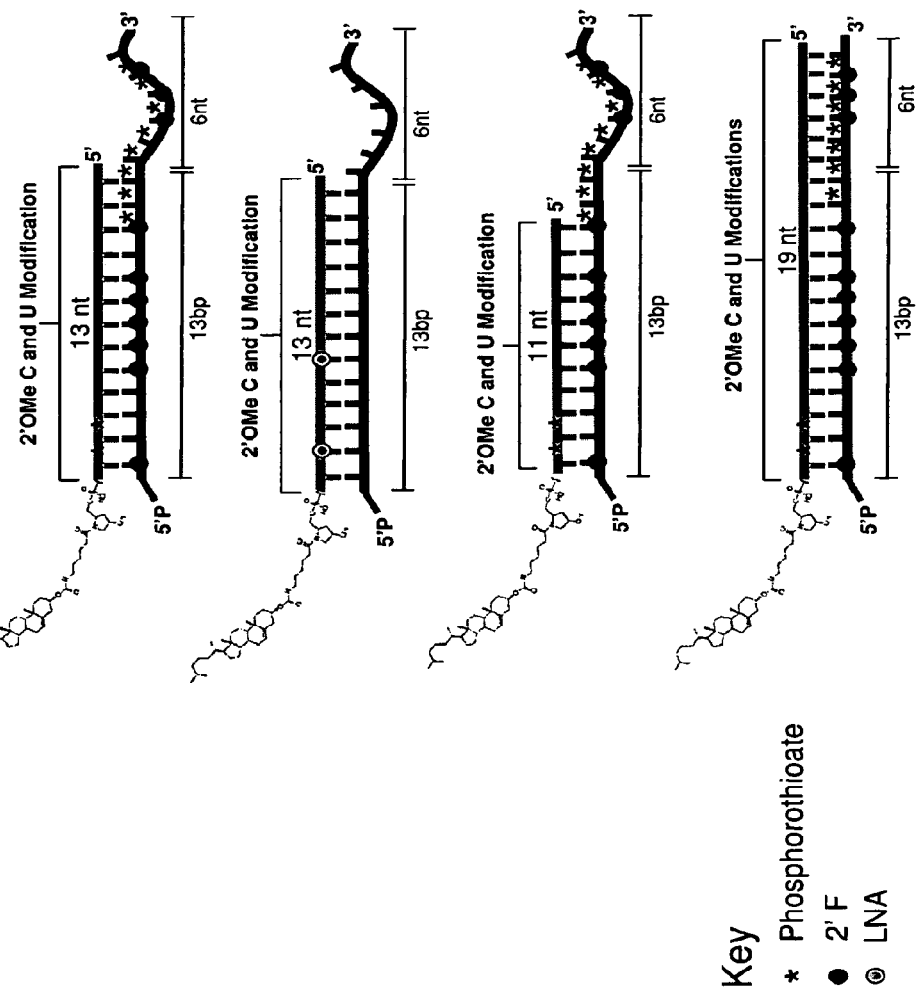
FIG. 46 is a schematic depicting sense strand modifications.
Figure 47:
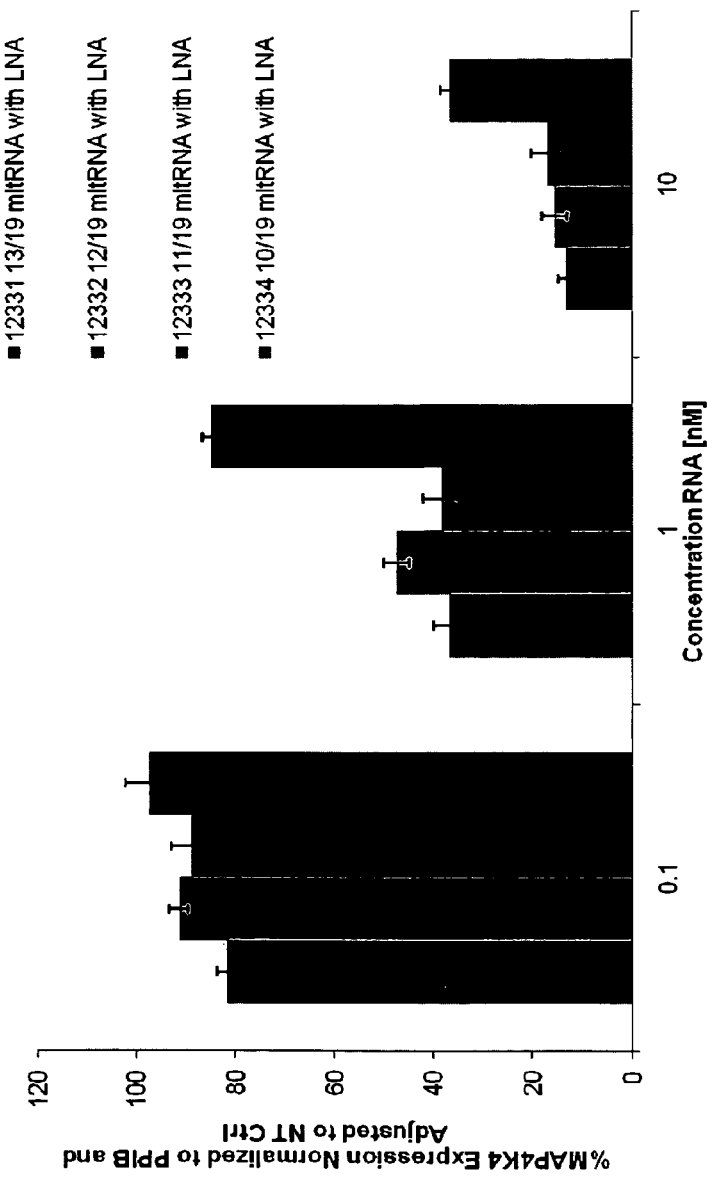
FIG. 47 is a graph demonstrating sense strand length optimization. A sense strand length between 10-15 bases was found to be optimal in this assay. Increasing sense strand length resulted in a reduction of passive uptake of these compounds but may be tolerated for other compounds. Sense strands containing LNA modification demonstrated similar efficacy to non-LNA containing compounds. In some embodiments, the addition of LNA or other thermodynamically stabilizing compounds can be beneficial, resulting in converting non-functional sequences into functional sequences.
Figure 48:
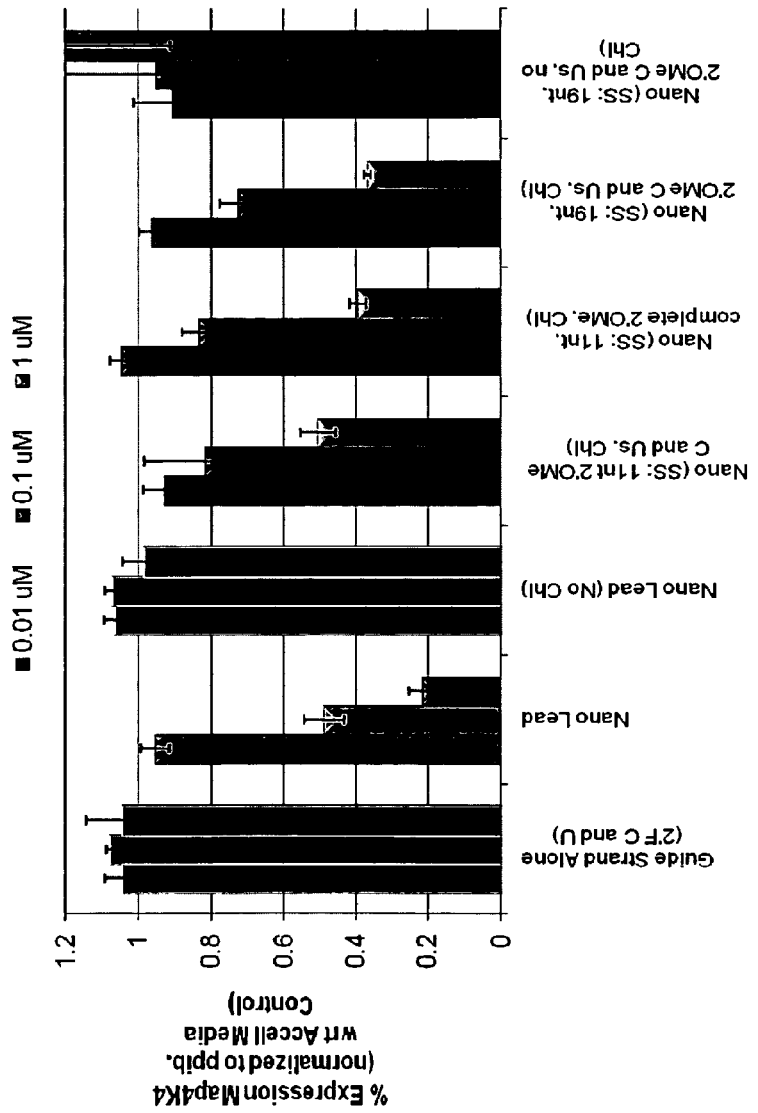
FIG. 48 is a graph showing percent MAP4K4 expression in HeLa cells following passive uptake transfection of: Guide Strand Alone (2'F C and U); Nano Lead; Nano Lead (No Chl); Nano (SS: 11 nt 2'OMe C and Us, Chl); Nano (SS: 11 nt, complete 2'OMe, Chl); Nano (SS: 19 nt, 2'OMe C and Us, Chl); Nano (SS: 19 nt, 2'OMe C and Us, no Chl).
Figure 49:
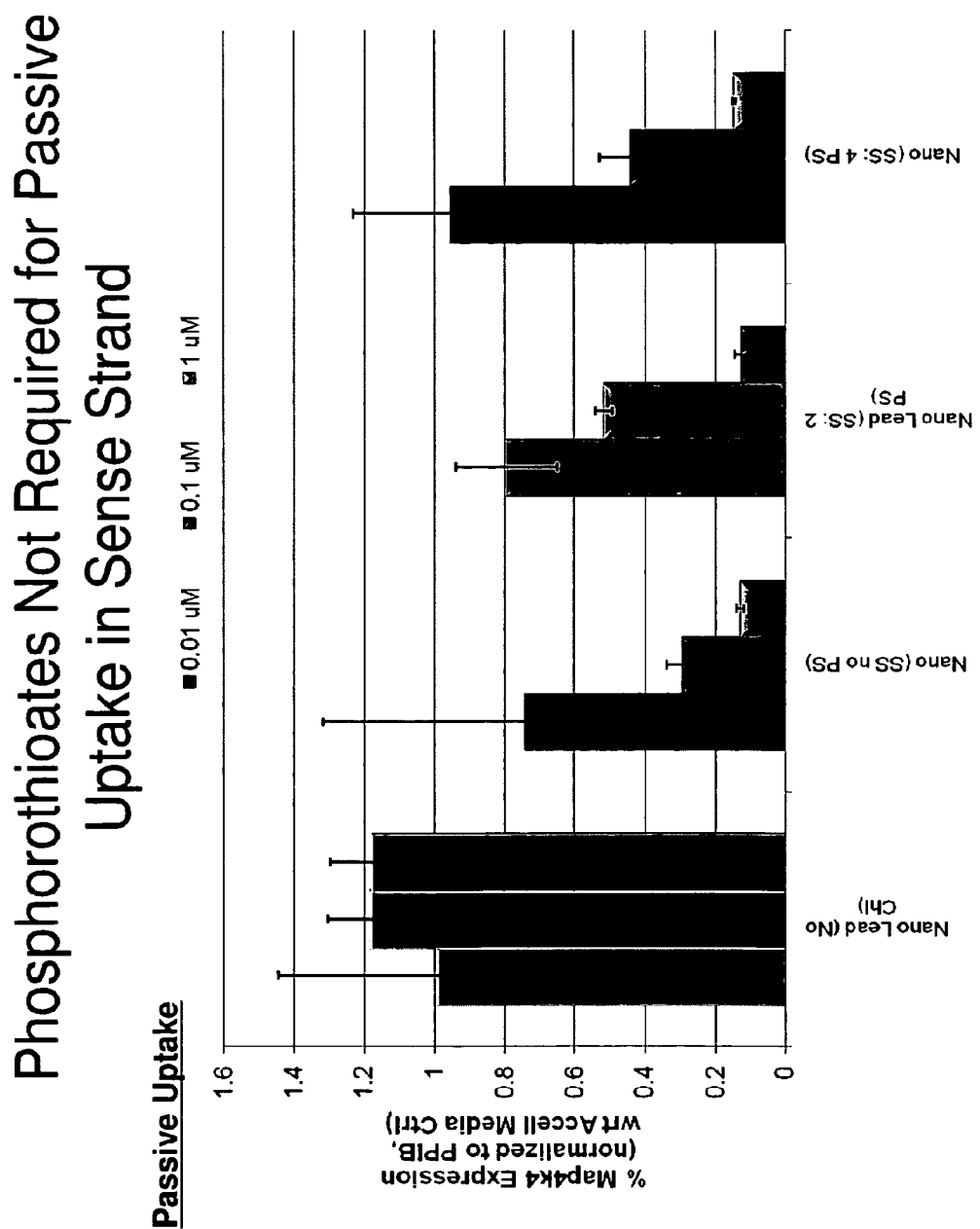
FIG. 49 is a graph showing percent MAP4K4 expression in HeLa cells following passive uptake transfection of: Nano Lead (No Chl); Nano (SS no PS); Nano Lead (SS:2 PS); Nano (SS:4 PS).

Modifications to the sense strand were also developed and tested, as depicted in FIG. 46. FIG. 47 reveals that in some instances, a sense strand length between 10-15 bases was found to be optimal. For the molecules tested in FIG. 47, an increase in the sense strand length resulted in reduction of passive uptake, however an increase in sense strand length may be tolerated for some compounds. FIG. 47 also reveals that LNA modification of the sense strand demonstrated similar efficacy to non-LNA containing compounds. In general, the addition of LNA or other thermodynamically stabilizing compounds has been found to be beneficial, in some instances resulting in converting non-functional sequences to functional sequences. FIG. 48 also presents data on sense strand length optimization, while FIG. 49 shows that phosphorothioate modification of the sense strand is not required for passive uptake.

Figure 50:
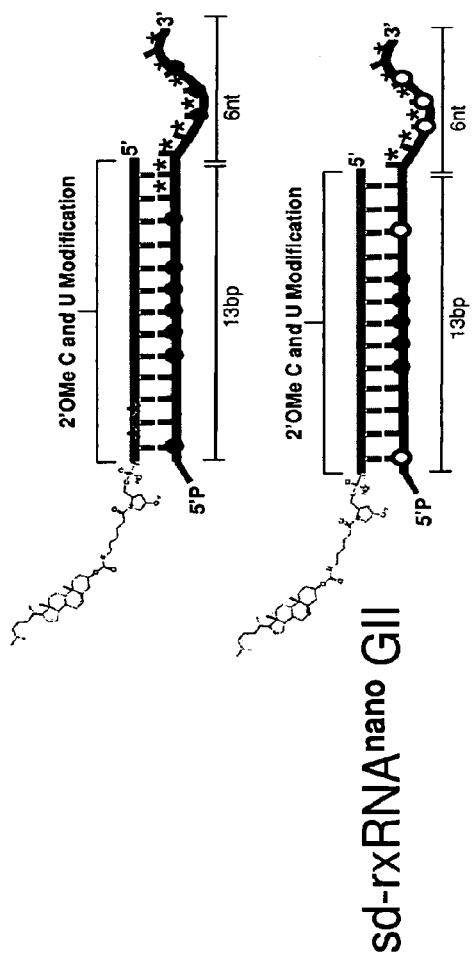
FIG. 50 is a schematic depicting a sd-rxRNA$^{nano}$ second generation (GII) lead molecule.
Figure 52:
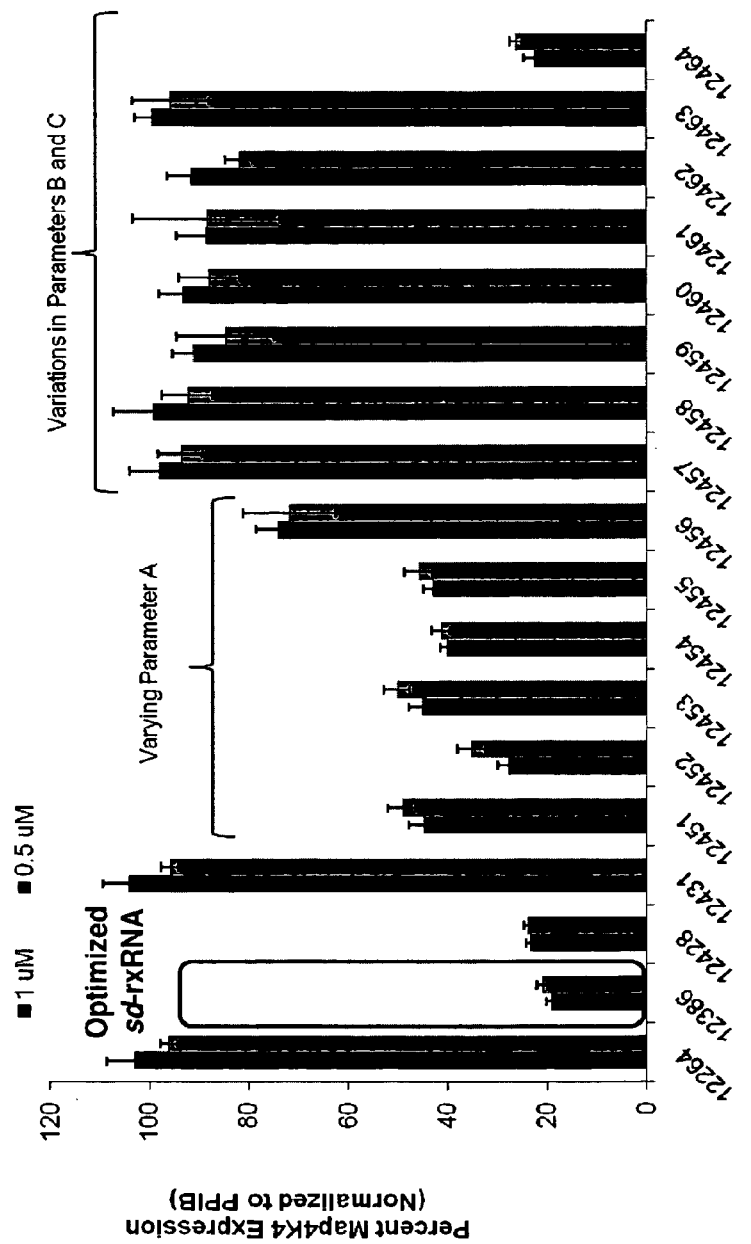
FIG. 52 is a graph showing percent MAP4K4 expression in HeLa cells in the presence of optimized sd-rxRNA molecules.
Figure 53:
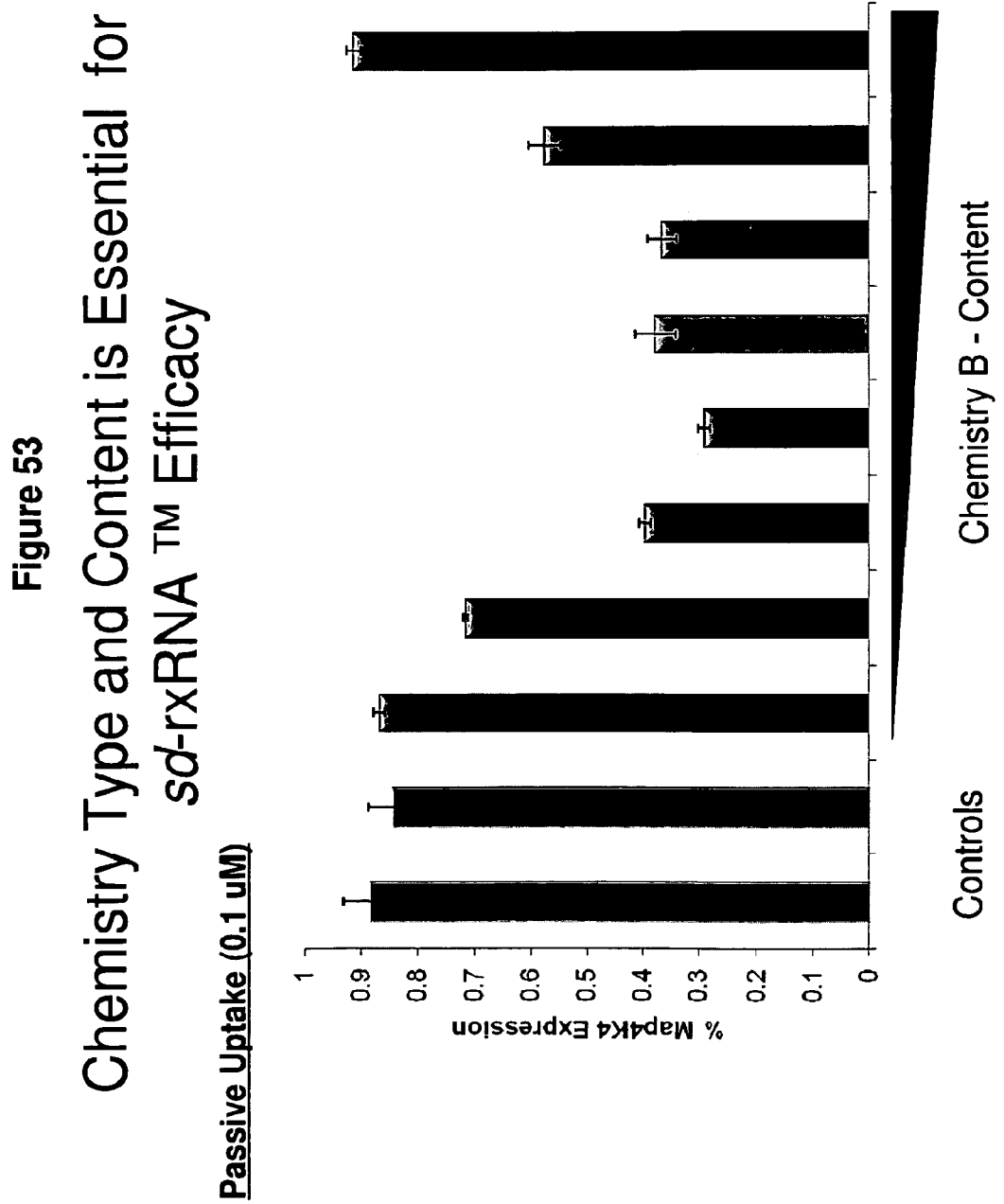
FIG. 53 is a graph depicting the relevance of chemistry content in optimization of sd-rxRNA efficacy.

Based on the above-described optimization experiments, $2^{nd}$ generation RNA molecules were developed. As shown in FIG. 50, these molecules contained reduced phosphorothioate modification content and reduced 2'F modification content, relative to $1^{st}$ generation RNA molecules. Significantly, these RNA molecules exhibit spontaneous cellular uptake and efficacy without a delivery vehicle (FIG. 51). These molecules can achieve self-delivery (i.e., with no transfection reagent) and following self-delivery can exhibit nanomolar activity in cell culture. These molecules can also be delivered using lipid-mediated transfection, and exhibit picomolar activity levels following transfection. Significantly, these molecules exhibit highly efficient uptake, 95% by most cells in cell culture, and are stable for more than three days in the presence of 100% human serum. These molecules are also highly specific and exhibit little or no immune induction. FIGS. 52 and 53 reveal the significance of chemical modifications and the configurations of such modifications in influencing the properties of the RNA molecules associated with the invention.

Figure 54:
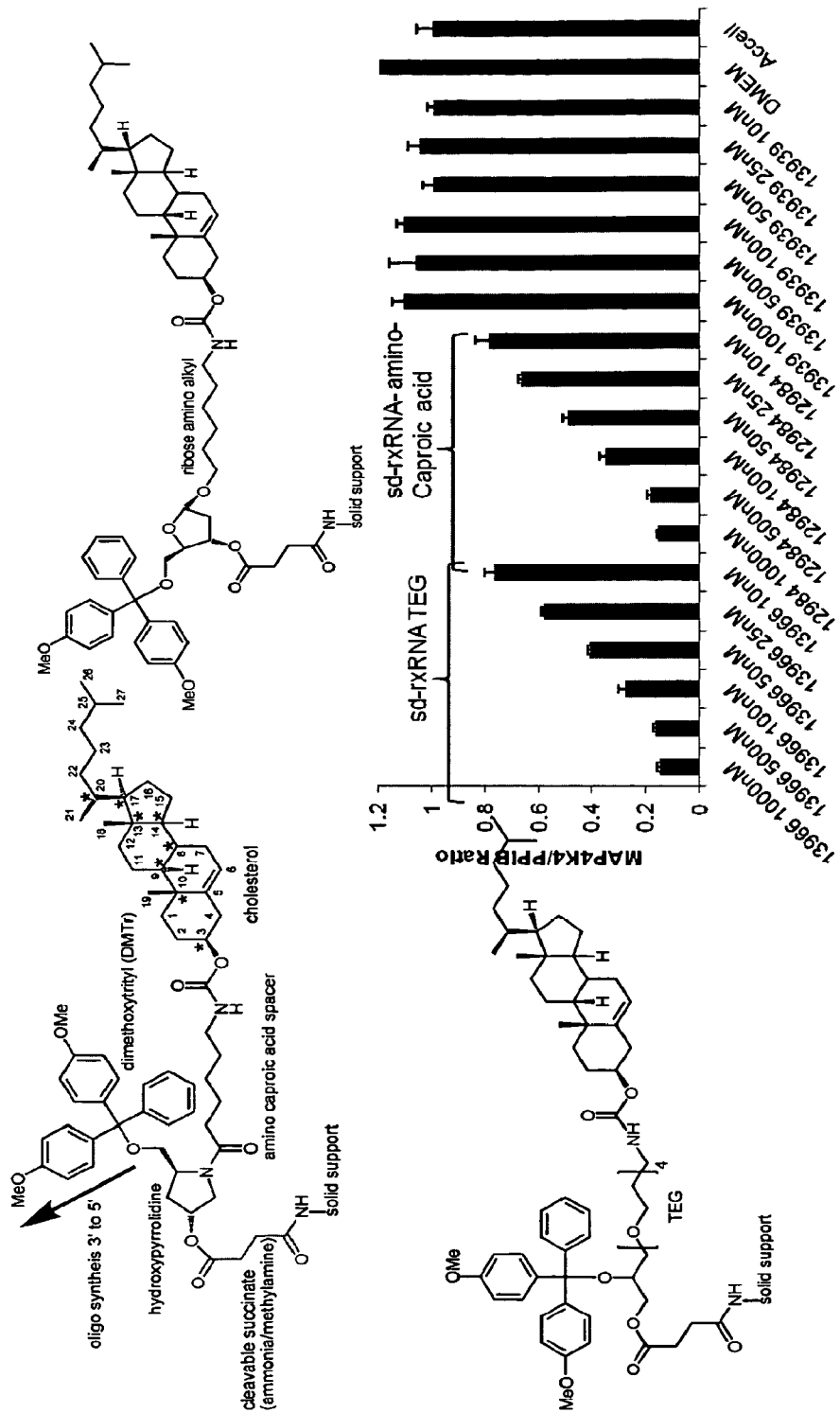
FIG. 54 presents schematics of sterol-type molecules and a graph revealing that sd-rxRNA compounds are fully functional with a variety of linker chemistries. GII asymmetric compounds were synthesized with sterol type molecules attached through TEG and amino caproic acid linkers. Both linkers showed identical potency. This functionality independent of linker chemistry indicates a significant difference between the molecules described herein and previously described molecules, and offers significant advantages for the molecules described herein in terms of scale up and synthesis.

Linker chemistry was also tested in conjunction with the RNA molecules associated with the invention. As depicted in FIG. 54, $2^{nd}$ generation RNA molecules were synthesized with sterol-type molecules attached through TEG and amino caproic acid linkers. Both linkers showed identical potency. This functionality of the RNA molecules, independent of linker chemistry offers additional advantages in terms of scale up and synthesis and demonstrates that the mechanism of function of these RNA molecules is very different from other previously described RNA molecules.

Figure 55:
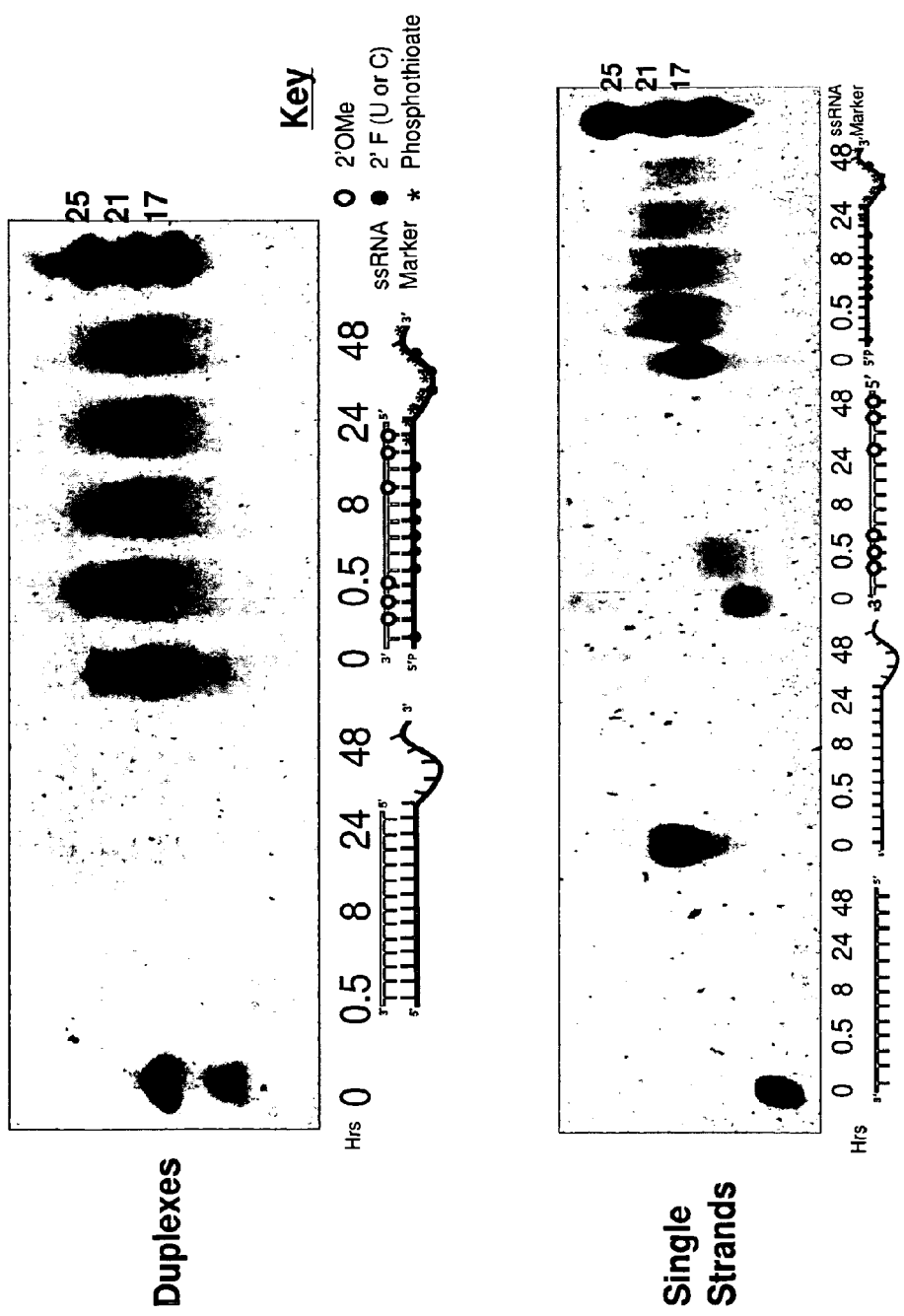
FIG. 55 demonstrates the stability of chemically modified sd-rxRNA compounds in human serum in comparison to non modified RNA. The oligonucleotides were incubated in 75% serum at 37° C. for the number of hours indicated. The level of degradation was determined by running the samples on non-denaturing gels and staining with SYBGR.

Stability of the chemically modified sd-rxRNA molecules described herein in human serum is shown in FIG. 55 in comparison to unmodified RNA. The duplex molecules were incubated in 75% serum at 37° C. for the indicated periods of time. The level of degradation was determined by running the samples on non-denaturing gels and staining with SYBGR.

Figure 56:
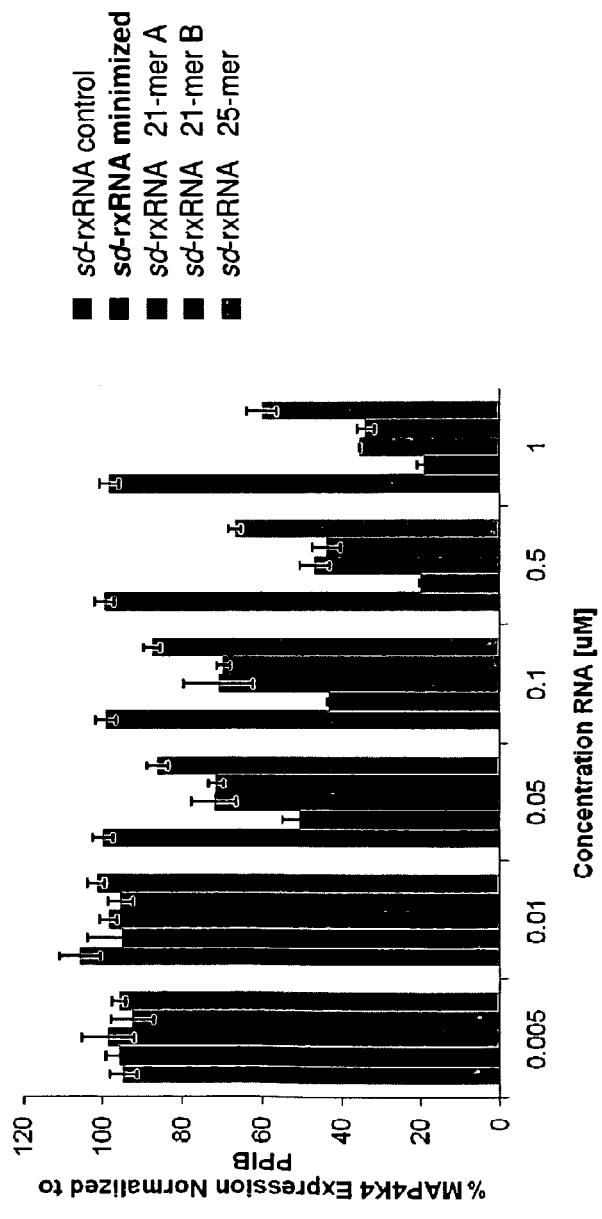
FIG. 56 is a graph depicting optimization of cellular uptake of sd-rxRNA through minimizing oligonucleotide content.
Figure 57:
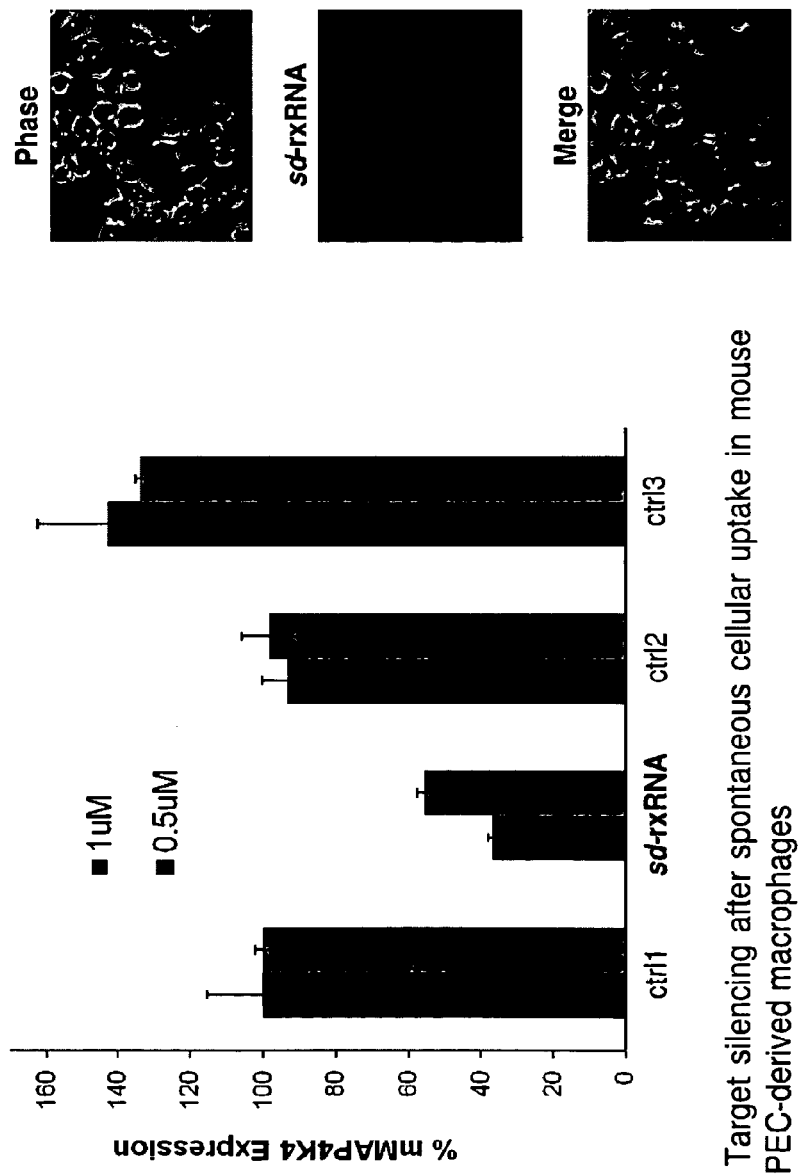
FIG. 57 is a graph showing percent MAP4K4 expression after spontaneous cellular uptake of sd-rxRNA in mouse PEC-derived macrophages, and phase and fluorescent images showing localization of sd-rxRNA.
Figure 58:
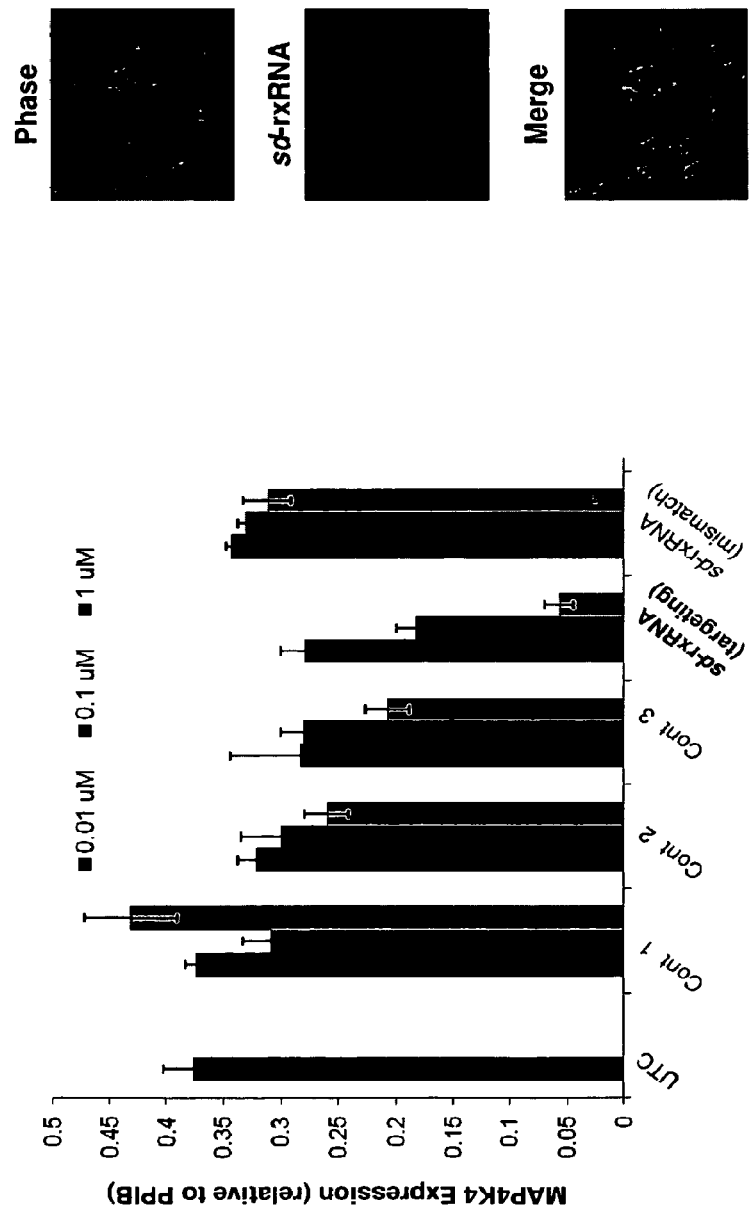
FIG. 58 is a graph showing percent MAP4K4 expression after spontaneous cellular uptake of sd-rxRNA (targeting) and sd-rxRNA (mismatch) in mouse primary hepatocytes, and phase and fluorescent images showing localization of sd-rxRNA.
Figure 59:
FIG. 59 presents images depicting localization of DY547-labeled sd-rxRNA delivered to RPE cells with no formulation.
Figure 60:
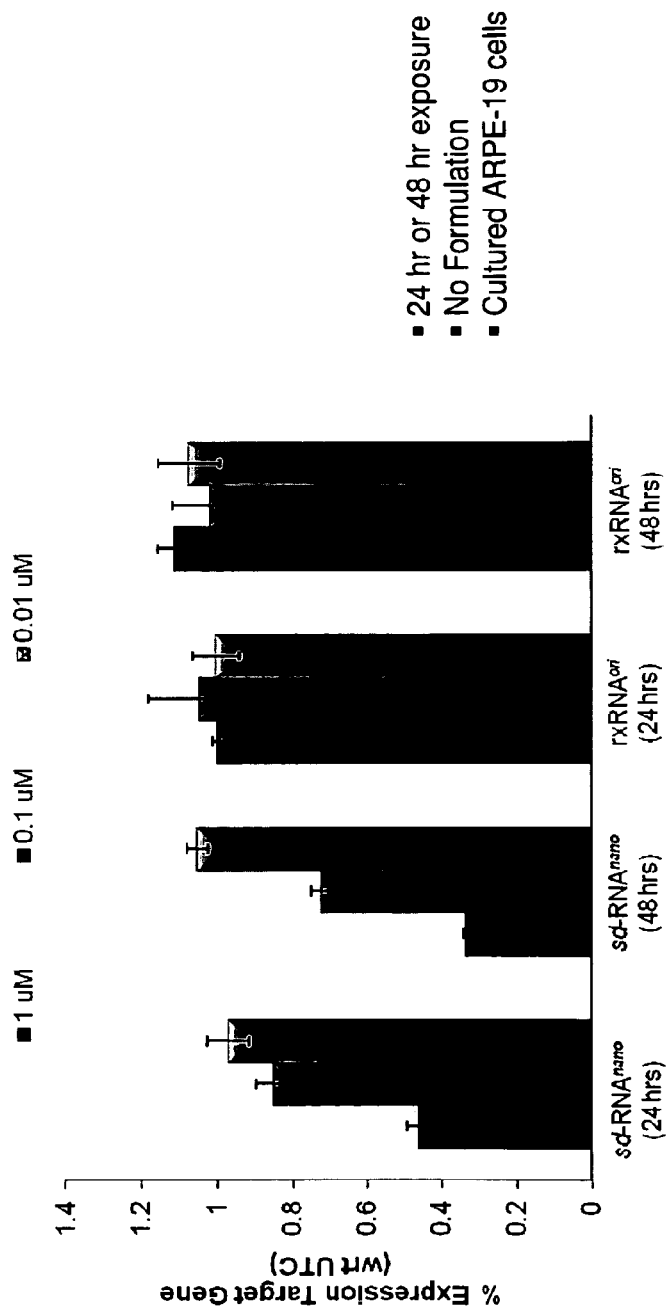
FIG. 60 is a graph showing silencing of MAP4K4 expression in RPE cells treated with sd-rxRNA$^{nano}$ without formulation.

FIGS. 56 and 57 present data on cellular uptake of the sd-rxRNA molecules. FIG. 56 shows that minimizing the length of the RNA molecule is importance for cellular uptake, while FIG. 57 presents data showing target gene silencing after spontaneous cellular uptake in mouse PEC-derived macrophages. FIG. 58 demonstrates spontaneous uptake and target gene silencing in primary cells. FIG. 59 shows the results of delivery of sd-rxRNA molecules associated with the invention to RPE cells with no formulation. Imaging with Hoechst and DY547 reveals the clear presence of a signal representing the RNA molecule in the sd-rxRNA sample, while no signal is detectable in the other samples including the samples competing a competing conjugate, an rxRNA, and an untransfected control. FIG. 60 reveals silencing of target gene expression in RPE cells treated with sd-rxRNA molecules associated with the invention following 24-48 hours without any transfection formulation.

Figure 61:
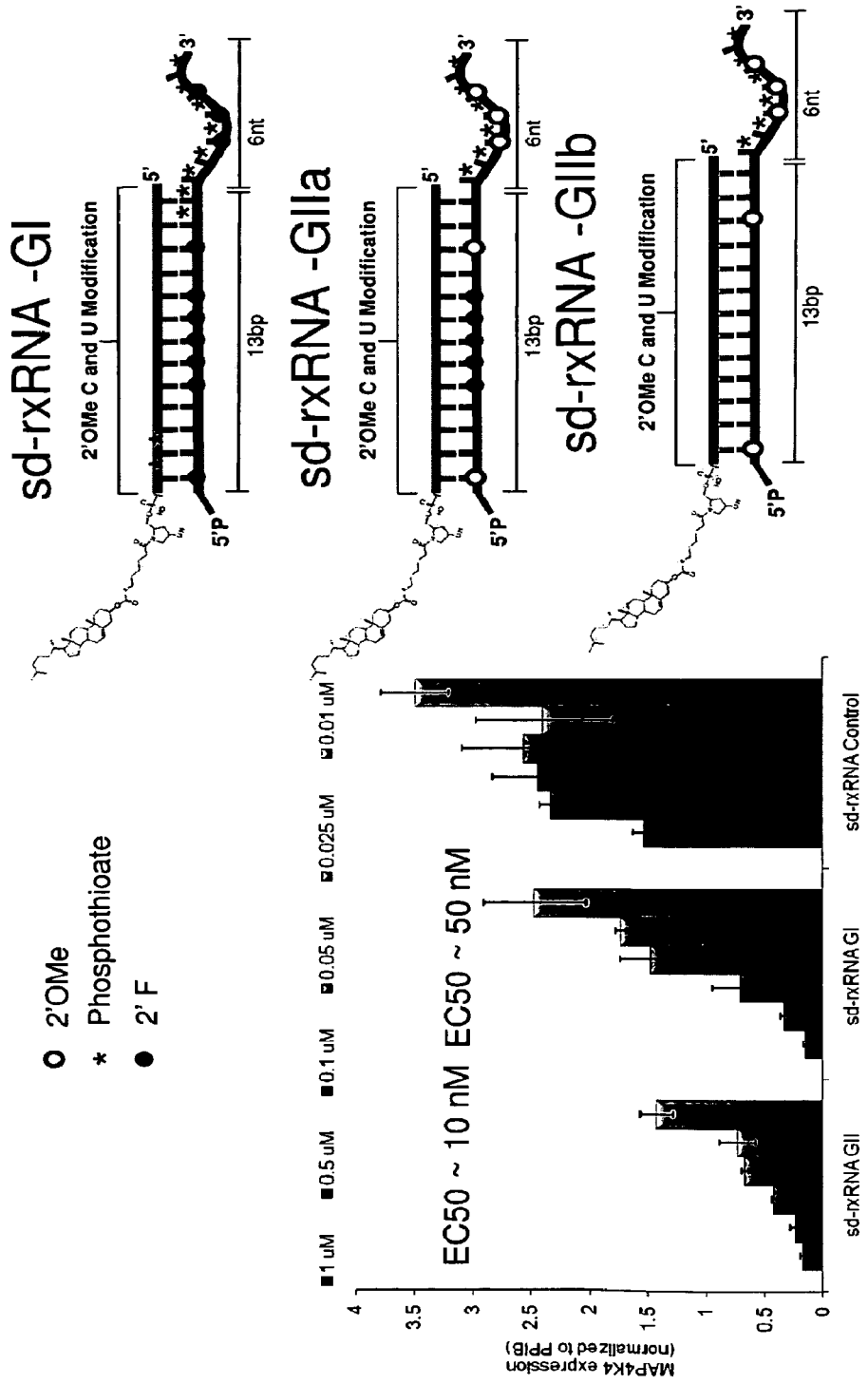
FIG. 61 presents a graph and schematics of RNAi compounds showing the chemical/structural composition of highly effective sd-rxRNA compounds. Highly effective compounds were found to have the following characteristics: antisense strands of 17-21 nucleotides, sense strands of 10-15 nucleotides, single-stranded regions that contained 2-12 phosphorothioate modifications, preferentially 6-8 phosphorothioate modifications, and sense strands in which the majority of nucleotides were 2'OMe modified, with or without phosphorothioate modification. Any linker chemistry can be used to attach these molecules to hydrophobic moieties such as cholesterol at the 3' end of the sense strand. Version GIIa-b of these RNA compounds demonstrate that elimination of 2'F content has no impact on efficacy.

FIG. 61 shows further optimization of the chemical/structural composition of sd-rxRNA compounds. In some instances, preferred properties included an antisense strand that was 17-21 nucleotides long, a sense strand that was 10-15 nucleotides long, phosphorothioate modification of 2-12 nucleotides within the single stranded region of the molecule, preferentially phosphorothioate modification of 6-8 nucleotides within the single stranded region, and 2'OMe modification at the majority of positions within the sense strand, with or without phosphorothioate modification. Any linker chemistry can be used to attach the hydrophobic moiety, such as cholesterol, to the 3' end of the sense strand. Version GIIb molecules, as shown in FIG. 61, have no 2'F modifications. Significantly, there is was no impact on efficacy in these molecules.

Figure 62:
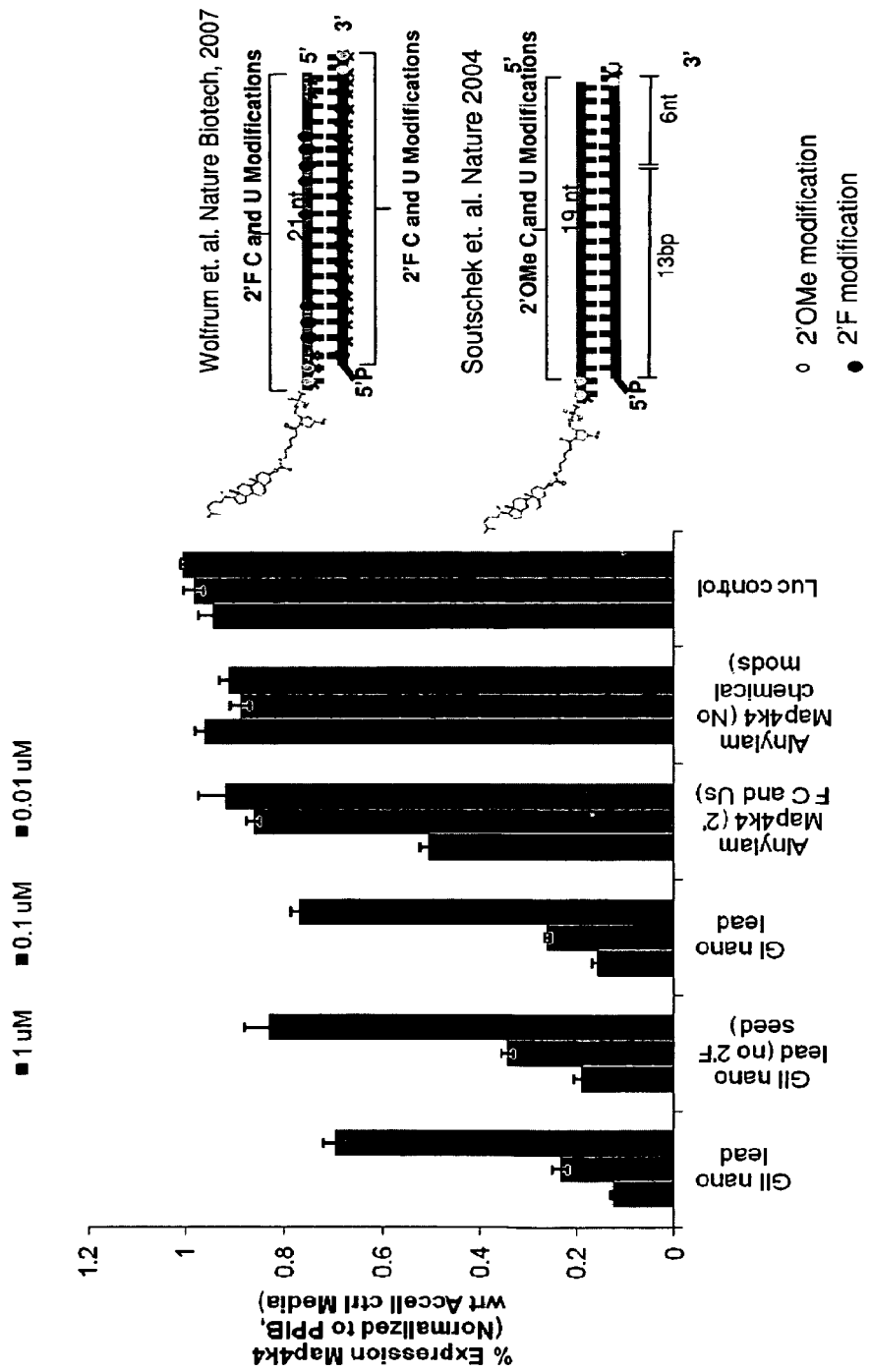
FIG. 62 presents a graph and schematics of RNAi compounds demonstrating the superior performance of sd-rxRNA compounds compared to compounds published by Wolfrum et. al. Nature Biotech, 2007. Both generation I and II compounds (GI and GIIa) developed herein show great efficacy. By contrast, when the chemistry described in Wolfrum et al. (all oligos contain cholesterol conjugated to the 3' end of the sense strand) was applied to the same sequence in a context of conventional siRNA (19 bp duplex with two overhang) the compound was practically inactive. These data emphasize the significance of the combination of chemical modifications and assymetrical molecules described herein, producing highly effective RNA compounds.

FIG. 62 demonstrates the superior performance of sd-rxRNA compounds compared to compounds published by Wolfrum et. al. Nature Biotech, 2007. Both generation I and II compounds (GI and GIIa) developed herein show great efficacy in reducing target gene expression. By contrast, when the chemistry described in Wolfrum et al. (all oligos contain cholesterol conjugated to the 3' end of the sense strand) was applied to the same sequence in a context of conventional siRNA (19 bp duplex with two overhang) the compound was practically inactive. These data emphasize the significance of the combination of chemical modifications and assymetrical molecules described herein, producing highly effective RNA compounds.

Figure 63:
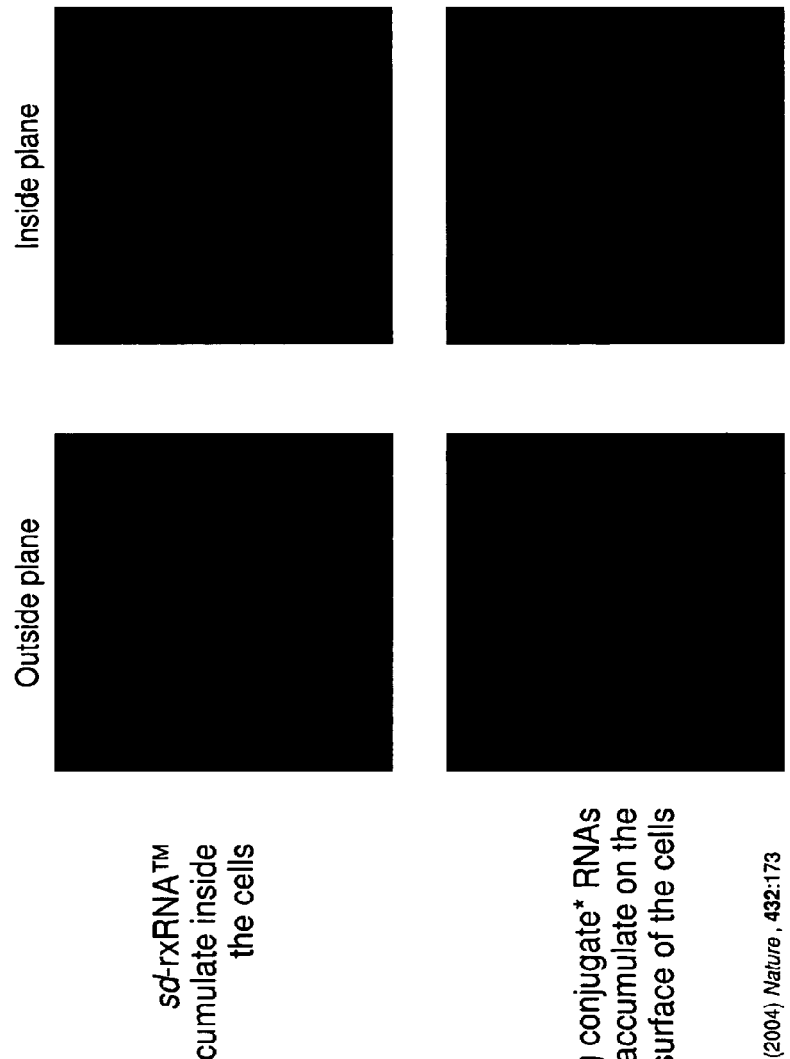
FIG. 63 presents images showing that sd-rxRNA accumulates inside cells while other less effective conjugate RNAs accumulate on the surface of cells.
Figure 64:
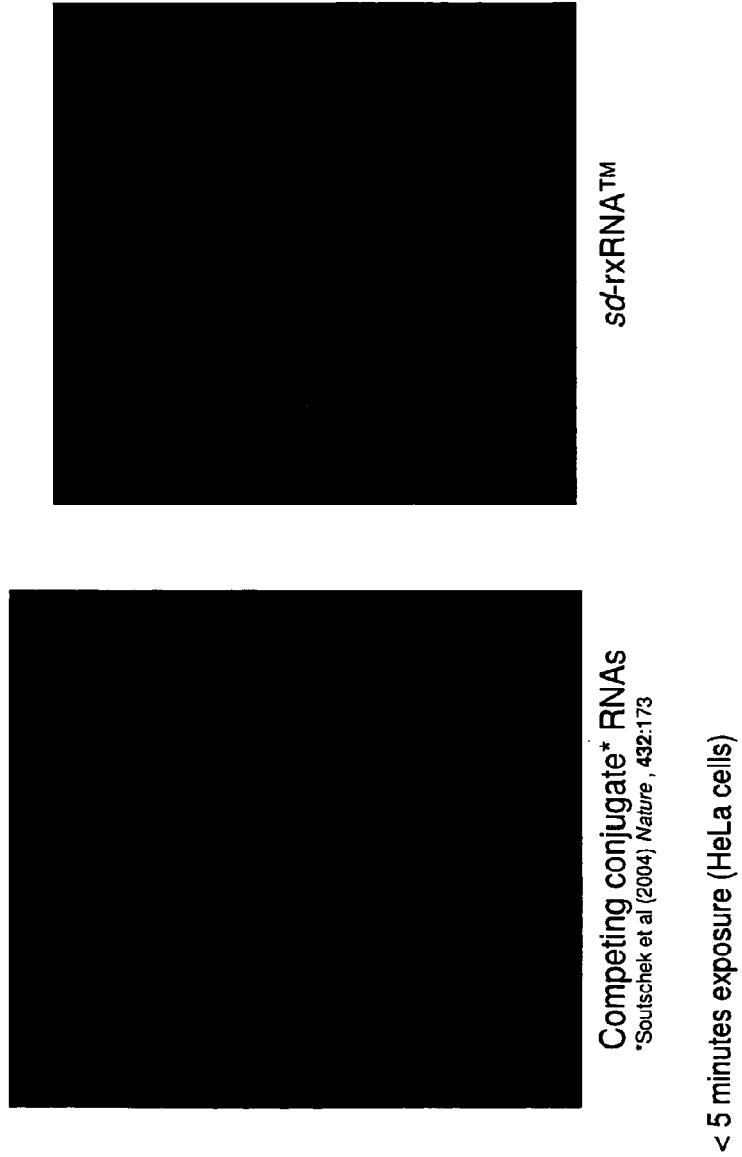
FIG. 64 presents images showing that sd-rxRNA molecules, but not other molecules, are internalized into cells within minutes.

FIG. 63 shows localization of sd-rxRNA molecules developed herein compared to localization of other RNA molecules such as those described in Soutschek et al. (2004) Nature, 432:173. sd-rxRNA molecules accumulate inside the cells whereas competing conjugate RNAs accumulate on the surface of cells. Significantly, FIG. 64 shows that sd-rxRNA molecules, but not competitor molecules such as those described in Soutschek et al. are internalized within minutes. FIG. 65 compares localization of sd-rxRNA molecules compared to regular siRNA-cholesterol, as described in Soutschek et al. A signal representing the RNA molecule is clearly detected for the sd-rxRNA molecule in tissue culture RPE cells, following local delivery to compromised skin, and following systemic delivery where uptake to the liver is seen. In each case, no signal is detected for the regular siRNA-cholesterol molecule. The sd-rxRNA molecule thus has drastically better cellular and tissue uptake characteristics when compared to conventional cholesterol conjugated siRNAs such as those described in Soutschek et al. The level of uptake is at least order of magnitude higher and is due at least in part to the unique combination of chemistries and conjugated structure. Superior delivery of sd-rxRNA relative to previously described RNA molecules is also demonstrated in FIGS. 66 and 67.

Based on the analysis of $2^{nd}$ generation RNA molecules associated with the invention, a screen was performed to identify functional molecules for targeting the SPP1/PPIB gene. As revealed in FIG. 68, several effective molecules were identified, with 14131 being the most effective. The compounds were added to A-549 cells and then the level of SPP1/PPIB ratio was determined by B-DNA after 48 hours.

Figure 69:
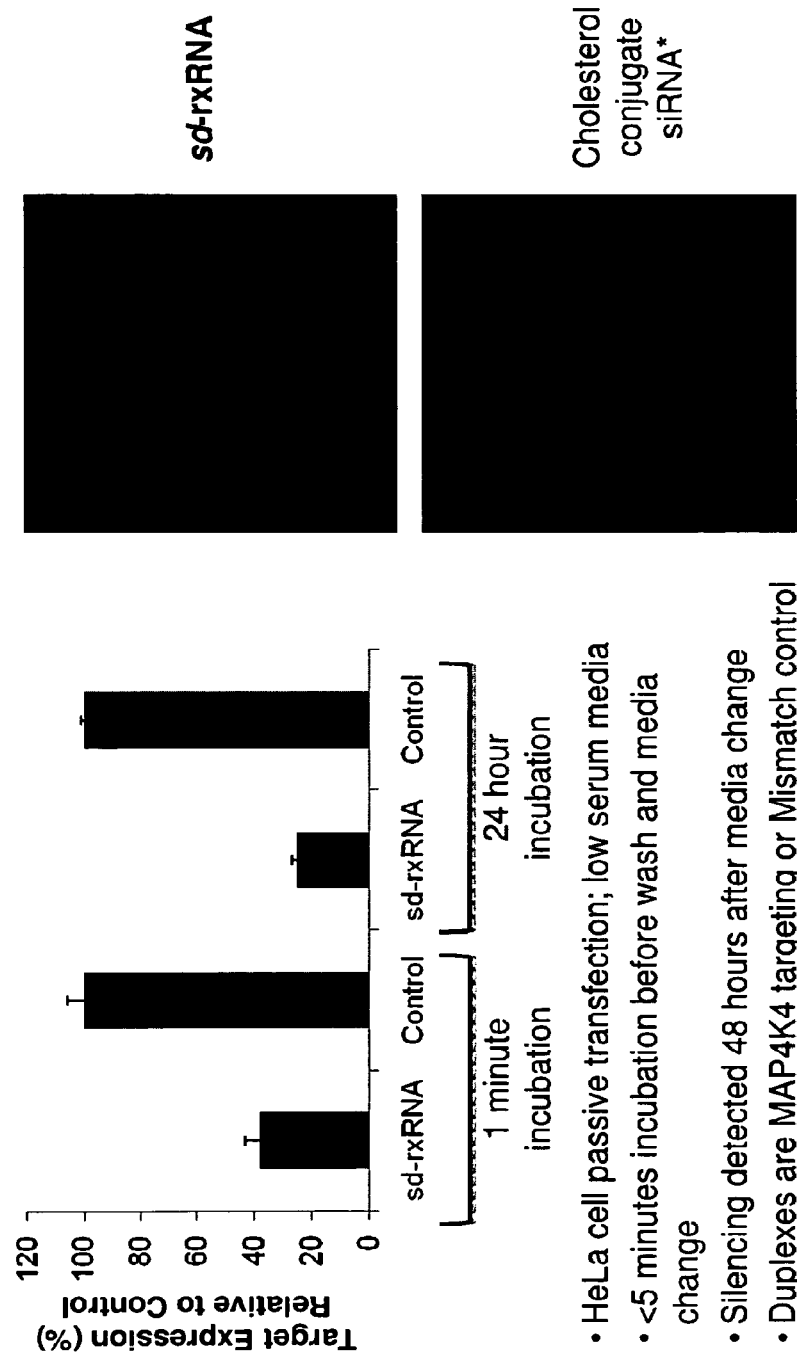
FIG. 69 presents a graph and several images demonstrating efficient cellular uptake of sd-rxRNA within minutes of exposure. This is a unique characteristics of the sd-rxRNA compounds described herein, not observed with any other RNAi compounds. The Soutschek et al. compound was used as a negative control.

FIG. 69 reveals efficient cellular uptake of sd-rxRNA within minutes of exposure. This is a unique characteristics of these molecules, not observed with any other RNAi compounds. Compounds described in Soutschek et al. were used as negative controls. FIG. 70 reveals that the uptake and gene silencing of the sd-rxRNA is effective in multiple different cell types including SH-SY5Y neuroblastoma derived cells, ARPE-19 (retinal pigment epithelium) cells, primary hepatocytes, and primary macrophages. In each case silencing was confirmed by looking at target gene expression by a Branched DNA assay.

FIG. 70 reveals that sd-rxRNA is active in the presence or absence of serum. While a slight reduction in efficacy (2-5 fold) was observed in the presence of serum, this small reduction in efficacy in the presence of serum differentiate the sd-rxRNA molecules from previously described molecules which exhibited a larger reduction in efficacy in the presence of serum. This demonstrated level of efficacy in the presence of serum creates a foundation for in vivo efficacy.

Figure 74:
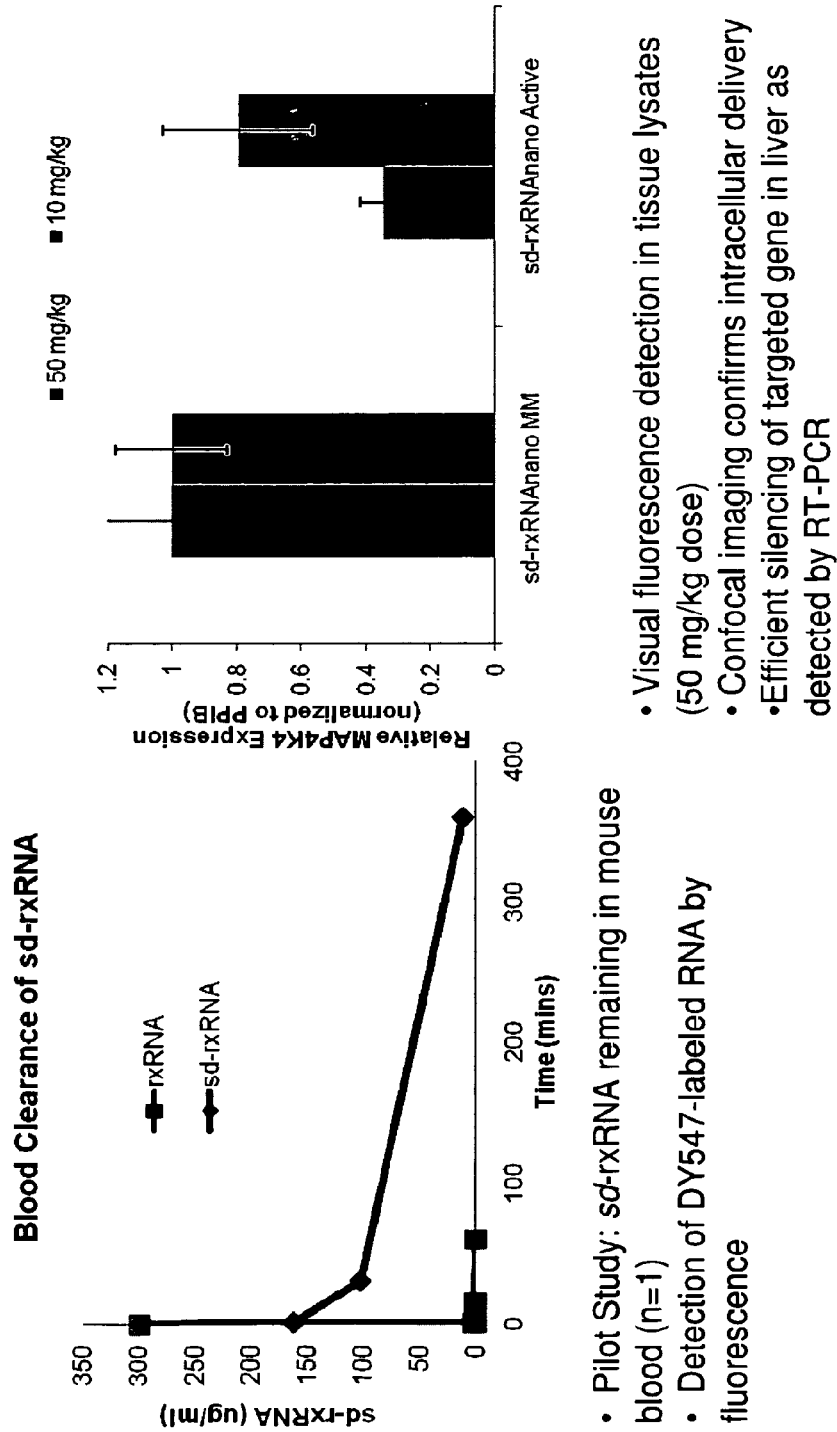
FIG. 74 presents graphs demonstrating that sd-rxRNA compounds have improved blood clearance and induce effective gene silencing in vivo in the liver upon systemic administration.

FIG. 72 reveals efficient tissue penetration and cellular uptake upon single intradermal injection. This data indicates the potential of the sd-rxRNA compounds described herein for silencing genes in any dermatology applications, and also represents a model for local delivery of sd-rxRNA compounds. FIG. 73 also demonstrates efficient cellular uptake and in vivo silencing with sd-rxRNA following intradermal injection. Silencing is determined as the level of MAP4K4 knockdown in several individual biopsies taken from the site of injection as compared to biopsies taken from a site injected with a negative control. FIG. 74 reveals that sd-rxRNA compounds has improved blood clearance and induced effective gene silencing in vivo in the liver upon systemic administration. In comparison to the RNA molecules described by Soutschek et al., the level of liver uptake at identical dose level is at least 50 fold higher with the sd-rxRNA molecules. The uptake results in productive silencing. sd-rxRNA compounds are also characterized by improved blood clearance kinetics.

Figure 75:
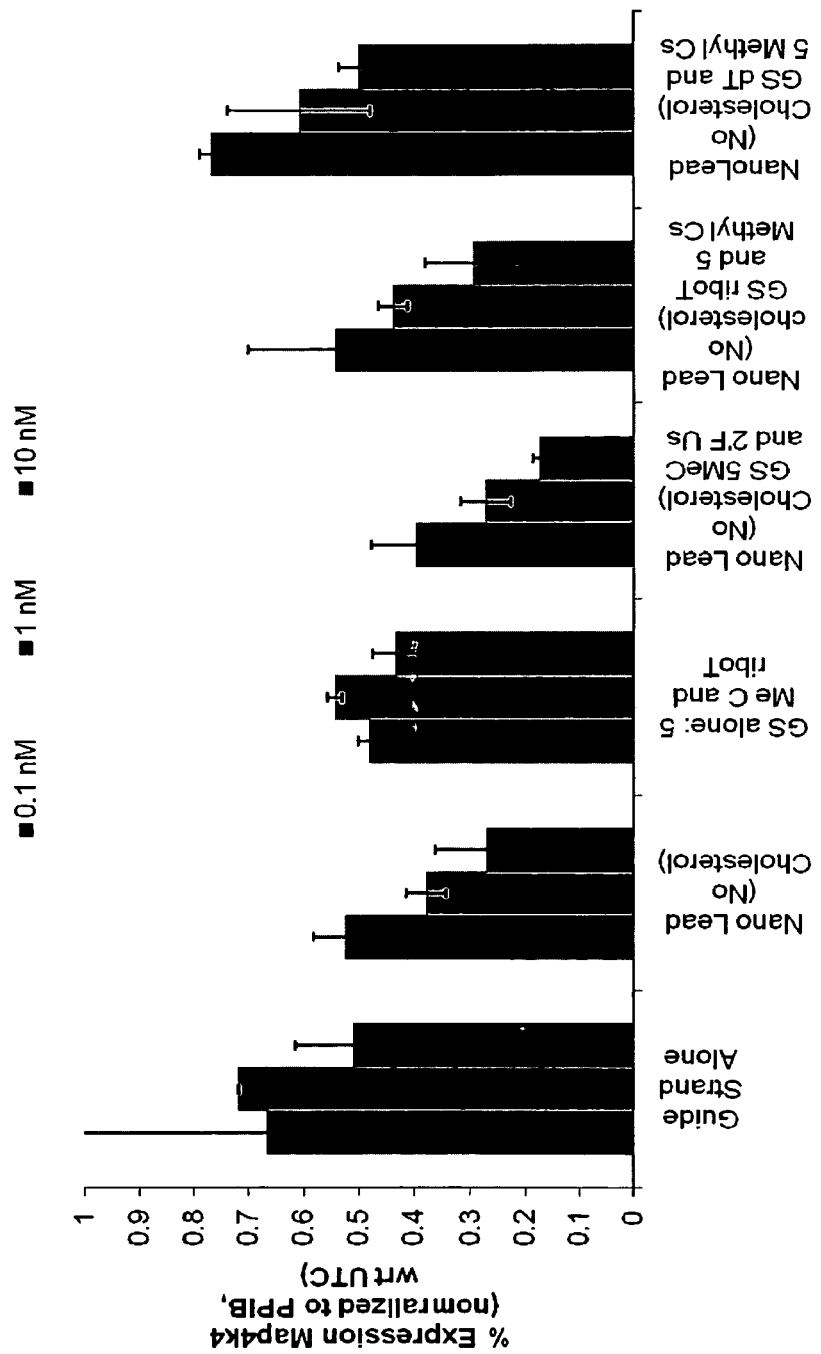
FIG. 75 presents a graph demonstrating that the presence of 5-Methyl C in an RNAi compound resulted in an increase in potency of lipid mediated transfection, demonstrating that hydrophobic modification of Cs and Us in the content of RNAi compounds can be beneficial. In some embodiments, these types of modifications can be used in the context of 2' ribose modified bases to insure optimal stability and efficacy.
Figure 76:
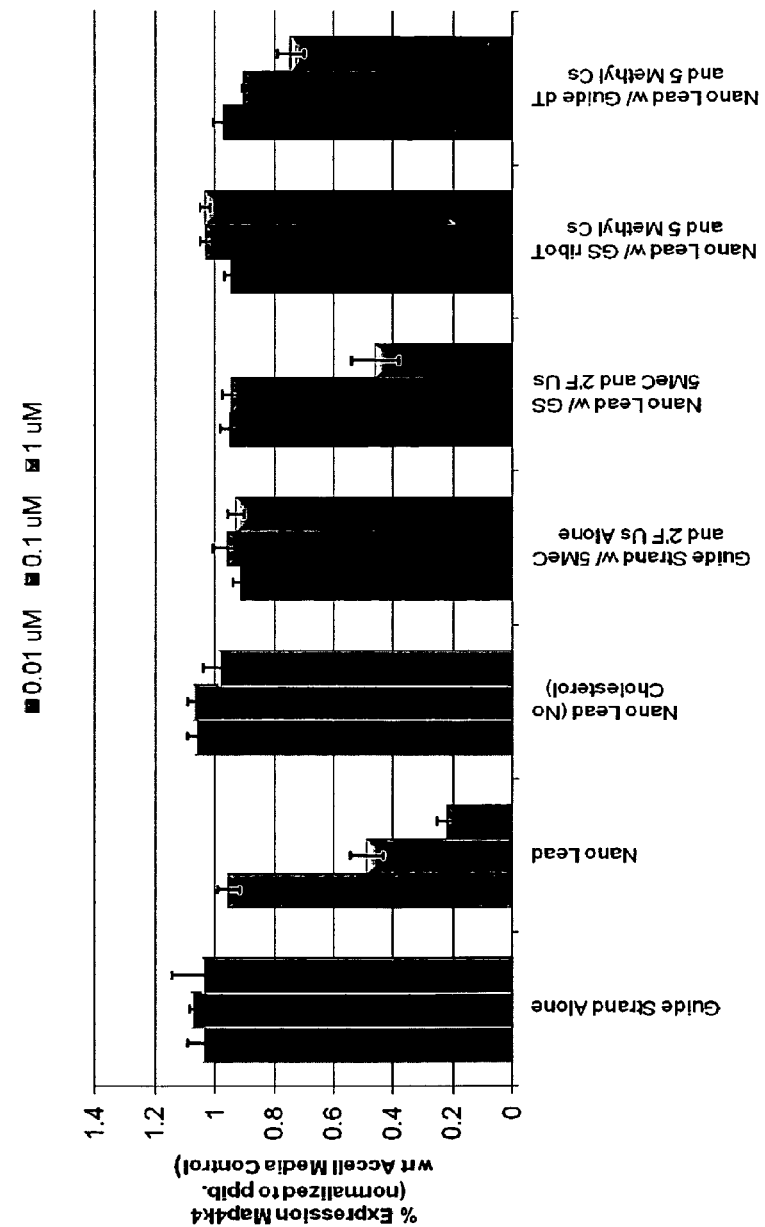
FIG. 76 presents a graph showing percent MAP4K4 expression in HeLa cells following passive uptake transfection of: Guide strand alone; Nano Lead; Nano Lead (No cholesterol); Guide Strand w/5MeC and 2'F Us Alone; Nano Lead w/GS 5MeC and 2'F Us; Nano Lead w/GS riboT and 5 Methyl Cs; and Nano Lead w/Guide dT and 5 Methyl Cs.

The effect of 5-Methyl C modifications was also examined. FIG. 75 demonstrates that the presence of 5-Methyl C in an RNAi molecule resulted in increased potency in lipid mediated transfection. This suggests that hydrophobic modification of Cs and Us in an RNAi molecule can be beneficial. These types of modifications can also be used in the context 2' ribose modified bases to ensure optimal stability and efficacy. FIG. 76 presents data showing that incorporation of 5-Methyl C and/or ribothymidine in the guide strand can in some instances reduce efficacy.

Figure 77:
FIG. 77 presents images comparing localization of sd-rxRNA and other RNA conjugates following systemic delivery to the liver.

FIG. 77 reveals that sd-rxRNA molecules are more effective than competitor molecules such as molecules described in Soutschek et al., in systemic delivery to the liver. A signal representing the RNA molecule is clearly visible in the sample containing sd-rxRNA, while no signal representing the RNA molecule is visible in the sample containing the competitor RNA molecule.

Figure 78:
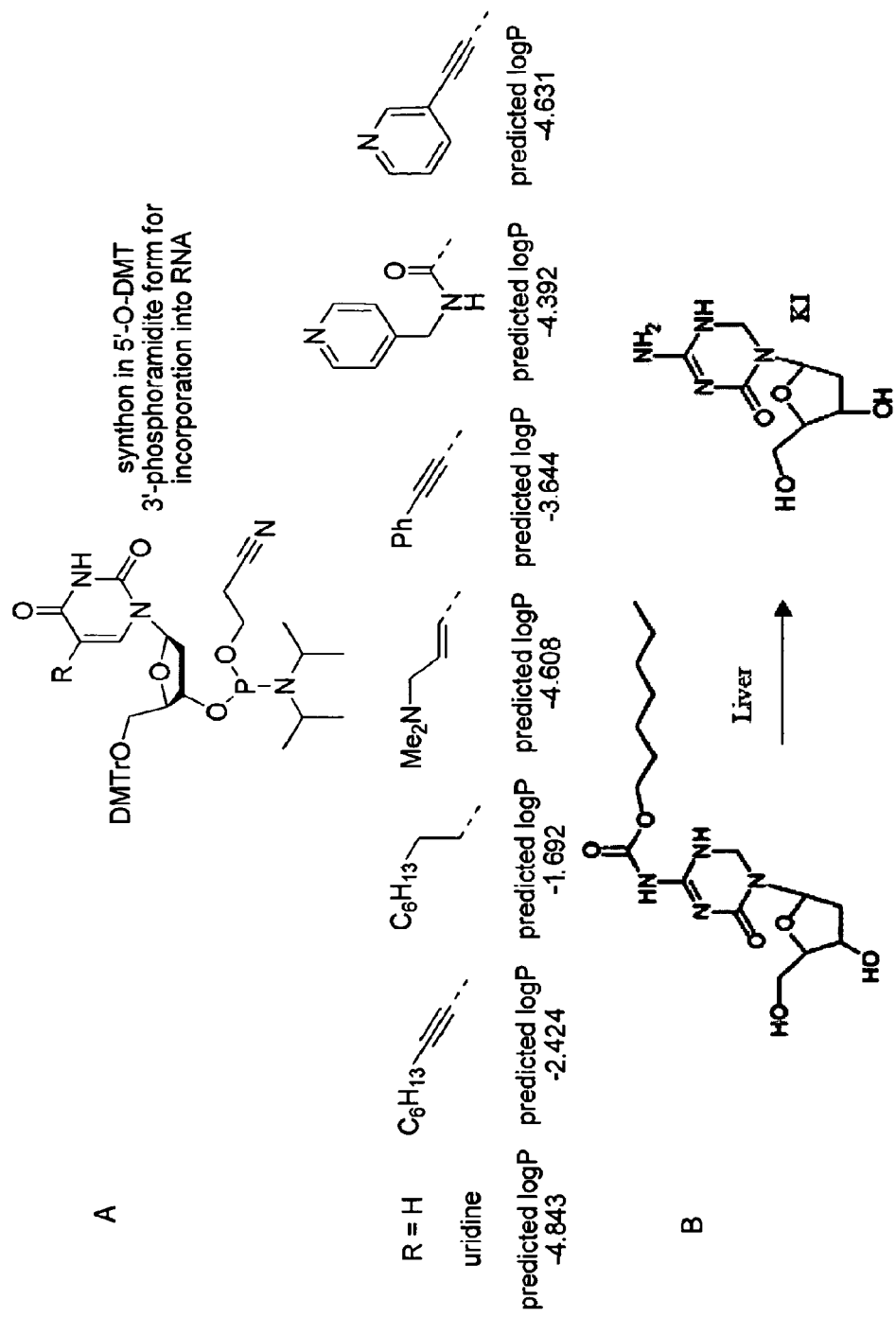
FIG. 78A presents schematics demonstrating 5-uridyl modifications with improved hydrophobicity characteristics. Incorporation of such modifications into sd-rxRNA compounds can increase cellular and tissue uptake properties.
FIG. 78B presents a new type of RNAi compound modification which can be applied to compounds to improve cellular uptake and pharmacokinetic behavior. This type of modification, when applied to sd-rxRNA compounds, may contribute to making such compounds orally available.
Figure 79:
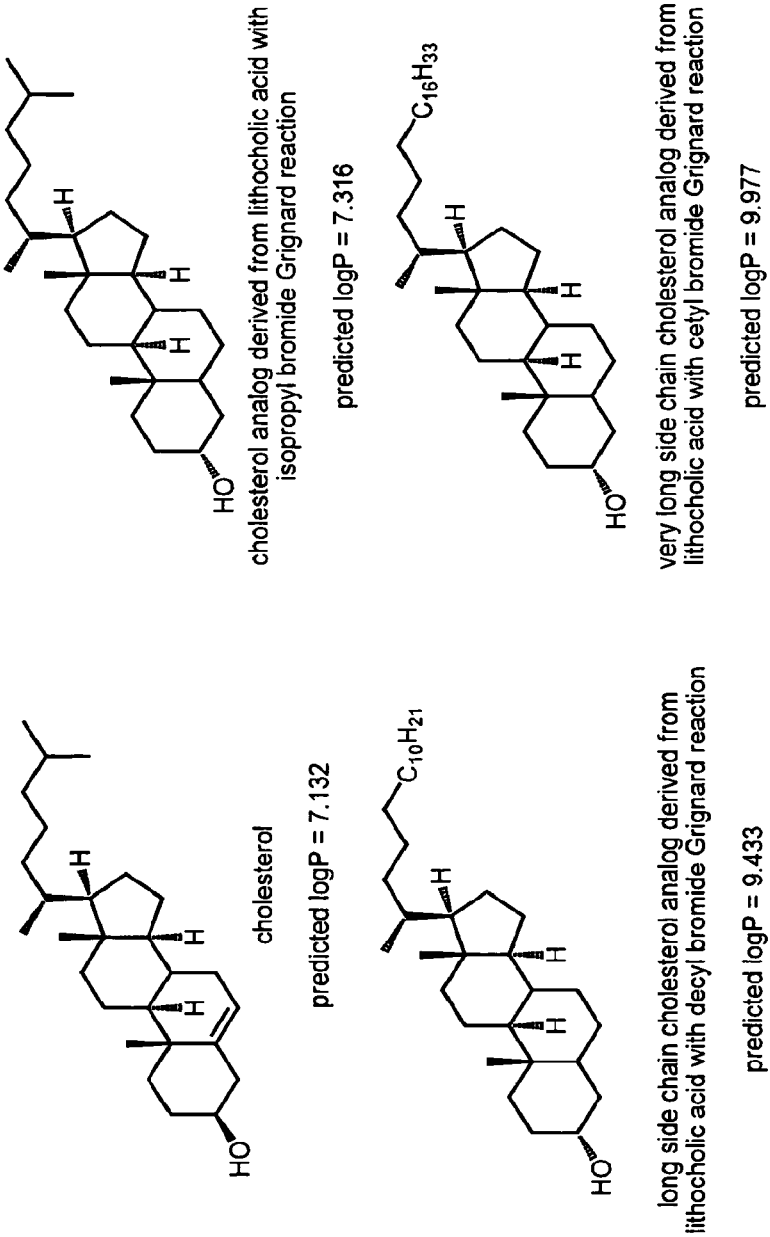
FIG. 79 presents schematics revealing the structures of synthesized modified sterol type molecules, where the length and structure of the C17 attached tail is modified. Without wishing to be bound by any theory, the length of the C17 attached tail may contribute to improving in vitro and in vivo efficacy of sd-rxRNA compounds.

The addition of hydrophobic conjugates to the sd-rxRNA molecules was also explored (FIGS. 78-83). FIG. 78 presents schematics demonstrating 5-uridyl modifications with improved hydrophobicity characteristics. Incorporation of such modifications into sd-rxRNA compounds can increase cellular and tissue uptake properties. FIG. 78B presents a new type of RNAi compound modification which can be applied to compounds to improve cellular uptake and pharmacokinetic behavior. Significantly, this type of modification, when applied to sd-rxRNA compounds, may contribute to making such compounds orally available. FIG. 79 presents schematics revealing the structures of synthesized modified sterol-type molecules, where the length and structure of the C17 attached tail is modified. Without wishing to be bound by any theory, the length of the C17 attached tail may contribute to improving in vitro and in vivo efficacy of sd-rxRNA compounds.

Figure 80:
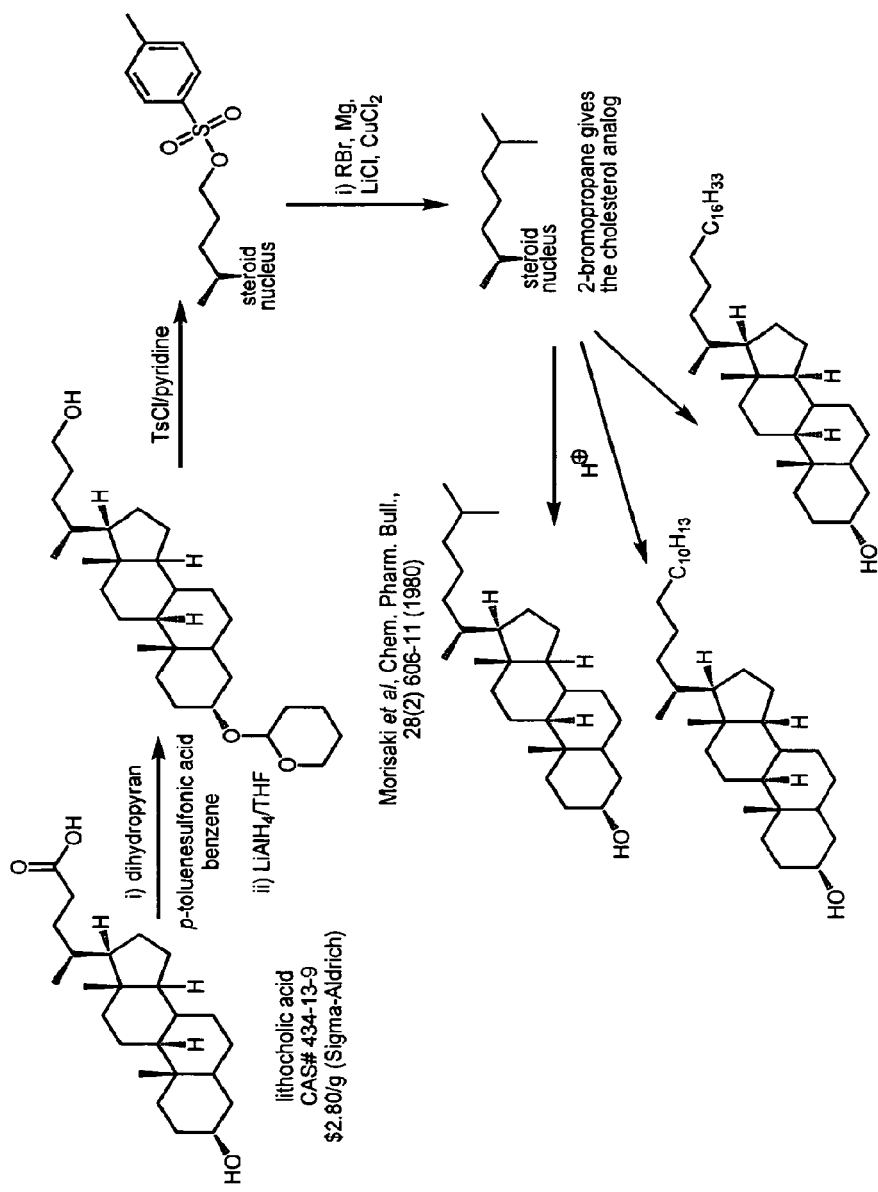
FIG. 80 presents a schematic demonstrating the lithocholic acid route to long side chain cholesterols.
Figure 81:
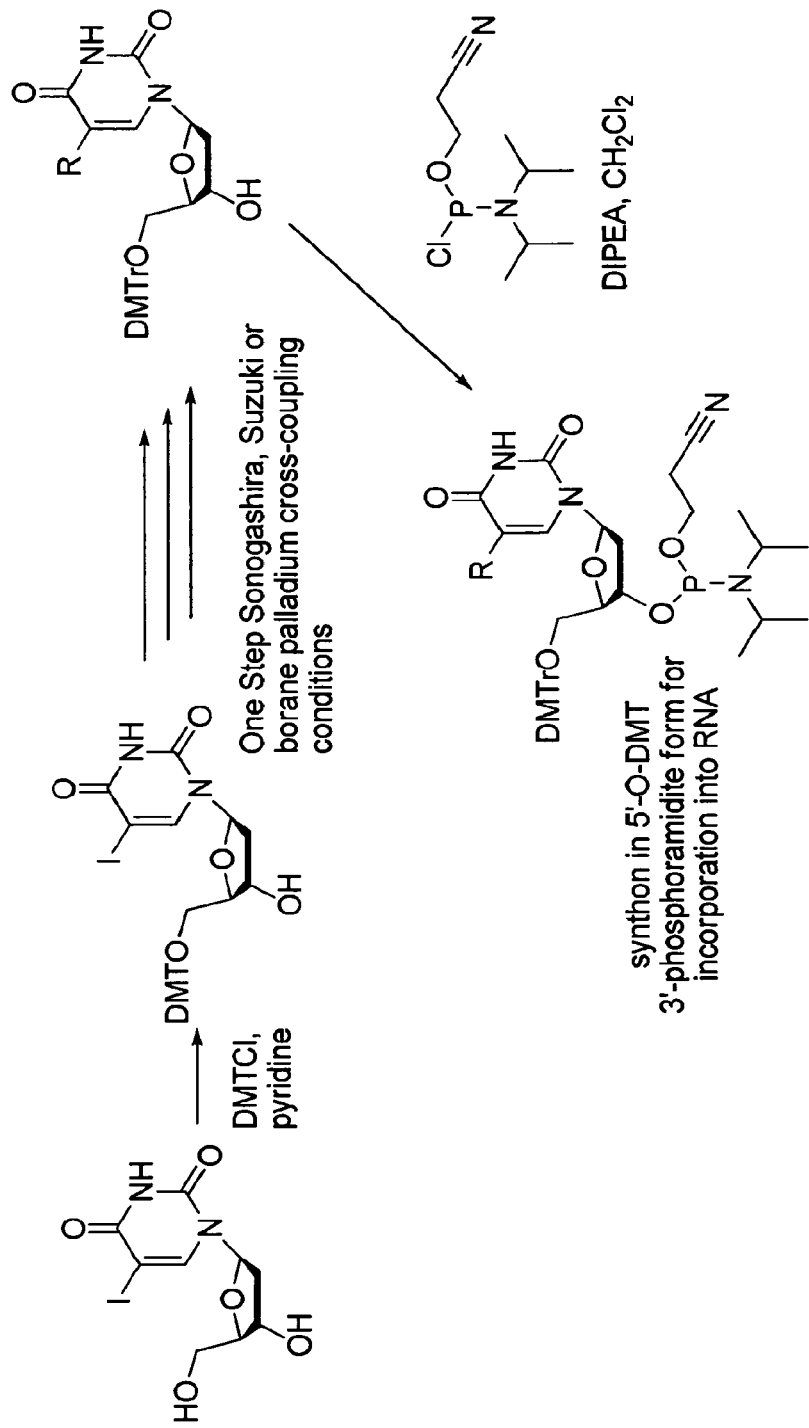
FIG. 81 presents a schematic demonstrating a route to 5-uridyl phosphoramidite synthesis.
Figure 82:
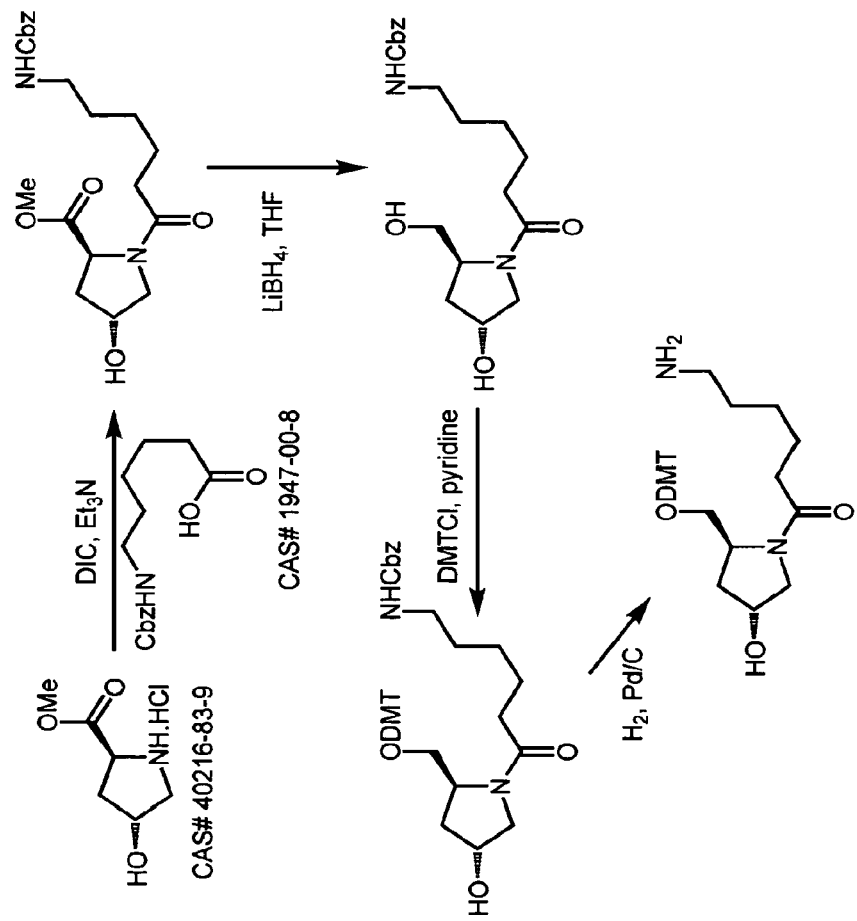
FIG. 82 presents a schematic demonstrating synthesis of tri-functional hydroxyprolinol linker for 3'-cholesterol attachment.
Figure 83:
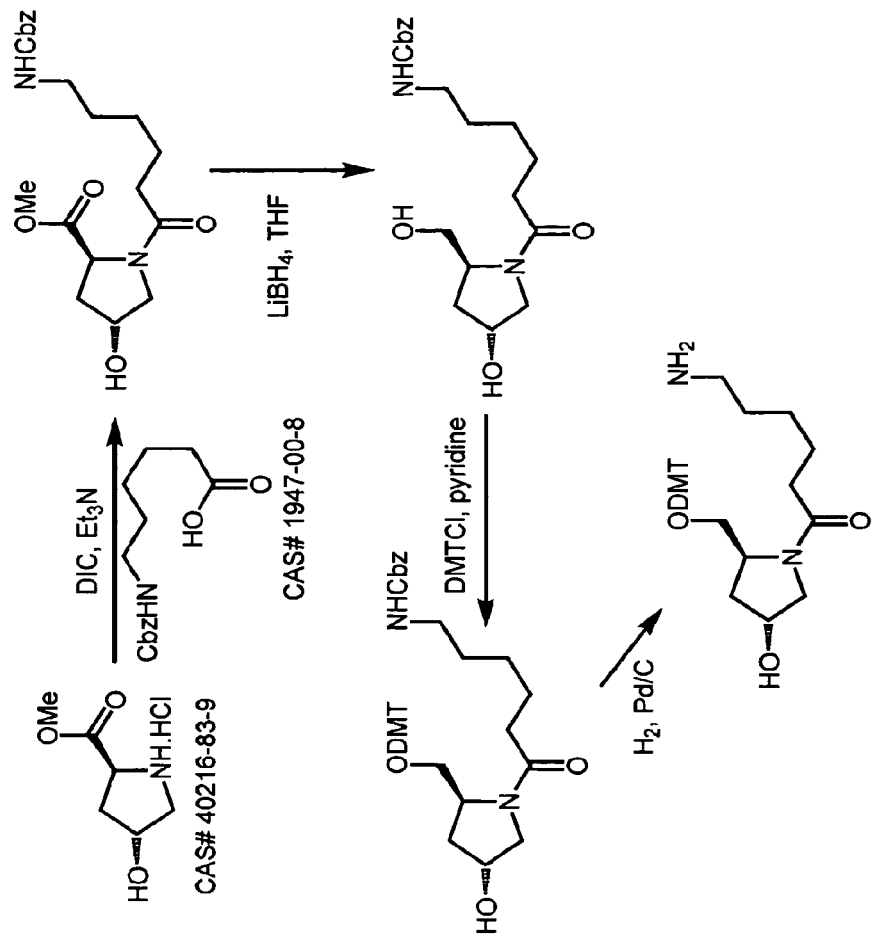
FIG. 83 presents a schematic demonstrating synthesis of solid support for the manufacture of a shorter asymmetric RNAi compound strand.

FIG. 80 presents a schematic demonstrating the lithocholic acid route to long side chain cholesterols. FIG. 81 presents a schematic demonstrating a route to 5-uridyl phosphoramidite synthesis. FIG. 82 presents a schematic demonstrating synthesis of tri-functional hydroxyprolinol linker for 3'-cholesterol attachment. FIG. 83 presents a schematic demonstrating synthesis of solid support for the manufacture of a shorter asymmetric RNAi compound strand.

Figure 84:
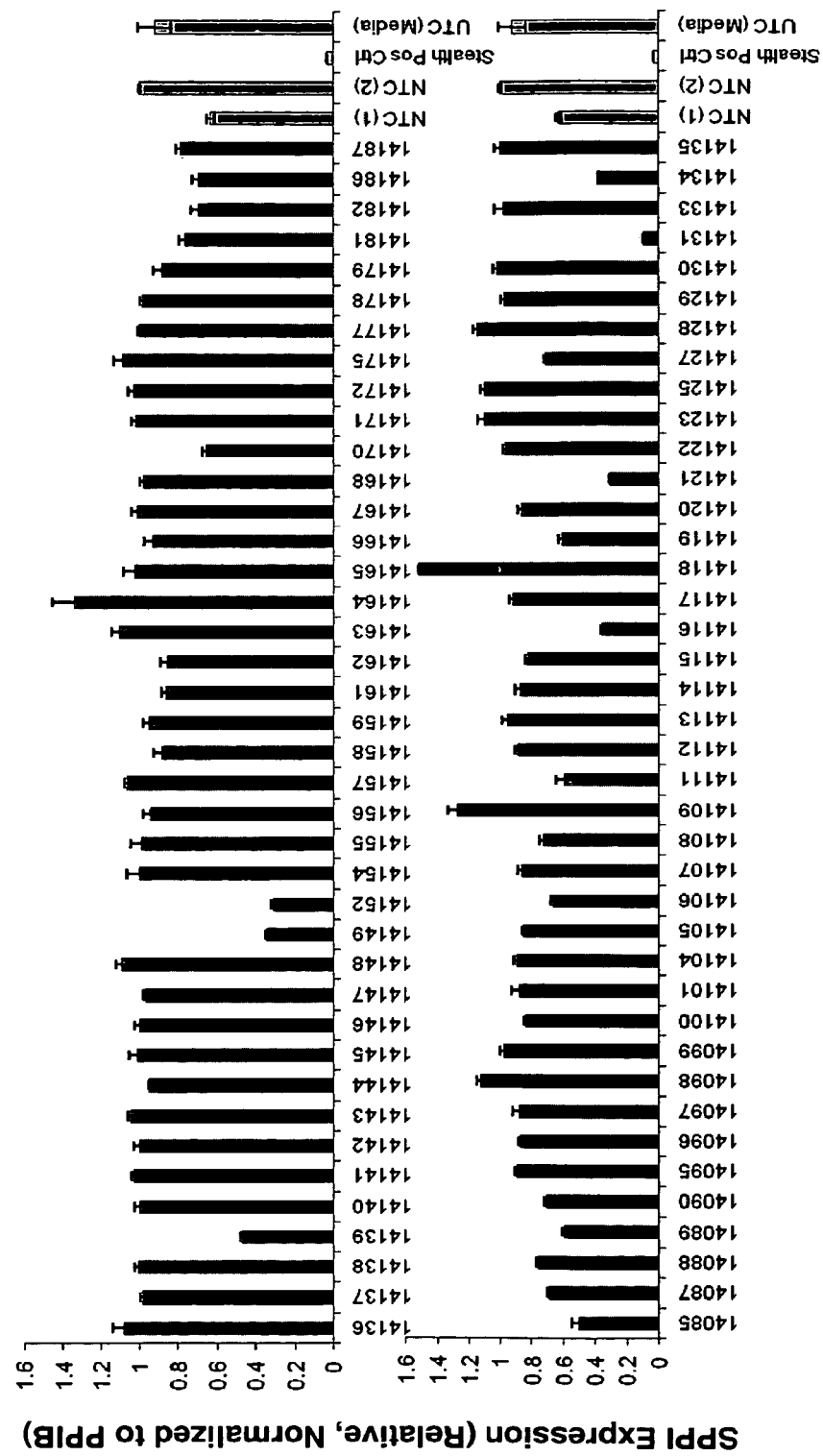
FIG. 84 demonstrates SPPI sd-rxRNA compound selection. Sd-rxRNA compounds targeting SPP1 were added to A549 cells (using passive transfection) and the level of SPP1 expression was evaluated after 48 hours. Several novel compounds effective in SPP1 silencing were identified, the most potent of which was compound 14131.
Figure 85:
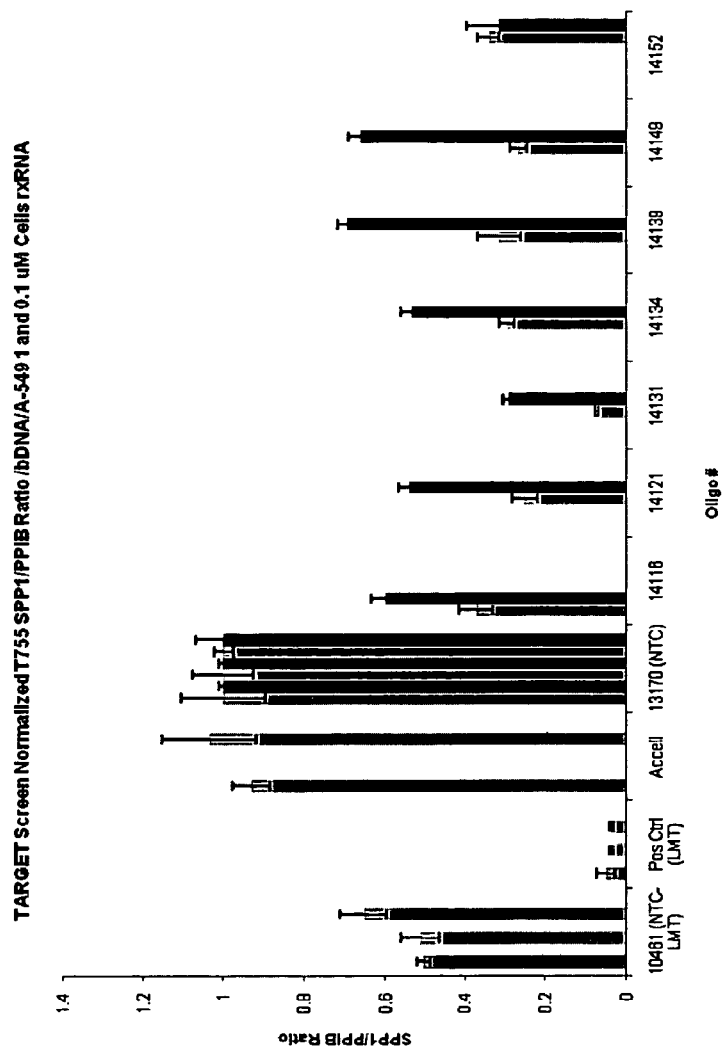
FIG. 85 demonstrates independent validation of sd-rxRNA compounds 14116, 14121, 14131, 14134, 14139, 14149, and 14152 efficacy in SPP1 silencing.
Figure 86:
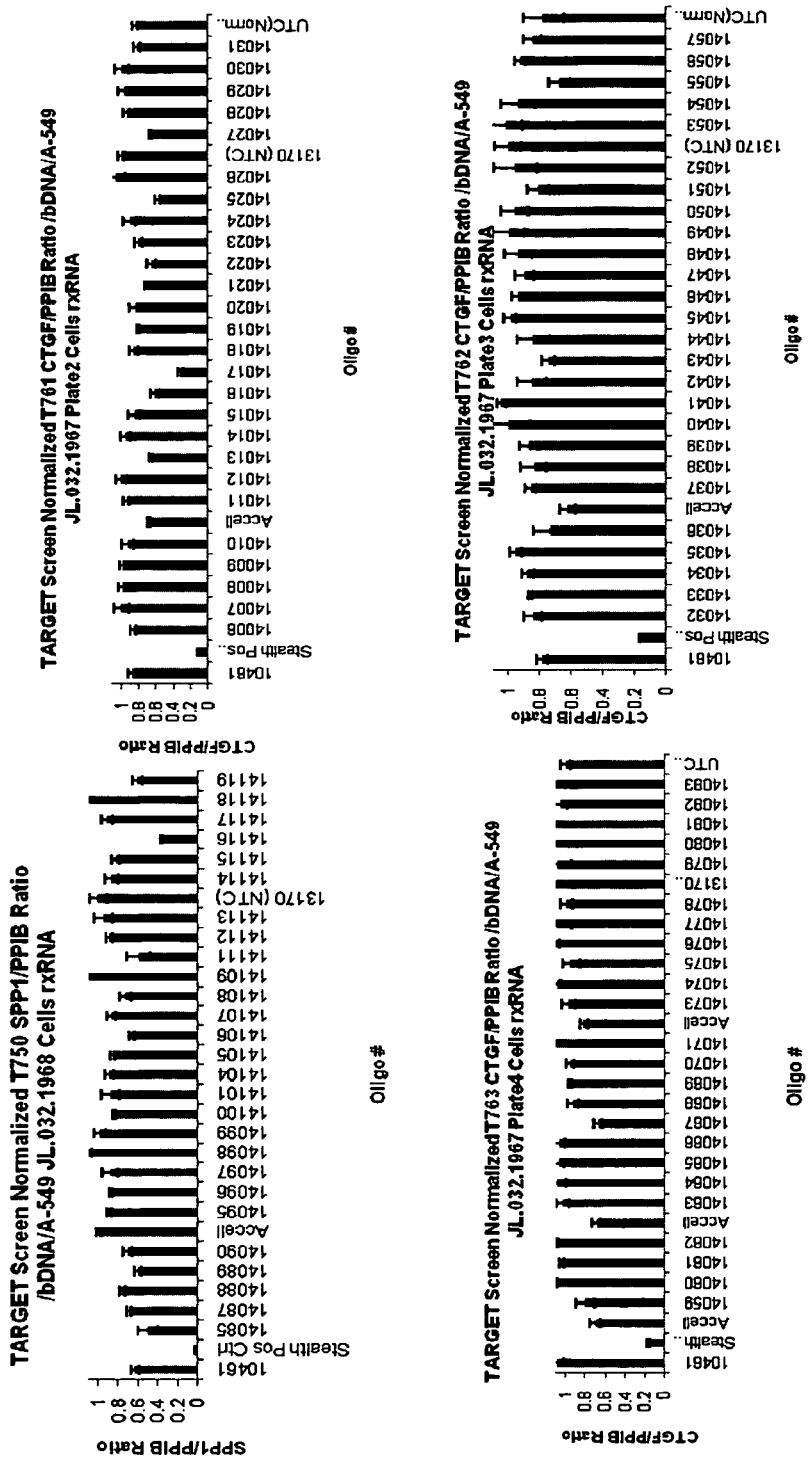
FIG. 86 demonstrates results of sd-rxRNA compound screens to identify sd-rxRNA compounds functional in CTGF knockdown.

A screen was conducted to identify compounds that could effectively silence expression of SPP1 (Osteopontin). Compounds targeting SPP1 were added to A549 cells (using passive transfection), and the level of SPP1 expression was evaluated at 48 hours. Several novel compounds effective in SPP1 silencing were identified. Compounds that were effective in silencing of SPP1 included 14116, 14121, 14131, 14134, 14139, 14149, and 14152 (FIGS. 84-86). The most potent compound in this assay was 14131 (FIG. 84). The efficacy of these sd-rxRNA compounds in silencing SPP1 expression was independently validated (FIG. 85).

Figure 87:
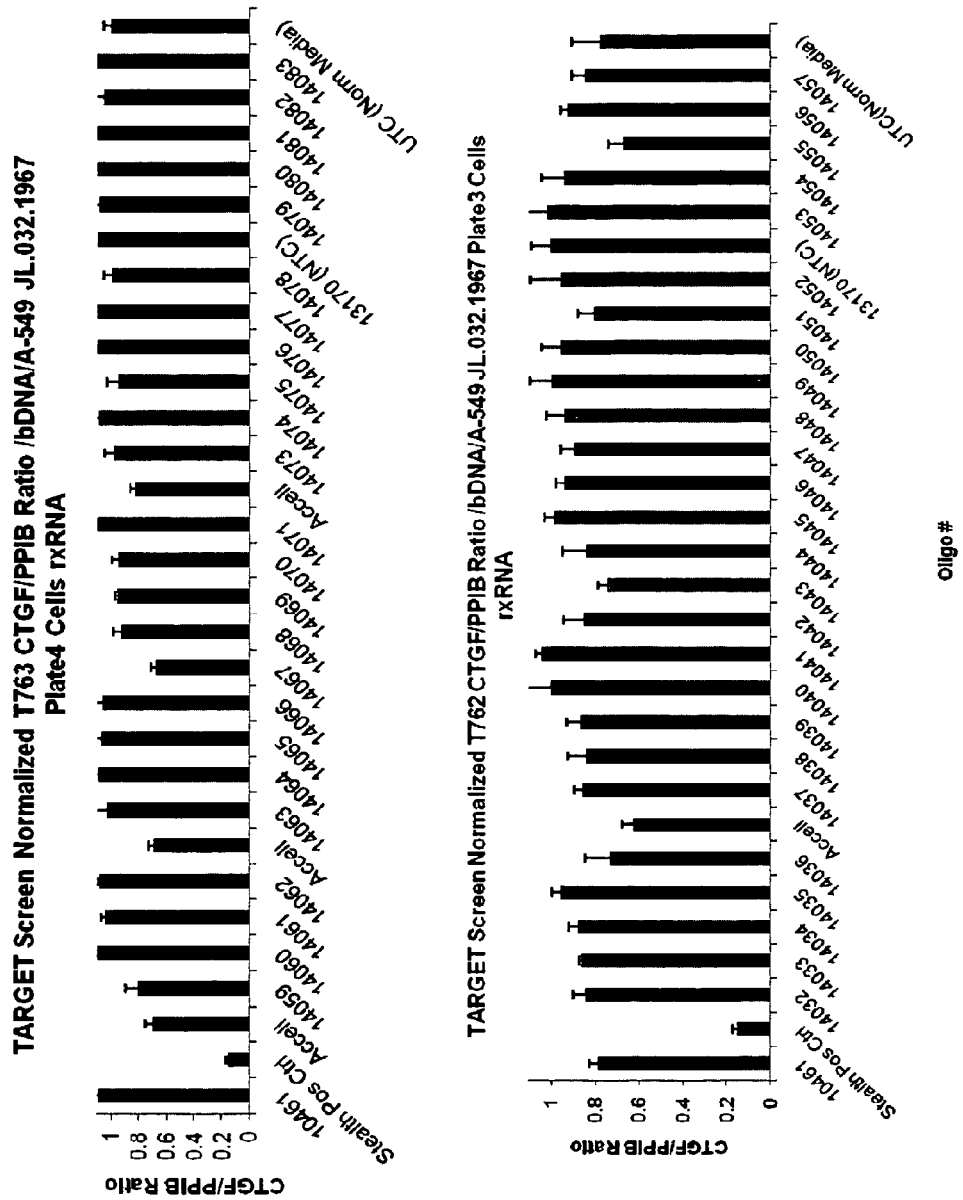
FIG. 87 demonstrates results of sd-rxRNA compound screens to identify sd-rxRNA functional in CTGF knockdown.

A similar screen was conducted to identify compounds that could effectively silence expression of CTGF (FIGS. 86-87). Compounds that were effective in silencing of CTGF included 14017, 14013, 14016, 14022, 14025, 14027.

Methods
Transfection of sd-rxRNA$^{nano}$
Lipid Mediated Transfection sd-rxRNA$^{nano}$ constructs were chemically synthesized (Dharmacon, Lafayette, Colo.) and transfected into HEK293 cells (ATCC, Manassas, Va.) using Lipofectamine RNAiMAX (Invitrogen, Carlsbad, Calif.) according to the manufacturer's instructions. In brief, RNA was diluted to a 12× concentration in Opti-MEM® 1 Reduced Serum Media (Invitrogen, Carlsbad, Calif.) and then combined with a 12× concentration of Lipofectamine RNAiMAX. The RNA and transfection reagent were allowed to complex at room temperature for 20 minutes and make a 6× concentration. While complexing, HEK293 cells were washed, trypsinized and counted. The cells were diluted to a concentration recommended by the manufacturer and previously described of $1 \times 10^5$ cells/ml. When RNA had completed complexing with the RNAiMAX transfection reagent, 20 ul of the complexes were added to the appropriate well of the 96-well plate in triplicate. Cells were added to each well (100 ul volume) to make the final cell count per well $1 \times 10^4$ cells/well. The volume of cells diluted the 6× concentration of complex to 1× (between 10-0.05 nM). Cells were incubated for 24 or 48 hours under normal growth conditions. After 24 or 48 hour incubation, cells were lysed and gene silencing activity was measured using the QuantiGene assay (Panomics, Freemont, Calif.) which employs bDNA hybridization technology. The assay was carried out according to manufacturer's instructions.

Passive Uptake Transfection sd-rxRNA$^{nano}$ constructs were chemically synthesized (Dharmacon, Lafayette, Colo.). 24 hours prior to transfection, HeLa cells (ATCC, Manassas, Va.) were plated at $1 \times 10^4$ cells/well in a 96 well plate under normal growth conditions (DMEM, 10% FBS and 1% Penicillin and Streptomycin). Prior to transfection of HeLa cells, sd-rxRNA$^{nano}$ were diluted to a final concentration of 0.01 uM to 1 uM in Accell siRNA Delivery Media (Dharmacon, Lafayette, Colo.). Normal growth media was aspirated off cells and 100 uL of Accell Delivery media containing the appropriate concentration of sd-rxRNAnano was applied to the cells. 48 hours post transfection, delivery media was aspirated off the cells and normal growth media was applied to cells for an additional 24 hours.

After 48 or 72 hour incubation, cells were lysed and gene silencing activity was measured using the QuantiGene assay (Panomics, Freemont, Calif.) according to manufacturer's instructions.

TABLE 1

| ID Number | Oligo Number | Accession number | Gene Name | Gene Symbol |
|---|---|---|---|---|
| APOB-10167-20-12138 | 12138 | NM_000384 | Apolipoprotein B (including Ag(x) antigen) | APOB |
| APOB-10167-20-12139 | 12139 | NM_000384 | Apolipoprotein B (including Ag(x) antigen) | APOB |
| MAP4K4-2931-13-12266 | 12266 | NM_004834 | Mitogen-Activated Protein Kinase Kinase Kinase Kinase 4 (MAP4K4), transcript variant 1 | MAP4K4 |
| MAP4K4-2931-16-12293 | 12293 | NM_004834 | Mitogen-Activated Protein Kinase Kinase Kinase Kinase 4 (MAP4K4), transcript variant 1 | MAP4K4 |
| MAP4K4-2931-16-12383 | 12383 | NM_004834 | Mitogen-Activated Protein Kinase Kinase Kinase Kinase 4 (MAP4K4), transcript variant 1 | MAP4K4 |
| MAP4K4-2931-16-12384 | 12384 | NM_004834 | Mitogen-Activated Protein Kinase Kinase Kinase Kinase 4 (MAP4K4), transcript variant 1 | MAP4K4 |
| MAP4K4-2931-16-12385 | 12385 | NM_004834 | Mitogen-Activated Protein Kinase Kinase Kinase Kinase 4 (MAP4K4), transcript variant 1 | MAP4K4 |
| MAP4K4-2931-16-12386 | 12386 | NM_004834 | Mitogen-Activated Protein Kinase Kinase Kinase Kinase 4 (MAP4K4), transcript variant 1 | MAP4K4 |
| MAP4K4-2931-16-12387 | 12387 | NM_004834 | Mitogen-Activated Protein Kinase Kinase Kinase Kinase 4 (MAP4K4), transcript variant 1 | MAP4K4 |
| MAP4K4-2931-15-12388 | 12388 | NM_004834 | Mitogen-Activated Protein Kinase Kinase Kinase Kinase 4 (MAP4K4), transcript variant 1 | MAP4K4 |
| MAP4K4-2931-13-12432 | 12432 | NM_004834 | Mitogen-Activated Protein Kinase Kinase Kinase Kinase 4 (MAP4K4), transcript variant 1 | MAP4K4 |
| MAP4K4-2931-13-12266.2 | 12266.2 | NM_004834 | Mitogen-Activated Protein Kinase Kinase Kinase Kinase 4 (MAP4K4), transcript variant 1 | MAP4K4 |
| APOB--21-12434 | 12434 | NM_000384 | Apolipoprotein B (including Ag(x) antigen) | APOB |
| APOB--21-12435 | 12435 | NM_000384 | Apolipoprotein B (including Ag(x) antigen) | APOB |
| MAP4K4-2931-16-12451 | 12451 | NM_004834 | Mitogen-Activated Protein Kinase Kinase Kinase Kinase 4 (MAP4K4), transcript variant 1 | MAP4K4 |
| MAP4K4-2931-16-12452 | 12452 | NM_004834 | Mitogen-Activated Protein Kinase Kinase Kinase Kinase 4 (MAP4K4), transcript variant 1 | MAP4K4 |
| MAP4K4-2931-16-12453 | 12453 | NM_004834 | Mitogen-Activated Protein Kinase Kinase Kinase Kinase 4 (MAP4K4), transcript variant 1 | MAP4K4 |
| MAP4K4-2931-17-12454 | 12454 | NM_004834 | Mitogen-Activated Protein Kinase Kinase Kinase Kinase 4 (MAP4K4), transcript variant 1 | MAP4K4 |
| MAP4K4-2931-17-12455 | 12455 | NM_004834 | Mitogen-Activated Protein Kinase Kinase Kinase Kinase 4 (MAP4K4), transcript variant 1 | MAP4K4 |
| MAP4K4-2931-19-12456 | 12456 | NM_004834 | Mitogen-Activated Protein Kinase Kinase Kinase Kinase 4 (MAP4K4), transcript variant 1 | MAP4K4 |
| --27-12480 | 12480 | | | |
| --27-12481 | 12481 | | | |
| APOB-10167-21-12505 | 12505 | NM_000384 | Apolipoprotein B (including Ag(x) antigen) | APOB |
| APOB-10167-21-12506 | 12506 | NM_000384 | Apolipoprotein B (including Ag(x) antigen) | APOB |

TABLE 1-continued

| ID Number | Oligo Number | Accession number | Gene Name | Gene Symbol |
|---|---|---|---|---|
| MAP4K4-2931-16-12539 | 12539 | NM_004834 | Mitogen-Activated Protein Kinase Kinase Kinase Kinase 4 (MAP4K4), transcript variant 1 | MAP4K4 |
| APOB-10167-21-12505.2 | 12505.2 | NM_000384 | Apolipoprotein B (including Ag(x) antigen) | APOB |
| APOB-10167-21-12506.2 | 12506.2 | NM_000384 | Apolipoprotein B (including Ag(x) antigen) | APOB |
| MAP4K4--13-12565 | 12565 | | | MAP4K4 |
| MAP4K4-2931-16-12386.2 | 12386.2 | NM_004834 | Mitogen-Activated Protein Kinase Kinase Kinase Kinase 4 (MAP4K4), transcript variant 1 | MAP4K4 |
| MAP4K4-2931-13-12815 | 12815 | NM_004834 | Mitogen-Activated Protein Kinase Kinase Kinase Kinase 4 (MAP4K4), transcript variant 1 | MAP4K4 |
| APOB--13-12957 | 12957 | NM_000384 | Apolipoprotein B (including Ag(x) antigen) | APOB |
| MAP4K4--16-12983 | 12983 | | Mitogen-Activated Protein Kinase Kinase Kinase Kinase 4 (MAP4K4), transcript variant 1 | MAP4K4 |
| MAP4K4--16-12984 | 12984 | | Mitogen-Activated Protein Kinase Kinase Kinase Kinase 4 (MAP4K4), transcript variant 1 | MAP4K4 |
| MAP4K4--16-12985 | 12985 | | Mitogen-Activated Protein Kinase Kinase Kinase Kinase 4 (MAP4K4), transcript variant 1 | MAP4K4 |
| MAP4K4--16-12986 | 12986 | | Mitogen-Activated Protein Kinase Kinase Kinase Kinase 4 (MAP4K4), transcript variant 1 | MAP4K4 |
| MAP4K4--16-12987 | 12987 | | Mitogen-Activated Protein Kinase Kinase Kinase Kinase 4 (MAP4K4), transcript variant 1 | MAP4K4 |
| MAP4K4--16-12988 | 12988 | | Mitogen-Activated Protein Kinase Kinase Kinase Kinase 4 (MAP4K4), transcript variant 1 | MAP4K4 |
| MAP4K4--16-12989 | 12989 | | Mitogen-Activated Protein Kinase Kinase Kinase Kinase 4 (MAP4K4), transcript variant 1 | MAP4K4 |
| MAP4K4--16-12990 | 12990 | | Mitogen-Activated Protein Kinase Kinase Kinase Kinase 4 (MAP4K4), transcript variant 1 | MAP4K4 |
| MAP4K4--16-12991 | 12991 | | Mitogen-Activated Protein Kinase Kinase Kinase Kinase 4 (MAP4K4), transcript variant 1 | MAP4K4 |
| MAP4K4--16-12992 | 12992 | | Mitogen-Activated Protein Kinase Kinase Kinase Kinase 4 (MAP4K4), transcript variant 1 | MAP4K4 |
| MAP4K4--16-12993 | 12993 | | Mitogen-Activated Protein Kinase Kinase Kinase Kinase 4 (MAP4K4), transcript variant 1 | MAP4K4 |
| MAP4K4--16-12994 | 12994 | | Mitogen-Activated Protein Kinase Kinase Kinase Kinase 4 (MAP4K4), transcript variant 1 | MAP4K4 |
| MAP4K4--16-12995 | 12995 | | Mitogen-Activated Protein Kinase Kinase Kinase Kinase 4 (MAP4K4), transcript variant 1 | MAP4K4 |
| MAP4K4-2931-19-13012 | 13012 | NM_004834 | Mitogen-Activated Protein Kinase Kinase Kinase Kinase 4 (MAP4K4), transcript variant 1 | MAP4K4 |
| MAP4K4-2931-19-13016 | 13016 | NM_004834 | Mitogen-Activated Protein Kinase Kinase Kinase Kinase 4 (MAP4K4), transcript variant 1 | MAP4K4 |
| PPIB--13-13021 | 13021 | NM_000942 | Peptidylprolyl Isomerase B (cyclophilin B) | PPIB |
| pGL3-1172-13-13038 | 13038 | U47296 | Cloning vector pGL3-Control | pGL3 |
| pGL3-1172-13-13040 | 13040 | U47296 | Cloning vector pGL3-Control | pGL3 |
| --16-13047 | 13047 | | | |
| SOD1-530-13-13090 | 13090 | NM_000454 | Superoxide Dismutase 1, soluble (amyotrophic lateral sclerosis 1 (adult)) | SOD1 |
| SOD1-523-13-13091 | 13091 | NM_000454 | Superoxide Dismutase 1, soluble (amyotrophic lateral sclerosis 1 (adult)) | SOD1 |
| SOD1-535-13-13092 | 13092 | NM_000454 | Superoxide Dismutase 1, soluble (amyotrophic lateral sclerosis 1 (adult)) | SOD1 |
| SOD1-536-13-13093 | 13093 | NM_000454 | Superoxide Dismutase 1, soluble (amyotrophic lateral sclerosis 1 (adult)) | SOD1 |
| SOD1-396-13-13094 | 13094 | NM_000454 | Superoxide Dismutase 1, soluble (amyotrophic lateral sclerosis 1 (adult)) | SOD1 |
| SOD1-385-13-13095 | 13095 | NM_000454 | Superoxide Dismutase 1, soluble (amyotrophic lateral sclerosis 1 (adult)) | SOD1 |
| SOD1-195-13-13096 | 13096 | NM_000454 | Superoxide Dismutase 1, soluble (amyotrophic lateral sclerosis 1 (adult)) | SOD1 |
| APOB-4314-13-13115 | 13115 | NM_000384 | Apolipoprotein B (including Ag(x) antigen) | APOB |
| APOB-3384-13-13116 | 13116 | NM_000384 | Apolipoprotein B (including Ag(x) antigen) | APOB |
| APOB-3547-13-13117 | 13117 | NM_000384 | Apolipoprotein B (including Ag(x) antigen) | APOB |
| APOB-4318-13-13118 | 13118 | NM_000384 | Apolipoprotein B (including Ag(x) antigen) | APOB |
| APOB-3741-13-13119 | 13119 | NM_000384 | Apolipoprotein B (including Ag(x) antigen) | APOB |
| PPIB--16-13136 | 13136 | NM_000942 | Peptidylprolyl Isomerase B (cyclophilin B) | PPIB |

TABLE 1-continued

| ID Number | Oligo Number | Accession number | Gene Name | Gene Symbol |
|---|---|---|---|---|
| APOB-4314-15-13154 | 13154 | NM_000384 | Apolipoprotein B (including Ag(x) antigen) | APOB |
| APOB-3547-15-13155 | 13155 | NM_000384 | Apolipoprotein B (including Ag(x) antigen) | APOB |
| APOB-4318-15-13157 | 13157 | NM_000384 | Apolipoprotein B (including Ag(x) antigen) | APOB |
| APOB-3741-15-13158 | 13158 | NM_000384 | Apolipoprotein B (including Ag(x) antigen) | APOB |
| APOB--13-13159 | 13159 | NM_000384 | Apolipoprotein B (including Ag(x) antigen) | APOB |
| APOB--15-13160 | 13160 | NM_000384 | Apolipoprotein B (including Ag(x) antigen) | APOB |
| SOD1-530-16-13163 | 13163 | NM_000454 | Superoxide Dismutase 1, soluble (amyotrophic lateral sclerosis 1 (adult)) | SOD1 |
| SOD1-523-16-13164 | 13164 | NM_000454 | Superoxide Dismutase 1, soluble (amyotrophic lateral sclerosis 1 (adult)) | SOD1 |
| SOD1-535-16-13165 | 13165 | NM_000454 | Superoxide Dismutase 1, soluble (amyotrophic lateral sclerosis 1 (adult)) | SOD1 |
| SOD1-536-16-13166 | 13166 | NM_000454 | Superoxide Dismutase 1, soluble (amyotrophic lateral sclerosis 1 (adult)) | SOD1 |
| SOD1-396-16-13167 | 13167 | NM_000454 | Superoxide Dismutase 1, soluble (amyotrophic lateral sclerosis 1 (adult)) | SOD1 |
| SOD1-385-16-13168 | 13168 | NM_000454 | Superoxide Dismutase 1, soluble (amyotrophic lateral sclerosis 1 (adult)) | SOD1 |
| SOD1-195-16-13169 | 13169 | NM_000454 | Superoxide Dismutase 1, soluble (amyotrophic lateral sclerosis 1 (adult)) | SOD1 |
| pGL3-1172-16-13170 | 13170 | U47296 | Cloning vector pGL3-Control | pGL3 |
| pGL3-1172-16-13171 | 13171 | U47296 | Cloning vector pGL3-Control | pGL3 |
| MAP4k4-2931-19-13189 | 13189 | NM_004834 | Mitogen-Activated Protein Kinase Kinase Kinase Kinase 4 (MAP4K4), transcript variant 1 | MAP4k4 |
| CTGF-1222-13-13190 | 13190 | NM_001901.2 | connective tissue growth factor | CTGF |
| CTGF-813-13-13192 | 13192 | NM_001901.2 | connective tissue growth factor | CTGF |
| CTGF-747-13-13194 | 13194 | NM_001901.2 | connective tissue growth factor | CTGF |
| CTGF-817-13-13196 | 13196 | NM_001901.2 | connective tissue growth factor | CTGF |
| CTGF-1174-13-13198 | 13198 | NM_001901.2 | connective tissue growth factor | CTGF |
| CTGF-1005-13-13200 | 13200 | NM_001901.2 | connective tissue growth factor | CTGF |
| CTGF-814-13-13202 | 13202 | NM_001901.2 | connective tissue growth factor | CTGF |
| CTGF-816-13-13204 | 13204 | NM_001901.2 | connective tissue growth factor | CTGF |
| CTGF-1001-13-13206 | 13206 | NM_001901.2 | connective tissue growth factor | CTGF |
| CTGF-1173-13-13208 | 13208 | NM_001901.2 | connective tissue growth factor | CTGF |
| CTGF-749-13-13210 | 13210 | NM_001901.2 | connective tissue growth factor | CTGF |
| CTGF-792-13-13212 | 13212 | NM_001901.2 | connective tissue growth factor | CTGF |
| CTGF-1162-13-13214 | 13214 | NM_001901.2 | connective tissue growth factor | CTGF |
| CTGF-811-13-13216 | 13216 | NM_001901.2 | connective tissue growth factor | CTGF |
| CTGF-797-13-13218 | 13218 | NM_001901.2 | connective tissue growth factor | CTGF |
| CTGF-1175-13-13220 | 13220 | NM_001901.2 | connective tissue growth factor | CTGF |
| CTGF-1172-13-13222 | 13222 | NM_001901.2 | connective tissue growth factor | CTGF |
| CTGF-1177-13-13224 | 13224 | NM_001901.2 | connective tissue growth factor | CTGF |
| CTGF-1176-13-13226 | 13226 | NM_001901.2 | connective tissue growth factor | CTGF |
| CTGF-812-13-13228 | 13228 | NM_001901.2 | connective tissue growth factor | CTGF |
| CTGF-745-13-13230 | 13230 | NM_001901.2 | connective tissue growth factor | CTGF |
| CTGF-1230-13-13232 | 13232 | NM_001901.2 | connective tissue growth factor | CTGF |

TABLE 1-continued

| ID Number | Oligo Number | Accession number | Gene Name | Gene Symbol |
|---|---|---|---|---|
| CTGF-920-13-13234 | 13234 | NM_001901.2 | connective tissue growth factor | CTGF |
| CTGF-679-13-13236 | 13236 | NM_001901.2 | connective tissue growth factor | CTGF |
| CTGF-992-13-13238 | 13238 | NM_001901.2 | connective tissue growth factor | CTGF |
| CTGF-1045-13-13240 | 13240 | NM_001901.2 | connective tissue growth factor | CTGF |
| CTGF-1231-13-13242 | 13242 | NM_001901.2 | connective tissue growth factor | CTGF |
| CTGF-991-13-13244 | 13244 | NM_001901.2 | connective tissue growth factor | CTGF |
| CTGF-998-13-13246 | 13246 | NM_001901.2 | connective tissue growth factor | CTGF |
| CTGF-1049-13-13248 | 13248 | NM_001901.2 | connective tissue growth factor | CTGF |
| CTGF-1044-13-13250 | 13250 | NM_001901.2 | connective tissue growth factor | CTGF |
| CTGF-1327-13-13252 | 13252 | NM_001901.2 | connective tissue growth factor | CTGF |
| CTGF-1196-13-13254 | 13254 | NM_001901.2 | connective tissue growth factor | CTGF |
| CTGF-562-13-13256 | 13256 | NM_001901.2 | connective tissue growth factor | CTGF |
| CTGF-752-13-13258 | 13258 | NM_001901.2 | connective tissue growth factor | CTGF |
| CTGF-994-13-13260 | 13260 | NM_001901.2 | connective tissue growth factor | CTGF |
| CTGF-1040-13-13262 | 13262 | NM_001901.2 | connective tissue growth factor | CTGF |
| CTGF-1984-13-13264 | 13264 | NM_001901.2 | connective tissue growth factor | CTGF |
| CTGF-2195-13-13266 | 13266 | NM_001901.2 | connective tissue growth factor | CTGF |
| CTGF-2043-13-13268 | 13268 | NM_001901.2 | connective tissue growth factor | CTGF |
| CTGF-1892-13-13270 | 13270 | NM_001901.2 | connective tissue growth factor | CTGF |
| CTGF-1567-13-13272 | 13272 | NM_001901.2 | connective tissue growth factor | CTGF |
| CTGF-1780-13-13274 | 13274 | NM_001901.2 | connective tissue growth factor | CTGF |
| CTGF-2162-13-13276 | 13276 | NM_001901.2 | connective tissue growth factor | CTGF |
| CTGF-1034-13-13278 | 13278 | NM_001901.2 | connective tissue growth factor | CTGF |
| CTGF-2264-13-13280 | 13280 | NM_001901.2 | connective tissue growth factor | CTGF |
| CTGF-1032-13-13282 | 13282 | NM_001901.2 | connective tissue growth factor | CTGF |
| CTGF-1535-13-13284 | 13284 | NM_001901.2 | connective tissue growth factor | CTGF |
| CTGF-1694-13-13286 | 13286 | NM_001901.2 | connective tissue growth factor | CTGF |
| CTGF-1588-13-13288 | 13288 | NM_001901.2 | connective tissue growth factor | CTGF |
| CTGF-928-13-13290 | 13290 | NM_001901.2 | connective tissue growth factor | CTGF |
| CTGF-1133-13-13292 | 13292 | NM_001901.2 | connective tissue growth factor | CTGF |
| CTGF-912-13-13294 | 13294 | NM_001901.2 | connective tissue growth factor | CTGF |
| CTGF-753-13-13296 | 13296 | NM_001901.2 | connective tissue growth factor | CTGF |
| CTGF-918-13-13298 | 13298 | NM_001901.2 | connective tissue growth factor | CTGF |
| CTGF-744-13-13300 | 13300 | NM_001901.2 | connective tissue growth factor | CTGF |
| CTGF-466-13-13302 | 13302 | NM_001901.2 | connective tissue growth factor | CTGF |
| CTGF-917-13-13304 | 13304 | NM_001901.2 | connective tissue growth factor | CTGF |
| CTGF-1038-13-13306 | 13306 | NM_001901.2 | connective tissue growth factor | CTGF |
| CTGF-1048-13-13308 | 13308 | NM_001901.2 | connective tissue growth factor | CTGF |

TABLE 1-continued

| ID Number | Oligo Number | Accession number | Gene Name | Gene Symbol |
|---|---|---|---|---|
| CTGF-1235-13-13310 | 13310 | NM_001901.2 | connective tissue growth factor | CTGF |
| CTGF-868-13-13312 | 13312 | NM_001901.2 | connective tissue growth factor | CTGF |
| CTGF-1131-13-13314 | 13314 | NM_001901.2 | connective tissue growth factor | CTGF |
| CTGF-1043-13-13316 | 13316 | NM_001901.2 | connective tissue growth factor | CTGF |
| CTGF-751-13-13318 | 13318 | NM_001901.2 | connective tissue growth factor | CTGF |
| CTGF-1227-13-13320 | 13320 | NM_001901.2 | connective tissue growth factor | CTGF |
| CTGF-867-13-13322 | 13322 | NM_001901.2 | connective tissue growth factor | CTGF |
| CTGF-1128-13-13324 | 13324 | NM_001901.2 | connective tissue growth factor | CTGF |
| CTGF-756-13-13326 | 13326 | NM_001901.2 | connective tissue growth factor | CTGF |
| CTGF-1234-13-13328 | 13328 | NM_001901.2 | connective tissue growth factor | CTGF |
| CTGF-916-13-13330 | 13330 | NM_001901.2 | connective tissue growth factor | CTGF |
| CTGF-925-13-13332 | 13332 | NM_001901.2 | connective tissue growth factor | CTGF |
| CTGF-1225-13-13334 | 13334 | NM_001901.2 | connective tissue growth factor | CTGF |
| CTGF-445-13-13336 | 13336 | NM_001901.2 | connective tissue growth factor | CTGF |
| CTGF-446-13-13338 | 13338 | NM_001901.2 | connective tissue growth factor | CTGF |
| CTGF-913-13-13340 | 13340 | NM_001901.2 | connective tissue growth factor | CTGF |
| CTGF-997-13-13342 | 13342 | NM_001901.2 | connective tissue growth factor | CTGF |
| CTGF-277-13-13344 | 13344 | NM_001901.2 | connective tissue growth factor | CTGF |
| CTGF-1052-13-13346 | 13346 | NM_001901.2 | connective tissue growth factor | CTGF |
| CTGF-887-13-13348 | 13348 | NM_001901.2 | connective tissue growth factor | CTGF |
| CTGF-914-13-13350 | 13350 | NM_001901.2 | connective tissue growth factor | CTGF |
| CTGF-1039-13-13352 | 13352 | NM_001901.2 | connective tissue growth factor | CTGF |
| CTGF-754-13-13354 | 13354 | NM_001901.2 | connective tissue growth factor | CTGF |
| CTGF-1130-13-13356 | 13356 | NM_001901.2 | connective tissue growth factor | CTGF |
| CTGF-919-13-13358 | 13358 | NM_001901.2 | connective tissue growth factor | CTGF |
| CTGF-922-13-13360 | 13360 | NM_001901.2 | connective tissue growth factor | CTGF |
| CTGF-746-13-13362 | 13362 | NM_001901.2 | connective tissue growth factor | CTGF |
| CTGF-993-13-13364 | 13364 | NM_001901.2 | connective tissue growth factor | CTGF |
| CTGF-825-13-13366 | 13366 | NM_001901.2 | connective tissue growth factor | CTGF |
| CTGF-926-13-13368 | 13368 | NM_001901.2 | connective tissue growth factor | CTGF |
| CTGF-923-13-13370 | 13370 | NM_001901.2 | connective tissue growth factor | CTGF |
| CTGF-866-13-13372 | 13372 | NM_001901.2 | connective tissue growth factor | CTGF |
| CTGF-563-13-13374 | 13374 | NM_001901.2 | connective tissue growth factor | CTGF |
| CTGF-823-13-13376 | 13376 | NM_001901.2 | connective tissue growth factor | CTGF |
| CTGF-1233-13-13378 | 13378 | NM_001901.2 | connective tissue growth factor | CTGF |
| CTGF-924-13-13380 | 13380 | NM_001901.2 | connective tissue growth factor | CTGF |
| CTGF-921-13-13382 | 13382 | NM_001901.2 | connective tissue growth factor | CTGF |
| CTGF-443-13-13384 | 13384 | NM_001901.2 | connective tissue growth factor | CTGF |

TABLE 1-continued

| ID Number | Oligo Number | Accession number | Gene Name | Gene Symbol |
|---|---|---|---|---|
| CTGF-1041-13-13386 | 13386 | NM_001901.2 | connective tissue growth factor | CTGF |
| CTGF-1042-13-13388 | 13388 | NM_001901.2 | connective tissue growth factor | CTGF |
| CTGF-755-13-13390 | 13390 | NM_001901.2 | connective tissue growth factor | CTGF |
| CTGF-467-13-13392 | 13392 | NM_001901.2 | connective tissue growth factor | CTGF |
| CTGF-995-13-13394 | 13394 | NM_001901.2 | connective tissue growth factor | CTGF |
| CTGF-927-13-13396 | 13396 | NM_001901.2 | connective tissue growth factor | CTGF |
| SPP1-1025-13-13398 | 13398 | NM_000582.2 | Osteopontin | SPP1 |
| SPP1-1049-13-13400 | 13400 | NM_000582.2 | Osteopontin | SPP1 |
| SPP1-1051-13-13402 | 13402 | NM_000582.2 | Osteopontin | SPP1 |
| SPP1-1048-13-13404 | 13404 | NM_000582.2 | Osteopontin | SPP1 |
| SPP1-1050-13-13406 | 13406 | NM_000582.2 | Osteopontin | SPP1 |
| SPP1-1047-13-13408 | 13408 | NM_000582.2 | Osteopontin | SPP1 |
| SPP1-800-13-13410 | 13410 | NM_000582.2 | Osteopontin | SPP1 |
| SPP1-492-13-13412 | 13412 | NM_000582.2 | Osteopontin | SPP1 |
| SPP1-612-13-13414 | 13414 | NM_000582.2 | Osteopontin | SPP1 |
| SPP1-481-13-13416 | 13416 | NM_000582.2 | Osteopontin | SPP1 |
| SPP1-614-13-13418 | 13418 | NM_000582.2 | Osteopontin | SPP1 |
| SPP1-951-13-13420 | 13420 | NM_000582.2 | Osteopontin | SPP1 |
| SPP1-482-13-13422 | 13422 | NM_000582.2 | Osteopontin | SPP1 |
| SPP1-856-13-13424 | 13424 | NM_000582.2 | Osteopontin | SPP1 |
| SPP1-857-13-13426 | 13426 | NM_000582.2 | Osteopontin | SPP1 |
| SPP1-365-13-13428 | 13428 | NM_000582.2 | Osteopontin | SPP1 |
| SPP1-359-13-13430 | 13430 | NM_000582.2 | Osteopontin | SPP1 |
| SPP1-357-13-13432 | 13432 | NM_000582.2 | Osteopontin | SPP1 |
| SPP1-858-13-13434 | 13434 | NM_000582.2 | Osteopontin | SPP1 |
| SPP1-1012-13-13436 | 13436 | NM_000582.2 | Osteopontin | SPP1 |
| SPP1-1014-13-13438 | 13438 | NM_000582.2 | Osteopontin | SPP1 |
| SPP1-356-13-13440 | 13440 | NM_000582.2 | Osteopontin | SPP1 |
| SPP1-368-13-13442 | 13442 | NM_000582.2 | Osteopontin | SPP1 |
| SPP1-1011-13-13444 | 13444 | NM_000582.2 | Osteopontin | SPP1 |
| SPP1-754-13-13446 | 13446 | NM_000582.2 | Osteopontin | SPP1 |
| SPP1-1021-13-13448 | 13448 | NM_000582.2 | Osteopontin | SPP1 |
| SPP1-1330-13-13450 | 13450 | NM_000582.2 | Osteopontin | SPP1 |
| SPP1-346-13-13452 | 13452 | NM_000582.2 | Osteopontin | SPP1 |
| SPP1-869-13-13454 | 13454 | NM_000582.2 | Osteopontin | SPP1 |
| SPP1-701-13-13456 | 13456 | NM_000582.2 | Osteopontin | SPP1 |
| SPP1-896-13-13458 | 13458 | NM_000582.2 | Osteopontin | SPP1 |
| SPP1-1035-13-13460 | 13460 | NM_000582.2 | Osteopontin | SPP1 |

TABLE 1-continued

| ID Number | Oligo Number | Accession number | Gene Name | Gene Symbol |
|---|---|---|---|---|
| SPP1-1170-13-13462 | 13462 | NM_000582.2 | Osteopontin | SPP1 |
| SPP1-1282-13-13464 | 13464 | NM_000582.2 | Osteopontin | SPP1 |
| SPP1-1537-13-13466 | 13466 | NM_000582.2 | Osteopontin | SPP1 |
| SPP1-692-13-13468 | 13468 | NM_000582.2 | Osteopontin | SPP1 |
| SPP1-840-13-13470 | 13470 | NM_000582.2 | Osteopontin | SPP1 |
| SPP1-1163-13-13472 | 13472 | NM_000582.2 | Osteopontin | SPP1 |
| SPP1-789-13-13474 | 13474 | NM_000582.2 | Osteopontin | SPP1 |
| SPP1-841-13-13476 | 13476 | NM_000582.2 | Osteopontin | SPP1 |
| SPP1-852-13-13478 | 13478 | NM_000582.2 | Osteopontin | SPP1 |
| SPP1-209-13-13480 | 13480 | NM_000582.2 | Osteopontin | SPP1 |
| SPP1-1276-13-13482 | 13482 | NM_000582.2 | Osteopontin | SPP1 |
| SPP1-137-13-13484 | 13484 | NM_000582.2 | Osteopontin | SPP1 |
| SPP1-711-13-13486 | 13486 | NM_000582.2 | Osteopontin | SPP1 |
| SPP1-582-13-13488 | 13488 | NM_000582.2 | Osteopontin | SPP1 |
| SPP1-839-13-13490 | 13490 | NM_000582.2 | Osteopontin | SPP1 |
| SPP1-1091-13-13492 | 13492 | NM_000582.2 | Osteopontin | SPP1 |
| SPP1-884-13-13494 | 13494 | NM_000582.2 | Osteopontin | SPP1 |
| SPP1-903-13-13496 | 13496 | NM_000582.2 | Osteopontin | SPP1 |
| SPP1-1090-13-13498 | 13498 | NM_000582.2 | Osteopontin | SPP1 |
| SPP1-474-13-13500 | 13500 | NM_000582.2 | Osteopontin | SPP1 |
| SPP1-575-13-13502 | 13502 | NM_000582.2 | Osteopontin | SPP1 |
| SPP1-671-13-13504 | 13504 | NM_000582.2 | Osteopontin | SPP1 |
| SPP1-924-13-13506 | 13506 | NM_000582.2 | Osteopontin | SPP1 |
| SPP1-1185-13-13508 | 13508 | NM_000582.2 | Osteopontin | SPP1 |
| SPP1-1221-13-13510 | 13510 | NM_000582.2 | Osteopontin | SPP1 |
| SPP1-347-13-13512 | 13512 | NM_000582.2 | Osteopontin | SPP1 |
| SPP1-634-13-13514 | 13514 | NM_000582.2 | Osteopontin | SPP1 |
| SPP1-877-13-13516 | 13516 | NM_000582.2 | Osteopontin | SPP1 |
| SPP1-1033-13-13518 | 13518 | NM_000582.2 | Osteopontin | SPP1 |
| SPP1-714-13-13520 | 13520 | NM_000582.2 | Osteopontin | SPP1 |
| SPP1-791-13-13522 | 13522 | NM_000582.2 | Osteopontin | SPP1 |
| SPP1-813-13-13524 | 13524 | NM_000582.2 | Osteopontin | SPP1 |
| SPP1-939-13-13526 | 13526 | NM_000582.2 | Osteopontin | SPP1 |
| SPP1-1161-13-13528 | 13528 | NM_000582.2 | Osteopontin | SPP1 |
| SPP1-1164-13-13530 | 13530 | NM_000582.2 | Osteopontin | SPP1 |
| SPP1-1190-13-13532 | 13532 | NM_000582.2 | Osteopontin | SPP1 |
| SPP1-1333-13-13534 | 13534 | NM_000582.2 | Osteopontin | SPP1 |
| SPP1-537-13-13536 | 13536 | NM_000582.2 | Osteopontin | SPP1 |

TABLE 1-continued

| ID Number | Oligo Number | Accession number | Gene Name | Gene Symbol |
|---|---|---|---|---|
| SPP1-684-13-13538 | 13538 | NM_000582.2 | Osteopontin | SPP1 |
| SPP1-707-13-13540 | 13540 | NM_000582.2 | Osteopontin | SPP1 |
| SPP1-799-13-13542 | 13542 | NM_000582.2 | Osteopontin | SPP1 |
| SPP1-853-13-13544 | 13544 | NM_000582.2 | Osteopontin | SPP1 |
| SPP1-888-13-13546 | 13546 | NM_000582.2 | Osteopontin | SPP1 |
| SPP1-1194-13-13548 | 13548 | NM_000582.2 | Osteopontin | SPP1 |
| SPP1-1279-13-13550 | 13550 | NM_000582.2 | Osteopontin | SPP1 |
| SPP1-1300-13-13552 | 13552 | NM_000582.2 | Osteopontin | SPP1 |
| SPP1-1510-13-13554 | 13554 | NM_000582.2 | Osteopontin | SPP1 |
| SPP1-1543-13-13556 | 13556 | NM_000582.2 | Osteopontin | SPP1 |
| SPP1-434-13-13558 | 13558 | NM_000582.2 | Osteopontin | SPP1 |
| SPP1-600-13-13560 | 13560 | NM_000582.2 | Osteopontin | SPP1 |
| SPP1-863-13-13562 | 13562 | NM_000582.2 | Osteopontin | SPP1 |
| SPP1-902-13-13564 | 13564 | NM_000582.2 | Osteopontin | SPP1 |
| SPP1-921-13-13566 | 13566 | NM_000582.2 | Osteopontin | SPP1 |
| SPP1-154-13-13568 | 13568 | NM_000582.2 | Osteopontin | SPP1 |
| SPP1-217-13-13570 | 13570 | NM_000582.2 | Osteopontin | SPP1 |
| SPP1-816-13-13572 | 13572 | NM_000582.2 | Osteopontin | SPP1 |
| SPP1-882-13-13574 | 13574 | NM_000582.2 | Osteopontin | SPP1 |
| SPP1-932-13-13576 | 13576 | NM_000582.2 | Osteopontin | SPP1 |
| SPP1-1509-13-13578 | 13578 | NM_000582.2 | Osteopontin | SPP1 |
| SPP1-157-13-13580 | 13580 | NM_000582.2 | Osteopontin | SPP1 |
| SPP1-350-13-13582 | 13582 | NM_000582.2 | Osteopontin | SPP1 |
| SPP1-511-13-13584 | 13584 | NM_000582.2 | Osteopontin | SPP1 |
| SPP1-605-13-13586 | 13586 | NM_000582.2 | Osteopontin | SPP1 |
| SPP1-811-13-13588 | 13588 | NM_000582.2 | Osteopontin | SPP1 |
| SPP1-892-13-13590 | 13590 | NM_000582.2 | Osteopontin | SPP1 |
| SPP1-922-13-13592 | 13592 | NM_000582.2 | Osteopontin | SPP1 |
| SPP1-1169-13-13594 | 13594 | NM_000582.2 | Osteopontin | SPP1 |
| SPP1-1182-13-13596 | 13596 | NM_000582.2 | Osteopontin | SPP1 |
| SPP1-1539-13-13598 | 13598 | NM_000582.2 | Osteopontin | SPP1 |
| SPP1-1541-13-13600 | 13600 | NM_000582.2 | Osteopontin | SPP1 |
| SPP1-427-13-13602 | 13602 | NM_000582.2 | Osteopontin | SPP1 |
| SPP1-533-13-13604 | 13604 | NM_000582.2 | Osteopontin | SPP1 |
| APOB--13-13763 | 13763 | NM_000384 | Apolipoprotein B (including Ag(x) antigen) | APOB |
| APOB--13-13764 | 13764 | NM_000384 | Apolipoprotein B (including Ag(x) antigen) | APOB |
| MAP4K4--16-13766 | 13766 | | | MAP4K4 |
| PPIB--13-13767 | 13767 | NM_000942 | peptidylprolyl isomerase B (cyclophilin B) | PPIB |

TABLE 1-continued

| ID Number | Oligo Number | Accession number | Gene Name | Gene Symbol |
|---|---|---|---|---|
| PPIB--15-13768 | 13768 | NM_000942 | peptidylprolyl isomerase B (cyclophilin B) | PPIB |
| PPIB--17-13769 | 13769 | NM_000942 | peptidylprolyl isomerase B (cyclophilin B) | PPIB |
| MAP4K4--16-13939 | 13939 | | | MAP4K4 |
| APOB-4314-16-13940 | 13940 | NM_000384 | Apolipoprotein B (including Ag(x) antigen) | APOB |
| APOB-4314-17-13941 | 13941 | NM_000384 | Apolipoprotein B (including Ag(x) antigen) | APOB |
| APOB--16-13942 | 13942 | NM_000384 | Apolipoprotein B (including Ag(x) antigen) | APOB |
| APOB--18-13943 | 13943 | NM_000384 | Apolipoprotein B (including Ag(x) antigen) | APOB |
| APOB--17-13944 | 13944 | NM_000384 | Apolipoprotein B (including Ag(x) antigen) | APOB |
| APOB--19-13945 | 13945 | NM_000384 | Apolipoprotein B (including Ag(x) antigen) | APOB |
| APOB-4314-16-13946 | 13946 | NM_000384 | Apolipoprotein B (including Ag(x) antigen) | APOB |
| APOB-4314-17-13947 | 13947 | NM_000384 | Apolipoprotein B (including Ag(x) antigen) | APOB |
| APOB--16-13948 | 13948 | NM_000384 | Apolipoprotein B (including Ag(x) antigen) | APOB |
| APOB--17-13949 | 13949 | NM_000384 | Apolipoprotein B (including Ag(x) antigen) | APOB |
| APOB--16-13950 | 13950 | NM_000384 | Apolipoprotein B (including Ag(x) antigen) | APOB |
| APOB--18-13951 | 13951 | NM_000384 | Apolipoprotein B (including Ag(x) antigen) | APOB |
| APOB--17-13952 | 13952 | NM_000384 | Apolipoprotein B (including Ag(x) antigen) | APOB |
| APOB--19-13953 | 13953 | NM_000384 | Apolipoprotein B (including Ag(x) antigen) | APOB |
| MAP4K4--16-13766.2 | 13766.2 | | | MAP4K4 |
| CTGF-1222-16-13980 | 13980 | NM_001901.2 | connective tissue growth factor | CTGF |
| CTGF-813-16-13981 | 13981 | NM_001901.2 | connective tissue growth factor | CTGF |
| CTGF-747-16-13982 | 13982 | NM_001901.2 | connective tissue growth factor | CTGF |
| CTGF-817-16-13983 | 13983 | NM_001901.2 | connective tissue growth factor | CTGF |
| CTGF-1174-16-13984 | 13984 | NM_001901.2 | connective tissue growth factor | CTGF |
| CTGF-1005-16-13985 | 13985 | NM_001901.2 | connective tissue growth factor | CTGF |
| CTGF-814-16-13986 | 13986 | NM_001901.2 | connective tissue growth factor | CTGF |
| CTGF-816-16-13987 | 13987 | NM_001901.2 | connective tissue growth factor | CTGF |
| CTGF-1001-16-13988 | 13988 | NM_001901.2 | connective tissue growth factor | CTGF |
| CTGF-1173-16-13989 | 13989 | NM_001901.2 | connective tissue growth factor | CTGF |
| CTGF-749-16-13990 | 13990 | NM_001901.2 | connective tissue growth factor | CTGF |
| CTGF-792-16-13991 | 13991 | NM_001901.2 | connective tissue growth factor | CTGF |
| CTGF-1162-16-13992 | 13992 | NM_001901.2 | connective tissue growth factor | CTGF |
| CTGF-811-16-13993 | 13993 | NM_001901.2 | connective tissue growth factor | CTGF |
| CTGF-797-16-13994 | 13994 | NM_001901.2 | connective tissue growth factor | CTGF |
| CTGF-1175-16-13995 | 13995 | NM_001901.2 | connective tissue growth factor | CTGF |
| CTGF-1172-16-13996 | 13996 | NM_001901.2 | connective tissue growth factor | CTGF |
| CTGF-1177-16-13997 | 13997 | NM_001901.2 | connective tissue growth factor | CTGF |
| CTGF-1176-16-13998 | 13998 | NM_001901.2 | connective tissue growth factor | CTGF |
| CTGF-812-16-13999 | 13999 | NM_001901.2 | connective tissue growth factor | CTGF |

TABLE 1-continued

| ID Number | Oligo Number | Accession number | Gene Name | Gene Symbol |
|---|---|---|---|---|
| CTGF-745-16-14000 | 14000 | NM_001901.2 | connective tissue growth factor | CTGF |
| CTGF-1230-16-14001 | 14001 | NM_001901.2 | connective tissue growth factor | CTGF |
| CTGF-920-16-14002 | 14002 | NM_001901.2 | connective tissue growth factor | CTGF |
| CTGF-679-16-14003 | 14003 | NM_001901.2 | connective tissue growth factor | CTGF |
| CTGF-992-16-14004 | 14004 | NM_001901.2 | connective tissue growth factor | CTGF |
| CTGF-1045-16-14005 | 14005 | NM_001901.2 | connective tissue growth factor | CTGF |
| CTGF-1231-16-14006 | 14006 | NM_001901.2 | connective tissue growth factor | CTGF |
| CTGF-991-16-14007 | 14007 | NM_001901.2 | connective tissue growth factor | CTGF |
| CTGF-998-16-14008 | 14008 | NM_001901.2 | connective tissue growth factor | CTGF |
| CTGF-1049-16-14009 | 14009 | NM_001901.2 | connective tissue growth factor | CTGF |
| CTGF-1044-16-14010 | 14010 | NM_001901.2 | connective tissue growth factor | CTGF |
| CTGF-1327-16-14011 | 14011 | NM_001901.2 | connective tissue growth factor | CTGF |
| CTGF-1196-16-14012 | 14012 | NM_001901.2 | connective tissue growth factor | CTGF |
| CTGF-562-16-14013 | 14013 | NM_001901.2 | connective tissue growth factor | CTGF |
| CTGF-752-16-14014 | 14014 | NM_001901.2 | connective tissue growth factor | CTGF |
| CTGF-994-16-14015 | 14015 | NM_001901.2 | connective tissue growth factor | CTGF |
| CTGF-1040-16-14016 | 14016 | NM_001901.2 | connective tissue growth factor | CTGF |
| CTGF-1984-16-14017 | 14017 | NM_001901.2 | connective tissue growth factor | CTGF |
| CTGF-2195-16-14018 | 14018 | NM_001901.2 | connective tissue growth factor | CTGF |
| CTGF-2043-16-14019 | 14019 | NM_001901.2 | connective tissue growth factor | CTGF |
| CTGF-1892-16-14020 | 14020 | NM_001901.2 | connective tissue growth factor | CTGF |
| CTGF-1567-16-14021 | 14021 | NM_001901.2 | connective tissue growth factor | CTGF |
| CTGF-1780-16-14022 | 14022 | NM_001901.2 | connective tissue growth factor | CTGF |
| CTGF-2162-16-14023 | 14023 | NM_001901.2 | connective tissue growth factor | CTGF |
| CTGF-1034-16-14024 | 14024 | NM_001901.2 | connective tissue growth factor | CTGF |
| CTGF-2264-16-14025 | 14025 | NM_001901.2 | connective tissue growth factor | CTGF |
| CTGF-1032-16-14026 | 14026 | NM_001901.2 | connective tissue growth factor | CTGF |
| CTGF-1535-16-14027 | 14027 | NM_001901.2 | connective tissue growth factor | CTGF |
| CTGF-1694-16-14028 | 14028 | NM_001901.2 | connective tissue growth factor | CTGF |
| CTGF-1588-16-14029 | 14029 | NM_001901.2 | connective tissue growth factor | CTGF |
| CTGF-928-16-14030 | 14030 | NM_001901.2 | connective tissue growth factor | CTGF |
| CTGF-1133-16-14031 | 14031 | NM_001901.2 | connective tissue growth factor | CTGF |
| CTGF-912-16-14032 | 14032 | NM_001901.2 | connective tissue growth factor | CTGF |
| CTGF-753-16-14033 | 14033 | NM_001901.2 | connective tissue growth factor | CTGF |
| CTGF-918-16-14034 | 14034 | NM_001901.2 | connective tissue growth factor | CTGF |
| CTGF-744-16-14035 | 14035 | NM_001901.2 | connective tissue growth factor | CTGF |
| CTGF-466-16-14036 | 14036 | NM_001901.2 | connective tissue growth factor | CTGF |
| CTGF-917-16-14037 | 14037 | NM_001901.2 | connective tissue growth factor | CTGF |

TABLE 1-continued

| ID Number | Oligo Number | Accession number | Gene Name | Gene Symbol |
|---|---|---|---|---|
| CTGF-1038-16-14038 | 14038 | NM_001901.2 | connective tissue growth factor | CTGF |
| CTGF-1048-16-14039 | 14039 | NM_001901.2 | connective tissue growth factor | CTGF |
| CTGF-1235-16-14040 | 14040 | NM_001901.2 | connective tissue growth factor | CTGF |
| CTGF-868-16-14041 | 14041 | NM_001901.2 | connective tissue growth factor | CTGF |
| CTGF-1131-16-14042 | 14042 | NM_001901.2 | connective tissue growth factor | CTGF |
| CTGF-1043-16-14043 | 14043 | NM_001901.2 | connective tissue growth factor | CTGF |
| CTGF-751-16-14044 | 14044 | NM_001901.2 | connective tissue growth factor | CTGF |
| CTGF-1227-16-14045 | 14045 | NM_001901.2 | connective tissue growth factor | CTGF |
| CTGF-867-16-14046 | 14046 | NM_001901.2 | connective tissue growth factor | CTGF |
| CTGF-1128-16-14047 | 14047 | NM_001901.2 | connective tissue growth factor | CTGF |
| CTGF-756-16-14048 | 14048 | NM_001901.2 | connective tissue growth factor | CTGF |
| CTGF-1234-16-14049 | 14049 | NM_001901.2 | connective tissue growth factor | CTGF |
| CTGF-916-16-14050 | 14050 | NM_001901.2 | connective tissue growth factor | CTGF |
| CTGF-925-16-14051 | 14051 | NM_001901.2 | connective tissue growth factor | CTGF |
| CTGF-1225-16-14052 | 14052 | NM_001901.2 | connective tissue growth factor | CTGF |
| CTGF-445-16-14053 | 14053 | NM_001901.2 | connective tissue growth factor | CTGF |
| CTGF-446-16-14054 | 14054 | NM_001901.2 | connective tissue growth factor | CTGF |
| CTGF-913-16-14055 | 14055 | NM_001901.2 | connective tissue growth factor | CTGF |
| CTGF-997-16-14056 | 14056 | NM_001901.2 | connective tissue growth factor | CTGF |
| CTGF-277-16-14057 | 14057 | NM_001901.2 | connective tissue growth factor | CTGF |
| CTGF-1052-16-14058 | 14058 | NM_001901.2 | connective tissue growth factor | CTGF |
| CTGF-887-16-14059 | 14059 | NM_001901.2 | connective tissue growth factor | CTGF |
| CTGF-914-16-14060 | 14060 | NM_001901.2 | connective tissue growth factor | CTGF |
| CTGF-1039-16-14061 | 14061 | NM_001901.2 | connective tissue growth factor | CTGF |
| CTGF-754-16-14062 | 14062 | NM_001901.2 | connective tissue growth factor | CTGF |
| CTGF-1130-16-14063 | 14063 | NM_001901.2 | connective tissue growth factor | CTGF |
| CTGF-919-16-14064 | 14064 | NM_001901.2 | connective tissue growth factor | CTGF |
| CTGF-922-16-14065 | 14065 | NM_001901.2 | connective tissue growth factor | CTGF |
| CTGF-746-16-14066 | 14066 | NM_001901.2 | connective tissue growth factor | CTGF |
| CTGF-993-16-14067 | 14067 | NM_001901.2 | connective tissue growth factor | CTGF |
| CTGF-825-16-14068 | 14068 | NM_001901.2 | connective tissue growth factor | CTGF |
| CTGF-926-16-14069 | 14069 | NM_001901.2 | connective tissue growth factor | CTGF |
| CTGF-923-16-14070 | 14070 | NM_001901.2 | connective tissue growth factor | CTGF |
| CTGF-866-16-14071 | 14071 | NM_001901.2 | connective tissue growth factor | CTGF |
| CTGF-563-16-14072 | 14072 | NM_001901.2 | connective tissue growth factor | CTGF |
| CTGF-823-16-14073 | 14073 | NM_001901.2 | connective tissue growth factor | CTGF |
| CTGF-1233-16-14074 | 14074 | NM_001901.2 | connective tissue growth factor | CTGF |
| CTGF-924-16-14075 | 14075 | NM_001901.2 | connective tissue growth factor | CTGF |

TABLE 1-continued

| ID Number | Oligo Number | Accession number | Gene Name | Gene Symbol |
|---|---|---|---|---|
| CTGF-921-16-14076 | 14076 | NM_001901.2 | connective tissue growth factor | CTGF |
| CTGF-443-16-14077 | 14077 | NM_001901.2 | connective tissue growth factor | CTGF |
| CTGF-1041-16-14078 | 14078 | NM_001901.2 | connective tissue growth factor | CTGF |
| CTGF-1042-16-14079 | 14079 | NM_001901.2 | connective tissue growth factor | CTGF |
| CTGF-755-16-14080 | 14080 | NM_001901.2 | connective tissue growth factor | CTGF |
| CTGF-467-16-14081 | 14081 | NM_001901.2 | connective tissue growth factor | CTGF |
| CTGF-995-16-14082 | 14082 | NM_001901.2 | connective tissue growth factor | CTGF |
| CTGF-927-16-14083 | 14083 | NM_001901.2 | connective tissue growth factor | CTGF |
| SPP1-1091-16-14131 | 14131 | NM_000582.2 | Osteopontin | SPP1 |
| PPIB--16-14188 | 14188 | NM_000942 | peptidylprolyl isomerase B (cyclophilin B) | PPIB |
| PPIB--17-14189 | 14189 | NM_000942 | peptidylprolyl isomerase B (cyclophilin B) | PPIB |
| PPIB--18-14190 | 14190 | NM_000942 | peptidylprolyl isomerase B (cyclophilin B) | PPIB |
| pGL3-1172-16-14386 | 14386 | U47296 | Cloning vector pGL3-Control | pGL3 |
| pGL3-1172-16-14387 | 14387 | U47296 | Cloning vector pGL3-Control | pGL3 |
| MAP4K4-2931-25-14390 | 14390 | NM_004834 | Mitogen-Activated Protein Kinase Kinase Kinase Kinase 4 (MAP4K4), transcript variant 1 | MAP4K4 |
| miR-122--23-14391 | 14391 | | | miR-122 |
| | 14084 | NM_000582.2 | Osteopontin | SPP1 |
| | 14085 | NM_000582.2 | Osteopontin | SPP1 |
| | 14086 | NM_000582.2 | Osteopontin | SPP1 |
| | 14087 | NM_000582.2 | Osteopontin | SPP1 |
| | 14088 | NM_000582.2 | Osteopontin | SPP1 |
| | 14089 | NM_000582.2 | Osteopontin | SPP1 |
| | 14090 | NM_000582.2 | Osteopontin | SPP1 |
| | 14091 | NM_000582.2 | Osteopontin | SPP1 |
| | 14092 | NM_000582.2 | Osteopontin | SPP1 |
| | 14093 | NM_000582.2 | Osteopontin | SPP1 |
| | 14094 | NM_000582.2 | Osteopontin | SPP1 |
| | 14095 | NM_000582.2 | Osteopontin | SPP1 |
| | 14096 | NM_000582.2 | Osteopontin | SPP1 |
| | 14097 | NM_000582.2 | Osteopontin | SPP1 |
| | 14098 | NM_000582.2 | Osteopontin | SPP1 |
| | 14099 | NM_000582.2 | Osteopontin | SPP1 |
| | 14100 | NM_000582.2 | Osteopontin | SPP1 |
| | 14101 | NM_000582.2 | Osteopontin | SPP1 |
| | 14102 | NM_000582.2 | Osteopontin | SPP1 |
| | 14103 | NM_000582.2 | Osteopontin | SPP1 |
| | 14104 | NM_000582.2 | Osteopontin | SPP1 |
| | 14105 | NM_000582.2 | Osteopontin | SPP1 |
| | 14106 | NM_000582.2 | Osteopontin | SPP1 |
| | 14107 | NM_000582.2 | Osteopontin | SPP1 |
| | 14108 | NM_000582.2 | Osteopontin | SPP1 |
| | 14109 | NM_000582.2 | Osteopontin | SPP1 |
| | 14110 | NM_000582.2 | Osteopontin | SPP1 |
| | 14111 | NM_000582.2 | Osteopontin | SPP1 |
| | 14112 | NM_000582.2 | Osteopontin | SPP1 |
| | 14113 | NM_000582.2 | Osteopontin | SPP1 |
| | 14114 | NM_000582.2 | Osteopontin | SPP1 |
| | 14115 | NM_000582.2 | Osteopontin | SPP1 |
| | 14116 | NM_000582.2 | Osteopontin | SPP1 |
| | 14117 | NM_000582.2 | Osteopontin | SPP1 |
| | 14118 | NM_000582.2 | Osteopontin | SPP1 |
| | 14119 | NM_000582.2 | Osteopontin | SPP1 |
| | 14120 | NM_000582.2 | Osteopontin | SPP1 |
| | 14121 | NM_000582.2 | Osteopontin | SPP1 |
| | 14122 | NM_000582.2 | Osteopontin | SPP1 |
| | 14123 | NM_000582.2 | Osteopontin | SPP1 |
| | 14124 | NM_000582.2 | Osteopontin | SPP1 |
| | 14125 | NM_000582.2 | Osteopontin | SPP1 |
| | 14126 | NM_000582.2 | Osteopontin | SPP1 |
| | 14127 | NM_000582.2 | Osteopontin | SPP1 |
| | 14128 | NM_000582.2 | Osteopontin | SPP1 |

TABLE 1-continued

| ID Number | Oligo Number | Accession number | Gene Name | Gene Symbol |
|---|---|---|---|---|
| | 14129 | NM_000582.2 | Osteopontin | SPP1 |
| | 14130 | NM_000582.2 | Osteopontin | SPP1 |
| | 14132 | NM_000582.2 | Osteopontin | SPP1 |
| | 14133 | NM_000582.2 | Osteopontin | SPP1 |
| | 14134 | NM_000582.2 | Osteopontin | SPP1 |
| | 14135 | NM_000582.2 | Osteopontin | SPP1 |
| | 14136 | NM_000582.2 | Osteopontin | SPP1 |
| | 14137 | NM_000582.2 | Osteopontin | SPP1 |
| | 14138 | NM_000582.2 | Osteopontin | SPP1 |
| | 14139 | NM_000582.2 | Osteopontin | SPP1 |
| | 14140 | NM_000582.2 | Osteopontin | SPP1 |
| | 14141 | NM_000582.2 | Osteopontin | SPP1 |
| | 14142 | NM_000582.2 | Osteopontin | SPP1 |
| | 14143 | NM_000582.2 | Osteopontin | SPP1 |
| | 14144 | NM_000582.2 | Osteopontin | SPP1 |
| | 14145 | NM_000582.2 | Osteopontin | SPP1 |
| | 14146 | NM_000582.2 | Osteopontin | SPP1 |
| | 14147 | NM_000582.2 | Osteopontin | SPP1 |
| | 14148 | NM_000582.2 | Osteopontin | SPP1 |
| | 14149 | NM_000582.2 | Osteopontin | SPP1 |
| | 14150 | NM_000582.2 | Osteopontin | SPP1 |
| | 14151 | NM_000582.2 | Osteopontin | SPP1 |
| | 14152 | NM_000582.2 | Osteopontin | SPP1 |
| | 14153 | NM_000582.2 | Osteopontin | SPP1 |
| | 14154 | NM_000582.2 | Osteopontin | SPP1 |
| | 14155 | NM_000582.2 | Osteopontin | SPP1 |
| | 14156 | NM_000582.2 | Osteopontin | SPP1 |
| | 14157 | NM_000582.2 | Osteopontin | SPP1 |
| | 14158 | NM_000582.2 | Osteopontin | SPP1 |
| | 14159 | NM_000582.2 | Osteopontin | SPP1 |
| | 14160 | NM_000582.2 | Osteopontin | SPP1 |
| | 14161 | NM_000582.2 | Osteopontin | SPP1 |
| | 14162 | NM_000582.2 | Osteopontin | SPP1 |
| | 14163 | NM_000582.2 | Osteopontin | SPP1 |
| | 14164 | NM_000582.2 | Osteopontin | SPP1 |
| | 14165 | NM_000582.2 | Osteopontin | SPP1 |
| | 14166 | NM_000582.2 | Osteopontin | SPP1 |
| | 14167 | NM_000582.2 | Osteopontin | SPP1 |
| | 14168 | NM_000582.2 | Osteopontin | SPP1 |
| | 14169 | NM_000582.2 | Osteopontin | SPP1 |
| | 14170 | NM_000582.2 | Osteopontin | SPP1 |
| | 14171 | NM_000582.2 | Osteopontin | SPP1 |
| | 14172 | NM_000582.2 | Osteopontin | SPP1 |
| | 14173 | NM_000582.2 | Osteopontin | SPP1 |
| | 14174 | NM_000582.2 | Osteopontin | SPP1 |
| | 14175 | NM_000582.2 | Osteopontin | SPP1 |
| | 14176 | NM_000582.2 | Osteopontin | SPP1 |
| | 14177 | NM_000582.2 | Osteopontin | SPP1 |
| | 14178 | NM_000582.2 | Osteopontin | SPP1 |
| | 14179 | NM_000582.2 | Osteopontin | SPP1 |
| | 14180 | NM_000582.2 | Osteopontin | SPP1 |
| | 14181 | NM_000582.2 | Osteopontin | SPP1 |
| | 14182 | NM_000582.2 | Osteopontin | SPP1 |
| | 14183 | NM_000582.2 | Osteopontin | SPP1 |
| | 14184 | NM_000582.2 | Osteopontin | SPP1 |
| | 14185 | NM_000582.2 | Osteopontin | SPP1 |
| | 14186 | NM_000582.2 | Osteopontin | SPP1 |
| | 14187 | NM_000582.2 | Osteopontin | SPP1 |

TABLE 2

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| APOB-10167-20-12138 | 12138 | oooooooooooooooooooo | ooooooooooooooooooooom | AUUGGUAUUCAGUGUGAUG | 1 |
| APOB-10167-20-12139 | 12139 | oooooooooooooooooooo | ooooooooooooooooooooom | AUUCGUAUUGAGUCUGAUC | 2 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| MAP4K4-2931-13-12266 | 12266 | | | | |
| MAP4K4-2931-16-12293 | 12293 | oooooooooooooooooo | Pf000fffff0f0000fff0 | UAGACUUCCACAGAACUCU | 3 |
| MAP4K4-2931-16-12383 | 12383 | oooooooooooooooooo | 00000000000000000000 | UAGACUUCCACAGAACUCU | 4 |
| MAP4K4-2931-16-12384 | 12384 | oooooooooooooooooo | P0000000000000000000 | UAGACUUCCACAGAACUCU | 5 |
| MAP4K4-2931-16-12385 | 12385 | oooooooooooooooooo | Pf000fffff0f0000fff0 | UAGACUUCCACAGAACUCU | 6 |
| MAP4K4-2931-16-12386 | 12386 | ooooooooooosssssssso | Pf000fffff0f0000fff0 | UAGACUUCCACAGAACUCU | 7 |
| MAP4K4-2931-16-12387 | 12387 | ooooooooooosssssssso | P0000000000000000000 | UAGACUUCCACAGAACUCU | 8 |
| MAP4K4-2931-15-12388 | 12388 | oooooooooooooooo | 000000000000000000 | UAGACUUCCACAGAACU | 9 |
| MAP4K4-2931-13-12432 | 12432 | | | | |
| MAP4K4-2931-13-12266.2 | 12266.2 | | | | |
| APOB--21-12434 | 12434 | ooooooooooooooooooooo | 000000000000000000000m | AUUGGUAUUCAGUGUGAUGAC | 10 |
| APOB--21-12435 | 12435 | ooooooooooooooooooooo | 000000000000000000000m | AUUCGUAUUGAGUCUGAUCAC | 11 |
| MAP4K4 -2931-16-12451 | 12451 | ooooooooooosssssssso | Pf000fffff0f0000ffmm | UAGACUUCCACAGAACUCU | 12 |
| MAP4K4-2931-16-12452 | 12452 | ooooooooooosssssssso | Pm000fffff0f0000ffmm | UAGACUUCCACAGAACUCU | 13 |
| MAP4K4-2931-16-12453 | 12453 | ooooooossssssssssssso | Pm000fffff0f0000ffmm | UAGACUUCCACAGAACUCU | 14 |
| MAP4K4-2931-17-12454 | 12454 | ooooooooooossssssso | Pm000fffff0f0000ffffmm | UAGACUUCCACAGAACUCUUC | 15 |
| MAP4K4-2931-17-12455 | 12455 | ooooooooosssssssssso | Pm000fffff0f0000ffffmm | UAGACUUCCACAGAACUCUUC | 16 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| MAP4K4-2931-19-12456 | 12456 | ooooooooooooss ssssssssssso | Pm000fffff0f0000ffff ff00mm | UAGACUUCCACAGAACUCUU CAAAG | 17 |
| --27-12480 | 12480 | | | | |
| --27-12481 | 12481 | | | | |
| APOB-10167-21-12505 | 12505 | oooooooooooooo oooooooos | 00000000000000000000 m | AUUGGUAUUCAGUGUGAUGA C | 18 |
| APOB-10167-21-12506 | 12506 | oooooooooooooo ooooooos | 00000000000000000000 m | AUUCGUAUUGAGUCUGAUCA C | 19 |
| MAP4K4-2931-16-12539 | 12539 | oooooooooooss ssssss | Pf000fffff0f0000fff0 | UAGACUUCCACAGAACUCU | 20 |
| APOB-10167-21-12505.2 | 12505.2 | oooooooooooooo ooooooo | 00000000000000000000 m | AUUGGUAUUCAGUGUGAUGA C | 21 |
| APOB-10167-21-12506.2 | 12506.2 | oooooooooooooo ooooooo | 00000000000000000000 m | AUUCGUAUUGAGUCUGAUCA C | 22 |
| MAP4K4--13-12565 | 12565 | | | | |
| MAP4K4-2931-16-12386.2 | 12386.2 | oooooooooosss sssso | Pf000fffff0f0000fff0 | UAGACUUCCACAGAACUCU | 23 |
| MAP4K4-2931-13-12815 | 12815 | | | | |
| APOB--13-12957 | 12957 | | | | |
| MAP4K4 16-12983 | 12983 | oooooooooooos sssso | Pm000fffff0m0000mmm0 | uagacuuccacagaacucu | 24 |
| MAP4K4--16-12984 | 12984 | oooooooooooos sssss | Pm000fffff0m0000mmm0 | uagacuuccacagaacucu | 25 |
| MAP4K4--16-12985 | 12985 | oooooooooooos sssso | Pm000fffff0m0000mmm0 | uagacuuccacagaacucu | 26 |
| MAP4K4--16-12986 | 12986 | oooooooooosss sssso | Pf000fffff0f0000fff0 | UAGACUUCCACAGAACUCU | 27 |
| MAP4K4--16-12987 | 12987 | oooooooooooo sssss | P0000f00ff0m0000m0m0 | UagacUUccacagaacUcU | 28 |
| MAP4K4--16-12988 | 12988 | oooooooooooo sssss | P0000f00ff0m0000m0m0 | UagacUUccacagaacUcu | 29 |
| MAP4K4--16-12989 | 12989 | oooooooooooo sssss | P0000ff0ff0m0000m0m0 | UagacuUccacagaacUcu | 30 |
| MAP4K4--16-12990 | 12990 | oooooooooooo sssss | Pf0000ff000000000m00 | uagaCuuCCaCagaaCuCu | 31 |
| MAP4K4--16-12991 | 12991 | oooooooooooo sssss | Pf0000fff00m00000mm0 | uagaCuucCacagaaCucu | 32 |
| MAP4K4--16-12992 | 12992 | oooooooooooo sssss | Pf000fffff0000000m00 | uagacuuccaCagaaCuCu | 33 |
| MAP4K4--16-12993 | 12993 | oooooooooooo sssss | P0000000000000000000 | UagaCUUCCaCagaaCUCU | 34 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| MAP4K4--16-12994 | 12994 | ooooooooooooosssss | P0000f0f0f0000000m00 | UagacUuCcaCagaaCuCu | 35 |
| MAP4K4-16-12995 | 12995 | ooooooooooooosssssso | Pf000fffff0000000000 | uagacuuccaCagaaCUCU | 36 |
| MAP4K4-2931-19-13012 | 13012 | | | | |
| MAP4K4-2931-19-13016 | 13016 | | | | |
| PPIB--13-13021 | 13021 | | | | |
| pGL3-1172-13-13038 | 13038 | | | | |
| pGL3-1172-13-13040 | 13040 | | | | |
| --16-13047 | 13047 | ooooooooooooossssss | Pm000000000m0000mmm0 | UAGACUUCCACAGAACUCU | 37 |
| SOD1-530-13-13090 | 13090 | | | | |
| SOD1-523-13-13091 | 13091 | | | | |
| SOD1-535-13-13092 | 13092 | | | | |
| SOD1-536-13-13093 | 13093 | | | | |
| SOD1-396-13-13094 | 13094 | | | | |
| SOD1-385-13-13095 | 13095 | | | | |
| SOD1-195-13-13096 | 13096 | | | | |
| APOB-4314-13-13115 | 13115 | | | | |
| APOB-3384-13-13116 | 13116 | | | | |
| APOB-3547-13-13117 | 13117 | | | | |
| APOB-4318-13-13118 | 13118 | | | | |
| APOB-3741-13-13119 | 13119 | | | | |
| PPIB--16-13136 | 13136 | ooooooooooooossssss | Pm0fffff0f00mm000mm0 | UGUUUUGUAGCCAAAUCC | 38 |
| APOB-4314-15-13154 | 13154 | | | | |
| APOB-3547-15-13155 | 13155 | | | | |
| APOB-4318-15-13157 | 13157 | | | | |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| APOB-3741-15-13158 | 13158 | | | | |
| APOB--13-13159 | 13159 | | | | |
| APOB--15-13160 | 13160 | | | | |
| SOD1-530-16-13163 | 13163 | ooooooooooooos ssssso | Pm0fffffffff0mmmmm0m0 | UACUUUCUUCAUUUCCACC | 39 |
| SOD1-523-16-13164 | 13164 | ooooooooooooos ssssso | Pmff0fffff0fmmmm0mm0 | UUCAUUUCCACCUUUGCCC | 40 |
| SOD1-535-16-13165 | 13165 | ooooooooooooos ssssso | Pmfff0f0ffffmmmm0mm0C | UUUGUACUUUCUUCAUUU | 41 |
| SOD1-536-16-13166 | 13166 | ooooooooooooos ssssso | Pmffff0f0fffmmmmm0m0 | UCUUUGUACUUUCUUCAUU | 42 |
| SOD1-396-16-13167 | 13167 | ooooooooooooos ssssso | Pmf00f00ff0f0mm0mmm0 | UCAGCAGUCACAUUGCCCA | 43 |
| SOD1-385-16-13168 | 13168 | ooooooooooooos ssssso | Pmff0fff000fmmmm00m0 | AUUGCCCAAGUCUCCAACA | 44 |
| SOD1-195-16-13169 | 13169 | ooooooooooooos ssssso | Pmfff0fff0000mm00m00 | UUCUGCUCGAAAUUGAUGA | 45 |
| pGL3-1172-16-13170 | 13170 | ooooooooooooos ssssso | Pm00ff0f0ffm0ff0mm0 | AAAUCGUAUUUGUCAAUCA | 46 |
| pGL3-1172-16-13171 | 13171 | ooooooooooooos ssssss | Pm00ff0f0ffm0ff0mm0 | AAAUCGUAUUUGUCAAUCA | 47 |
| MAP4k4-2931-19-13189 | 13189 | oooooooooooooo oooooo | 000000000000000000 | UAGACUUCCACAGAACUCU | 48 |
| CTGF-1222-13-13190 | 13190 | | | | |
| CTGF-813-13-13192 | 13192 | | | | |
| CTGF-747-13-13194 | 13194 | | | | |
| CTGF-817-13-13196 | 13196 | | | | |
| CTGF-1174-13-13198 | 13198 | | | | |
| CTGF-1005-13-13200 | 13200 | | | | |
| CTGF-814-13-13202 | 13202 | | | | |
| CTGF-816-13-13204 | 13204 | | | | |
| CTGF-1001-13-13206 | 13206 | | | | |
| CTGF-1173-13-13208 | 13208 | | | | |
| CTGF-749-13-13210 | 13210 | | | | |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| CTGF-792-13-13212 | 13212 | | | | |
| CTGF-1162-13-13214 | 13214 | | | | |
| CTGF-811-13-13216 | 13216 | | | | |
| CTGF-797-13-13218 | 13218 | | | | |
| CTGF-1175-13-13220 | 13220 | | | | |
| CTGF-1172-13-13222 | 13222 | | | | |
| CTGF-1177-13-13224 | 13224 | | | | |
| CTGF-1176-13-13226 | 13226 | | | | |
| CTGF-812-13-13228 | 13228 | | | | |
| CTGF-745-13-13230 | 13230 | | | | |
| CTGF-1230-13-13232 | 13232 | | | | |
| CTGF-920-13-13234 | 13234 | | | | |
| CTGF-679-13-13236 | 13236 | | | | |
| CTGF-992-13-13238 | 13238 | | | | |
| CTGF-1045-13-13240 | 13240 | | | | |
| CTGF-1231-13-13242 | 13242 | | | | |
| CTGF-991-13-13244 | 13244 | | | | |
| CTGF-998-13-13246 | 13246 | | | | |
| CTGF-1049-13-13248 | 13248 | | | | |
| CTGF-1044-13-13250 | 13250 | | | | |
| CTGF-1327-13-13252 | 13252 | | | | |
| CTGF-1196-13-13254 | 13254 | | | | |
| CTGF-562-13-13256 | 13256 | | | | |
| CTGF-752-13-13258 | 13258 | | | | |
| CTGF-994-13-13260 | 13260 | | | | |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| CTGF-1040-13-13262 | 13262 | | | | |
| CTGF-1984-13-13264 | 13264 | | | | |
| CTGF-2195-13-13266 | 13266 | | | | |
| CTGF-2043-13-13268 | 13268 | | | | |
| CTGF-1892-13-13270 | 13270 | | | | |
| CTGF-1567-13-13272 | 13272 | | | | |
| CTGF-1780-13-13274 | 13274 | | | | |
| CTGF-2162-13-13276 | 13276 | | | | |
| CTGF-1034-13-13278 | 13278 | | | | |
| CTGF-2264-13-13280 | 13280 | | | | |
| CTGF-1032-13-13282 | 13282 | | | | |
| CTGF-1535-13-13284 | 13284 | | | | |
| CTGF-1694-13-13286 | 13286 | | | | |
| CTGF-1588-13-13288 | 13288 | | | | |
| CTGF-928-13-13290 | 13290 | | | | |
| CTGF-1133-13-13292 | 13292 | | | | |
| CTGF-912-13-13294 | 13294 | | | | |
| CTGF-753-13-13296 | 13296 | | | | |
| CTGF-918-13-13298 | 13298 | | | | |
| CTGF-744-13-13300 | 13300 | | | | |
| CTGF-466-13-13302 | 13302 | | | | |
| CTGF-917-13-13304 | 13304 | | | | |
| CTGF-1038-13-13306 | 13306 | | | | |
| CTGF-1048-13-13308 | 13308 | | | | |
| CTGF-1235-13-13310 | 13310 | | | | |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| CTGF-868-13-13312 | 13312 | | | | |
| CTGF-1131-13-13314 | 13314 | | | | |
| CTGF-1043-13-13316 | 13316 | | | | |
| CTGF-751-13-13318 | 13318 | | | | |
| CTGF-1227-13-13320 | 13320 | | | | |
| CTGF-867-13-13322 | 13322 | | | | |
| CTGF-1128-13-13324 | 13324 | | | | |
| CTGF-756-13-13326 | 13326 | | | | |
| CTGF-1234-13-13328 | 13328 | | | | |
| CTGF-916-13-13330 | 13330 | | | | |
| CTGF-925-13-13332 | 13332 | | | | |
| CTGF-1225-13-13334 | 13334 | | | | |
| CTGF-445-13-13336 | 13336 | | | | |
| CTGF-446-13-13338 | 13338 | | | | |
| CTGF-913-13-13340 | 13340 | | | | |
| CTGF-997-13-13342 | 13342 | | | | |
| CTGF-277-13-13344 | 13344 | | | | |
| CTGF-1052-13-13346 | 13346 | | | | |
| CTGF-887-13-13348 | 13348 | | | | |
| CTGF-914-13-13350 | 13350 | | | | |
| CTGF-1039-13-13352 | 13352 | | | | |
| CTGF-754-13-13354 | 13354 | | | | |
| CTGF-1130-13-13356 | 13356 | | | | |
| CTGF-919-13-13358 | 13358 | | | | |
| CTGF-922-13-13360 | 13360 | | | | |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| CTGF-746-13-13362 | 13362 | | | | |
| CTGF-993-13-13364 | 13364 | | | | |
| CTGF-825-13-13366 | 13366 | | | | |
| CTGF-926-13-13368 | 13368 | | | | |
| CTGF-923-13-13370 | 13370 | | | | |
| CTGF-866-13-13372 | 13372 | | | | |
| CTGF-563-13-13374 | 13374 | | | | |
| CTGF-823-13-13376 | 13376 | | | | |
| CTGF-1233-13-13378 | 13378 | | | | |
| CTGF-924-13-13380 | 13380 | | | | |
| CTGF-921-13-13382 | 13382 | | | | |
| CTGF-443-13-13384 | 13384 | | | | |
| CTGF-1041-13-13386 | 13386 | | | | |
| CTGF-1042-13-13388 | 13388 | | | | |
| CTGF-755-13-13390 | 13390 | | | | |
| CTGF-467-13-13392 | 13392 | | | | |
| CTGF-995-13-13394 | 13394 | | | | |
| CTGF-927-13-13396 | 13396 | | | | |
| SPP1-1025-13-13398 | 13398 | | | | |
| SPP1-1049-13-13400 | 13400 | | | | |
| SPP1-1051-13-13402 | 13402 | | | | |
| SPP1-1048-13-13404 | 13404 | | | | |
| SPP1-1050-13-13406 | 13406 | | | | |
| SPP1-1047-13-13408 | 13408 | | | | |
| SPP1-800-13-13410 | 13410 | | | | |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| SPP1-492-13-13412 | 13412 | | | | |
| SPP1-612-13-13414 | 13414 | | | | |
| SPP1-481-13-13416 | 13416 | | | | |
| SPP1-614-13-13418 | 13418 | | | | |
| SPP1-951-13-13420 | 13420 | | | | |
| SPP1-482-13-13422 | 13422 | | | | |
| SPP1-856-13-13424 | 13424 | | | | |
| SPP1-857-13-13426 | 13426 | | | | |
| SPP1-365-13-13428 | 13428 | | | | |
| SPP1-359-13-13430 | 13430 | | | | |
| SPP1-357-13-13432 | 13432 | | | | |
| SPP1-858-13-13434 | 13434 | | | | |
| SPP1-1012-13-13436 | 13436 | | | | |
| SPP1-1014-13-13438 | 13438 | | | | |
| SPP1-356-13-13440 | 13440 | | | | |
| SPP1-368-13-13442 | 13442 | | | | |
| SPP1-1011-13-13444 | 13444 | | | | |
| SPP1-754-13-13446 | 13446 | | | | |
| SPP1-1021-13-13448 | 13448 | | | | |
| SPP1-1330-13-13450 | 13450 | | | | |
| SPP1-346-13-13452 | 13452 | | | | |
| SPP1-869-13-13454 | 13454 | | | | |
| SPP1-701-13-13456 | 13456 | | | | |
| SPP1-896-13-13458 | 13458 | | | | |
| SPP1-1035-13-13460 | 13460 | | | | |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| SPP1-1170-13-13462 | 13462 | | | | |
| SPP1-1282-13-13464 | 13464 | | | | |
| SPP1-1537-13-13466 | 13466 | | | | |
| SPP1-692-13-13468 | 13468 | | | | |
| SPP1-840-13-13470 | 13470 | | | | |
| SPP1-1163-13-13472 | 13472 | | | | |
| SPP1-789-13-13474 | 13474 | | | | |
| SPP1-841-13-13476 | 13476 | | | | |
| SPP1-852-13-13478 | 13478 | | | | |
| SPP1-209-13-13480 | 13480 | | | | |
| SPP1-1276-13-13482 | 13482 | | | | |
| SPP1-137-13-13484 | 13484 | | | | |
| SPP1-711-13-13486 | 13486 | | | | |
| SPP1-582-13-13488 | 13488 | | | | |
| SPP1-839-13-13490 | 13490 | | | | |
| SPP1-1091-13-13492 | 13492 | | | | |
| SPP1-884-13-13494 | 13494 | | | | |
| SPP1-903-13-13496 | 13496 | | | | |
| SPP1-1090-13-13498 | 13498 | | | | |
| SPP1-474-13-13500 | 13500 | | | | |
| SPP1-575-13-13502 | 13502 | | | | |
| SPP1-671-13-13504 | 13504 | | | | |
| SPP1-924-13-13506 | 13506 | | | | |
| SPP1-1185-13-13508 | 13508 | | | | |
| SPP1-1221-13-13510 | 13510 | | | | |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| SPP1-347-13-13512 | 13512 | | | | |
| SPP1-634-13-13514 | 13514 | | | | |
| SPP1-877-13-13516 | 13516 | | | | |
| SPP1-1033-13-13518 | 13518 | | | | |
| SPP1-714-13-13520 | 13520 | | | | |
| SPP1-791-13-13522 | 13522 | | | | |
| SPP1-813-13-13524 | 13524 | | | | |
| SPP1-939-13-13526 | 13526 | | | | |
| SPP1-1161-13-13528 | 13528 | | | | |
| SPP1-1164-13-13530 | 13530 | | | | |
| SPP1-1190-13-13532 | 13532 | | | | |
| SPP1-1333-13-13534 | 13534 | | | | |
| SPP1-537-13-13536 | 13536 | | | | |
| SPP1-684-13-13538 | 13538 | | | | |
| SPP1-707-13-13540 | 13540 | | | | |
| SPP1-799-13-13542 | 13542 | | | | |
| SPP1-853-13-13544 | 13544 | | | | |
| SPP1-888-13-13546 | 13546 | | | | |
| SPP1-1194-13-13548 | 13548 | | | | |
| SPP1-1279-13-13550 | 13550 | | | | |
| SPP1-1300-13-13552 | 13552 | | | | |
| SPP1-1510-13-13554 | 13554 | | | | |
| SPP1-1543-13-13556 | 13556 | | | | |
| SPP1-434-13-13558 | 13558 | | | | |
| SPP1-600-13-13560 | 13560 | | | | |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| SPP1-863-13-13562 | 13562 | | | | |
| SPP1-902-13-13564 | 13564 | | | | |
| SPP1-921-13-13566 | 13566 | | | | |
| SPP1-154-13-13568 | 13568 | | | | |
| SPP1-217-13-13570 | 13570 | | | | |
| SPP1-816-13-13572 | 13572 | | | | |
| SPP1-882-13-13574 | 13574 | | | | |
| SPP1-932-13-13576 | 13576 | | | | |
| SPP1-1509-13-13578 | 13578 | | | | |
| SPP1-157-13-13580 | 13580 | | | | |
| SPP1-350-13-13582 | 13582 | | | | |
| SPP1-511-13-13584 | 13584 | | | | |
| SPP1-605-13-13586 | 13586 | | | | |
| SPP1-811-13-13588 | 13588 | | | | |
| SPP1-892-13-13590 | 13590 | | | | |
| SPP1-922-13-13592 | 13592 | | | | |
| SPP1-1169-13-13594 | 13594 | | | | |
| SPP1-1182-13-13596 | 13596 | | | | |
| SPP1-1539-13-13598 | 13598 | | | | |
| SPP1-1541-13-13600 | 13600 | | | | |
| SPP1-427-13-13602 | 13602 | | | | |
| SPP1-533-13-13604 | 13604 | | | | |
| APOB--13-13763 | 13763 | | | | |
| APOB--13-13764 | 13764 | | | | |
| MAP4K4--16-13766 | 13766 | ooooooooooooos ssssso | Pm000fffff0m0000mmm0 | UAGACUUCCACAGAACUCU | 49 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| PPIB--13-13767 | 13767 | | | | |
| PPIB--15-13768 | 13768 | | | | |
| PPIB--17-13769 | 13769 | | | | |
| MAP4K4--16-13939 | 13939 | ooooooooooooosssssso | m000f0ffff0m0m00m0m | UAGACAUCCUACACAGCAC | 50 |
| APOB-4314-16-13940 | 13940 | ooooooooooooosssssso | Pm0fffffff000mmmmm00 | UGUUUCUCCAGAUCCUUGC | 51 |
| APOB-4314-17-13941 | 13941 | ooooooooooooosssssso | Pm0fffffff000mmmmm00 | UGUUUCUCCAGAUCCUUGC | 52 |
| APOB--16-13942 | 13942 | ooooooooooooosssssso | Pm00f000f000mmm0mmm0 | UAGCAGAUGAGUCCAUUUG | 53 |
| APOB--18-13943 | 13943 | oooooooooooooooossssssso | Pm00f000f000mmm0mmm00000 | UAGCAGAUGAGUCCAUUUGGAGA | 54 |
| APOB--17-13944 | 13944 | ooooooooooooosssssso | Pm0f000f000mmm0mmm0 | UAGCAGAUGAGUCCAUUUG | 55 |
| APOB--19-13945 | 13945 | oooooooooooooooossssssso | Pm0f000f000mmm0mmm00000 | UAGCAGAUGAGUCCAUUUGGAGA | 56 |
| APOB-4314-16-13946 | 13946 | ooooooooooooosssssso | Pmf0ff0ffffmmm000mm0 | AUGUUGUUUCUCCAGAUCC | 57 |
| APOB-4314-17-13947 | 13947 | ooooooooooooosssssso | Pmf0ff0ffffmmm000mm0 | AUGUUGUUUCUCCAGAUCC | 58 |
| APOB--16-13948 | 13948 | ooooooooooooosssssso | Pm0fff000000mmmm0m00 | UGUUUGAGGGACUCUGUGA | 59 |
| APOB--17-13949 | 13949 | ooooooooooooosssssso | Pm0fff000000mmmm0m00 | UGUUUGAGGGACUCUGUGA | 60 |
| APOB--16-13950 | 13950 | ooooooooooooosssssso | Pmff00f0fff00m0m00m0 | AUUGGUAUUCAGUGUGAUG | 61 |
| APOB--18-13951 | 13951 | oooooooooooooooossssssso | Pmff00f0fff00m0m00m0m00 | AUUGGUAUUCAGUGUGAUGACAC | 62 |
| APOB--17-13952 | 13952 | ooooooooooooosssssso | Pmff00f0fff00m0m00m0 | AUUGGUAUUCAGUGUGAUG | 63 |
| APOB--19-13953 | 13953 | oooooooooooooooossssssso | Pmff00f0fff00m0m00m0m00 | AUUGGUAUUCAGUGUGAUGACAC | 64 |
| MAP4K4--16-13766.2 | 13766.2 | ooooooooooooosssssso | Pm000fffff0m0000mmm0 | UAGACUUCCACAGAACUCU | 65 |
| CTGF-1222-16-13980 | 13980 | ooooooooooooosssssso | Pm0f0ffffffm0m00m0m0 | UACAUCUUCCUGUAGUACA | 66 |
| CTGF-813-16-13981 | 13981 | ooooooooooooosssssso | Pm0f0ffff0mmmm0m000 | AGGCGCUCCACUCUGUGGU | 67 |
| CTGF-747-16-13982 | 13982 | ooooooooooooosssssso | Pm0ffffff00mm0m0000 | UGUCUUCCAGUCGGUAAGC | 68 |
| CTGF-817-16-13983 | 13983 | ooooooooooooosssssso | Pm00f000f0fmmm0mmmm0 | GAACAGGCGCUCCACUCUG | 69 |
| CTGF-1174-16-13984 | 13984 | ooooooooooooosssssso | Pm00ff0f00f00m000m00 | CAGUUGUAAUGGCAGGCAC | 70 |
| CTGF-1005-16-13985 | 13985 | ooooooooooooosssssso | Pmff000000mmm000mm0 | AGCCAGAAAGCUCAAACUU | 71 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| CTGF-814-16-13986 | 13986 | ooooooooooooos sssso | Pm000f0ffff0mmm0m00 | CAGGCGCUCCACUCUGUGG | 72 |
| CTGF-816-16-13987 | 13987 | ooooooooooooos sssso | Pm0f000f0ffmm0mmmm00 | AACAGGCGCUCCACUCUGU | 73 |
| CTGF-1001-16-13988 | 13988 | ooooooooooooos sssso | Pm0000fff000mmm00m0 | AGAAAGCUCAAACUUGAUA | 74 |
| CTGF-1173-16-13989 | 13989 | ooooooooooooos sssso | Pmff0f00f00m000m0m0 | AGUUGUAAUGGCAGGCACA | 75 |
| CTGF-749-16-13990 | 13990 | ooooooooooooos sssso | Pmf0ffffff00mm00m00 | CGUGUCUUCCAGUCGGUAA | 76 |
| CTGF-792-16-13991 | 13991 | ooooooooooooos sssso | Pm00ff000f00mm0mmm0 | GGACCAGGCAGUUGGCUCU | 77 |
| CTGF-1162-16-13992 | 13992 | ooooooooooooos sssso | Pm000f0f000mmmm00m0 | CAGGCACAGGUCUUGAUGA | 78 |
| CTGF-811-16-13993 | 13993 | ooooooooooooos sssso | Pmf0ffff0ffmm0m0mmm0 | GCGCUCCACUCUGUGGUCU | 79 |
| CTGF-797-16-13994 | 13994 | ooooooooooooos sssso | Pm0fff000ff000m0mmm0 | GGUCUGGACCAGGCAGUUG | 80 |
| CTGF-1175-16-13995 | 13995 | ooooooooooooos sssso | Pmf00ff0f00m00m000m0 | ACAGUUGUAAUGGCAGGCA | 81 |
| CTGF-1172-16-13996 | 13996 | ooooooooooooos sssso | Pmff0f00f00m000m0m00 | GUUGUAAUGGCAGGCACAG | 82 |
| CTGF-1177-16-13997 | 13997 | ooooooooooooos sssso | Pm00f00ff0f00m00m000 | GGACAGUUGUAAUGGCAGG | 83 |
| CTGF-1176-16-13998 | 13998 | ooooooooooooos sssso | Pm0f00ff0f00m00m0000 | GACAGUUGUAAUGGCAGGC | 84 |
| CTGF-812-16-13999 | 13999 | ooooooooooooos sssso | Pm0f0ffff0fmmm0m00m0 | GGCGCUCCACUCUGUGGUC | 85 |
| CTGF-745-16-14000 | 14000 | ooooooooooooos sssso | Pmfffff00ff00m000mm0 | UCUUCCAGUCGGUAAGCCG | 86 |
| CTGF-1230-16-14001 | 14001 | ooooooooooooos sssso | Pm0fffff0f0m0mmmmm0 | UGUCUCCGUACAUCUUCCU | 87 |
| CTGF-920-16-14002 | 14002 | ooooooooooooos sssso | Pmffff0f0000mmm00m0 | AGCUUCGCAAGGCCUGACC | 88 |
| CTGF-679-16-14003 | 14003 | ooooooooooooos sssso | Pm0fffffff0f00m0mmmm0 | CACUCCUCGCAGCAUUUCC | 89 |
| CTGF-992-16-14004 | 14004 | ooooooooooooos sssso | Pm00fff00f000mmm0000 | AAACUUGAUAGGCUUGGAG | 90 |
| CTGF-1045-16-14005 | 14005 | ooooooooooooos sssso | Pmffff0f0000mmm00mm0 | ACUCCACAGAAUUUAGCUC | 91 |
| CTGF-1231-16-14006 | 14006 | ooooooooooooos sssso | Pmf0fffff0f0m0mmmmm0 | AUGUCUCCGUACAUCUUCC | 92 |
| CTGF-991-16-14007 | 14007 | ooooooooooooos sssso | Pm0fff00f000mmm00000 | AACUUGAUAGGCUUGGAGA | 93 |
| CTGF-998-16-14008 | 14008 | ooooooooooooos sssso | Pm00fff000fmm00m0000 | AAGCUCAAACUUGAUAGGC | 94 |
| CTGF-1049-16-14009 | 14009 | ooooooooooooos sssso | Pmf0f0ffff0m0000mmm0 | ACAUACUCCACAGAAUUUA | 95 |
| CTGF-1044-16-14010 | 14010 | ooooooooooooos sssso | Pmfff0f0000mmm00mmm0 | CUCCACAGAAUUUAGCUCG | 96 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| CTGF-1327-16-14011 | 14011 | ooooooooooooos ssssso | Pm0f0ff0ff0000mm0mm0 | UGUGCUACUGAAAUCAUUU | 97 |
| CTGF-1196-16-14012 | 14012 | ooooooooooooos ssssso | Pm0000f0ff0mm0mmmmm0 | AAAGAUGUCAUUGUCUCCG | 98 |
| CTGF-562-16-14013 | 14013 | ooooooooooooos ssssso | Pmf0f0ff00f0mmm0m000 | GUGCACUGGUACUUGCAGC | 99 |
| CTGF-752-16-14014 | 14014 | ooooooooooooos ssssso | Pm00f0f0fffmmm00mm00 | AAACGUGUCUUCCAGUCGG | 100 |
| CTGF-994-16-14015 | 14015 | ooooooooooooos ssssso | Pmf000fff00m000mmm00 | UCAAACUUGAUAGGCUUGG | 101 |
| CTGF-1040-16-14016 | 14016 | ooooooooooooos ssssso | Pmf0000fff00mmm00m00 | ACAGAAUUUAGCUCGGUAU | 102 |
| CTGF-1984-16-14017 | 14017 | ooooooooooooos ssssso | Pmf0f0ffff0mmm0m0m0 | UUACAUUCUACCUAUGGUG | 103 |
| CTGF-2195-16-14018 | 14018 | ooooooooooooos ssssso | Pm00ff00ff00mm0m0m00 | AAACUGAUCAGCUAUAUAG | 104 |
| CTGF-2043-16-14019 | 14019 | ooooooooooooos ssssso | Pm0fff000f0000mmmmm0 | UAUCUGAGCAGAAUUUCCA | 105 |
| CTGF-1892-16-14020 | 14020 | ooooooooooooos ssssso | Pmf00fff000m00mm0m00 | UUAACUUAGAUAACUGUAC | 106 |
| CTGF-1567-16-14021 | 14021 | ooooooooooooos ssssso | Pm0ff0fff0f0m0000m00 | UAUUACUCGUAUAAGAUGC | 107 |
| CTGF-1780-16-14022 | 14022 | ooooooooooooos ssssso | Pm00ff0fff00mmm00mm0 | AAGCUGUCCAGUCUAAUCG | 108 |
| CTGF-2162-16-14023 | 14023 | ooooooooooooos ssssso | Pm00f00000fm0mmm0mm0 | UAAUAAGGCCAUUUGUUC | 109 |
| CTGF-1034-16-14024 | 14024 | ooooooooooooos ssssso | Pmff00fff00m0m0mmmm0 | UUUAGCUCGGUAUGUCUUC | 110 |
| CTGF-2264-16-14025 | 14025 | ooooooooooooos ssssso | Pm0fffff00m000m0000 | ACACUCUCAACAAAUAAAC | 111 |
| CTGF-1032-16-14026 | 14026 | ooooooooooooos ssssso | Pm00fff00f0m0mmmmm00 | UAGCUCGGUAUGUCUUCAU | 112 |
| CTGF-1535-16-14027 | 14027 | ooooooooooooos ssssso | Pm00ffffffff0mm00m0m0 | UAACCUUUCUGCUGGUACC | 113 |
| CTGF-1694-16-14028 | 14028 | ooooooooooooos ssssso | Pmf000000f00mmm00mm0 | UUAAGGAACAACUUGACUC | 114 |
| CTGF-1588-16-14029 | 14029 | ooooooooooooos ssssso | Pm0f0ffff000m00m000 | UUACACUUCAAAUAGCAGG | 115 |
| CTGF-928-16-14030 | 14030 | ooooooooooooos ssssso | Pmff000ff00mmmm0m000 | UCCAGGUCAGCUUCGCAAG | 116 |
| CTGF-1133-16-14031 | 14031 | ooooooooooooos ssssso | Pmffffff0f00mmmm0mm0 | CUUCUUCAUGACCUCGCCG | 117 |
| CTGF-912-16-14032 | 14032 | ooooooooooooos ssssso | Pm000fff00fm0m0m0m0 | AAGGCCUGACCAUGCACAG | 118 |
| CTGF-753-16-14033 | 14033 | ooooooooooooos ssssso | Pm000f0f0ffmmmm00mm0 | CAAACGUGUCUUCCAGUCG | 119 |
| CTGF-918-16-14034 | 14034 | ooooooooooooos ssssso | Pmfff0f0000mmm00mm00 | CUUCGCAAGGCCUGACCAU | 120 |
| CTGF-744-16-14035 | 14035 | ooooooooooooos ssssso | Pmffff00ff00m000mm00 | CUUCCAGUCGGUAAGCCGC | 121 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| CTGF-466-16-14036 | 14036 | oooooooooooossssso | Pmf00ffff0f00mm00mm0 | CCGAUCUUGCGGUUGGCCG | 122 |
| CTGF-917-16-14037 | 14037 | oooooooooooossssso | Pmff0f0000fmm00mm0m0 | UUCGCAAGGCCUGACCAUG | 123 |
| CTGF-1038-16-14038 | 14038 | oooooooooooossssso | Pm00fff00fmm0m0m00 | AGAAUUUAGCUCGGUAUGU | 124 |
| CTGF-1048-16-14039 | 14039 | oooooooooooossssso | Pmf0ffff0f0000mmm00 | CAUACUCCACAGAAUUUAG | 125 |
| CTGF-1235-16-14040 | 14040 | oooooooooooossssso | Pm0ff0f0fffmmm0m0m0 | UGCCAUGUCUCCGUACAUC | 126 |
| CTGF-868-16-14041 | 14041 | oooooooooooossssso | Pm000f0ff0fm0mm00m00 | GAGGCGUUGUCAUUGGUAA | 127 |
| CTGF-1131-16-14042 | 14042 | oooooooooooossssso | Pmffff0f00fmmm0mm0m0 | UCUUCAUGACCUCGCCGUC | 128 |
| CTGF-1043-16-14043 | 14043 | oooooooooooossssso | Pmff0f0000fmm00mmm00 | UCCACAGAAUUUAGCUCGG | 129 |
| CTGF-751-16-14044 | 14044 | oooooooooooossssso | Pm0f0f0fffmm00mm000 | AACGUGUCUUCCAGUCGGU | 130 |
| CTGF-1227-16-14045 | 14045 | oooooooooooossssso | Pmfff0f0f0fmmmmmm0m0 | CUCCGUACAUCUUCCUGUA | 131 |
| CTGF-867-16-14046 | 14046 | oooooooooooossssso | Pm0f0ff0ff0mm0m000 | AGGCGUUGUCAUUGGUAAC | 132 |
| CTGF-1128-16-14047 | 14047 | oooooooooooossssso | Pmf0f00ffff0mm0mm000 | UCAUGACCUCGCCGUCAGG | 133 |
| CTGF-756-16-14048 | 14048 | oooooooooooossssso | Pm0ff000f0f0mmmmmm00 | GGCCAAACGUGUCUUCCAG | 134 |
| CTGF-1234-16-14049 | 14049 | oooooooooooossssso | Pmff0f0ffffmm0m0mm0 | GCCAUGUCUCCGUACAUCU | 135 |
| CTGF-916-16-14050 | 14050 | oooooooooooossssso | Pmf0f0000ffm00mm0m00 | UCGCAAGGCCUGACCAUGC | 136 |
| CTGF-925-16-14051 | 14051 | oooooooooooossssso | Pm0ff00fffmm0000m0 | AGGUCAGCUUCGCAAGGCC | 137 |
| CTGF-1225-16-14052 | 14052 | oooooooooooossssso | Pmf0f0f0fffmmmm0m000 | CCGUACAUCUUCCUGUAGU | 138 |
| CTGF-445-16-14053 | 14053 | oooooooooooossssso | Pm00ff0000fm0m000000 | GAGCCGAAGUCACAGAAGA | 139 |
| CTGF-446-16-14054 | 14054 | oooooooooooossssso | Pm000ff0000mm0m00000 | GGAGCCGAAGUCACAGAAG | 140 |
| CTGF-913-16-14055 | 14055 | oooooooooooossssso | Pm0000fff00mm0m0m0m0 | CAAGGCCUGACCAUGCACA | 141 |
| CTGF-997-16-14056 | 14056 | oooooooooooossssso | Pmfff000ffm00m000m0 | AGCUCAAACUUGAUAGGCU | 142 |
| CTGF-277-16-14057 | 14057 | oooooooooooossssso | Pmf0f00ffff00mm0m00 | CUGCAGUUCUGGCCGACGG | 143 |
| CTGF-1052-16-14058 | 14058 | oooooooooooossssso | Pm0f0f0f0ffmm0m00000 | GGUACAUACUCCACAGAAU | 144 |
| CTGF-887-16-14059 | 14059 | oooooooooooossssso | Pmf0fffffff00mmm0m00 | CUGCUUCUCUAGCCUGCAG | 145 |
| CTGF-914-16-14060 | 14060 | oooooooooooossssso | Pmf0000fff00mm0m0m00 | GCAAGGCCUGACCAUGCAC | 146 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| CTGF-1039-16-14061 | 14061 | ooooooooooooos ssssso | Pm0000fff00mmm00m0m0 | CAGAAUUUAGCUCGGUAUG | 147 |
| CTGF-754-16-14062 | 14062 | ooooooooooooos ssssso | Pmf000f0f0fmmmmm00m0 | CCAAACGUGUCUUCCAGUC | 148 |
| CTGF-1130-16-14063 | 14063 | ooooooooooooos ssssso | Pmfff0f00ffmmmm0mm0 | CUUCAUGACCUCGCCGUCA | 149 |
| CTGF-919-16-14064 | 14064 | ooooooooooooos ssssso | Pmffff0f0000mmm00mm0 | GCUUCGCAAGGCCUGACCA | 150 |
| CTGF-922-16-14065 | 14065 | ooooooooooooos ssssso | Pmf00ffff0f0000mmm00 | UCAGCUUCGCAAGGCCUGA | 151 |
| CTGF-746-16-14066 | 14066 | ooooooooooooos ssssso | Pmffffff00fm0m000m0 | GUCUUCCAGUCGGUAAGCC | 152 |
| CTGF-993-16-14067 | 14067 | ooooooooooooos ssssso | Pm000fff00f000mmm000 | CAAACUUGAUAGGCUUGGA | 153 |
| CTGF-825-16-14068 | 14068 | ooooooooooooos ssssso | Pm0ffff0000m000m0m0 | AGGUCUUGGAACAGGCGCU | 154 |
| CTGF-926-16-14069 | 14069 | ooooooooooooos ssssso | Pm000ff00ffmmm00000 | CAGGUCAGCUUCGCAAGGC | 155 |
| CTGF-923-16-14070 | 14070 | ooooooooooooos ssssso | Pmff00ffff0m0000mmm0 | GUCAGCUUCGCAAGGCCUG | 156 |
| CTGF-866-16-14071 | 14071 | ooooooooooooos ssssso | Pm0f0ff0f0mm0m00m0 | GGCGUUGUCAUUGGUAACC | 157 |
| CTGF-563-16-14072 | 14072 | ooooooooooooos ssssso | Pmf0f0ff00m0mmm0m00 | CGUGCACUGGUACUUGCAG | 158 |
| CTGF-823-16-14073 | 14073 | ooooooooooooos ssssso | Pmffff0000f000m0mmm0 | GUCUUGGAACAGGCGCUCC | 159 |
| CTGF-1233-16-14074 | 14074 | ooooooooooooos ssssso | Pmf0f0ffffff0m0m0mmm0 | CCAUGUCUCCGUACAUCUU | 160 |
| CTGF-924-16-14075 | 14075 | ooooooooooooos ssssso | Pm0ff00ffff0m0000mm0 | GGUCAGCUUCGCAAGGCCU | 161 |
| CTGF-921-16-14076 | 14076 | ooooooooooooos ssssso | Pm00ffff0f0000mmm000 | CAGCUUCGCAAGGCCUGAC | 162 |
| CTGF-443-16-14077 | 14077 | ooooooooooooos ssssso | Pmff0000ff0m00000000 | GCCGAAGUCACAGAAGAGG | 163 |
| CTGF-1041-16-14078 | 14078 | ooooooooooooos ssssso | Pm0f0000fff00mmm00m0 | CACAGAAUUUAGCUCGGUA | 164 |
| CTGF-1042-16-14079 | 14079 | ooooooooooooos ssssso | Pmf0f0000ffm00mmm000 | CCACAGAAUUUAGCUCGGU | 165 |
| CTGF-755-16-14080 | 14080 | ooooooooooooos ssssso | Pmff000f0f0mmmmm000 | GCCAAACGUGUCUUCCAGU | 166 |
| CTGF-467-16-14081 | 14081 | ooooooooooooos ssssso | Pmf0f00ffff0m0mm0m0 | GCCGAUCUUGCGGUUGGCC | 167 |
| CTGF-995-16-14082 | 14082 | ooooooooooooos ssssso | Pmff000fff00m000mmm0 | CUCAAACUUGAUAGGCUUG | 168 |
| CTGF-927-16-14083 | 14083 | ooooooooooooos ssssso | Pmf000ff00fmmm0m0000 | CCAGGUCAGCUUCGCAAGG | 169 |
| SPP1-1091-16-14131 | 14131 | ooooooooooooos ssssso | Pmff00ff000m0m0000m0 | UUUGACUAAAUGCAAAGUG | 170 |
| PPIB--16-14188 | 14188 | oooooooooooooo ssssss | Pm0fffff0f00mm000mm0 | UGUUUUUGUAGCCAAAUCC | 171 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| PPIB--17-14189 | 14189 | ooooooooooooossssss | Pm0fffff0f00mm000mm0 | UGUUUUUGUAGCCAAAUCC | 172 |
| PPIB--18-14190 | 14190 | ooooooooooooossssss | Pm0fffff0f00mm000mm0 | UGUUUUUGUAGCCAAAUCC | 173 |
| pGL3-1172-16-14386 | 14386 | ooooooooooooosssssso | Pm00ff0f0ffm0mm00mm0 | AAAUCGUAUUUGUCAAUCA | 174 |
| pGL3-1172-16-14387 | 14387 | ooooooooooooosssssso | Pm00ff0f0ffm0mm00mm0 | AAAUCGUAUUUGUCAAUCA | 175 |
| MAP4K4-2931-25-14390 | 14390 | | | | |
| miR-122--23-14391 | 14391 | | | | |
| | 14084 | ooooooooooooosssssso | Pmff00fff0f000000m00 | UCUAAUUCAUGAGAAAUAC | 616 |
| | 14085 | ooooooooooooosssssso | Pm00ff00fffm000000m0 | UAAUUGACCUCAGAAGAUG | 617 |
| | 14086 | ooooooooooooosssssso | Pmff00ff00fmmm000000 | UUUAAUUGACCUCAGAAGA | 618 |
| | 14087 | ooooooooooooosssssso | Pm0ff00ffff000000m00 | AAUUGACCUCAGAAGAUGC | 619 |
| | 14088 | ooooooooooooosssssso | Pmf00ff00ffmm0000000 | UUAAUUGACCUCAGAAGAU | 620 |
| | 14089 | ooooooooooooosssssso | Pmff00ffff000000m0m0 | AUUGACCUCAGAAGAUGCA | 621 |
| | 14090 | ooooooooooooosssssso | Pmf0fff00ff00mmm0mm0 | UCAUCCAGCUGACUCGUUU | 622 |
| | 14091 | ooooooooooooosssssso | Pm0fff0ff0000m00m00 | AGAUUCAUCAGAAUGGUGA | 623 |
| | 14092 | ooooooooooooosssssso | Pm00ffff00fmm0m000m0 | UGACCUCAGUCCAUAAACC | 624 |
| | 14093 | ooooooooooooosssssso | Pm0f00f0000mmm0mm000 | AAUGGUGAGACUCAUCAGA | 625 |
| | 14094 | ooooooooooooosssssso | Pmff00ffff00mmm0m000 | UUUGACCUCAGUCCAUAAA | 626 |
| | 14095 | ooooooooooooosssssso | Pmff0f00ff0m0000mmm0 | UUCAUGGCUGUGAAAUUCA | 627 |
| | 14096 | ooooooooooooosssssso | Pm00f00f0000mmm0mm00 | GAAUGGUGAGACUCAUCAG | 628 |
| | 14097 | ooooooooooooosssssso | Pm00ffffff0mmm0m0m00 | UGGCUUUCCGCUUAUAUAA | 629 |
| | 14098 | ooooooooooooosssssso | Pmf00ffffff0mm0m0m00 | UUGGCUUUCCGCUUAUAUA | 630 |
| | 14099 | ooooooooooooosssssso | Pmf0fff0f0f00mm0m000 | UCAUCCAUGUGGUCAUGGC | 631 |
| | 14100 | ooooooooooooosssssso | Pmf0f00ff0f00mmmmm00 | AUGUGGUCAUGGCUUUCGU | 632 |
| | 14101 | ooooooooooooosssssso | Pmf00ff0f00mmmmm0mm0 | GUGGUCAUGGCUUUCGUUG | 633 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| | 14102 | ooooooooooooos sssso | Pmff00fffffmmmm0m00 | AUUGGCUUUCCGCUUAUAU | 634 |
| | 14103 | ooooooooooooos sssso | Pm00f0f0000mmmm000m0 | AAAUACGAAAUUUCAGGUG | 635 |
| | 14104 | ooooooooooooos sssso | Pm000f0f0000mmmm000 | AGAAAUACGAAAUUUCAGG | 636 |
| | 14105 | ooooooooooooos sssso | Pm00ff0f00fmmmm0mm00 | UGGUCAUGGCUUUCGUUGG | 637 |
| | 14106 | ooooooooooooos sssso | Pmf0ff0fff0m0m00mm00 | AUAUCAUCCAUGUGGUCAU | 638 |
| | 14107 | ooooooooooooos sssso | Pm0f0f0000fmmm000m0 | AAUACGAAAUUUCAGGUGU | 639 |
| | 14108 | ooooooooooooos sssso | Pm0ff000000mm0mmm0 | AAUCAGAAGGCGCGUUCAG | 640 |
| | 14109 | ooooooooooooos sssso | Pmfff0f000000m0m0000 | AUUCAUGAGAAAUACGAAA | 641 |
| | 14110 | ooooooooooooos sssso | Pmf0fff0f0000000m000 | CUAUUCAUGAGAGAAUAAC | 642 |
| | 14111 | ooooooooooooos sssso | Pmfff0ff000mmm0mmm00 | UUUCGUUGGACUUACUUGG | 643 |
| | 14112 | ooooooooooooos sssso | Pmf0fffff0fm0mm00mm0 | UUGCUCUCAUCAUUGGCUU | 644 |
| | 14113 | ooooooooooooos sssso | Pmff00fffffmmmmmmm0 | UUCAACUCCUCGCUUUCCA | 645 |
| | 14114 | ooooooooooooos sssso | Pm00ff0ff00mm0m0mm00 | UGACUAUCAAUCACAUCGG | 646 |
| | 14115 | ooooooooooooos sssso | Pm0f0f0ff0mmm00mmm0 | AGAUGCACUAUCUAAUUCA | 647 |
| | 14116 | ooooooooooooos sssso | Pm0f000f0f0m0mmm00m0 | AAUAGAUACACAUUCAACC | 648 |
| | 14117 | ooooooooooooos sssso | Pmffffff0f0000m000m0 | UUCUUCUAUAGAAUGAACA | 649 |
| | 14118 | ooooooooooooos sssso | Pm0ff0ff000m00mm0m00 | AAUUGCUGGACAACCGUGG | 650 |
| | 14119 | ooooooooooooos sssso | Pmf0fffiff0m0m0m0000 | UCGCUUUCCAUGUGUGAGG | 651 |
| | 14120 | ooooooooooooos sssso | Pm00fff000fm0mmm0m00 | UAAUCUGGACUGCUUGUGG | 652 |
| | 14121 | ooooooooooooos sssso | Pmf0f0fff00mm00m0000 | ACACAUUCAACCAAUAAAC | 653 |
| | 14122 | ooooooooooooos sssso | Pmfff0fffff0m00mm0mm0 | ACUCGUUUCAUAACUGUCC | 654 |
| | 14123 | ooooooooooooos sssso | Pmf00fff000mm0mmm0m0 | AUAAUCUGGACUGCUUGUG | 655 |
| | 14124 | ooooooooooooos sssso | Pmffff0fff0m0m00mmm0 | UUUCCGCUUAUAUAAUCUG | 656 |
| | 14125 | ooooooooooooos sssso | Pm0fff00ff0m0m00mm00 | UGUUUAACUGGUAUGGCAC | 657 |
| | 14126 | ooooooooooooos sssso | Pm0f0000f000m0m000m0 | UAUAGAAUGAACAUAGACA | 658 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| | 14127 | oooooooooooooos sssso | Pmfffff00fm0m0mmm0 | UUUCCUUGGUCGGCGUUUG | 659 |
| | 14128 | oooooooooooooos sssso | Pmf0f0f0ff0mmm00mmm0 | GUAUGCACCAUUCAACUCC | 660 |
| | 14129 | oooooooooooooos sssso | Pmf00ff0ff0m0m0mm0 | UCGGCCAUCAUAUGUGUCU | 661 |
| | 14130 | oooooooooooooos sssso | Pm0fff000ff0mmm0m000 | AAUCUGGACUGCUUGUGGC | 662 |
| | 14132 | oooooooooooooos sssso | Pmf0ff0000f0mmm0mm00 | ACAUCGGAAUGCUCAUUGC | 663 |
| | 14133 | oooooooooooooos sssso | Pm00fffff00mm0mm00m0 | AAGUUCCUGACUAUCAAUC | 664 |
| | 14134 | oooooooooooooos sssso | Pmf00ff000f0m0000m00 | UUGACUAAAUGCAAAGUGA | 665 |
| | 14135 | oooooooooooooos sssso | Pm0fff0ff000mm00m00 | AGACUCAUCAGACUGGUGA | 666 |
| | 14136 | oooooooooooooos sssso | Pmf0f0f0f0fmmm0m0m00 | UCAUAUGUGUCUACUGUGG | 667 |
| | 14137 | oooooooooooooos sssso | Pmf0fffff0fmm0m00m00 | AUGUCCUCGUCUGUAGCAU | 668 |
| | 14138 | oooooooooooooos sssso | Pm00fff0f00mm00mmmm0 | GAAUUCACGGCUGACUUUG | 669 |
| | 14139 | oooooooooooooos sssso | Pmf0fffff000mmm000m0 | UUAUUCCAGACUCAAAUA | 670 |
| | 14140 | oooooooooooooos sssso | Pm000ff0f000mm000mm0 | GAAGCCACAAACUAAACUA | 671 |
| | 14141 | oooooooooooooos sssso | Pmffff0ff000mmm0mmm0 | CUUUCGUUGGACUUACUUG | 672 |
| | 14142 | oooooooooooooos sssso | Pmfff0f0000mmmmmm000 | GUCUGCGAAACUUCUUAGA | 673 |
| | 14143 | oooooooooooooos sssso | Pm0f0fff0ff0mmmmm0m0 | AAUGCUCAUUGCUCUCAUC | 674 |
| | 14144 | oooooooooooooos sssso | Pmf0f0ff0ffm00mmm0m0 | AUGCACUAUCUAAUUCAUG | 675 |
| | 14145 | oooooooooooooos sssso | Pmff0f0f0f0mm0mmm000 | CUUGUAUGCACCAUUCAAC | 676 |
| | 14146 | oooooooooooooos sssso | Pm00fff0fffm0m00mm00 | UGACUCGUUUCAUAACUGU | 677 |
| | 14147 | oooooooooooooos sssso | Pmff00f0fffm0mm0mm0 | UUCAGCACUCUGGUCAUCC | 678 |
| | 14148 | oooooooooooooos sssso | Pm00fff0f00mm0m00000 | AAAUUCAUGGCUGUGGAAU | 679 |
| | 14149 | oooooooooooooos sssso | Pmf0fff00ff00m000mm0 | ACAUUCAACCAAUAAACUG | 680 |
| | 14150 | oooooooooooooos sssso | Pm0f0f0fff00mm00m000 | UACACAUUCAACCAAUAAA | 681 |
| | 14151 | oooooooooooooos sssso | Pmff00ff0ffmmm000mm0 | AUUAGUUAUUCCAGACUC | 682 |
| | 14152 | oooooooooooooos sssso | Pmffff0fff0m00000000 | UUUCUAUUCAUGAGAGAAU | 683 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| | 14153 | ooooooooooooos sssso | Pmff00ff0ff00m000mm0 | UUCGGUUGCUGGCAGGUCC | 684 |
| | 14154 | ooooooooooooos sssso | Pm0f0f0f0000m00m0mm0 | CAUGUGUGAGGUGAUGUCC | 685 |
| | 14155 | ooooooooooooos sssso | Pmf0ff0fff00mmmmmm00 | GCACCAUUCAACUCCUCGC | 686 |
| | 14156 | ooooooooooooos sssso | Pm0fff00ff00mm0mm0 | CAUCCAGCUGACUCGUUUC | 687 |
| | 14157 | ooooooooooooos sssso | Pmfffff0fff0m0m00mm0 | CUUUCCGCUUAUAUAAUCU | 688 |
| | 14158 | ooooooooooooos sssso | Pmff0f0ff0000m0mm0 | AAUCACAUCGGAAUGCUCA | 689 |
| | 14159 | ooooooooooooos sssso | Pmf0f0ff00fm0mmmmm00 | ACACAUUAGUUAUUCCAG | 690 |
| | 14160 | ooooooooooooos sssso | Pmfff0f0000m000m0m00 | UUCUAUAGAAUGAACAUAG | 691 |
| | 14161 | ooooooooooooos sssso | Pm0f00f00f00mmm0m0m0 | UACAGUGAUAGUUUGCAUU | 692 |
| | 14162 | ooooooooooooos sssso | Pmf000f00ff00m0mm0mm0 | AUAAGCAAUUGACACCACC | 693 |
| | 14163 | ooooooooooooos sssso | Pmff0ff00ff0mm000m00 | UUUAUUAAUUGCUGGACAA | 694 |
| | 14164 | ooooooooooooos sssso | Pmf0ff0000fmmmm0000 | UCAUCAGAGUCGUUCGAGU | 695 |
| | 14165 | ooooooooooooos sssso | Pmf000ff0f0mm0mm0m0 | AUAAACCACACUAUCACCU | 696 |
| | 14166 | ooooooooooooos sssso | Pm0ff0ff00mmmmmm0m0 | UCAUCAUUGGCUUUCCGCU | 697 |
| | 14167 | ooooooooooooos sssso | Pmfffff00fm0mm00mm0 | AGUUCCUGACUAUCAAUCA | 698 |
| | 14168 | ooooooooooooos sssso | Pmff0f00ff00mmmm0000 | UUCACGGCUGACUUUGGAA | 699 |
| | 14169 | ooooooooooooos sssso | Pmffff0f00f0m000mm0 | UUCUCAUGGUAGUGAGUUU | 700 |
| | 14170 | ooooooooooooos sssso | Pm0ff00fff0mmm00mm00 | AAUCAGCCUGUUUAACUGG | 701 |
| | 14171 | ooooooooooooos sssso | Pm0ffff00f0mmmm00mm0 | GGUUUCAGCACUCUGGUCA | 702 |
| | 14172 | ooooooooooooos sssso | Pmff0000f0fmm0mm0m0 | AUCGGAAUGCUCAUUGCUC | 703 |
| | 14173 | ooooooooooooos sssso | Pm00ff0f0000mmm0m000 | UGGCUGUGGAAUUCACGGC | 704 |
| | 14174 | ooooooooooooos sssso | Pm000f00ff00m0mm0mm0 | UAAGCAAUUGACACCACCA | 705 |
| | 14175 | ooooooooooooos sssso | Pm00fffff0f00m00m0m000 | CAAUUCUCAUGGUAGUGAG | 706 |
| | 14176 | ooooooooooooos sssso | Pm00fffff0fm000mmm00 | UGGCUUUCGUUGGACUUAC | 707 |
| | 14177 | ooooooooooooos sssso | Pm0ff00f00fm00mmm0m0 | AAUCAGUGACCAGUUCAUC | 708 |

TABLE 2-continued

Antisense backbone, chemistry, and sequence information.

| ID Number | Oligo Number | AntiSense Backbone | AntiSense Chemistry | AntiSense Sequence | SEQ ID NO: |
|---|---|---|---|---|---|
| | 14178 | ooooooooooooos ssssso | Pmfff0f000mm0m0mm00 | AGUCCAUAAACCACACUAU | 709 |
| | 14179 | ooooooooooooos ssssso | Pm00f0fff00mm0mmm00 | CAGCACUCUGGUCAUCCAG | 710 |
| | 14180 | ooooooooooooos ssssso | Pm0ff00ff0f0mm0000m0 | UAUCAAUCACAUCGGAAUG | 711 |
| | 14181 | ooooooooooooos ssssso | Pmfff0f00ff00mmmm000 | AUUCACGGCUGACUUUGGA | 712 |
| | 14182 | ooooooooooooos ssssso | Pmf000f0f0f0mmm00mm0 | AUAGAUACACAUUCAACCA | 713 |
| | 14183 | ooooooooooooos ssssso | Pmffff000ffm000m0000 | UUUCCAGACUCAAAUAGAU | 714 |
| | 14184 | ooooooooooooos ssssso | Pmf00ff0ff000m00mm00 | UUAAUUGCUGGACAACCGU | 715 |
| | 14185 | ooooooooooooos ssssso | Pm0ff00ff0fm000m00m0 | UAUUAAUUGCUGGACAACC | 716 |
| | 14186 | ooooooooooooos ssssso | Pmff0fff000mm00m000 | AGUCGUUCGAGUCAAUGGA | 717 |
| | 14187 | ooooooooooooos ssssso | Pmff0ff00f000mmm0m00 | GUUGCUGGCAGGUCCGUGG | 718 | o: phosphodiester; s: phosphorothioate; P: 5' phosphorylation; 0: 2'-OH; F: 2'-fluoro; m: 2' O-methyl; +: LNA modification. Capital letters in the sequence signify riobonucleotides, lower case letters signify deoxyribonucleotides.

TABLE 3

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| APOB-10167-20-12138 | 12138 | chl | oooooooooooooooo oooso | 00000000000000000 000 | GUCAUCACACUGAAUAC CAAU | 176 |
| APOB-10167-20-12139 | 12139 | chl | oooooooooooooooo oooso | 00000000000000000 000 | GUGAUCAGACUCAAUAC GAAU | 177 |
| MAP4K4-2931-13-12266 | 12266 | chl | ooooooooooosso | mm0m00000mmm0 | CUGUGGAAGUCUA | 178 |
| MAP4K4-2931-16-12293 | 12293 | chl | ooooooooooosso | mm0m00000mmm0 | CUGUGGAAGUCUA | 179 |
| MAP4K4-2931-16-12383 | 12383 | chl | ooooooooooooo | mm0m00000mmm0 | CUGUGGAAGUCUA | 180 |
| MAP4K4-2931-16-12384 | 12384 | chl | ooooooooooooo | mm0m00000mmm0 | CUGUGGAAGUCUA | 181 |
| MAP4K4-2931-16-12385 | 12385 | chl | ooooooooooooo | mm0m00000mmm0 | CUGUGGAAGUCUA | 182 |
| MAP4K4-2931-16-12386 | 12386 | chl | ooooooooosso | 0mm0m00000mmm0 | CUGUGGAAGUCUA | 183 |
| MAP4K4-2931-16-12387 | 12387 | chl | ooooooooooooo | mm0m00000mmm0 | CUGUGGAAGUCUA | 184 |
| MAP4K4-2931-15-12388 | 12388 | chl | ooooooooooooo | mm0m00000mmm0 | CUGUGGAAGUCUA | 185 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| MAP4K4-2931-13-12432 | 12432 | chl | oooooooooooo | DY547mm0m00000mmm0 | CUGUGGAAGUCUA | 186 |
| MAP4K4-2931-13-12266.2 | 12266.2 | chl | ooooooooooss | mm0m00000mmm0 | CUGUGGAAGUCUA | 187 |
| APOB--21-12434 | 12434 | chl | ooooooooooooooooooso | 00000000000000000000 | GUCAUCACACUGAAUACCAAU | 188 |
| APOB--21-12435 | 12435 | chl | ooooooooooooooooooso | DY54700000000000000000000 | GUGAUCAGACUCAAUACGAAU | 189 |
| MAP4K4-2931-16-12451 | 12451 | chl | ooooooooooss | 0mm0m00000mmm0 | CUGUGGAAGUCUA | 190 |
| MAP4K4-2931-16-12452 | 12452 | chl | ooooooooooss | mm0m00000mmm0 | CUGUGGAAGUCUA | 191 |
| MAP4K4-2931-16-12453 | 12453 | chl | ooooooooooss | mm0m00000mmm0 | CUGUGGAAGUCUA | 192 |
| MAP4K4-2931-17-12454 | 12454 | chl | ooooooooooss | 0mm0m00000mmm0 | CUGUGGAAGUCUA | 193 |
| MAP4K4-2931-17-12455 | 12455 | chl | ooooooooooss | mm0m00000mmm0 | CUGUGGAAGUCUA | 194 |
| MAP4K4-2931-19-12456 | 12456 | chl | ooooooooooss | mm0m00000mmm0 | CUGUGGAAGUCUA | 195 |
| --27-12480 | 12480 | chl | ooooooooooooooooooooosso | DY547mm0f000f0055f5f00mm00000m000 | UCAUAGGUAACCUCGGUUGAAAGUGA | 196 |
| --27-12481 | 12481 | chl | ooooooooooooooooooooosso | DY547mm05f05000f05ff0m00000000m00 | CGGCUACAGGUGCUUAUGAAGAAAGUA | 197 |
| APOB-10167-21-12505 | 12505 | chl | ooooooooooooooooooos | 0000000000000000000 | GUCAUCACACUGAAUACCAAU | 198 |
| APOB-10167-21-12506 | 12506 | chl | ooooooooooooooooooos | 0000000000000000000 | GUGAUCAGACUCAAUACGAAU | 199 |
| MAP4K4-2931-16-12539 | 12539 | chl | ooooooooooss | DY547mm0m00000mmm0 | CUGUGGAAGUCUA | 200 |
| APOB-10167-21-12505.2 | 12505.2 | chl | ooooooooooooooooooso | 00000000000000000000 | GUCAUCACACUGAAUACCAAU | 201 |
| APOB-10167-21-12506.2 | 12506.2 | chl | ooooooooooooooooooso | 00000000000000000000 | GUGAUCAGACUCAAUACGAAU | 202 |
| MAP4K4--13-12565 | 12565 | Chl | oooooooooooo | m0m0000m0mmm0 | UGUAGGAUGUCUA | 203 |
| MAP4K4-2931-16-12386.2 | 12386.2 | chl | oooooooooooo | 0mm0m00000mmm0 | CUGUGGAAGUCUA | 204 |
| MAP4K4-2931-13-12815 | 12815 | chl | oooooooooooo | m0m0m0m0m0m0m0m0m0m0 | CUGUGGAAGUCUA | 205 |
| APOB--13-12957 | 12957 | Chl TEG | ooooooooooss | 0mmmmmmmmmmmm | ACUGAAUACCAAU | 206 |
| MAP4K4--16-12983 | 12983 | chl | ooooooooooss | mm0m00000mmm0 | CUGUGGAAGUCUA | 207 |
| MAP4K4--16-12984 | 12984 | Chl | 0ooooooooooo | mm0m00000mmm0 | CUGUGGAAGUCUA | 208 |
| MAP4K4--16-12985 | 12985 | chl | ooooooooooosso | mmmmmmmmmmmmm | CUGUGGAAGUCUA | 209 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| MAP4K4--16-12986 | 12986 | chl | ooooooooooosso | mmmmmmmmmmmmm | CUGUGGAAGUCUA | 210 |
| MAP4K4--16-12987 | 12987 | chl | ooooooooooosso | mm0m00000mmm0 | CUGUGGAAGUCUA | 211 |
| MAP4K4--16-12988 | 12988 | chl | ooooooooooosso | mm0m00000mmm0 | CUGUGGAAGUCUA | 212 |
| MAP4K4--16-12989 | 12989 | chl | ooooooooooosso | mm0m00000mmm0 | CUGUGGAAGUCUA | 213 |
| MAP4K4--16-12990 | 12990 | chl | ooooooooooosso | mm0m00000mmm0 | CUGUGGAAGUCUA | 214 |
| MAP4K4--16-12991 | 12991 | chl | ooooooooooosso | mm0m00000mmm0 | CUGUGGAAGUCUA | 215 |
| MAP4K4--16-12992 | 12992 | chl | ooooooooooosso | mm0m00000mmm0 | CUGUGGAAGUCUA | 216 |
| MAP4K4--16-12993 | 12993 | chl | ooooooooooosso | mm0m00000mmm0 | CUGUGGAAGUCUA | 217 |
| MAP4K4--16-12994 | 12994 | chl | ooooooooooosso | mm0m00000mmm0 | CUGUGGAAGUCUA | 218 |
| MAP4K4--16-12995 | 12995 | chl | ooooooooooosso | mm0m00000mmm0 | CUGUGGAAGUCUA | 219 |
| MAP4K4-2931-19-13012 | 13012 | chl | oooooooooooooooooo | 00000000000000000000 | AGAGUUCUGUGGAAGUCUA | 220 |
| MAP4K4-2931-19-13016 | 13016 | chl | oooooooooooooooooo | DY547000000000000000000000 | AGAGUUCUGUGGAAGUCUA | 221 |
| PPIB--13-13021 | 13021 | Chl | ooooooooooooo | 0mmm00mm0m000 | AUUUGGCUACAAA | 222 |
| pGL3-1172-13-13038 | 13038 | chl | ooooooooooo | 00m000m0m00mmm | ACAAAUACGAUUU | 223 |
| pGL3-1172-13-13040 | 13040 | chl | ooooooooooo | DY5470m000m0m00mmm | ACAAAUACGAUUU | 224 |
| --16-13047 | 13047 | Chl | ooooooooooooo | mm0m00000mmm0 | CUGUGGAAGUCUA | 225 |
| SOD1-530-13-13090 | 13090 | chl | ooooooooooo | 00m00000000m0 | AAUGAAGAAAGUA | 226 |
| SOD1-523-13-13091 | 13091 | chl | ooooooooooo | 000m00000m000 | AGGUGGAAAUGAA | 227 |
| SOD1-535-13-13092 | 13092 | chl | ooooooooooo | 000000m0m0000 | AGAAAGUACAAAG | 228 |
| SOD1-536-13-13093 | 13093 | chl | ooooooooooo | 00000m0m00000 | GAAAGUACAAAGA | 229 |
| SOD1-396-13-13094 | 13094 | chl | ooooooooooo | 0m0m00mm0m00 | AUGUGACUGCUGA | 230 |
| SOD1-385-13-13095 | 13095 | chl | ooooooooooo | 000mmm000m00m | AGACUUGGGCAAU | 231 |
| SOD1-195-13-13096 | 13096 | chl | ooooooooooo | 0mmmm000m0000 | AUUUCGAGCAGAA | 232 |
| APOB-4314-13-13115 | 13115 | Chl | ooooooooooo | 0mmm0000000m0 | AUCUGGAGAAACA | 233 |
| APOB-3384-13-13116 | 13116 | Chl | ooooooooooo | mm0000m000000 | UCAGAACAAGAAA | 234 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| APOB-3547-13-13117 | 13117 | Chl | ooooooooooo | o0mmm0mmm0mm0 | GACUCAUCUGCUA | 235 |
| APOB-4318-13-13118 | 13118 | Chl | ooooooooooo | o000000m00m0m | GGAGAAACAACAU | 236 |
| APOB-3741-13-13119 | 13119 | Chl | ooooooooooo | o0mmmmm000m0 | AGUCCCUCAAACA | 237 |
| PPIB--16-13136 | 13136 | Chl | ooooooooooo | o0mm0m00000m0 | GGCUACAAAAACA | 238 |
| APOB-4314-15-13154 | 13154 | chl | ooooooooooo | o00mmm0000000m0 | AGAUCUGGAGAAACA | 239 |
| APOB-3547-15-13155 | 13155 | chl | ooooooooooo | m000mmm0mmm0mm0 | UGGACUCAUCUGCUA | 240 |
| APOB-4318-15-13157 | 13157 | chl | ooooooooooo | mm0000000m00m0m | CUGGAGAAACAACAU | 241 |
| APOB-3741-15-13158 | 13158 | chl | ooooooooooo | o000mmmmm000m0 | AGAGUCCCUCAAACA | 242 |
| APOB--13-13159 | 13159 | chl | oooooooooo | o0mm000m0mm00m | ACUGAAUACCAAU | 243 |
| APOB--15-13160 | 13160 | chl | ooooooooooo | o0m0mm000m0mm00m | ACACUGAAUACCAAU | 244 |
| SOD1-530-16-13163 | 13163 | chl | ooooooooooo | o0m00000000m0 | AAUGAAGAAAGUA | 245 |
| SOD1-523-16-13164 | 13164 | chl | ooooooooooo | o000m00000m000 | AGGUGGAAAUGAA | 246 |
| SOD1-535-16-13165 | 13165 | chl | ooooooooooo | o00000m0m0000 | AGAAAGUACAAAG | 247 |
| SOD1-536-16-13166 | 13166 | chl | ooooooooooo | o0000m0m00000 | GAAAGUACAAAGA | 248 |
| SOD1-396-16-13167 | 13167 | chl | ooooooooooo | 0m0m00mm0mm00 | AUGUGACUGCUGA | 249 |
| SOD1-385-16-13168 | 13168 | chl | ooooooooooo | o000mmm000m00m | AGACUUGGGCAAU | 250 |
| SOD1-195-16-13169 | 13169 | chl | ooooooooooo | 0mmmm000m0000 | AUUUCGAGCAGAA | 251 |
| pGL3-1172-16-13170 | 13170 | chl | ooooooooooo | 0m000m0m00mmm | ACAAAUACGAUUU | 252 |
| pGL3-1172-16-13171 | 13171 | chl | ooooooooooo | DY5470m000m0m00mmm | ACAAAUACGAUUU | 253 |
| MAP4k4-2931-19-13189 | 13189 | chl | ooooooooooooooo oooo | o00000000000000000 0000 | AGAGUUCUGUGGAAGUC UA | 254 |
| CTGF-1222-13-13190 | 13190 | Chl | ooooooooooo | 0m0000000m0 | ACAGGAAGAUGUA | 255 |
| CTGF-813-13-13192 | 13192 | Chl | ooooooooooo | o000m0000m0mmm | GAGUGGAGCGCCU | 256 |
| CTGF-747-13-13194 | 13194 | Chl | ooooooooooo | m00mm000000m0 | CGACUGGAAGACA | 257 |
| CTGF-817-13-13196 | 13196 | Chl | ooooooooooo | o0000m0mmm0mmm | GGAGCGCCUGUUC | 258 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| CTGF-1174-13-13198 | 13198 | Chl | oooooooooooo | 0mm0mm0m00mm0 | GCCAUUACAACUG | 259 |
| CTGF-1005-13-13200 | 13200 | Chl | oooooooooooo | 000mmmmmm00mm | GAGCUUUCUGGCU | 260 |
| CTGF-814-13-13202 | 13202 | Chl | oooooooooooo | 00m0000m0mmm0 | AGUGGAGCGCCUG | 261 |
| CTGF-816-13-13204 | 13204 | Chl | oooooooooooo | m0000m0mmm0mm | UGGAGCGCCUGUU | 262 |
| CTGF-1001-13-13206 | 13206 | Chl | oooooooooooo | 0mm000mmmmmm | GUUUGAGCUUUCU | 263 |
| CTGF-1173-13-13208 | 13208 | Chl | oooooooooooo | m0mm0mm0m00mm | UGCCAUUACAACU | 264 |
| CTGF-749-13-13210 | 13210 | Chl | oooooooooooo | 0mm000000m0m0 | ACUGGAAGACACG | 265 |
| CTGF-792-13-13212 | 13212 | Chl | oooooooooooo | 00mm0mmm00mmm | AACUGCCUGGUCC | 266 |
| CTGF-1162-13-13214 | 13214 | Chl | oooooooooooo | 000mmm0m0mmm0 | AGACCUGUGCCUG | 267 |
| CTGF-811-13-13216 | 13216 | Chl | oooooooooooo | m0000m0000m0m | CAGAGUGGAGCGC | 268 |
| CTGF-797-13-13218 | 13218 | Chl | oooooooooooo | mmm00mmm000mm | CCUGGUCCAGACC | 269 |
| CTGF-1175-13-13220 | 13220 | Chl | oooooooooooo | mm0mm0m00mm0m | CCAUUACAACUGU | 270 |
| CTGF-1172-13-13222 | 13222 | Chl | oooooooooooo | mm0mm0m0m00m | CUGCCAUUACAAC | 271 |
| CTGF-1177-13-13224 | 13224 | Chl | oooooooooooo | 0mm0m00mm0mmm | AUUACAACUGUCC | 272 |
| CTGF-1176-13-13226 | 13226 | Chl | oooooooooooo | m0mm0m00mm0mm | CAUUACAACUGUC | 273 |
| CTGF-812-13-13228 | 13228 | Chl | oooooooooooo | 0000m0000m0mm | AGAGUGGAGCGCC | 274 |
| CTGF-745-13-13230 | 13230 | Chl | oooooooooooo | 0mm00mm000000 | ACCGACUGGAAGA | 275 |
| CTGF-1230-13-13232 | 13232 | Chl | oooooooooooo | 0m0m0m00000m0 | AUGUACGGAGACA | 276 |
| CTGF-920-13-13234 | 13234 | Chl | oooooooooooo | 0mmmm0m0000mm | GCCUUGCGAAGCU | 277 |
| CTGF-679-13-13236 | 13236 | Chl | oooooooooooo | 0mm0m000000m0 | GCUGCGAGGAGUG | 278 |
| CTGF-992-13-13238 | 13238 | Chl | oooooooooooo | 0mmm0mm000mmm | GCCAUCAAGUUU | 279 |
| CTGF-1045-13-13240 | 13240 | Chl | oooooooooooo | 00mmmm0m0000m | AAUUCUGUGGAGU | 280 |
| CTGF-1231-13-13242 | 13242 | Chl | oooooooooooo | m0m0m00000m0m | UGUACGGAGACAU | 281 |
| CTGF-991-13-13244 | 13244 | Chl | oooooooooooo | 00mmm0mm000mm | AGCCAUCAAGUU | 282 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| CTGF-998-13-13246 | 13246 | Chl | oooooooooooo | mooommmooommm | CAAGUUUGAGCUU | 283 |
| CTGF-1049-13-13248 | 13248 | Chl | oooooooooooo | mmomooooomomom | CUGUGGAGUAUGU | 284 |
| CTGF-1044-13-13250 | 13250 | Chl | oooooooooooo | ooommmmomoooo | AAAUUCUGUGGAG | 285 |
| CTGF-1327-13-13252 | 13252 | Chl | oooooooooooo | mmmmoomomomo | UUUCAGUAGCACA | 286 |
| CTGF-1196-13-13254 | 13254 | Chl | oooooooooooo | moomooommmmm | CAAUGACAUCUUU | 287 |
| CTGF-562-13-13256 | 13256 | Chl | oooooooooooo | oomommomomom | AGUACCAGUGCAC | 288 |
| CTGF-752-13-13258 | 13258 | Chl | oooooooooooo | oooooomomommm | GGAAGACACGUUU | 289 |
| CTGF-994-13-13260 | 13260 | Chl | oooooooooooo | mmommooommmoo | CUAUCAAGUUUGA | 290 |
| CTGF-1040-13-13262 | 13262 | Chl | oooooooooooo | oommooommmmom | AGCUAAAUUCUGU | 291 |
| CTGF-1984-13-13264 | 13264 | Chl | oooooooooooo | ooomooooomoo | AGGUAGAAUGUAA | 292 |
| CTGF-2195-13-13266 | 13266 | Chl | oooooooooooo | oomoommoommm | AGCUGAUCAGUUU | 293 |
| CTGF-2043-13-13268 | 13268 | Chl | oooooooooooo | mmmmommmooomo | UUCUGCUCAGAUA | 294 |
| CTGF-1892-13-13270 | 13270 | Chl | oooooooooooo | mmommmooommoo | UUAUCUAAGUUAA | 295 |
| CTGF-1567-13-13272 | 13272 | Chl | oooooooooooo | momomooomoom | UAUACGAGUAAUA | 296 |
| CTGF-1780-13-13274 | 13274 | Chl | oooooooooooo | oommooomommm | GACUGGACAGCUU | 297 |
| CTGF-2162-13-13276 | 13276 | Chl | oooooooooooo | omoommmmmommo | AUGGCCUUUAUUA | 298 |
| CTGF-1034-13-13278 | 13278 | Chl | oooooooooooo | omommooommooo | AUACCGAGCUAAA | 299 |
| CTGF-2264-13-13280 | 13280 | Chl | oooooooooooo | mmommooooomom | UUGUUGAGAGUGU | 300 |
| CTGF-1032-13-13282 | 13282 | Chl | oooooooooooo | omomommooommo | ACAUACCGAGCUA | 301 |
| CTGF-1535-13-13284 | 13284 | Chl | oooooooooooo | oomoooooommo | AGCAGAAAGGUUA | 302 |
| CTGF-1694-13-13286 | 13286 | Chl | oooooooooooo | oommommmmmmoo | AGUUGUUCCUUAA | 303 |
| CTGF-1588-13-13288 | 13288 | Chl | oooooooooooo | ommmooooomoo | AUUUGAAGUGUAA | 304 |
| CTGF-928-13-13290 | 13290 | Chl | oooooooooooo | ooommoommmooo | AAGCUGACCUGGA | 305 |
| CTGF-1133-13-13292 | 13292 | Chl | oooooooooooo | oommomooooooo | GGUCAUGAAGAAG | 306 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| CTGF-912-13-13294 | 13294 | Chl | oooooooooooo | 0m00mm000mmmm | AUGGUCAGGCCUU | 307 |
| CTGF-753-13-13296 | 13296 | Chl | oooooooooooo | 00000m0m0mmm0 | GAAGACACGUUUG | 308 |
| CTGF-918-13-13298 | 13298 | Chl | oooooooooooo | 000mmmm0m0000 | AGGCCUUGCGAAG | 309 |
| CTGF-744-13-13300 | 13300 | Chl | oooooooooooo | m0mm0mm00000 | UACCGACUGGAAG | 310 |
| CTGF-466-13-13302 | 13302 | Chl | oooooooooooo | 0mm0m0000mm0 | ACCGCAAGAUCGG | 311 |
| cTGF-917-13-13304 | 13304 | Chl | oooooooooooo | m000mmmm0m000 | CAGGCCUUGCGAA | 312 |
| CTGF-1038-13-13306 | 13306 | Chl | oooooooooooo | m000mm000mmmm | CGAGCUAAAUUCU | 313 |
| CTGF-1048-13-13308 | 13308 | Chl | oooooooooooo | mmm0m0000m0m0 | UCUGUGGAGUAUG | 314 |
| CTGF-1235-13-13310 | 13310 | Chl | oooooooooooo | m00000m0m00m0 | CGGAGACAUGGCA | 315 |
| CTGF-868-13-13312 | 13312 | Chl | oooooooooooo | 0m00m00m0mmmm | AUGACAACGCCUC | 316 |
| CTGF-1131-13-13314 | 13314 | Chl | oooooooooooo | 0000mm0m00000 | GAGGUCAUGAAGA | 317 |
| CTGF-1043-13-13316 | 13316 | Chl | oooooooooooo | m000mmmm0m000 | UAAAUUCUGUGGA | 318 |
| CTGF-751-13-13318 | 13318 | Chl | oooooooooooo | m000000m0m0mm | UGGAAGACACGUU | 319 |
| CTGF-1227-13-13320 | 13320 | Chl | oooooooooooo | 0000m0m0m0000 | AAGAUGUACGGAG | 320 |
| CTGF-867-13-13322 | 13322 | Chl | oooooooooooo | 00m00m0m0mmmm | AAUGACAACGCCU | 321 |
| CTGF-1128-13-13324 | 13324 | Chl | oooooooooooo | 00m0000mm0m00 | GGCGAGGUCAUGA | 322 |
| CTGF-756-13-13326 | 13326 | Chl | oooooooooooo | 00m0m0mmm00mm | GACACGUUUGGCC | 323 |
| cTGF-1234-13-13328 | 13328 | Chl | oooooooooooo | 0m00000m0m00m | ACGGAGACAUGGC | 324 |
| CTGF-916-13-13330 | 13330 | Chl | oooooooooooo | mm000mmmm0m00 | UCAGGCCUUGCGA | 325 |
| CTGF-925-13-13332 | 13332 | Chl | oooooooooooo | 0m0000mm00mmm | GCGAAGCUGACCU | 326 |
| CTGF-1225-13-13334 | 13334 | Chl | oooooooooooo | 000000m0m0m00 | GGAAGAUGUACGG | 327 |
| CTGF-445-13-13336 | 13336 | Chl | oooooooooooo | 0m00mmmm00mmm | GUGACUUCGGCUC | 328 |
| CTGF-446-13-13338 | 13338 | Chl | oooooooooooo | m00mmmm00mmm | UGACUUCGGCUCC | 329 |
| CTGF-913-13-13340 | 13340 | Chl | oooooooooooo | m00mm000mmmm0 | UGGUCAGGCCUUG | 330 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| cTGF-997-13-13342 | 13342 | Chl | oooooooooooo | mm000mmm000mm | UCAAGUUUGAGCU | 331 |
| CTGF-277-13-13344 | 13344 | Chl | oooooooooooo | 0mm0000mm0m00 | GCCAGAACUGCAG | 332 |
| CTGF-1052-13-13346 | 13346 | Chl | oooooooooooo | m0000m0m0m0mm | UGGAGUAUGUACC | 333 |
| CTGF-887-13-13348 | 13348 | Chl | oooooooooooo | 0mm0000000m00 | GCUAGAGAAGCAG | 334 |
| CTGF-914-13-13350 | 13350 | Chl | oooooooooooo | 00mm000mmmm0m | GGUCAGGCCUUGC | 335 |
| CTGF-1039-13-13352 | 13352 | Chl | oooooooooooo | 000mm000mmmm0 | GAGCUAAAUUCUG | 336 |
| CTGF-754-13-13354 | 13354 | Chl | oooooooooooo | 0000m0m0mmm00 | AAGACACGUUUGG | 337 |
| CTGF-1130-13-13356 | 13356 | Chl | oooooooooooo | m0000mm0m0000 | CGAGGUCAUGAAG | 338 |
| CTGF-919-13-13358 | 13358 | Chl | oooooooooooo | 00mmmm0m0000m | GGCCUUGCGAAGC | 339 |
| CTGF-922-13-13360 | 13360 | Chl | oooooooooooo | mmm0m000mm00 | CUUGCGAAGCUGA | 340 |
| CTGF-746-13-13362 | 13362 | Chl | oooooooooooo | mm00mm000000m | CCGACUGGAAGAC | 341 |
| CTGF-993-13-13364 | 13364 | Chl | oooooooooooo | mmm0m000mmm0 | CCUAUCAAGUUUG | 342 |
| CTGF-825-13-13366 | 13366 | Chl | oooooooooooo | m0mmmm0000mmm | UGUUCCAAGACCU | 343 |
| CTGF-926-13-13368 | 13368 | Chl | oooooooooooo | m0000mm00mmm0 | CGAAGCUGACCUG | 344 |
| CTGF-923-13-13370 | 13370 | Chl | oooooooooooo | mm0m0000mm00m | UUGCGAAGCUGAC | 345 |
| CTGF-866-13-13372 | 13372 | Chl | oooooooooooo | m00m00m0m0mm | CAAUGACAACGCC | 346 |
| CTGF-563-13-13374 | 13374 | Chl | oooooooooooo | 0m0mm00m0m0m0 | GUACCAGUGCACG | 347 |
| CTGF-823-13-13376 | 13376 | Chl | oooooooooooo | mmm0mmmm0000m | CCUGUUCCAAGAC | 348 |
| CTGF-1233-13-13378 | 13378 | Chl | oooooooooooo | m0m0000m0m00 | UACGGAGACAUGG | 349 |
| CTGF-924-13-13380 | 13380 | Chl | oooooooooooo | m0m0000mm00mm | UGCGAAGCUGACC | 350 |
| CTGF-921-13-13382 | 13382 | Chl | oooooooooooo | mmmm0m0000mm0 | CCUUGCGAAGCUG | 351 |
| CTGF-443-13-13384 | 13384 | Chl | oooooooooooo | mm0m0mmmm00m | CUGUGACUUCGGC | 352 |
| CTGF-1041-13-13386 | 13386 | Chl | oooooooooooo | 0mm000mmmm0m0 | GCUAAAUUCUGUG | 353 |
| CTGF-1042-13-13388 | 13388 | Chl | oooooooooooo | mm000mmmm0m00 | CUAAAUUCUGUGG | 354 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| CTGF-755-13-13390 | 13390 | Chl | oooooooooooo | ooomomommmoom | AGACACGUUUGGC | 355 |
| CTGF-467-13-13392 | 13392 | Chl | oooooooooooo | mmoooooommoom | CCGCAAGAUCGGC | 356 |
| CTGF-995-13-13394 | 13394 | Chl | oooooooooooo | mommooommmooo | UAUCAAGUUUGAG | 357 |
| CTGF-927-13-13396 | 13396 | Chl | oooooooooooo | ooooommoommmoo | GAAGCUGACCUGG | 358 |
| SPP1-1025-13-13398 | 13398 | Chl | oooooooooooo | mmmomoommooo | CUCAUGAAUUAGA | 359 |
| SPP1-1049-13-13400 | 13400 | Chl | oooooooooooo | mmoooommoommo | CUGAGGUCAAUUA | 360 |
| SPP1-1051-13-13402 | 13402 | Chl | oooooooooooo | ooooommoommooo | GAGGUCAAUUAAA | 361 |
| SPP1-1048-13-13404 | 13404 | Chl | oooooooooooo | mmmoooommoomm | UCUGAGGUCAAUU | 362 |
| SPP1-1050-13-13406 | 13406 | Chl | oooooooooooo | moooommoommoo | UGAGGUCAAUUAA | 363 |
| SPP1-1047-13-13408 | 13408 | Chl | oooooooooooo | mmmmoooommoom | UUCUGAGGUCAAU | 364 |
| SPP1-800-13-13410 | 13410 | Chl | oooooooooooo | ommoommooomoo | GUCAGCUGGAUGA | 365 |
| SPP1-492-13-13412 | 13412 | Chl | oooooooooooo | mmmmoomooommm | UUCUGAUGAAUCU | 366 |
| SPP1-612-13-13414 | 13414 | Chl | oooooooooooo | mooommooooommo | UGGACUGAGGUCA | 367 |
| SPP1-481-13-13416 | 13416 | Chl | oooooooooooo | ooommmmommomm | GAGUCUCACCAUU | 368 |
| SPP1-614-13-13418 | 13418 | Chl | oooooooooooo | oommoooommooo | GACUGAGGUCAAA | 369 |
| SPP1-951-13-13420 | 13420 | Chl | oooooooooooo | mmomoommomooo | UCACAGCCAUGAA | 370 |
| SPP1-482-13-13422 | 13422 | Chl | oooooooooooo | oommmmommomm | AGUCUCACCAUUC | 371 |
| SPP1-856-13-13424 | 13424 | Chl | oooooooooooo | ooomoooooommo | AAGCGGAAAGCCA | 372 |
| SPP1-857-13-13426 | 13426 | Chl | oooooooooooo | oomoooooommoo | AGCGGAAAGCCAA | 373 |
| SPP1-365-13-13428 | 13428 | Chl | oooooooooooo | ommomomoooomoo | ACCACAUGGAUGA | 374 |
| SPP1-359-13-13430 | 13430 | Chl | oooooooooooo | ommomoommomom | GCCAUGACCACAU | 375 |
| SPP1-357-13-13432 | 13432 | Chl | oooooooooooo | ooommomoommom | AAGCCAUGACCAC | 376 |
| SPP1-858-13-13434 | 13434 | Chl | oooooooooooo | omoooooommoom | GCGGAAAGCCAAU | 377 |
| SPP1-1012-13-13436 | 13436 | Chl | oooooooooooo | ooommmmomommm | AAAUUCGUAUUU | 378 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| SPP1-1014-13-13438 | 13438 | Chl | oooooooooooo | 0mmmm0m0mmmmm | AUUUCGUAUUUCU | 379 |
| SPP1-356-13-13440 | 13440 | Chl | oooooooooooo | 0000mm0m00mm0 | AAAGCCAUGACCA | 380 |
| SPP1-368-13-13442 | 13442 | Chl | oooooooooooo | 0m0m000m0m0m | ACAUGGAUGAUAU | 381 |
| SPP1-1011-13-13444 | 13444 | Chl | oooooooooooo | 0000mmmm0m0mm | GAAAUUUCGUAUU | 382 |
| SPP1-754-13-13446 | 13446 | Chl | oooooooooooo | 0m0mmmmmm00mm | GCGCCUUCUGAUU | 383 |
| SPP1-1021-13-13448 | 13448 | Chl | oooooooooooo | 0mmmmmm0m000m | AUUUCUCAUGAAU | 384 |
| SPP1-1330-13-13450 | 13450 | Chl | oooooooooooo | mmmmm0m000m00 | CUCUCAUGAAUAG | 385 |
| SPP1-346-13-13452 | 13452 | Chl | oooooooooooo | 000mmm00m0000 | AAGUCCAACGAAA | 386 |
| SPP1-869-13-13454 | 13454 | Chl | oooooooooooo | 0m00m00000m00 | AUGAUGAGAGCAA | 387 |
| SPP1-701-13-13456 | 13456 | Chl | oooooooooooo | 0m000000mm000 | GCGAGGAGUUGAA | 388 |
| SPP1-896-13-13458 | 13458 | Chl | oooooooooooo | m00mm00m00mm0 | UGAUUGAUAGUCA | 389 |
| SPP1-1035-13-13460 | 13460 | Chl | oooooooooooo | 000m0m0m0mmm | AGAUAGUGCAUCU | 390 |
| SPP1-1170-13-13462 | 13462 | Chl | oooooooooooo | 0m0m0m0mmm0mm | AUGUGUAUCUAUU | 391 |
| SPP1-1282-13-13464 | 13464 | Chl | oooooooooooo | mmmm0m0000000 | UUCUAUAGAAGAA | 392 |
| SPP1-1537-13-13466 | 13466 | Chl | oooooooooooo | mm0mmm00m00mm | UUGUCCAGCAAUU | 393 |
| SPP1-692-13-13468 | 13468 | Chl | oooooooooooo | 0m0m000000m00 | ACAUGGAAAGCGA | 394 |
| SPP1-840-13-13470 | 13470 | Chl | oooooooooooo | 0m00mmm000mm0 | GCAGUCCAGAUUA | 395 |
| SPP1-1163-13-13472 | 13472 | Chl | oooooooooooo | m00mm000m0m0m | UGGUUGAAUGUGU | 396 |
| SPP1-789-13-13474 | 13474 | Chl | oooooooooooo | mm0m0000m000m | UUAUGAAACGAGU | 397 |
| SPP1-841-13-13476 | 13476 | Chl | oooooooooooo | m00mm000mm0m | CAGUCCAGAUUAU | 398 |
| SPP1-852-13-13478 | 13478 | Chl | oooooooooooo | 0m0m000m00000 | AUAUAAGCGGAAA | 399 |
| SPP1-209-13-13480 | 13480 | Chl | oooooooooooo | m0mm0mm000m0 | UACCAGUUAAACA | 400 |
| SPP1-1276-13-13482 | 13482 | Chl | oooooooooooo | m0mmm0mmmm0m0 | UGUUCAUUCUAUA | 401 |
| SPP1-137-13-13484 | 13484 | Chl | oooooooooooo | mm00mm0000000 | CCGACCAAGGAAA | 402 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| SPP1-711-13-13486 | 13486 | Chl | oooooooooooo | oooOm0Om0m0m | GAAUGGUGCAUAC | 403 |
| SPP1-582-13-13488 | 13488 | Chl | oooooooooooo | 0m0m00m00mm00 | AUAUGAUGGCCGA | 404 |
| SPP1-839-13-13490 | 13490 | Chl | oooooooooooo | 00m00mmm000mm | AGCAGUCCAGAUU | 405 |
| SPP1-1091-13-13492 | 13492 | Chl | oooooooooooo | 0m0mmm00mm000 | GCAUUUAGUCAAA | 406 |
| SPP1-884-13-13494 | 13494 | Chl | oooooooooooo | 00m0mmmm00m0m | AGCAUUCCGAUGU | 407 |
| SPP1-903-13-13496 | 13496 | Chl | oooooooooooo | m00mm00000mmm | UAGUCAGGAACUU | 408 |
| SPP1-1090-13-13498 | 13498 | Chl | oooooooooooo | m0m0mmm00mm00 | UGCAUUUAGUCAA | 409 |
| SPP1-474-13-13500 | 13500 | Chl | oooooooooooo | 0mmm0m000mmm | GUCUGAUGAGUCU | 410 |
| SPP1-575-13-13502 | 13502 | Chl | oooooooooooo | m000m0m0m00 | UAGACACAUAUGA | 411 |
| SPP1-671-13-13504 | 13504 | Chl | oooooooooooo | m000m00000m0m | CAGACGAGGACAU | 412 |
| SPP1-924-13-13506 | 13506 | Chl | oooooooooooo | m00mm0m000mmm | CAGCCGUGAAUUC | 413 |
| SPP1-1185-13-13508 | 13508 | Chl | oooooooooooo | 00mmm00000m00 | AGUCUGGAAAUAA | 414 |
| SPP1-1221-13-13510 | 13510 | Chl | oooooooooooo | 00mmm0m00mmmm | AGUUUGUGGCUUC | 415 |
| SPP1-347-13-13512 | 13512 | Chl | oooooooooooo | 00mmm00m00000 | AGUCCAACGAAAG | 416 |
| SPP1-634-13-13514 | 13514 | Chl | oooooooooooo | 000mmmm0m000m | AAGUUUCGCAGAC | 417 |
| SPP1-877-13-13516 | 13516 | Chl | oooooooooooo | 00m00m000m0mm | AGCAAUGAGCAUU | 418 |
| SPP1-1033-13-13518 | 13518 | Chl | oooooooooooo | mm000m00m0m0m | UUAGAUAGUGCAU | 419 |
| SPP1-714-13-13520 | 13520 | Chl | oooooooooooo | m00m0m0m0m000 | UGGUGCAUACAAG | 420 |
| SPP1-791-13-13522 | 13522 | Chl | oooooooooooo | 0m0000m000mm0 | AUGAAACGAGUCA | 421 |
| SPP1-813-13-13524 | 13524 | Chl | oooooooooooo | mm0000m0mm000 | CCAGAGUGCUGAA | 422 |
| SPP1-939-13-13526 | 13526 | Chl | oooooooooooo | m00mm0m000mmm | CAGCCAUGAAUUU | 423 |
| SPP1-1161-13-13528 | 13528 | Chl | oooooooooooo | 0mm00mm000m0m | AUUGGUUGAAUGU | 424 |
| SPP1-1164-13-13530 | 13530 | Chl | oooooooooooo | 00mm000m0m0m0 | GGUUGAAUGUGUA | 425 |
| SPP1-1190-13-13532 | 13532 | Chl | oooooooooooo | 00000m00mm00m | GGAAAUAACUAAU | 426 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| SPP1-1333-13-13534 | 13534 | Chl | ooooooooooooo | mm0m000m00000 | UCAUGAAUAGAAA | 427 |
| SPP1-537-13-13536 | 13536 | Chl | ooooooooooooo | 0mm00m00mm000 | GCCAGCAACCGAA | 428 |
| SPP1-684-13-13538 | 13538 | Chl | ooooooooooooo | m0mmmm0m0m0 | CACCUCACACAUG | 429 |
| SPP1-707-13-13540 | 13540 | Chl | ooooooooooooo | 00mm000m00m0m | AGUUGAAUGGUGC | 430 |
| SPP1-799-13-13542 | 13542 | Chl | ooooooooooooo | 00mm00mm000m0 | AGUCAGCUGGAUG | 431 |
| SPP1-853-13-13544 | 13544 | Chl | ooooooooooooo | m0m0m000000 | UAUAAGCGGAAAG | 432 |
| SPP1-888-13-13546 | 13546 | Chl | ooooooooooooo | mmmm00m0m00mm | UUCCGAUGUGAUU | 433 |
| SPP1-1194-13-13548 | 13548 | Chl | ooooooooooooo | 0m00mm00m0m0m | AUAACUAAUGUGU | 434 |
| SPP1-1279-13-13550 | 13550 | Chl | ooooooooooooo | mm0mmmm0m0000 | UCAUUCUAUAGAA | 435 |
| SPP1-1300-13-13552 | 13552 | Chl | ooooooooooooo | 00mm0mm0m0m0 | AACUAUCACUGUA | 436 |
| SPP1-1510-13-13554 | 13554 | Chl | ooooooooooooo | 0mm00mm0mmm0m | GUCAAUUGCUUAU | 437 |
| SPP1-1543-13-13556 | 13556 | Chl | ooooooooooooo | 00m00mm00m000 | AGCAAUUAAUAAA | 438 |
| SPP1-434-13-13558 | 13558 | Chl | ooooooooooooo | 0m00mmmm00m00 | ACGACUCUGAUGA | 439 |
| SPP1-600-13-13560 | 13560 | Chl | ooooooooooooo | m00m0m00mmm0m | UAGUGUGGUUUAU | 440 |
| SPP1-863-13-13562 | 13562 | Chl | ooooooooooooo | 000mm00m00m00 | AAGCCAAUGAUGA | 441 |
| SPP1-902-13-13564 | 13564 | Chl | ooooooooooooo | 0m00mm00000mm | AUAGUCAGGAACU | 442 |
| SPP1-921-13-13566 | 13566 | Chl | ooooooooooooo | 00mm00mm0m000 | AGUCAGCCGUGAA | 443 |
| SPP1-154-13-13568 | 13568 | Chl | ooooooooooooo | 0mm0mm0m00000 | ACUACCAUGAGAA | 444 |
| SPP1-217-13-13570 | 13570 | Chl | ooooooooooooo | 000m000mm00mm | AAACAGGCUGAUU | 445 |
| SPP1-816-13-13572 | 13572 | Chl | ooooooooooooo | 000m0mm0000mm | GAGUGCUGAAACC | 446 |
| SPP1-882-13-13574 | 13574 | Chl | ooooooooooooo | m000m0mmmm00m | UGAGCAUUCCGAU | 447 |
| SPP1-932-13-13576 | 13576 | Chl | ooooooooooooo | 00mmmm0m00mm0 | AAUUCCACAGCCA | 448 |
| SPP1-1509-13-13578 | 13578 | Chl | ooooooooooooo | m0mm00mm0mmm0 | UGUCAAUUGCUUA | 449 |
| SPP1-157-13-13580 | 13580 | Chl | ooooooooooooo | 0mm0m00000mm0 | ACCAUGAGAAUUG | 450 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| SPP1-350-13-13582 | 13582 | Chl | oooooooooooo | mm00m00000mm0 | CCAACGAAAGCCA | 451 |
| SPP1-511-13-13584 | 13584 | Chl | oooooooooooo | mm00mm0mm00mm | CUGGUCACUGAUU | 452 |
| SPP1-605-13-13586 | 13586 | Chl | oooooooooooo | m00mmm0m000mm | UGGUUUAUGGACU | 453 |
| SPP1-811-13-13588 | 13588 | Chl | oooooooooooo | 00mm0000m0mm0 | GACCAGAGUGCUG | 454 |
| SPP1-892-13-13590 | 13590 | Chl | oooooooooooo | 00m0m00mm00m0 | GAUGUGAUUGAUA | 455 |
| SPP1-922-13-13592 | 13592 | Chl | oooooooooooo | 0mm00mm0m000m | GUCAGCCGUGAAU | 456 |
| SPP1-1169-13-13594 | 13594 | Chl | oooooooooooo | 00m0m0mmm0m | AAUGUGUAUCUAU | 457 |
| SPP1-1182-13-13596 | 13596 | Chl | oooooooooooo | mm000mmm00000 | UUGAGUCUGGAAA | 458 |
| SPP1-1539-13-13598 | 13598 | Chl | oooooooooooo | 0mmm0m00mm00 | GUCCAGCAAUUAA | 459 |
| SPP1-1541-13-13600 | 13600 | Chl | oooooooooooo | mm00m00mm00m0 | 0CCAGCAAUUAAUA | 460 |
| SPP1-427-13-13602 | 13602 | Chl | oooooooooooo | 00mmm000m0mm | GACUCGAACGACU | 461 |
| SPP1-533-13-13604 | 13604 | Chl Chl | oooooooooooo | 0mmm0mm00m00m | ACCUGCCAGCAAC | 462 |
| APOB--13-13763 | 13763 | TEG Chl | oooooooooooo | 0m + 00 + m0 + m0 + m | ACtGAaUAcCAaU | 463 |
| APOB--13-13764 | 13764 | TEG | oooooooooooo | 0mm000mmm00m | ACUGAAUACCAAU | 464 |
| MAP4K4--16-13766 | 13766 | Chl | oooooooooooo | DY547mm0m0000mmm 0 | CUGUGGAAGUCUA | 465 |
| PPIB--13-13767 | 13767 | Chl | oooooooooooo | mmmmmmmmmmmm | GGCUACAAAAACA | 466 |
| PPIB--15-13768 | 13768 | Chl | oooooooooooooo | mm00mm0m00000m0 | UUGGCUACAAAAACA | 467 |
| PPIB--17-13769 | 13769 | Chl | oooooooooooooooo | 0mmm00mm0m00000m0 | AUUJGGCUACAAAAACA | 468 |
| MAP4K4--16-13939 | 13939 | Chl | oooooooooooo | m0m0000m0mmm0 | UGUAGGAUGUCUA | 469 |
| APOB-4314-16-13940 | 13940 | Chl | oooooooooooooo | 0mmm0000000m0 | AUCUGGAGAAACA | 470 |
| APOB-4314-17-13941 | 13941 | Chl | oooooooooooooo | 000mmm0000000m0 | AGAUCUGGAGAAACA | 471 |
| APOB--16-13942 | 13942 | Chl | oooooooooooooo | 00mmm0mm0mm0 | GACUCAUCUGCUA | 472 |
| APOB--18-13943 | 13943 | Chl | oooooooooooooo | 00mmm0mm0mm0 | GACUCAUCUGCUA | 473 |
| APOB--17-13944 | 13944 | Chl | oooooooooooooo | m00mmm0mmm0mm0 | UGGACUCAUCUGCUA | 474 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| APOB--19-13945 | 13945 | Chl | oooooooooooooo | m000mmm0mmm0mm0 | UGGACUCAUCUGCUA | 475 |
| APOB-4314-16-13946 | 13946 | Chl | oooooooooooo | 0000000m00m0m | GGAGAAACAACAU | 476 |
| APOB-4314-17-13947 | 13947 | Chl | ooooooooooooo | mm0000000m00m0m | CUGGAGAAACAACAU | 477 |
| APOB--16-13948 | 13948 | Chl | oooooooooooo | 00mmmmmm000m | AGUCCCUCAAACA | 478 |
| APOB--17-13949 | 13949 | Chl | ooooooooooooo | 0000mmmmmm000m | AGAGUCCCUCAAACA | 479 |
| APOB--16-13950 | 13950 | Chl | oooooooooooo | 0mm000m0mm00m | ACUGAAUACCAAU | 480 |
| APOB--18-13951 | 13951 | Chl | oooooooooooo | 0mm000m0mm00m | ACUGAAUACCAAU | 481 |
| APOB--17-13952 | 13952 | Chl | ooooooooooooo | 0m0mm000m0mm00m | ACACUGAAUACCAAU | 482 |
| APOB--19-13953 | 13953 | Chl | ooooooooooooo | 0m0mm000m0mm00m | ACACUGAAUACCAAU | 483 |
| MAP4K4--16-13766.2 | 13766.2 | Chl | oooooooooooo | DY547mm0m00000mmm0 | CUGUGGAAGUCUA | 484 |
| CTGF-1222-16-13980 | 13980 | Chl | oooooooooooo | 0m0000000m0m0 | ACAGGAAGAUGUA | 485 |
| CTGF-813-16-13981 | 13981 | Chl | oooooooooooo | 000m0000mmmm | GAGUGGAGCGCCU | 486 |
| CTGF-747-16-13982 | 13982 | Chl | oooooooooooo | m0mm000000m0 | CGACUGGAAGACA | 487 |
| CTGF-817-16-13983 | 13983 | Chl | oooooooooooo | 0000mmmm0mmm | GGAGCGCCUGUUC | 488 |
| CTGF-1174-16-13984 | 13984 | Chl | oooooooooooo | 0mm0m0m00mm0 | GCCAUUACAACUG | 489 |
| CTGF-1005-16-13985 | 13985 | Chl | oooooooooooo | 000mmmmmm00mm | GAGCUUUCUGGCU | 490 |
| CTGF-814-16-13986 | 13986 | Chl | oooooooooooo | 00m0000mmmm0 | AGUGGAGCGCCUG | 491 |
| CTGF-816-16-13987 | 13987 | Chl | oooooooooooo | m0000mmmm0mm | UGGAGCGCCUGUU | 492 |
| CTGF-1001-16-13988 | 13988 | Chl | oooooooooooo | 0mmm000mmmmmm | GUUUGAGCUUUCU | 493 |
| CTGF-1173-16-13989 | 13989 | Chl | oooooooooooo | m0mm0mm0m00mm | UGCCAUUACAACU | 494 |
| CTGF-749-16-13990 | 13990 | Chl | oooooooooooo | 0mm000000m0m | ACUGGAAGACACG | 495 |
| CTGF-792-16-13991 | 13991 | Chl | oooooooooooo | 00mm0mmm00mmm | AACUGCCUGGUCC | 496 |
| CTGF-1162-16-13992 | 13992 | Chl | oooooooooooo | 000mmm0m0mmm0 | AGACCUGUGCCUG | 497 |
| CTGF-811-16-13993 | 13993 | Chl | oooooooooooo | m0000m0000mm | CAGAGUGGAGCGC | 498 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| CTGF-797-16-13994 | 13994 | Chl | oooooooooooo | mmm00mmm000mm | CCUGGUCCAGACC | 499 |
| CTGF-1175-16-13995 | 13995 | Chl | oooooooooooo | mm0mm0m00mm0m | CCAUUACAACUGU | 500 |
| CTGF-1172-16-13996 | 13996 | Chl | oooooooooooo | mm0mm0mm00m | CUGCCAUUACAAC | 501 |
| CTGF-1177-16-13997 | 13997 | Chl | oooooooooooo | 0mm0m00mm0mmm | AUUACAACUGUCC | 502 |
| CTGF-1176-16-13998 | 13998 | Chl | oooooooooooo | m0mm0m00mm0mm | CAUUACAACUGUC | 503 |
| CTGF-812-16-13999 | 13999 | Chl | oooooooooooo | 0000m0000mmm | AGAGUGGAGCGCC | 504 |
| CTGF-745-16-14000 | 14000 | Chl | oooooooooooo | 0mm0mm000000 | ACCGACUGGAAGA | 505 |
| CTGF-1230-16-14001 | 14001 | Chl | oooooooooooo | 0m0m0m0000m0 | AUGUACGGAGACA | 506 |
| CTGF-920-16-14002 | 14002 | Chl | oooooooooooo | 0mmmm0m000mm | GCCUUGCGAAGCU | 507 |
| CTGF-679-16-14003 | 14003 | Chl | oooooooooooo | 0mm0m00000m0 | GCUGCGAGGAGUG | 508 |
| CTGF-992-16-14004 | 14004 | Chl | oooooooooooo | 0mmm0mm000mmm | GCCUAUCAAGUUU | 509 |
| CTGF-1045-16-14005 | 14005 | Chl | oooooooooooo | 00mmmm0m0000m | AAUUCUGUGGAGU | 510 |
| CTGF-1231-16-14006 | 14006 | Chl | oooooooooooo | m0m0m0000m0m | UGUACGGAGACAU | 511 |
| CTGF-991-16-14007 | 14007 | Chl | oooooooooooo | 00mmm0mm000mm | AGCCUAUCAAGUU | 512 |
| CTGF-998-16-14008 | 14008 | Chl | oooooooooooo | m000mmm000mmm | CAAGUUUGAGCUU | 513 |
| CTGF-1049-16-14009 | 14009 | Chl | oooooooooooo | mm0m0000m0m0m | CUGUGGAGUAUGU | 514 |
| CTGF-1044-16-14010 | 14010 | Chl | oooooooooooo | 000mmmm0m0000 | AAAUUCUGUGGAG | 515 |
| CTGF-1327-16-14011 | 14011 | Chl | oooooooooooo | mmmm00m00m0m0 | UUUCAGUAGCACA | 516 |
| CTGF-1196-16-14012 | 14012 | Chl | oooooooooooo | m00m0m0mmmmm | CAAUGACAUCUUU | 517 |
| CTGF-562-16-14013 | 14013 | Chl | oooooooooooo | 00m0mm0m0m0m | AGUACCAGUGCAC | 518 |
| CTGF-752-16-14014 | 14014 | Chl | oooooooooooo | 000000m0mmmm | GGAAGACACGUUU | 519 |
| CTGF-994-16-14015 | 14015 | Chl | oooooooooooo | mm0mm000mmmm00 | CUAUCAAGUUUGA | 520 |
| CTGF-1040-16-14016 | 14016 | Chl | oooooooooooo | 00mm000mmmm0m | AGCUAAAUUCUGU | 521 |
| CTGF-1984-16-14017 | 14017 | Chl | oooooooooooo | 000m0000m0m00 | AGGUAGAAUGUAA | 522 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| CTGF-2195-16-14018 | 14018 | Chl | ooooooooooooo | 00mm00mm00mmm | AGCUGAUCAGUUU | 523 |
| CTGF-2043-16-14019 | 14019 | Chl | ooooooooooooo | mmmm0mmm000m0 | UUCUGCUCAGAUA | 524 |
| CTGF-1892-16-14020 | 14020 | Chl | ooooooooooooo | mm0mmm000mm00 | UUAUCUAAGUUAA | 525 |
| CTGF-1567-16-14021 | 14021 | Chl | ooooooooooooo | m0m0m00m00m0 | UAUACGAGUAAUA | 526 |
| CTGF-1780-16-14022 | 14022 | Chl | ooooooooooooo | 00mm000m00mmm | GACUGGACAGCUU | 527 |
| CTGF-2162-16-14023 | 14023 | Chl | ooooooooooooo | 0m00mmmm0mm0 | AUGGCCUUUAUUA | 528 |
| CTGF-1034-16-14024 | 14024 | Chl | ooooooooooooo | 0m0mm00mm000 | AUACCGAGCUAAA | 529 |
| CTGF-2264-16-14025 | 14025 | Chl | ooooooooooooo | mm0mm00000m0m | UUGUUGAGAGUGU | 530 |
| CTGF-1032-16-14026 | 14026 | Chl | ooooooooooooo | 0m0m0mm00mm0 | ACAUACCGAGCUA | 531 |
| CTGF-1535-16-14027 | 14027 | Chl | ooooooooooooo | 00m0000000mm0 | AGCAGAAAGGUUA | 532 |
| CTGF-1694-16-14028 | 14028 | Chl | ooooooooooooo | 00mm0mmmmmm00 | AGUUGUUCCUUAA | 533 |
| CTGF-1588-16-14029 | 14029 | Chl | ooooooooooooo | 0mmm0000m0m00 | AUUUGAAGUGUAA | 534 |
| CTGF-928-16-14030 | 14030 | Chl | ooooooooooooo | 000mm00mmm000 | AAGCUGACCUGGA | 535 |
| CTGF-1133-16-14031 | 14031 | Chl | ooooooooooooo | 00mm0m0000000 | GGUCAUGAAGAAG | 536 |
| CTGF-912-16-14032 | 14032 | Chl | ooooooooooooo | 0m00mm000mmmm | AUGGUCAGGCCUU | 537 |
| CTGF-753-16-14033 | 14033 | Chl | ooooooooooooo | 00000m0mmmm0 | GAAGACACGUUUG | 538 |
| CTGF-918-16-14034 | 14034 | Chl | ooooooooooooo | 000mmmm0m000 | AGGCCUUGCGAAG | 539 |
| CTGF-744-16-14035 | 14035 | Chl | ooooooooooooo | m0mm0mm00000 | UACCGACUGGAAG | 540 |
| CTGF-466-16-14036 | 14036 | Chl | ooooooooooooo | 0mmm0000mm0 | ACCGCAAGAUCGG | 541 |
| CTGF-917-16-14037 | 14037 | Chl | ooooooooooooo | m000mmmm0m00 | CAGGCCUUGCGAA | 542 |
| CTGF-1038-16-14038 | 14038 | Chl | ooooooooooooo | m00mm000mmmm | CGAGCUAAAUUCU | 543 |
| CTGF-1048-16-14039 | 14039 | Chl | ooooooooooooo | mmm0m0000m0m0 | UCUGUGGAGUAUG | 544 |
| CTGF-1235-16-14040 | 14040 | Chl | ooooooooooooo | m0000m0m00m0 | CGGAGACAUGGCA | 545 |
| CTGF-868-16-14041 | 14041 | Chl | ooooooooooooo | 0m00m00mmmmm | AUGACAACGCCUC | 546 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| CTGF-1131-16-14042 | 14042 | Chl | oooooooooooo | 0000mm0m00000 | GAGGUCAUGAAGA | 547 |
| CTGF-1043-16-14043 | 14043 | Chl | oooooooooooo | m000mmmm0m000 | UAAAUUCUGUGGA | 548 |
| CTGF-751-16-14044 | 14044 | Chl | oooooooooooo | m000000m0mmm | UGGAAGACACGUU | 549 |
| CTGF-1227-16-14045 | 14045 | Chl | oooooooooooo | 0000m0m0m000 | AAGAUGUACGGAG | 550 |
| CTGF-867-16-14046 | 14046 | Chl | oooooooooooo | 00m00m00mmmm | AAUGACAACGCCU | 551 |
| CTGF-1128-16-14047 | 14047 | Chl | oooooooooooo | 00m000mm0m00 | GGCGAGGUCAUGA | 552 |
| CTGF-756-16-14048 | 14048 | Chl | oooooooooooo | 00m0m0mmm00mm | GACACGUUUGGCC | 553 |
| CTGF-1234-16-14049 | 14049 | Chl | oooooooooooo | 0m00000m0m00m | ACGGAGACAUGGC | 554 |
| CTGF-916-16-14050 | 14050 | Chl | oooooooooooo | mm000mmmm0m00 | UCAGGCCUUGCGA | 555 |
| CTGF-925-16-14051 | 14051 | Chl | oooooooooooo | 0m0000m00mmm | GCGAAGCUGACCU | 556 |
| CTGF-1225-16-14052 | 14052 | Chl | oooooooooooo | 000000m0m0m00 | GGAAGAUGUACGG | 557 |
| CTGF-445-16-14053 | 14053 | Chl | oooooooooooo | 0m00mmmm00mmm | GUGACUUCGGCUC | 558 |
| CTGF-446-16-14054 | 14054 | Chl | oooooooooooo | m00mmmm00mmmm | UGACUUCGGCUCC | 559 |
| CTGF-913-16-14055 | 14055 | Chl | oooooooooooo | m00mm000mmmm0 | UGGUCAGGCCUUG | 560 |
| CTGF-997-16-14056 | 14056 | Chl | oooooooooooo | mm000mmm000mm | UCAAGUUUGAGCU | 561 |
| CTGF-277-16-14057 | 14057 | Chl | oooooooooooo | 0mm0000mm0m00 | GCCAGAACUGCAG | 562 |
| CTGF-1052-16-14058 | 14058 | Chl | oooooooooooo | m0000m0m0m0mm | UGGAGUAUGUACC | 563 |
| CTGF-887-16-14059 | 14059 | Chl | oooooooooooo | 0mm0000000m00 | GCUAGAGAAGCAG | 564 |
| CTGF-914-16-14060 | 14060 | Chl | oooooooooooo | 00mm000mmmm0m | GGUCAGGCCUUGC | 565 |
| CTGF-1039-16-14061 | 14061 | Chl | oooooooooooo | 000mm000mmmm0 | GAGCUAAAUUCUG | 566 |
| CTGF-754-16-14062 | 14062 | Chl | oooooooooooo | 0000m0m0mmm00 | AAGACACGUUUGG | 567 |
| CTGF-1130-16-14063 | 14063 | Chl | oooooooooooo | m0000mm0m0000 | CGAGGUCAUGAAG | 568 |
| CTGF-919-16-14064 | 14064 | Chl | oooooooooooo | 00mmmm0m0000m | GGCCUUGCGAAGC | 569 |
| CTGF-922-16-14065 | 14065 | Chl | oooooooooooo | mmm0m0000mm00 | CUUGCGAAGCUGA | 570 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| CTGF-746-16-14066 | 14066 | Chl | oooooooooooo | mm00mm000000m | CCGACUGGAAGAC | 571 |
| CTGF-993-16-14067 | 14067 | Chl | oooooooooooo | mmm0mm000mmm0 | CCUAUCAAGUUUG | 572 |
| CTGF-825-16-14068 | 14068 | Chl | oooooooooooo | m0mmmm0000mmm | UGUUCCAAGACCU | 573 |
| CTGF-926-16-14069 | 14069 | Chl | oooooooooooo | m0000mm00mmm0 | CGAAGCUGACCUG | 574 |
| CTGF-923-16-14070 | 14070 | Chl | oooooooooooo | mm0m0000mm00m | UUGCGAAGCUGAC | 575 |
| CTGF-866-16-14071 | 14071 | Chl | oooooooooooo | m00m00m00m0mm | CAAUGACAACGCC | 576 |
| CTGF-563-16-14072 | 14072 | Chl | oooooooooooo | 0m0mm00m0m0m0 | GUACCAGUGCACG | 577 |
| CTGF-823-16-14073 | 14073 | Chl | oooooooooooo | mmm0mmmm0000m | CCUGUUCCAAGAC | 578 |
| CTGF-1233-16-14074 | 14074 | Chl | oooooooooooo | m0m00000m0m00 | UACGGAGACAUGG | 579 |
| CTGF-924-16-14075 | 14075 | Chl | oooooooooooo | m0m0000mm00mm | UGCGAAGCUGACC | 580 |
| CTGF-921-16-14076 | 14076 | Chl | oooooooooooo | mmmm0m0000mm0 | CCUUGCGAAGCUG | 581 |
| CTGF-443-16-14077 | 14077 | Chl | oooooooooooo | mm0m00mmmm00m | CUGUGACUUCGGC | 582 |
| CTGF-1041-16-14078 | 14078 | Chl | oooooooooooo | 0mm000mmmm0m0 | GCUAAAUUCUGUG | 583 |
| CTGF-1042-16-14079 | 14079 | Chl | oooooooooooo | mm000mmmm0m00 | CUAAAUUCUGUGG | 584 |
| CTGF-755-16-14080 | 14080 | Chl | oooooooooooo | 000m0m0mmm00m | AGACACGUUUGGC | 585 |
| CTGF-467-16-14081 | 14081 | Chl | oooooooooooo | mm0m0000mm00m | CCGCAAGAUCGGC | 586 |
| CTGF-995-16-14082 | 14082 | Chl | oooooooooooo | m0mm000mmm000 | UAUCAAGUUUGAG | 587 |
| CTGF-927-16-14083 | 14083 | Chl | oooooooooooo | 0000mm00mmm00 | GAAGCUGACCUGG | 588 |
| SPP1-1091-16-14131 | 14131 | Chl | oooooooooooo | 0m0mmm00mm000 | GCAUUUAGUCAAA | 589 |
| PPIB--16-14188 | 14188 | Chl | oooooooooooo | mmmmmmmmmmmmm | GGCUACAAAAACA | 590 |
| PPIB--17-14189 | 14189 | Chl | ooooooooooooo | mm00mm0m00000m | UUGGCUACAAAAACA | 591 |
| PPIB--18-14190 | 14190 | Chl | oooooooooooooooo | 0mmm00mm0m00000m | AUUUGGCUACAAAAACA | 592 |
| pGL3-1172-16-14386 | 14386 | chl | oooooooooooo | 0m000m00mmm | ACAAAUACGAUUU | 593 |
| pGL3-1172-16-14387 | 14387 | chl | oooooooooooo | DY5470m000m0m00mmm | ACAAAUACGAUUU | 594 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| MAP4K4-2931-25-14390 | 14390 | Chl | ooooooooooooooo oooooooooo | Pmmmmmmmmmmmm ooo m mmmmmmmmm | CUUUGAAGAGUUCUGUG GAAGUCUA | 595 |
| miR-122--23-14391 | 14391 | Chl | ssoooooooooooo ooossss | mmmmmmmmmmmmmmmm mmmmmm | ACAAACACCAUUGUCAC ACUCCA | 596 |
| | 14084 | Chl | oooooooooooo | mmm0m000mm000 | CUCAUGAAUUAGA | 719 |
| | 14085 | Chl | oooooooooooo | mm0000mm00mm0 | CUGAGGUCAAUUA | 720 |
| | 14086 | Chl | oooooooooooo | 0000mm00mm000 | GAGGUCAAUUAAA | 721 |
| | 14087 | Chl | oooooooooooo | mmm0000mm00mm | UCUGAGGUCAAUU | 722 |
| | 14088 | Chl | oooooooooooo | m0000mm00mm00 | UGAGGUCAAUUAA | 723 |
| | 14089 | Chl | oooooooooooo | mmmm0000mm00m | UUCUGAGGUCAAU | 724 |
| | 14090 | Chl | oooooooooooo | 0mm00mm000m0 | GUCAGCUGGAUGA | 725 |
| | 14091 | Chl | oooooooooooo | mmmm00m000mmm | UUCUGAUGAAUCU | 726 |
| | 14092 | Chl | oooooooooooo | m000mm0000mm0 | UGGACUGAGGUCA | 727 |
| | 14093 | Chl | oooooooooooo | 000mmmm0mm0mm | GAGUCUCACCAUU | 728 |
| | 14094 | Chl | oooooooooooo | 00mm0000mm000 | GACUGAGGUCAAA | 729 |
| | 14095 | Chl | oooooooooooo | mm0m00mm0m000 | UCACAGCCAUGAA | 730 |
| | 14096 | Chl | oooooooooooo | 00mmmm0m0mmm | AGUCUCACCAUUC | 731 |
| | 14097 | Chl | oooooooooooo | 000m00000mm0 | AAGCGGAAAGCCA | 732 |
| | 14098 | Chl | oooooooooooo | 00m00000mm00 | AGCGGAAAGCCAA | 733 |
| | 14099 | Chl | oooooooooooo | 0mm0m0m000m00 | ACCACAUGGAUGA | 734 |
| | 14100 | Chl | oooooooooooo | 0mm0m00mm0m0m | GCCAUGACCACAU | 735 |
| | 14101 | Chl | oooooooooooo | 000mm0m00mm0m | AAGCCAUGACCAC | 736 |
| | 14102 | Chl | oooooooooooo | 0m00000mm00m | GCGGAAAGCCAAU | 737 |
| | 14103 | Chl | oooooooooooo | 000mmmm0mmm | AAAUUCGUAUUU | 738 |
| | 14104 | Chl | oooooooooooo | 0mmmmm0mmmmm | AUUUCGUAUUUCU | 739 |
| | 14105 | Chl | oooooooooooo | 0000mm0m00mm0 | AAAGCCAUGACCA | 740 |
| | 14106 | Chl | oooooooooooo | 0m0m000m00m0m | ACAUGGAUGAUAU | 741 |
| | 14107 | Chl | oooooooooooo | 0000mmmm0mm | GAAAUUCGUAUU | 742 |
| | 14108 | Chl | oooooooooooo | 0mmmmmm00mm | GCGCCUUCUGAUU | 743 |
| | 14109 | Chl | oooooooooooo | 0mmmmm0m000m | AUUUCUCAUGAAU | 744 |
| | 14110 | Chl | oooooooooooo | mmmmm0m000m00 | CUCUCAUGAAUAG | 745 |
| | 14111 | Chl | oooooooooooo | 000mmm00m000 | AAGUCCAACGAAA | 746 |
| | 14112 | Chl | oooooooooooo | 0m00m00000m00 | AUGAUGAGAGCAA | 747 |
| | 14113 | Chl | oooooooooooo | 0m00000mm000 | GCGAGGAGUUGAA | 748 |
| | 14114 | Chl | oooooooooooo | m00mm00m00mm0 | UGAUUGAUAGUCA | 749 |
| | 14115 | Chl | oooooooooooo | 000m00m0m0mmm | AGAUAGUGCAUCU | 750 |
| | 14116 | Chl | oooooooooooo | 0m0m0m0mmm0mm | AUGUGUAUCUAUU | 751 |
| | 14117 | Chl | oooooooooooo | mmmm0m0000000 | UUCUAUAGAAGAA | 752 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| | 14118 | Chl | oooooooooooo | mm0mmm00m00mm | UUGUCCAGCAAUU | 753 |
| | 14119 | Chl | oooooooooooo | 0m0m000000m0 | ACAUGGAAAGCGA | 754 |
| | 14120 | Chl | oooooooooooo | 0m00mmm000mm0 | GCAGUCCAGAUUA | 755 |
| | 14121 | Chl | oooooooooooo | m00mm000m0m0m | UGGUUGAAUGUGU | 756 |
| | 14122 | Chl | oooooooooooo | mm00000m00m | UUAUGAAACGAGU | 757 |
| | 14123 | Chl | oooooooooooo | m00mm000mm0m | CAGUCCAGAUUAU | 758 |
| | 14124 | Chl | oooooooooooo | 0m0m000m0000 | AUAUAAGCGGAAA | 759 |
| | 14125 | Chl | oooooooooooo | m0mm00mm000m0 | UACCAGUUAAACA | 760 |
| | 14126 | Chl | oooooooooooo | m0mmm0mmmm0m0 | UGUUCAUUCUAUA | 761 |
| | 14127 | Chl | oooooooooooo | mm0mm0000000 | CCGACCAAGGAAA | 762 |
| | 14128 | Chl | oooooooooooo | 000m00m0m0m0m | GAAUGGUGCAUAC | 763 |
| | 14129 | Chl | oooooooooooo | 0m0m0m00mm0 | AUAUGAUGGCCGA | 764 |
| | 14130 | Chl | oooooooooooo | 00m00mmm000mm | AGCAGUCCAGAUU | 765 |
| | 14132 | Chl | oooooooooooo | 00m0mmmm0m0m | AGCAUUCCGAUGU | 766 |
| | 14133 | Chl | oooooooooooo | m00mm00000mmm | UAGUCAGGAACUU | 767 |
| | 14134 | Chl | oooooooooooo | m0m0mmm00mm00 | UGCAUUUAGUCAA | 768 |
| | 14135 | Chl | oooooooooooo | 0mmm00m000mmm | GUCUGAUGAGUCU | 769 |
| | 14136 | Chl | oooooooooooo | m000m0m0m0m00 | UAGACACAUAUGA | 770 |
| | 14137 | Chl | oooooooooooo | m000m0000m0m | CAGACGAGGACAU | 771 |
| | 14138 | Chl | oooooooooooo | m00mmm000mmm | CAGCCGUGAAUUC | 772 |
| | 14139 | Chl | oooooooooooo | 00mmm00000m00 | AGUCUGGAAAUAA | 773 |
| | 14140 | Chl | oooooooooooo | 00mmm0m00mmmm | AGUUUGUGGCUUC | 774 |
| | 14141 | Chl | oooooooooooo | 00mmm00m0000 | AGUCCAACGAAAG | 775 |
| | 14142 | Chl | oooooooooooo | 000mmmmm000m | AAGUUUCGCAGAC | 776 |
| | 14143 | Chl | oooooooooooo | 00m00m000m0mm | AGCAAUGAGCAUU | 777 |
| | 14144 | Chl | oooooooooooo | mm000m00m0m0m | UUAGAUAGUGCAU | 778 |
| | 14145 | Chl | oooooooooooo | m00m0m0m0m000 | UGGUGCAUACAAG | 779 |
| | 14146 | Chl | oooooooooooo | 0m0000m00mm0 | AUGAAACGAGUCA | 780 |
| | 14147 | Chl | oooooooooooo | mm0000m0mm000 | CCAGAGUGCUGAA | 781 |
| | 14148 | Chl | oooooooooooo | m00mm0m000mmm | CAGCCAUGAAUUU | 782 |
| | 14149 | Chl | oooooooooooo | 0mm00m000m0m | AUUGGUUGAAUGU | 783 |
| | 14150 | Chl | oooooooooooo | 00mm000m0m0m0 | GGUUGAAUGUGUA | 784 |
| | 14151 | Chl | oooooooooooo | 00000m00mm00m | GGAAAUAACUAAU | 785 |
| | 14152 | Chl | oooooooooooo | mm0m000m00000 | UCAUGAAUAGAAA | 786 |

TABLE 3-continued

Sense backbone, chemistry, and sequence information.

| ID Number | Oligo Number | OHang Sense Chem. | Sense Backbone | Sense Chemistry | Sense Sequence | SEQ ID NO: |
|---|---|---|---|---|---|---|
| | 14153 | Chl | oooooooooooo | 0mm00m00mm00 | GCCAGCAACCGAA | 787 |
| | 14154 | Chl | oooooooooooo | m0mmmm0m0m0m0 | CACCUCACACAUG | 788 |
| | 14155 | Chl | oooooooooooo | 00mm000m00m0m | AGUUGAAUGGUGC | 789 |
| | 14156 | Chl | oooooooooooo | 00mm00mm000m0 | AGUCAGCUGGAUG | 790 |
| | 14157 | Chl | oooooooooooo | m0m000m00000 | UAUAAGCGGAAAG | 791 |
| | 14158 | Chl | oooooooooooo | mmmm0m0m00mm | UUCCGAUGUGAUU | 792 |
| | 14159 | Chl | oooooooooooo | 0m00mm0m0m0m | AUAACUAAUGUGU | 793 |
| | 14160 | Chl | oooooooooooo | mm0mmmm0m0000 | UCAUUCUAUAGAA | 794 |
| | 14161 | Chl | oooooooooooo | 00mm0mm0mm0m0 | AACUAUCACUGUA | 795 |
| | 14162 | Chl | oooooooooooo | 0mm00mm0mmm0m | GUCAAUUGCUUAU | 796 |
| | 14163 | Chl | oooooooooooo | 00m00mm00m000 | AGCAAUUAAUAAA | 797 |
| | 14164 | Chl | oooooooooooo | 0m0mmmm00m00 | ACGACUCUGAUGA | 798 |
| | 14165 | Chl | oooooooooooo | m00m0m0mmm0m | UAGUGUGGUUUAU | 799 |
| | 14166 | Chl | oooooooooooo | 000mm00m00m00 | AAGCCAAUGAUGA | 800 |
| | 14167 | Chl | oooooooooooo | 0m00mm00000mm | AUAGUCAGGAACU | 801 |
| | 14168 | Chl | oooooooooooo | 00mm00mmm000 | AGUCAGCCGUGAA | 802 |
| | 14169 | Chl | oooooooooooo | 0mm0m0m00000 | ACUACCAUGAGAA | 803 |
| | 14170 | Chl | oooooooooooo | 000m000mm00m | AAACAGGCUGAUU | 804 |
| | 14171 | Chl | oooooooooooo | 000m0mm0000mm | GAGUGCUGAAACC | 805 |
| | 14172 | Chl | oooooooooooo | m000m0mmmm0m | UGAGCAUUCCGAU | 806 |
| | 14173 | Chl | oooooooooooo | 00mmmm0m00mm0 | AAUUCCACAGCCA | 807 |
| | 14174 | Chl | oooooooooooo | m0mm00mm0mmm0 | UGUCAAUUGCUUA | 808 |
| | 14175 | Chl | oooooooooooo | 0mm0m00000mm0 | ACCAUGAGAAUUG | 809 |
| | 14176 | Chl | oooooooooooo | mm00m0000mm0 | CCAACGAAAGCCA | 810 |
| | 14177 | Chl | oooooooooooo | mm00m0m00mm | CUGGUCACUGAUU | 811 |
| | 14178 | Chl | oooooooooooo | m00mmm0m000mm | UGGUUUAUGGACU | 812 |
| | 14179 | Chl | oooooooooooo | 00mm0000mm0 | GACCAGAGUGCUG | 813 |
| | 14180 | Chl | oooooooooooo | 00m0m0m0m0 | GAUGUGAUUGAUA | 814 |
| | 14181 | Chl | oooooooooooo | 0mm00mmm000m | GUCAGCCGUGAAU | 815 |
| | 14182 | Chl | oooooooooooo | 00m0m0m0mmm0m | AAUGUGUAUCUAU | 816 |
| | 14183 | Chl | oooooooooooo | mm000mmm00000 | UUGAGUCUGGAAA | 817 |
| | 14184 | Chl | oooooooooooo | 0mm00m0m00mm00 | GUCCAGCAAUUAA | 818 |
| | 14185 | Chl | oooooooooooo | mm00m0m00m0m0 | CCAGCAAUUAAUA | 819 |
| | 14186 | Chl | oooooooooooo | 00mmm00m0mm | GACUCGAACGACU | 820 |
| | 14187 | Chl | oooooooooooo | 0mmm0mm0m00m | ACCUGCCAGCAAC | 821 | o: phosphodiester; s: phosphorothioate; P: 5' phosphorylation; 0: 2'-OH; F: 2'-fluoro; m: 2' O-methyl; +: LNA modification. Capital letters in the sequence signify ribonucleotides, lower case letters signify deoxyribonucleotides.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety. This application incorporates by reference the entire contents, including all the drawings and all parts of the specification (including sequence listing or amino acid/polynucleotide sequences) of the co-pending U.S. Provisional Application No. 61/135,855, filed on Jul. 24, 2008, entitled "SHORT HAIRPIN RNAI CONSTRUCTS AND USES THEREOF," and U.S. Provisional Application No. 61/197,768, filed on Oct. 30, 2008, entitled "MINIRNA CONSTRUCTS AND USES THEREOF."

What is claimed is:

1. A method for treating compromised skin, the method comprising, administering to a subject a therapeutically effective amount for treating compromised skin of a double stranded nucleic acid molecule comprising a guide strand, with a minimal length of 16 nucleotides, and a passenger strand forming a double stranded nucleic acid molecule, having a double stranded region and a single stranded region, the double stranded region having 8-15 nucleotides in length, the single stranded region having 4-12 nucleotides in length, wherein position 1 of the guide strand is 5' phosphorylated or has a 2' O-methyl modification, wherein the passenger strand is linked to a lipophilic group, wherein at least 40% of the nucleotides of the double stranded nucleic acid are modified, and wherein the double stranded nucleic acid molecule has one end that is blunt or includes a one nucleotide overhang, wherein the double stranded nucleic acid molecule is directed against a gene encoding Connective Tissue Growth Factor (CTGF), and wherein treating compromised skin comprises preventing, reducing, or inhibiting dermal scarring in compromised skin.

2. The method of claim 1, wherein the subject has a wound.

3. The method of claim 2, wherein the wound is a result of elective surgery.

4. The method of claim 1, wherein the double stranded nucleic acid molecule is administered on the skin of the subject in need thereof.

5. The method of claim 1, wherein the nucleic acid molecule is administered by local injection.

6. The method of claim 1, wherein the single stranded region contains 3, 4, 5, 6, 7, 8, 9, 10, 11 or 12 phosphorothioate modifications.

7. A method for treating compromised skin, the method comprising, administering to a subject a therapeutically effective amount for treating compromised skin of a double stranded nucleic acid molecule comprising a guide strand, with a minimal length of 16 nucleotides, and a passenger strand forming a double stranded nucleic acid molecule, having a double stranded region and a single stranded region, the double stranded region having 8-15 nucleotides in length, the single stranded region having 4-12 nucleotides in length, wherein position 1 of the guide strand is 5' phosphorylated or has a 2' O-methyl modification, wherein at least 40% of the nucleotides of the double stranded nucleic acid are modified, and wherein the double stranded nucleic acid molecule has one end that is blunt or includes a one nucleotide overhang, wherein the double stranded nucleic acid molecule is directed against a gene encoding Connective Tissue Growth Factor (CTGF), and wherein treating compromised skin comprises preventing, reducing, or inhibiting dermal scarring in compromised skin.

8. The method of claim 7, wherein the subject has a wound.

9. The method of claim 8, wherein the wound is a result of elective surgery.

10. The method of claim 7, wherein the double stranded nucleic acid molecule is administered on the skin of the subject in need thereof.

11. The method of claim 7, wherein the nucleic acid molecule is administered by local injection.

12. The method of claim 7, wherein the single stranded region contains 3, 4, 5, 6, 7, 8, 9, 10, 11 or 12 phosphorothioate modifications.

* * * * *